US012790398B2

(12) United States Patent
Sapieha et al.

(10) Patent No.: US 12,790,398 B2

(45) Date of Patent: Nov. 10, 2026

(54) COMPOSITIONS AND METHODS FOR TREATING AND PREVENTING INFLAMMATION

(71) Applicant: RSEM, LIMITED PARTNERSHIP, Montréal (CA)

(72) Inventors: Przemyslaw Sapieha, Montréal (CA); Normand Beaulieu, Montréal (CA)

(73) Assignee: RSEM, LIMITED PARTNERSHIP, Montréal (CA)

( * ) Notice: Subject to any disclaimer, the term of this patent is extended or adjusted under 35 U.S.C. 154(b) by 807 days.

(21) Appl. No.: 18/188,707

(22) Filed: Mar. 23, 2023

(65) Prior Publication Data

US 2023/0265199 A1 Aug. 24, 2023

Related U.S. Application Data

(60) Continuation of application No. 16/983,185, filed on Aug. 3, 2020, now Pat. No. 11,649,292, which is a (Continued)

(51) Int. Cl.

| | |
|---|---|
| ***A61K 47/68*** | (2017.01) |
| ***A61K 31/7105*** | (2006.01) |
| ***A61K 31/713*** | (2006.01) |
| ***A61K 39/395*** | (2006.01) |
| ***C07K 14/71*** | (2006.01) |

(Continued)

(52) U.S. Cl.

CPC ...... *C07K 16/2863* (2013.01); *A61K 31/7105* (2013.01); *A61K 31/713* (2013.01); *A61K 39/395* (2013.01); *C07K 14/71* (2013.01); *C07K 16/22* (2013.01); *C12N 15/113* (2013.01); *A61K 38/00* (2013.01); *A61K 2039/505* (2013.01); *C07K 2319/30* (2013.01); *C12N 2310/14* (2013.01)

(58) Field of Classification Search

None

See application file for complete search history.

(56) References Cited

U.S. PATENT DOCUMENTS

| | | | |
|---|---|---|---|
| 2015/0368327 | A1 | 12/2015 | Goshima et al. |
| 2017/0283502 | A1 | 10/2017 | Sapieha et al. |

(Continued)

FOREIGN PATENT DOCUMENTS

| | | |
|---|---|---|
| CA | 2629028 | 5/2007 |
| CA | 2901946 | 8/2014 |

(Continued)

OTHER PUBLICATIONS

Skolnick et al (Trends Biotechnol. Jan. 2000;18(1):34-9), (Year: 2000).*

(Continued)

*Primary Examiner* — Aurora M Fontainhas

(74) *Attorney, Agent, or Firm* — Klarquist Sparkman, LLP

(57) ABSTRACT

The present invention provides novel compounds compositions and methods for (i) treating or preventing inflammation; and (ii) preventing or reducing hyperactivation of innate immune response, by inhibiting NRP1-dependent cell-signaling. Also provided are compounds, composition, and methods of specifically inhibiting SEMA3A-mediated cell signaling.

15 Claims, 86 Drawing Sheets

Specification includes a Sequence Listing.

Related U.S. Application Data continuation of application No. 16/422,273, filed on May 24, 2019, now Pat. No. 10,766,964, which is a division of application No. 15/507,407, filed as application No. PCT/CA2015/050862 on Sep. 8, 2015, now Pat. No. 10,738,122.

(60) Provisional application No. 62/046,459, filed on Sep. 5, 2014.

(51) Int. Cl.

| | |
|---|---|
| ***C07K 16/22*** | (2006.01) |
| ***C07K 16/28*** | (2006.01) |
| ***C12N 15/113*** | (2010.01) |
| ***C12N 15/62*** | (2006.01) |
| *A61K 38/00* | (2006.01) |
| *A61K 39/00* | (2006.01) |

(56) References Cited

U.S. PATENT DOCUMENTS

| | | | |
|---|---|---|---|
| 2019/0359718 | A1 | 11/2019 | Sapieha et al. |
| 2021/0061915 | A1 | 3/2021 | Sapieha et al. |

FOREIGN PATENT DOCUMENTS

| | | |
|---|---|---|
| EP | 2497498 | 9/2012 |
| JP | 2009-501521 | 1/2009 |
| KR | 10-2010-0020967 | 2/2010 |
| WO | WO 03/007803 | 1/2003 |
| WO | WO 03/035100 | 5/2003 |
| WO | WO 2007/009071 | 1/2007 |
| WO | WO 2008/143666 | 11/2008 |
| WO | WO 2009/060159 | 5/2009 |

OTHER PUBLICATIONS

Lazar et al. (Mol. Cell. Biol., 8:1247-1252, 1988) (Year: 1988).*
Burgess et al. (J. Cell Biol. 111:2129-2138, 1990) (Year: 1990).*
Kulmanov et al (Bioinformatics, 34(4), 2018, 660-668) (Year: 2018).*
Adamis et al., "Immunological mechanisms in the pathogenesis of diabetic retinopathy," *Semin Immunopathol,* vol. 30:65-84, 2008.
Ambati et al., "Mechanisms of age-related macular degeneration," *Neuron,* vol. 75:26-39, 2012.
Antonetti et al., "Diabetic retinopathy," *N Engl J Med,* vol. 366:1227-1239, 2012.
Appleton et al., "Structural studies of neuropilin/antibody complexes provide insights into semaphorin and VEGF binding," *EMBO J,* vol. 26:4902-4912, 2007.
Binet et al., "Neuronal ER Stress Impedes Myeloid-Cell-Induced Vascular Regeneration through IRE1α Degradation of Netrin-1," *Cell Metab,* vol. 17:353- 371,2013.
Bruder et al., "Neuropilin-1: a surface marker of regulatory T cells," *Eur J Immunol,* vol. 34:623-630, 2004.
Bussolino, et al., "Semaphoring vascular morphogenesis," *Endothelium,* vol. 13:81-91, 2006.
Carrer, et al., "Neuropilin-1 identifies a subset of bone marrow Gr1-monocytes that can induce tumor vessel normalization and inhibit tumor growth," *Cancer Res,* vol. 72:6371-6381, 2012.
Casazza, et al., "Impeding Macrophage Entry into Hypoxic Tumor Areas by SEMA3A/Nrp1 Signaling Blockade Inhibits Angiogenesis and Restores Antitumor Immunity," *Cancer Cell,* vol. 24:695-709, 2013.
Cerani, et al., "Neuron-Derived Semaphorin 3A is an Early Inducer of Vascular Permeability in Diabetic Retinopathy via Neuropilin-1," *Cell Metabolism,* vol. 18(4): 505-518, 2013.
Checchin, et al., "Potential role of microglia in retinal blood vessel formation," *Invest Ophthalmol Vis Sci,* vol. 47:3595-3602, 2006.
Clausen, et al., "Conditional gene targeting in macrophages and granulocytes using LysMcre mice," *Transgenic Res,* vol. 8:265-277, 1999.
Combadiere et al., "CX3CR1-dependent subretinal microglia cell accumulation is associated with cardinal features of age-related macular degeneration," *J Clin Invest* 117:2920-2928, 2007.
Communication pursuant to Article 94(3) EPC, dated May 9, 2019, from European Application No. 15838150.9, 5 pages.
Connor, et al., "Increased dietary intake of omega-3-polyunsaturated fatty acids reduces pathological retinal angiogenesis," *Nat Med,* vol. 13:868-873, 2007.
Dammann, "Inflammation and retinopathy of prematurity," *Acta Paediatr,* vol. 99:975-977, 2010.
Dammann, et al., "Immaturity, perinatal inflammation, and retinopathy of prematurity: a multi-hit hypothesis," *Early Hum Dev,* vol. 85:325-329, 2009.
Deutschman, et al., "Sepsis: current dogma and new perspectives," *Immunity,* vol. 40:463-475, 2014.
Fantin, et al., "Tissue macrophages act as cellular chaperones for vascular anastomosis downstream of VEGF-mediated endothelial tip cell induction," *Blood,* vol. 116:829-840, 2010.
George et al., "Novel Stroke Therapeutics: Unraveling Stroke Pathophysiology and its Impact on Clinical Treatments," *Neuron,* vol. 87:297-309, 2015.
Geretti et al., "Neuropilin structure governs VEGF and semaphorin binding and regulates angiogenesis," *Angiogenesis,* vol. 11:31-39, 2008.
Gluzman-Poltorak, et al., "Vascular endothelial growth factor receptor-1 and neuropilin-2 form complexes," *J Biol Chem,* vol. 276:18688-18694, 2001.
Gu et al., "Characterization of Neuropilin-1 Structural Features That Confer Binding to Semaphorin 3A and Vascular Endothelial Growth Factor 165*," *J Biol Chem* 277(20): 18069-18076, 2002.
Guttmann-Raviv, et al., "Semaphorin-3A and semaphorin-3F work together to repel endothelial cells and to inhibit their survival by induction of apoptosis," *J Biol Chem,* vol. 282:26294-26305, 2007.
Hartnett et al., "Mechanisms and management of retinopathy of prematurity," *N Engl J Med,* vol. 367:2515-2526, 2012.
Hellström et al., "Retinopathy of prematurity," *Lancet,* vol. 382:1445-1457, 2013.
International Search Report and Written Opinion of PCT/CA2015/050862, mailed Nov. 5, 2015.
International Preliminary Report on Patentability of PCT/CA2015/050862, mailed Mar. 7, 2017.
Jiang et al., "Neuropilin 1 Directly Interacts with Fer Kinase to Mediate Semaphorin 3A-induced Death of Cortical Neurons," *J. Biol. Chem.,* vol. 285:9908-9918, 2010.
Joussen et al., "A central role for inflammation in the pathogenesis of diabetic retinopathy," *FASEB J,* vol. 18:1450-1452, 2004.
Joyal et al., "Ischemic neurons prevent vascular regeneration of neural tissue by secreting semaphorin 3A," *Blood,* vol. 117:6024-6035, 2011.
Kaštelan et al., "Inflammation and pharmacological treatment in diabetic retinopathy," *Mediators Inflamm,* vol. 2013:1-8, 2013.
Kempen et al., "The prevalence of diabetic retinopathy among adults in the United States," *Arch Ophthalmol,* vol. 122:552-563, 2004.
Kern et al., "Retinal ganglion cells in diabetes," *J Physiol,* vol. 586:4401-4408, 2008.
Klagsbrun et al., "A role for axon guidance receptors and ligands in blood vessel development and tumor angiogenesis," *Cytokine Growth Factor Rev,* vol. 16:535-548, 2005.
Klagsbrun et al., "The role of neuropilin in vascular and tumor biology," *Adv Exp Med Biol,* vol. 515:33-48, 2002.
Klebanov et al., "Upregulation of Semaphorin 3A and the associated biochemical and cellular events in a rat model of retinal detachment," *Graefes Arch Clin Exp Ophthalmol,* vol. 247:73-86, 2009.
Koppel et al., "Collapsin-1 covalently dimerizes, and dimerization is necessary for collapsing activity," *J Biol Chem,* vol. 273:15708-15713, 1998.
Lampron et al., "Innate immunity in the CNS: redefining the relationship between the CNS and Its environment," *Neuron,* vol. 78:214-232, 2013.

(56) References Cited

OTHER PUBLICATIONS

Lee et al., "Neuropilin-1 is required for vascular development and is a mediator of VEGF-dependent angiogenesis in zebrafish," *Proc Natl Acad Sci USA,* vol. 99:10470-10475, 2002.
Mamluk et al., "Neuropilin-1 binds vascular endothelial growth factor 165, placenta growth factor-2, and heparin via its b1b2 domain," *J Biol Chem,* vol. 277:24818-24825, 2002.
Mamluk et al., "Soluble Neuropilin Targeted to the Skin Inhibits Vascular Permeability," *Angiogenesis,* vol. 8:217-227, 2005.
Mattapallil et al., "The Rd8 mutation of the Crb1 gene is present in vendor lines of C57BL/6N mice and embryonic stem cells, and confounds ocular induced mutant phenotypes," *Invest Ophthalmol Vis Sci,* vol. 53:2921-2927, 2012.
Miao et al., "Neuropilin-1 mediates collapsin-1/semaphorin III inhibition of endothelial cell motility: functional competition of collapsin-1 and vascular endothelial growth factor-165," *J Cell Biol,* vol. 146:233-242, 1999.
Miloudi et al., "Assessment of vascular regeneration in the CNS using the mouse retina," *J Vis Exp.,* vol. 88: e51351, 2014.
Neufeld et al., "The semaphorins: versatile regulators of tumour progression and tumour angiogenesis," *Nat Rev Cancer,* vol. 8:632-645, 2008.
Neufeld et al., "Semaphorins in angiogenesis and tumor progression," *Cold Spring Harb Perspect Med,* vol. 2:a006718, 2012.
Office Action mailed Aug. 27, 2019 in connection with corresponding Japanese Application No. 2017-531928 (in Japanese accompanied by an English translation, 7 pages total).
Office Action of Korean Application No. 10-2017-7007655, dated Oct. 11, 2022 (in Korean with English translation; 14 total pages).
Ousman et al., "Immune surveillance in the central nervous system," *Nat Neurosci,* vol. 15:1096-1101, 2012.
Ritter et al., "Myeloid progenitors differentiate into microglia and promote vascular repair in a model of ischemic retinopathy," *J Clin Invest,* vol. 116:3266-3276, 2006.
Robinson et al., "Nonvascular role for VEGF: VEGFR-1, 2 activity is critical for neural retinal development," *FASEB J,* vol. 15:1215-1217, 2001.
Rousselet et al., "Mouse model of intraluminal MCAO: cerebral infarct evaluation by cresyl violet staining," *J Vis Exp.* 69:e4038, doi:10.3791/4038, 2012.
Saint-Geniez et al., "Endogenous VEGF is required for visual function: evidence for a survival role on muller cells and photoreceptors," *PLoS ONE,* vol. 3:e3554, 2008.
Sapieha et al., "Proliferative retinopathies: angiogenesis that blinds," *Int J Biochem Cell Biol,* vol. 42:5-12, 2010.
Sapieha et al., "Retinopathy of prematurity: understanding ischemic retinal vasculopathies at an extreme of life," *J Clin Invest,* vol. 120:3022-3032, 2010.
Sapieha et al., "5-Lipoxygenase Metabolite 4-HDHA Is a Mediator of the Antiangiogenic Effect of {omega}-3 Polyunsaturated Fatty Acids," *Sci Transl Med,* 3:69ra12, 2011.
Sapieha, "Eyeing central neurons in vascular growth and reparative angiogenesis," *Blood,* vol. 120:2182-2194, 2012.
Sennlaub et al., "CCR2$^+$ monocytes infiltrate atrophic lesions in age-related macular disease and mediate photoreceptor degeneration in experimental subretinal inflammation in Cx3crl deficient mice," *EMBO Mol Med,* vol. 5:1775-1793, 2013.
Shao et al., "Choroid Sprouting Assay: An Ex Vivo Model of Microvascular Angiogenesis," *PLoS ONE,* vol. 8:e69552, 2013.
Silva et al., "Effect of systemic medications on onset and progression of diabetic retinopathy," *Nat Rev Endocrinol,* vol. 6:494-508, 2010.
Smith et al., "Oxygen-induced retinopathy in the mouse," *Invest Ophthalmol Vis Sci,* vol. 35:101-111, 1994.
Soker et al., "Neuropilin-1 is Expressed by Endothelial and Tumor Cells as an Isoform-Specific Receptor for Vascular Endothelial Growth Factor," *Cell,* vol. 92:735-745, 1998.
Soker et al., "$VEGF_{165}$ Mediates Formation of Complexes Containing VEGFR-2 and Neuropilin-1 that Enhance $VEGF_{165}$-Receptor Binding," *J Cell Biochem,* vol. 85:357-368, 2002.
Stahl et al., "Computer-aided quantification of retinal neovascularization," *Angiogenesis,* vol. 12:297-301, 2009.
Stahl et al., "Postnatal Weight Gain Modifies Severity and Functional Outcome of Oxygen-Induced Proliferative Retinopathy," *Am J Pathol,* vol. 177(6):2715-2733, 2010.
Stahl et al., "PPARγ mediates a direct antiangiogenic effect of omega 3-PUFAs in proliferative retinopathy," *Circ Res,* vol. 107(4):495-500, 2010.
Stahl et al., "The mouse retina as an angiogenesis model," *Invest Ophthalmol Vis Sci,* vol. 51:2813-2826, 2010.
Supplementary European Search Report, mailed Apr. 30, 2018, issued in connection with corresponding European Application No. EP15838150 (7 pages).
Takahashi et al., "Plexin-Neuropilin-1 Complexes Form Functional Semaphorin-3A Receptors," *Cell,* vol. 99:59-69, 1999.
Takamatsu et al., "Diverse Roles for Semaphorin-Plexin Signaling in the Immune System," *Trends Immunol.,* vol. 33:127-135, 2012.
Takeda et al., "CCR3 is a target for age-related macular degeneration diagnosis and therapy," *Nature,* vol. 460:225-230, 2009.
Tremblay et al., "Systemic inflammation perturbs developmental retinal angiogenesis and neuroretinal function," *Invest Ophthalmol Vis Sci,* vol. 54:8125-8139, 2013.
Van Rooijen et al., ""In vivo" depletion of macrophages by liposome-mediated "suicide"," *Methods Enzymol,* vol. 373:3-16, 2003.
Vieira et al., "Role of the neuropilin ligands VEGF164 and SEMA3A in neuronal and vascular patterning in the mouse," *Novartis Found Symp,* vol. 283:230-241, 2007.
Worthylake et al., "RhoA and ROCK Promote Migration by Limiting Membrane Protrusions," *J Biol Chem,* vol. 278:13578-13584, 2003.
Yancopoulos, "Clinical Application of Therapies Targeting VEGF," *Cell,* vol. 143:13-16, 2010.
Shirvan et al., "Anti-semaphorin 3A Antibodies Rescue Retinal Ganglion Cells from Cell Death following Optic Nerve Axotomy," *J Biol Chem* 277(51):49799-49807, 2002.

* cited by examiner

FIG. 1S
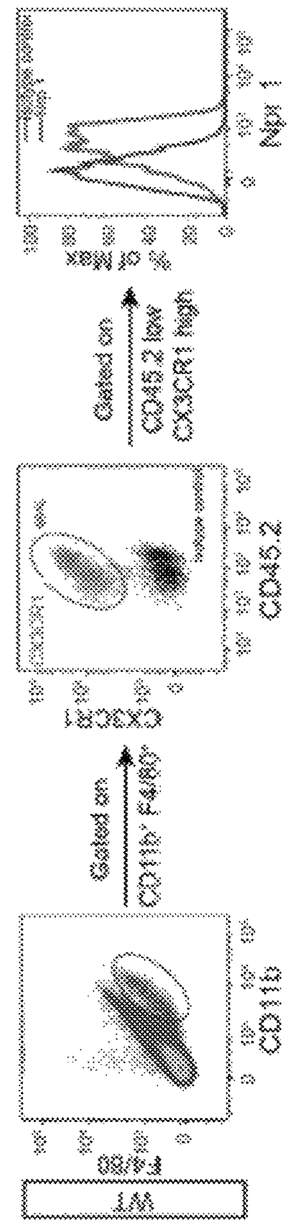
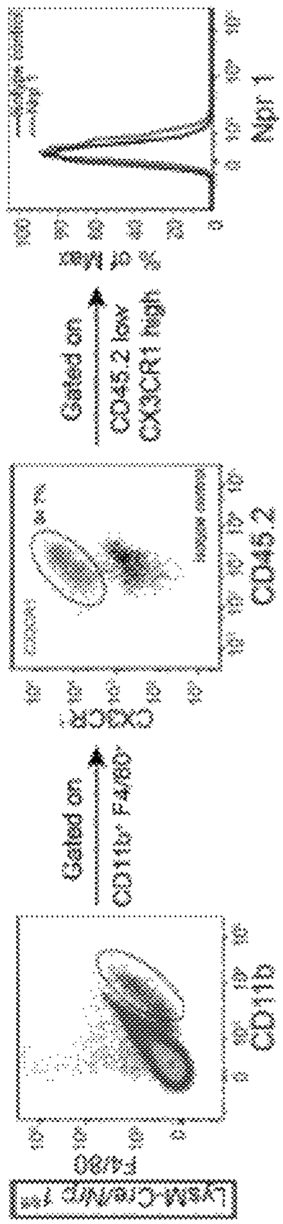
FIG. 1T
FIG. 1R
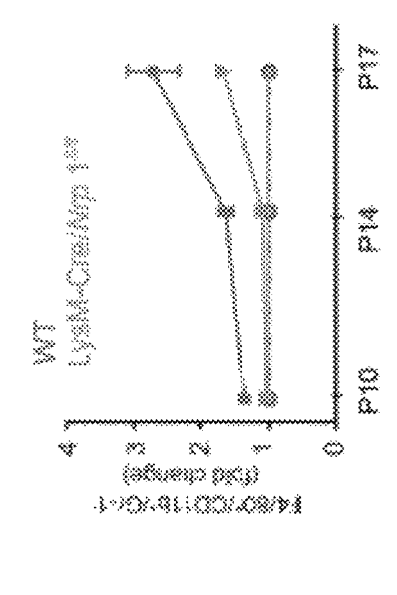

FIG. 2G
FIG. 2H
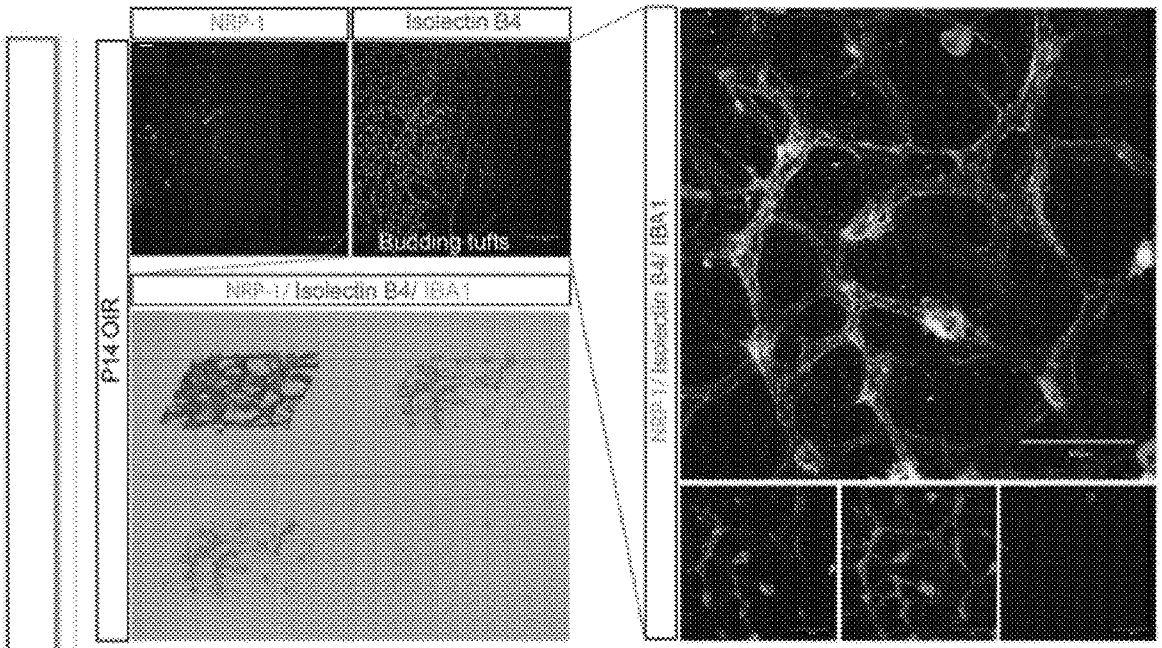
FIG. 2I
FIG. 2J
FIG. 2K
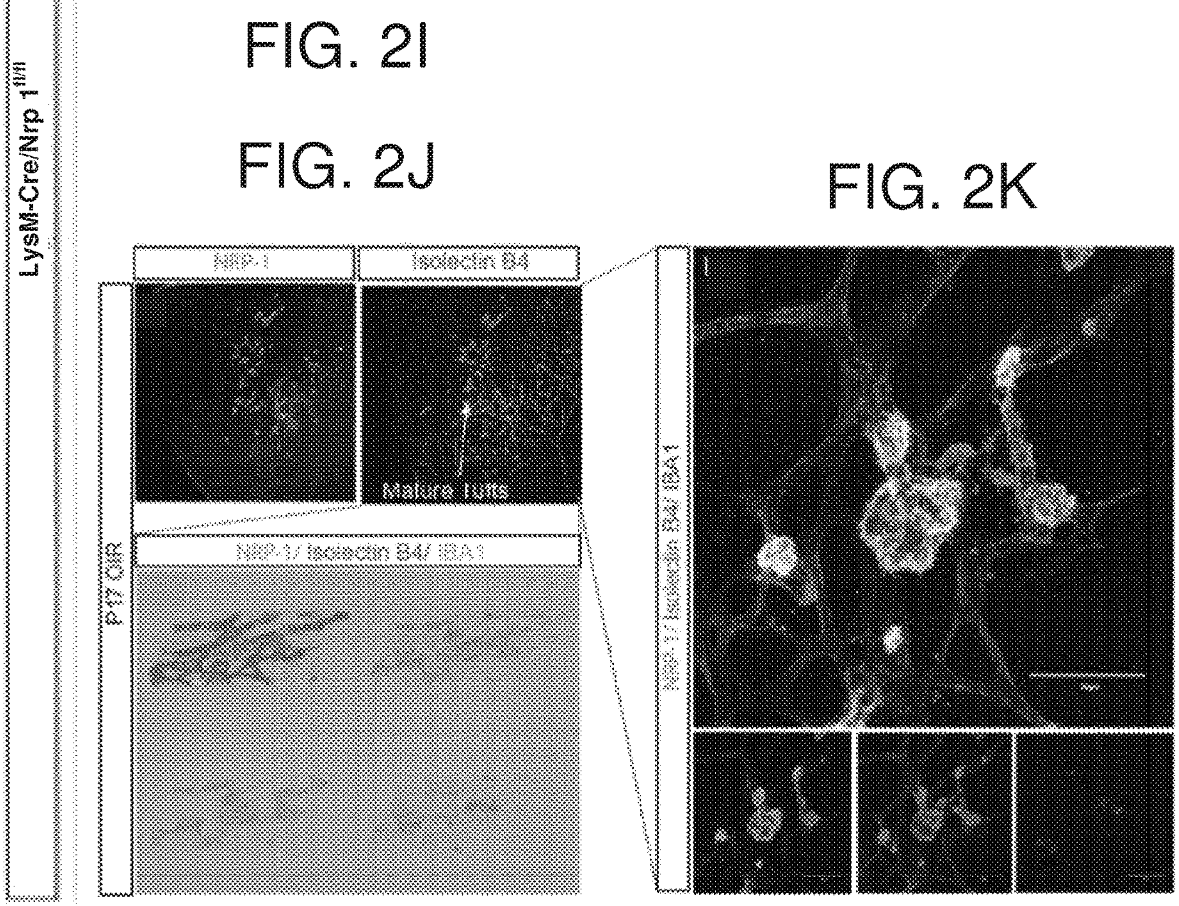
FIG. 2L

FIG. 8D
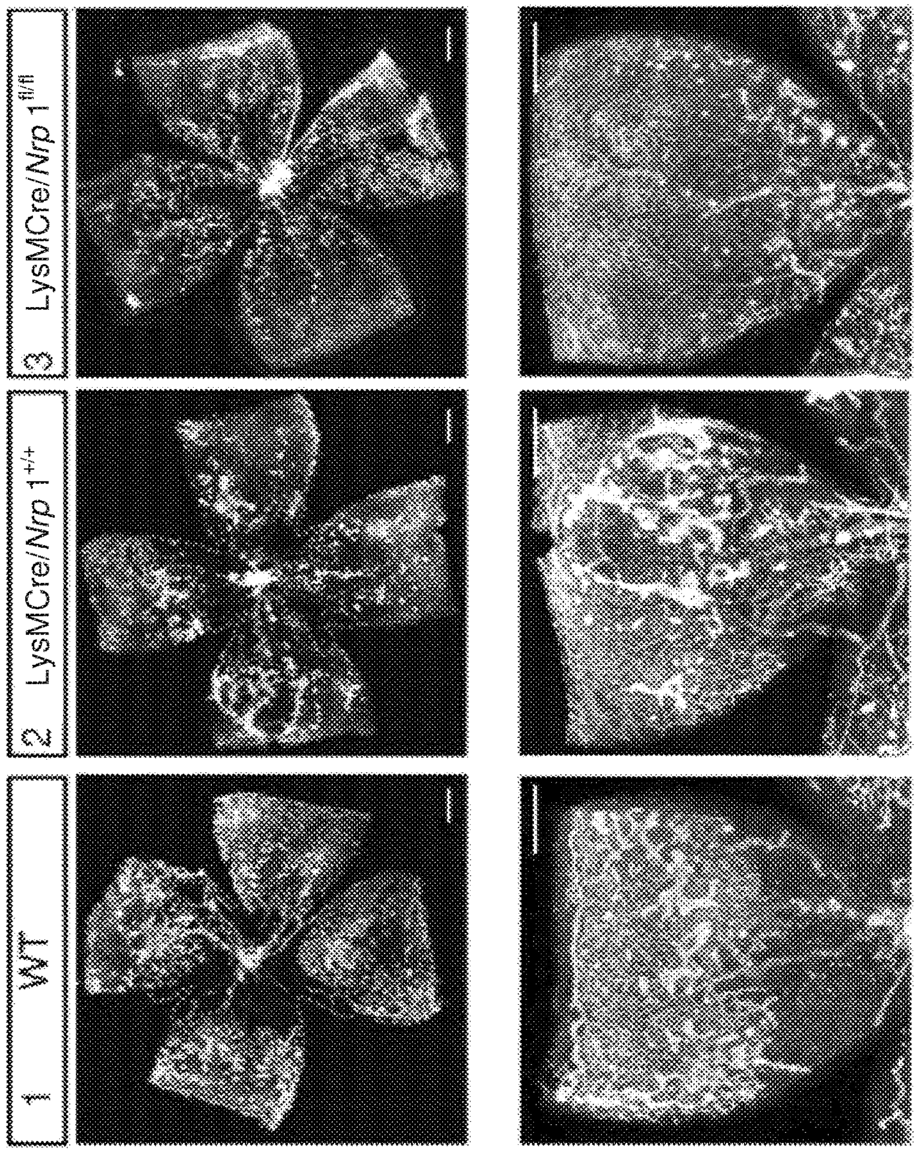
FIG. 8F
FIG. 8C
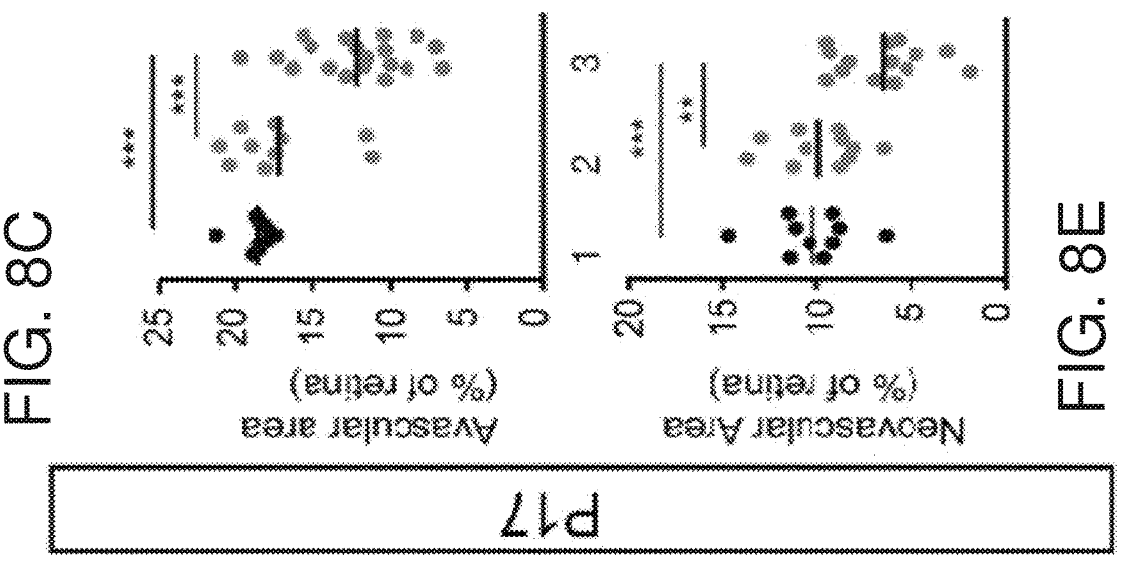
FIG. 8E

Vehicle

NRP-1-Trap

FIG. 20A atggagagggggctgccgctcctctgcgccgtgctcgccctcgtcctcgcccccgccggc
M E R G L P L L C A V L A L V L A P A G
gcttttcgcaacgataaatgtggcgatactataaaaattgaaagccccgggtaccttaca
A F R N D K C G D T I K I E S P G Y L T
tctcctggttatcctcattcttatcacccaagtgaaaaatgcgaatggctgattcaggct
S P G Y P H S Y H P S E K C E W L I Q A
ccggacccataccagagaattatgatcaacttcaaccctcacttcgatttggaggacaga
P D P Y Q R I M I N F N P H F D L E D R
gactgcaagtatgactacgtggaagtcttcgatggagaaaatgaaaatggacattttagg
D C K Y D Y V E V F D G E N E N G H F R
ggaaagttctgtggaaagatagcccctcctcctgttgtgtcttcagggccatttcttttt
G K F C G K I A P P P V V S S G P F L F
atcaaatttgtctctgactacgaaacacatggtgcaggattttccatacgttatgaactt
I K F V S D Y E T H G A G F S I R Y E L
ttcaagagaggtcctgaatgttcccagaactacacaacacctagtggagtgataaagtcc
F K R G P E C S Q N Y T T P S G V I K S
cccggattccctgaaaaatatcccaacagccttgaatgcacttatattgtctttgcgcca
P G F P E K Y P N S L E C T Y I V F A P
aagatgtcagagattatcctggaatttgaaagctttgacctggagcctgactcaaatcct
K M S E I I L E F E S F D L E P D S N P
ccaggggggatgttctgtcgctacgaccggctagaaatctgggatggattccctgatgtt
P G G M F C R Y D R L E I W D G F P D V
ggccctcacattgggcgttactgtggacagaaaacaccaggtcgaatccgatcctcatcg
G P H I G R Y C G Q K T P G R I R S S S
ggcattctctccatggttttttacaccgacagcgcgatagcaaaagaaggtttctcagca
G I L S M V F Y T D S A I A K E G F S A
aactacagtgtcttgcagagcagtgtctcagaagatttcaaatgtatggaagctctgggc
N Y S V L Q S S V S E D F K C M E A L G
atggaatcaggagaaattcattctgaccagatcacagcttcttcccagtatagcaccaac
M E S G E I H S D Q I T A S S Q Y S T N
tggtctgcagagcgctcccgcctgaactaccctgagaatgggtggactcccggagaggat
W S A E R S R L N Y P E N G W T P G E D
tcctaccgagagtggatacaggtagacttgggccttctgcgctttgtcacggctgtcggg
S Y R E W I Q V D L G L L R F V T A V G
acacagggcgccatttcaaaagaaaccaagaagaaatattatgtcaagacttacaagatc
T Q G A I S K E T K K K Y Y V K T Y K I
gacgttagctccaacggggaagactggatcaccataaaagaaggaaacaaacctgttctc
D V S S N G E D W I T I K E G N K P V L
tttcaggggaacaccaaccccacagatgttgtggttgcagtattccccaaaccactgata
F Q G N T N P T D V V V A V F P K P L I
actcgatttgtccgaatcaagcctgcaacttgggaaactggcatatctatgagatttgaa
T R F V R I K P A T W E T G I S M R F E
gtatatggttgcaagataacagattatccttgctctggaatgttgggtatggtgtctgga
V Y G C K I T D Y P C S G M L G M V S G
cttatttctgactcccagatcacatcatccaaccaaggggacagaaactggatgcctgaa
L I S D S Q I T S S N Q G D R N W M P E
aacatccgcctggtaaccagtcgctctggctgggcacttccacccgcacctcattcctac
N I R L V T S R S G W A L P P A P H S Y
atcaatgagtggctccaaatagacctgggggaggagaagatcgtgaggggcatcatcatt
I N E W L Q I D L G E E K I V R G I I I
cagggtgggaagcaccgagagaacaaggtgttcatgaggaagttcaagatcgggtacagc
Q G G K H R E N K V F M R K F K I G Y S
aacaacggctcggactggaagatgatcatggatgacagcaaacgcaaggcgaagtctttt
N N G S D W K M I M D D S K R K A K S F

FIG. 20B gagggcaacaacaactatgatacacctgagctgcggacttttccagctctctccacgcga
E G N N N Y D T P E L R T F P A L S T R ttcatcaggatctaccccgagagagccactcatggcggactggggctcagaatggagctg
F I R I Y P E R A T H G G L G L E M E L ctgggctgtgaagtggaagcccctacagctggaccgaccactcccaacgggaacttggtg
L G C E V E A P T A G P T T P N G N L V gatgaatgtgatgacgaccaggccaactgccacagtggaacaggtgatgacttccagctc
D E C D D D Q A N C H S G T G D D F Q L acaggtggcaccactgtgctggccacagaaaagcccacggtcatagacagcaccatacaa
T G G T T V L A T E K P T V I D S T I Q tcagagtttccaacatatggttttaactgtgaatttggctggggctctcacaagaccttc
S E F P T Y G F N C E F G W G S H K T F tgccactgggaacatgacaatcacgtgcagctcaagtggagtgtgttgaccagcaagacg
C H W E H D N H V Q L K W S V L T S K T ggacccattcaggatcacacaggagatggcaacttcatctattcccaagctgacgaaaat
G P I Q D H T G D G N F I Y S Q A D E N cagaagggcaaagtggctcgcctggtgagccctgtggtttattcccagaactctgcccac
Q K G K V A R L V S P V V Y S Q N S A H tgcatgaccttctggtatcacatgtctgggtcccacgtcggcacactcagggtcaaactg
C M T F W Y H M S G S H V G T L R V K L cgctaccagaagccagaggagtacgatcagctggtctggatggccattggacaccaaggt
R Y Q K P E E Y D Q L V W M A I G H Q G gaccactggaaggaagggcgtgtcttgctccacaagtctctgaaactttatcaggtgatt
D H W K E G R V L L H K S L K L Y Q V I ttcgagggcgaaatcggaaaaggaaaccttggtgggattgctgtggatgacattagtatt
F E G E I G K G N L G G I A V D D I S I aataaccacatttcacaagaagattgtgcaaaaccagcagacctggataaaaagaaccca
N N H I S Q E D C A K P A D L D K K N P gaaattaaaattgatgaaacagggagcacgccaggatacgaaggtgaaggagaaggtgac
E I K I D E T G S T P G Y E G E G E G D aagaacatctccaggaagccaggcaatgtgttgaagaccttagaccccagatctgacaaa
K N I S R K P G N V L K T L D P R S D K actcacacatgcccaccgtgcccagcacctgaactcctggggggaccgtcagtcttcctc
T H T C P P C P A P E L L G G P S V F L ttccccccaaaacccaaggacaccctcatgatctcccggacccctgaggtcacatgcgtg
F P P K P K D T L M I S R T P E V T C V gtggtggacgtgagccacgaagaccctgaggtcaagttcaactggtacgtggacggcgtg
V V D V S H E D P E V K F N W Y V D G V gaggtgcataatgccaagacaaagccgcgggaggagcagtacaacagcacgtaccgtgtg
E V H N A K T K P R E E Q Y N S T Y R V gtcagcgtcctcaccgtcctgcaccaggactggctgaatggcaaggagtacaagtgcaag
V S V L T V L H Q D W L N G K E Y K C K gtctccaacaaagccctcccagcccccatcgagaaaaccatctccaaagccaaagggcag
V S N K A L P A P I E K T I S K A K G Q ccccgagaaccacaggtgtacaccctgcccccatcccgggaggagatgaccaagaaccag
P R E P Q V Y T L P P S R E E M T K N Q gtcagcctgacctgcctggtcaaaggcttctatcccagcgacatcgccgtggagtgggag
V S L T C L V K G F Y P S D I A V E W E agcaatgggcagccggagaacaactacaagaccacgcctcccgtgctggactccgacggc
S N G Q P E N N Y K T T P P V L D S D G tccttcttcctctacagcaagctcaccgtggacaagagcaggtggcagcaggggaacgtc
S F F L Y S K L T V D K S R W Q Q G N V ttctcatgctccgtgatgcatgaggctctgcacaaccactacacgcagaagagcctctcc
F S C S V M H E A L H N H Y T Q K S L S ctgtctccgggtaaa
L S P G K

FIG. 20C

MERGLPLLCAVLALVLAPAGAFRNDKCGDTIKIESPGYLTSPGYPHSYHPSEKCEWLIQA
PDPYQRIMINFNPHFDLEDRDCKYDYVEVFDGENENGHFRGKFCGKIAPPPVVSSGPFLF
IKFVSDYETHGAGFSIRYELFKRGPECSQNYTTPSGVIKSPGFPEKYPNSLECTYIVFAP
KMSEIILEFESFDLEPDSNPPGGMFCRYDRLEIWDGFPDVGPHIGRYCGQKTPGRIRSSS
GILSMVFYTDSAIAKEGFSANYSVLQSSVSEDFKCMEALGMESGEIHSDQITASSQYSTN
WSAERSRLNYPENGWTPGEDSYREWIQVDLGLLRFVTAVGTQGAISKETKKKYYVKTYKI
DVSSNGEDWITIKEGNKPVLFQGNTNPTDVVVAVFPKPLITRFVRIKPATWETGISMRFE
VYGCKITDYPCSGMLGMVSGLISDSQITSSNQGDRNWMPENIRLVTSRSGWALPPAPHSY
INEWLQIDLGEEKIVRGIIIQGGKHRENKVFMRKFKIGYSNNGSDWKMIMDDSKRKAKSF
EGNNNYDTPELRTFPALSTRFIRIYPERATHGGLGLRMELLGCZZZZZZZZZZZZZZZZZ
ZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZ
ZZZZZZZZZZZZZZZZZZDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEYKCK
VSNKALPAPIEKTISKAKGQPREPQVYTLPPSREEMTKNQVSLTCLVKGFYPSDIAVEWE
SNGQPENNYKTTPPVLDSDGSFFLYSKLTVDKSRWQQGNVFSCSVMHEALHNHYTQKSLS
LSPGK

FIG. 20D

ATGGAGAGGGGGCTGCCGCTCCTCTGCGCCGTGCTCGCCCTCGTCCTCGCCCCGGCCGGCGCTTTTC
GCAACGATAAATGTGGCGATACTATAAAAATTGAAAGCCCCGGGTACCTTACATCTCCTGGTTATCC
TCATTCTTATCACCCAAGTGAAAAATGCGAATGGCTGATTCAGGCTCCGGACCCATACCAGAGAATT
ATGATCAACTTCAACCCTCACTTCGATTTGGAGGACAGAGACTGCAAGTATGACTACGTGGAAGTCT
TCGATGGAGAAAATGAAAATGGACATTTTAGGGGAAAGTTCTGTGGAAAGATAGCCCCTCCTCCTGT
TGTGTCTTCAGGGCCATTTCTTTTTATCAAATTTGTCTCTGACTACGAAACACATGGTGCAGGATTT
TCCATACGTTATGAACTTTTCAAGAGAGGTCCTGAATGTTCCCAGAACTACACAACACCTAGTGGAG
TGATAAAGTCCCCCGGATTCCCTGAAAAATATCCCAACAGCCTTGAATGCACTTATATTGTCTTTGC
GCCAAAGATGTCAGAGATTATCCTGGAATTTGAAAGCTTTGACCTGGAGCCTGACTCAAATCCTCCA
GGGGGGATGTTCTGTCGCTACGACCGGCTAGAAATCTGGGATGGATTCCCTGATGTTGGCCCTCACA
TTGGGCGTTACTGTGGACAGAAAACACCAGGTCGAATCCGATCCTCATCGGGCATTCTCTCCATGGT
TTTTTACACCGACAGCGCGATAGCAAAAGAAGGTTTCTCAGCAAACTACAGTGTCTTGCAGAGCAGT
GTCTCAGAAGATTTCAAATGTATGGAAGCTCTGGGCATGGAATCAGGAGAAATTCATTCTGACCAGA
TCACAGCTTCTTCCCAGTATAGCACCAACTGGTCTGCAGAGCGCTCCCGCCTGAACTACCCTGAGAA
TGGGTGGACTCCCGGAGAGGATTCCTACCGAGAGTGGATACAGGTAGACTTGGGCCTTCTGCGCTTT
GTCACGGCTGTCGGGACACAGGGCGCCATTTCAAAAGAAACCAAGAAGAAATATTATGTCAAGACTT
ACAAGATCGACGTTAGCTCCAACGGGGAAGACTGGATCACCATAAAAGAAGGAAACAAACCTGTTCT
CTTTCAGGGAAACACCAACCCTACAGATGTTGTGGTTGCAGTATTCCCCAAACCACTGATAACTCGA
TTTGTCCGAATCAAGCCTGCAACTTGGGAAACTGGCATATCTATGAGATTTGAAGTATATGGTTGCA
AGATAACAGATTATCCTTGCTCTGGAATGTTGGGTATGGTGTCTGGACTTATTTCTGACTCCCAGAT
CACATCATCCAACCAAGGGGACAGAAACTGGATGCCTGAAAACATCCGCCTGGTAACCAGTCGCTCT
GGCTGGGCACTTCCACCCGCACCTCATTCCTACATCAATGAGTGGCTCCAAATAGACCTGGGGGAGG
AGAAGATCGTGAGGGGCATCATCATTCAGGGTGGGAAGCACCGAGAGAACAAGGTGTTCATGAGGAA
GTTCAAGATCGGCTACAGCAACAACGGCTCGGACTGGAAGATGATCATGGATGACAGCAAACGCAAG
GCGAAGTCTTTTGAGGGCAACAACAACTATGATACACCTGAGCTGCGGACTTTTCCAGCTCTCTCCA
CGCGATTCATCAGGATCTACCCCGAGAGAGCCACTCATGGCGGACTGGGGCTCAGAATGGAGCTGCT
GGGCTGTNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNGACAAAACTCACACATGCCCACCGTGCCCAGCACCTGAA
CTCCTGGGGGGACCGTCAGTCTTCCTCTTCCCCCCAAAACCCAAGGACACCCTCATGATCTCCCGGA
CCCCTGAGGTCACATGCGTGGTGGTGGACGTGAGCCACGAAGACCCTGAGGTCAAGTTCAACTGGTA
CGTGGACGGCGTGGAGGTGCATAATGCCAAGACAAAGCCGCGGGAGGAGCAGTACAACAGCACGTAC
CGTGTGGTCAGCGTCCTCACCGTCCTGCACCAGGACTGGCTGAATGGCAAGGAGTACAAGTGCAAGG
TCTCCAACAAAGCCCTCCCAGCCCCCATCGAGAAAACCATCTCCAAAGCCAAAGGGCAGCCCCGAGA
ACCACAGGTGTACACCCTGCCCCCATCCCGGGAGGAGATGACCAAGAACCAGGTCAGCCTGACCTGC
CTGGTCAAAGGCTTCTATCCCAGCGACATCGCCGTGGAGTGGGAGAGCAATGGGCAGCCGGAGAACA
ACTACAAGACCACGCCTCCCGTGCTGGACTCCGACGGCTCCTTCTTCCTCTACAGCAAGCTCACCGT
GGACAAGAGCAGGTGGCAGCAGGGGAACGTCTTCTCATGCTCCGTGATGCACGAGGCTCTGCACAAC
CACTACACGCAGAAGAGCCTCTCCCTGTCTCCGGGTAAA

FIG. 20E

MKRGLPLLCAVLALVLAPAGAFRNDKCGDTIKIESPGYLTSPGYPHSYHPSEKCEWLIQAPDPYQRI
MINFNPHFDLEDRDCKYDYVEVFDGENENGHFRGKFCGKIAPPPVVSSGPFLFIKFVSDYETHGAGF
SIRYELFKRGPECSQNYTTPSGVIKSPGFPEKYPNSLECTYIVFAPKMSEIILEFESFDLEPDSNPP
GGMFCRYDRLEIWDGFPDVGPHIGRYCGQKTPGRIRSSSGILSMVFYTDSAIAKEGFSANYSVLQSS
VSEDFKCMEALGMESGEIHSDQITASSQYSTNWSAERSRLNYPENGWTPGEDSYREWIQVDLGLLRF
VTAVGTQGAISKETKKKYYVKTYKIDVSSNGEDWITIKEGNKPVLFQGNTNPTDVVVAVFPKPLITR
FVRIKPATWETGISMRFEVYCCZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZDKTHTCPPCPAPE
LLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTC
LVKGFYPSDIAVEWESNGQPENNYKTTPPVLDSDGSFFLYSKLTVDKSRWQQGNVFSCSVMHEALHN
HYTQKSLSLSPGK

FIG. 20F

ATGGAGACGGGGGCTGCCGCTCCTCTGCGCCGTGCTCGCCCTCGTCCTCGGCCCCGGCCGGCGCTTTTCGCAACGA
TAAATGTGGCGATACTATAAAAATTGAAAGCCCCGGGTACCTTACATCTCCTGGTTATCCTCATTCTTATCACC
CAAGTGAAAAATGCCAATGGCTGATTCAGGCTCCGGACCCATACCAGAGAATTATGATCAACTTCAACCCTCAC
TTCGATTTGGAGGACAGAGACTGCAAGTATGACTACGTGGAAGTCTTCGATGGAGAAAATGAAAATGGACATTT
TAGGGGAAAGTTCTGTGGAAAGATAGCCCCTCCTCCTGTTGTGTCTTCAGGGCCATTTCTTTTTATCAAATTTG
TCTCTGACTACGAAACACATGGTGCAGGATTTTCCATACGTTATGAACTTTTCAAGAGAGGTCCTGAATGTTCC
CAGAACTACACAACACCTAGTGGAGTGATAAAGTCCCCCGGATTCCCTGAAAAATATCCCAACAGCCTTGAATG
CACTTATATTGTCTTTGCGCCAAAGATGTCAGAGATTATCCTGGAATTTGAAAGCTTTGACCTGGAGCCTGACT
CAAATCCTCCAGGGGGGATGTTCTGTCGCTACGACCGGCTAGAAATCTGGGATGGATTCCCTGATGTTGGCCCT
CACATTGGGCGTTACTGTGGACAGAAAACACCAGGTCGAATCCGATCCTCATCGGGCATTCTCTCCATGGTTTT
TTACACCGACAGCGCGATAGCAAAAGAAGGTTTCTCAGCAAACTACAGTGTCTTGCAGAGCCAGTGTCTCAGAAG
ATTTCAAATGTATGGAAGCTCTGGGCATGGAATCAGGAGAAATTCATTCTGACCAGATCACAGCTTCTTCCCAG
TATAGCACCAACTGGTCTGCAGAGCGCTCCCGCCTGAACTACCCTGAGAATGGGTGGACTCCCGGAGAGGATTC
CTACCGAGAGTGGATACAGGTAGACTTGGGCCTTCTGCGCTTTGTCACGGCTGTCGGGACACAGGGCGCCATTT
CAAAAGAAACCAAGAAGAAATATTATGTCAAGACTTACAAGATCGACGTTAGCTCCAACGGGGAAGACTGGATC
ACCATAAAAGAAGGAAACAAACCTGTTCTCTTTCAGGGAAACACCAACCCTACAGATGTTGTGGTTGCAGTATT
CCCCAAACCACTGATAACTCGATTTGTCCGAATCAAGCCTGCAACTTGGGAAACTGGCATATCTATGAGATTTG
AAGTATATGGTTGCNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNGACAAAACTCACACAT
GCCCACCGTGCCCAGCACCTGAACTCCTGGGGGGACCGTCAGTCTTCCTCTTCCCCCCAAAACCCAAGGACACC
CTCATGATCTCCCGGACCCCTGAGGTCACATGCGTGGTGGTGGACGTGAGCCACGAAGACCCTGAGGTCAAGTT
CAACTGGTACGTGGACGGCGTGGAGGTGCATAATGCCAAGACAAAGCCGCGGGAGGAGCAGTACAACAGCACGT
ACCGTGTGGTCAGCGTCCTCACCGTCCTGCACCAGGACTGGCTGAATGGCAAGGAGTACAAGTGCAAGGTCTCC
AACAAAGCCCTCCCAGCCCCCATCGAGAAAACCATCTCCAAAGCCAAAGGGCAGCCCCGAGAACCACAGGTGTA
CACCCTGCCCCCATCCCGGGAGGAGATGACCAAGAACCAGGTCAGCCTGACCTGCCTGGTCAAAGGCTTCTATC
CCAGCGACATCGCCGTGGAGTGGGAGAGCAATGGGCAGCCGGAGAACAACTACAAGACCACGCCTCCCGTGCTG
GACTCCGACGGCTCCTTCTTCCTCTACAGCAAGCTCACCGTGGACAAGAGCAGGTGGCAGCAGGGGAACGTCTT
CTCATGCTCCGTGATGCATGAGGCTCTGCACAACCACTACACGCAGAAGAGCCTCTCCCTGTCTCCGGGTAAA

FIG. 20G

MERGLPLLCAVLALVLAPAGAFRNDKCGDTIKIESPGYLTSPGYPHSYHPSEKCEWLIQAP
DPYQRIMINFNPHFDLEDRDCKYDYVEVFDGENENGHFRGKFCGKIAPPPVVSSGPFLFIK
FVSDYETHGAGFSIRYELFKRGPECSQNYTTPSGVIKSPGFPEKYPNSLECTYIVFAPKMS
EIILEFESFDLEPDSNPPGGMFCRYDRLEIWDGFPDVGPHIGRYCGQKTPGRIRSSSGILS
MVFYTDSAIAKEGFSANYSVLZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZ
ZZZZDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKTTPPVLD
SDGSFFLYSKLTVDKSRWQQGNVFSCSVMHEALHNHYTQKSLSLSPGK

FIG. 20H

ATGGAGAGGGGGCTGCCGCTCCTCTGCGCCGTGCTCGCCCTCGTCCTCGCCCCGGCCGGCGCTTTTC
GCAACGATAAATGTGGCGATACTATAAAAATTGAAAGCCCCGGGTACCTTACATCTCCTGGTTATCC
TCATTCTTATCACCCAAGTGAAAAATGCGAATGGCTGATTCAGGCTCCGGACCCATACCAGAGAATT
ATGATCAACTTCAACCCTCACTTCGATTTGGAGGACAGAGACTGCAAGTATGACTACGTGGAAGTCT
TCGATGGAGAAAATGAAAATGGACATTTTAGGGGAAAGTTCTGTGGAAAGATAGCCCCTCCTCCTGT
TGTGTCTTCAGGGCCATTTCTTTTTATCAAATTTGTCTCTGACTACGAAACACATGGTGCAGGATTT
TCCATACGTTATGAACTTTTCAAGAGAGGTCCTGAATGTTCCCAGAACTACACAACACCTAGTGGAG
TGATAAAGTCCCCCGGATTCCCTGAAAAATATCCCAACAGCCTTGAATGCACTTATATTGTCTTTGC
GCCAAAGATGTCAGAGATTATCCTGGAATTTGAAAGCTTTGACCTGGAGCCTGACTCAAATCCTCCA
GGGGGGATGTTCTGTCGCTACGACCGGCTAGAAATCTGGGATGGATTCCCTGATGTTGGCCCTCACA
TTGGGCGTTACTGTGGACAGAAAACACCAGGTCGAATCCGATCCTCATCGGGCATTCTCTCCATGGT
TTTTTACACCGACAGCGCCGATAGCAAAAGAAGGTTTCTCAGCAAACTACAGTGTCTTGNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNGACAAAACTCACACATGCCCACCGTGCCCAGCACCTGAA
CTCCTGGGGGGACCGTCAGTCTTCCTCTTCCCCCCAAAACCCAAGGACACCCTCATGATCTCCCGGA
CCCCTGAGGTCACATGCGTGGTGGTGGACGTGAGCCACGAAGACCCTGAGGTCAAGTTCAACTGGTA
CGTGGACGGCGTGGAGGTGCATAATGCCAAGACAAAGCCGCGGGAGGAGCAGTACAACAGCACGTAC
CGTGTGGTCAGCGTCCTCACCGTCCTGCACCAGGACTGGCTGAATGGCAAGGAGTACAAGTGCAAGG
TCTCCAACAAAGCCCTCCCAGCCCCCATCGAGAAAACCATCTCCAAAGCCAAAGGGCAGCCCCGAGA
ACCACAGGTGTACACCCTGCCCCCATCCCGGGAGGAGATGACCAAGAACCAGGTCAGCCTGACCTGC
CTGGTCAAAGGCTTCTATCCCAGCGACATCGCCGTGGAGTGGGAGAGCAATGGGCAGCCGGAGAACA
ACTACAAGACCACGCCTCCCGTGCTGGACTCCGACGGCTCCTTCTTCCTCTACAGCAAGCTCACCGT
GGACAAGAGCAGGTGGCAGCAGGGGAACGTCTTCTCATGCTCCGTGATGCACGAGGCTCTGCACAAC
CACTACACGCAGAAGAGCCTCTCCCTGTCTCCGGGTAAA

FIG. 20I

```
atggagaggggctgccgctcctctgcgccgtgctcgccctcgtcctcgccccggccggc
 M  E  R  G  L  P  L  L  C  A  V  L  A  L  V  L  A  P  A  G
gcttttcgcaacgataaatgtggcgatactataaaaattgaaagccccgggtaccttaca
 A  F  R  N  D  K  C  G  D  T  I  K  I  E  S  P  G  Y  L  T
tctcctggttatcctcattcttatcacccaagtgaaaaatgcgaatggctgattcaggct
 S  P  G  Y  P  H  S  Y  H  P  S  E  K  C  E  W  L  I  Q  A
ccggacccataccagagaattatgatcaacttcaaccctcacttcgatttggaggacaga
 P  D  P  Y  Q  R  I  M  I  N  F  N  P  H  F  D  L  E  D  R
gactgcaagtatgactacgtggaagtcttcgatggagaaaatgaaaatggacattttagg
 D  C  K  Y  D  Y  V  E  V  F  D  G  E  N  E  N  G  H  F  R
ggaaagttctgtggaaagatagcccctcctcctgttgtgtcttcagggccatttcttttt
 G  K  F  C  G  K  I  A  P  P  P  V  V  S  S  G  P  F  L  F
atcaaatttgtctctgactacgaaacacatggtgcaggattttccatacgttatgaactt
 I  K  F  V  S  D  Y  E  T  H  G  A  G  F  S  I  R  Y  E  L
ttcaagagaggtcctgaatgttcccagaactacacaacacctagtggagtgataaagtcc
 F  K  R  G  P  E  C  S  Q  N  Y  T  T  P  S  G  V  I  K  S
cccggattccctgaaaaatatcccaacagccttgaatgcacttatattgtctttgcgcca
 P  G  F  P  E  K  Y  P  N  S  L  E  C  T  Y  I  V  F  A  P
aagatgtcagagattatcctggaatttgaaagctttgacctggagcctgactcaaatcct
 K  M  S  E  I  I  L  E  F  E  S  F  D  L  E  P  D  S  N  P
ccaggggggatgttctgtcgctacgaccggctagaaatctgggatggattccctgatgtt
 P  G  G  M  F  C  R  Y  D  R  L  E  I  W  D  G  F  P  D  V
ggccctcacattgggcgttactgtggacagaaaacaccaggtcgaatccgatcctcatcg
 G  P  H  I  G  R  Y  C  G  Q  K  T  P  G  R  I  R  S  S  S
ggcattctctccatggtttttttacaccgacagcgcgatagcaaaagaaggtttctcagca
 G  I  L  S  M  V  F  Y  T  D  S  A  I  A  K  E  G  F  S  A
aactacagtgtcttgcagagcagtgtctcagaagatttcaaatgtatggaagctctgggc
 N  Y  S  V  L  Q  S  S  V  S  E  D  F  K  C  M  E  A  L  G
atggaatcaggagaaattcattctgaccagatcacagcttcttcccagtatagcaccaac
 M  E  S  G  E  I  H  S  D  Q  I  T  A  S  S  Q  Y  S  T  N
tggtctgcagagcgctcccgcctgaactaccctgagaatgggtggactcccggagaggat
 W  S  A  E  R  S  R  L  N  Y  P  E  N  G  W  T  P  G  E  D
tcctaccgagagtggatacaggtagacttgggccttctgcgctttgtcacggctgtcggg
 S  Y  R  E  W  I  Q  V  D  L  G  L  L  R  F  V  T  A  V  G
acacagggcgccatttcaaaagaaaccaagaagaaatattatgtcaagacttacaagatc
 T  Q  G  A  I  S  K  E  T  K  K  K  Y  Y  V  K  T  Y  K  I
gacgttagctccaacggggaagactggatcaccataaaagaaggaaacaaacctgttctc
 D  V  S  S  N  G  E  D  W  I  T  I  K  E  G  N  K  P  V  L
tttcagggaaacaccaaccctacagatgttgtggttgcagtattccccaaaccactgata
 F  Q  G  N  T  N  P  T  D  V  V  V  A  V  F  P  K  P  L  I
actcgatttgtccgaatcaagcctgcaacttgggaaactggcatatctatgagatttgaa
 T  R  F  V  R  I  K  P  A  T  W  E  T  G  I  S  M  R  F  E
gtatatggttgcaagataacagattatccttgctctggaatgttgggtatggtgtctgga
 V  Y  G  C  K  I  T  D  Y  P  C  S  G  M  L  G  M  V  S  G
cttatttctgactcccagatcacatcatccaaccaaggggacagaaactggatgcctgaa
 L  I  S  D  S  Q  I  T  S  S  N  Q  G  D  R  N  W  M  P  E
aacatccgcctggtaaccagtcgctctggctgggcacttccacccgcacctcattcctac
 N  I  R  L  V  T  S  R  S  G  W  A  L  P  P  A  P  H  S  Y
atcaatgagtggctccaaatagacctgggggaggagaagatcgtgaggggcatcatcatt
 I  N  E  W  L  Q  I  D  L  G  E  E  K  I  V  R  G  I  I  I
cagggtgggaagcaccgagagaacaaggtgttcatgaggaagttcaagatcgggtacagc
 Q  G  G  K  H  R  E  N  K  V  F  M  R  K  F  K  I  G  Y  S
aacaacggctcggactggaagatgatcatggatgacagcaaacgcaaggcgaagtctttt
 N  N  G  S  D  W  K  M  I  M  D  D  S  K  R  K  A  K  S  F
```

FIG. 20J

```
gagggcaacaacaactatgatacacctgagctgcggactttcccagctctctccacgcga
 E  G  N  N  N  Y  D  T  P  E  L  R  T  F  P  A  L  S  T  R
ttcatcaggatctacccgagagagccactcatggcggactggggctcagaatggagctg
 F  I  R  I  Y  P  E  R  A  T  H  G  G  L  G  L  R  M  E  L
ctgggctgtagatctgacaaaactcacacatgcccaccgtgcccagcacctgaactcctg
 L  G  C  R  S  D  K  T  H  T  C  P  P  C  P  A  P  E  L  L
gggggaccgtcagtcttcctcttccccccaaaacccaaggacaccctcatgatctcccgg
 G  G  P  S  V  F  L  F  P  P  K  P  K  D  T  L  M  I  S  R
acccctgaggtcacatgcgtggtggtggacgtgagccacgaagaccctgaggtcaagttc
 T  P  E  V  T  C  V  V  V  D  V  S  H  E  D  P  E  V  K  F
aactggtacgtggacggcgtggaggtgcataatgccaagacaaagccgcgggaggagcag
 N  W  Y  V  D  G  V  E  V  H  N  A  K  T  K  P  R  E  E  Q
tacaacagcacgtaccgtgtggtcagcgtcctcaccgtcctgcaccaggactggctgaat
 Y  N  S  T  Y  R  V  V  S  V  L  T  V  L  H  Q  D  W  L  N
ggcaaggagtacaagtgcaaggtctccaacaaagccctcccagcccccatcgagaaaacc
 G  K  E  Y  K  C  K  V  S  N  K  A  L  P  A  P  I  E  K  T
atctccaaagccaaagggcagccccgagaaccacaggtgtacaccctgcccccatcccgg
 I  S  K  A  K  G  Q  P  R  E  P  Q  V  Y  T  L  P  P  S  R
gaggagatgaccaagaaccaggtcagcctgacctgcctggtcaaaggcttctatcccagc
 E  E  M  T  K  N  Q  V  S  L  T  C  L  V  K  G  F  Y  P  S
gacatcgccgtggagtgggagagcaatgggcagccggagaacaactacaagaccacgcct
 D  I  A  V  E  W  E  S  N  G  Q  P  E  N  N  Y  K  T  T  P
cccgtgctggactccgacggctccttcttcctctacagcaagctcaccgtggacaagagc
 P  V  L  D  S  D  G  S  F  F  L  Y  S  K  L  T  V  D  K  S
aggtggcagcaggggaacgtcttctcatgctccgtgatgcacgaggctctgcacaaccac
 R  W  Q  Q  G  N  V  F  S  C  S  V  M  H  E  A  L  H  N  H
tacacgcagaagagcctctccctgtctccgggtaaa
 Y  T  Q  K  S  L  S  L  S  P  G  K
```

FIG. 20K

```
atggagaggggctgccgctcctctgcgccgtgctcgccctcgtcctcgccccggccggc
 M  E  R  G  L  P  L  L  C  A  V  L  A  L  V  L  A  P  A  G
gcttttcgcaacgataaatgtggcgatactataaaaattgaaagccccgggtaccttaca
 A  F  R  N  D  K  C  G  D  T  I  K  I  E  S  P  G  Y  L  T
tctcctggttatcctcattcttatcacccaagtgaaaaatgcgaatggctgattcaggct
 S  P  G  Y  P  H  S  Y  H  P  S  E  K  C  E  W  L  I  Q  A
ccggacccataccagagaattatgatcaacttcaaccctcacttcgatttggaggacaga
 P  D  P  Y  Q  R  I  M  I  N  F  N  P  H  F  D  L  E  D  R
gactgcaagtatgactacgtggaagtcttcgatggagaaaatgaaaatggacattttagg
 D  C  K  Y  D  Y  V  E  V  F  D  G  E  N  E  N  G  H  F  R
ggaaagttctgtggaaagatagcccctcctcctgttgtgtcttcagggccatttcttttt
 G  K  F  C  G  K  I  A  P  P  P  V  V  S  S  G  P  F  L  F
atcaaatttgtctctgactacgaaacacatggtgcaggattttccatacgttatgaactt
 I  K  F  V  S  D  Y  E  T  H  G  A  G  F  S  I  R  Y  E  L
ttcaagagaggtcctgaatgttcccagaactacacaacacctagtggagtgataaagtcc
 F  K  R  G  P  E  C  S  Q  N  Y  T  T  P  S  G  V  I  K  S
cccggattccctgaaaaatatcccaacagccttgaatgcacttatattgtctttgcgcca
 P  G  F  P  E  K  Y  P  N  S  L  E  C  T  Y  I  V  F  A  P
aagatgtcagagattatcctggaatttgaaagctttgacctggagcctgactcaaatcct
 K  M  S  E  I  I  L  E  F  E  S  F  D  L  E  P  D  S  N  P
ccaggggggatgttctgtcgctacgaccggctagaaatctgggatggattccctgatgtt
 P  G  G  M  F  C  R  Y  D  R  L  E  I  W  D  G  F  P  D  V
ggccctcacattgggcgttactgtggacagaaaacaccaggtcgaatccgatcctcatcg
 G  P  H  I  G  R  Y  C  G  Q  K  T  P  G  R  I  R  S  S  S
ggcattctctccatggttttttacaccgacagcgcgatagcaaaagaaggtttctcagca
 G  I  L  S  M  V  F  Y  T  D  S  A  I  A  K  E  G  F  S  A
aactacagtgtcttgcagagcagtgtctcagaagatttcaaatgtatggaagctctgggc
 N  Y  S  V  L  Q  S  S  V  S  E  D  F  K  C  M  E  A  L  G
atggaatcaggagaaattcattctgaccagatcacagcttcttcccagtatagcaccaac
 M  E  S  G  E  I  H  S  D  Q  I  T  A  S  S  Q  Y  S  T  N
tggtctgcagagcgctcccgcctgaactaccctgagaatgggtggactcccggagaggat
 W  S  A  E  R  S  R  L  N  Y  P  E  N  G  W  T  P  G  E  D
tcctaccgagagtggatacaggtagacttgggccttctgcgctttgtcacggctgtcggg
 S  Y  R  E  W  I  Q  V  D  L  G  L  L  R  F  V  T  A  V  G
acacagggcgccatttcaaaagaaaccaagaagaaatattatgtcaagacttacaagatc
 T  Q  G  A  I  S  K  E  T  K  K  K  Y  Y  V  K  T  Y  K  I
gacgttagctccaacggggaagactggatcaccataaaagaaggaaacaaacctgttctc
 D  V  S  S  N  G  E  D  W  I  T  I  K  E  G  N  K  P  V  L
tttcagggaaacaccaaccccacagatgttgtggttgcagtattccccaaaccactgata
 F  Q  G  N  T  N  P  T  D  V  V  V  A  V  F  P  K  P  L  I
actcgatttgtccgaatcaagcctgcaacttgggaaactggcatatctatgagatttgaa
 T  R  F  V  R  I  K  P  A  T  W  E  T  G  I  S  M  R  F  E
gtatatggttgcagatctgacaaaactcacacatgcccaccgtgcccagcacctgaactc
 V  Y  G  C  R  S  D  K  T  H  T  C  P  P  C  P  A  P  E  L
ctggggggaccgtcagtcttcctcttccccccaaaacccaaggacaccctcatgatctcc
 L  G  G  P  S  V  F  L  F  P  P  K  P  K  D  T  L  M  I  S
cggacccctgaggtcacatgcgtggtggtggacgtgagccacgaagaccctgaggtcaag
 R  T  P  E  V  T  C  V  V  V  D  V  S  H  E  D  P  E  V  K
ttcaactggtacgtggacggcgtggaggtgcataatgccaagacaaagccgcgggaggag
 F  N  W  Y  V  D  G  V  E  V  H  N  A  K  T  K  P  R  E  E
cagtacaacagcacgtaccgtgtggtcagcgtcctcaccgtcctgcaccaggactggctg
 Q  Y  N  S  T  Y  R  V  V  S  V  L  T  V  L  H  Q  D  W  L
```

FIG. 20L

```
aatggcaaggagtacaagtgcaaggtctccaacaaagccctcccagcccccatcgagaaa
 N  G  K  E  Y  K  C  K  V  S  N  K  A  L  P  A  P  I  E  K
accatctccaaagccaaagggcagccccgagaaccacaggtgtacaccctgcccccatcc
 T  I  S  K  A  K  G  Q  P  R  E  P  Q  V  Y  T  L  P  P  S
cgggaggagatgaccaagaaccaggtcagcctgacctgcctggtcaaaggcttctatccc
 R  E  E  M  T  K  N  Q  V  S  L  T  C  L  V  K  G  F  Y  P
agcgacatcgccgtggagtgggagagcaatgggcagccggagaacaactacaagaccacg
 S  D  I  A  V  E  W  E  S  N  G  Q  P  E  N  N  Y  K  T  T
cctcccgtgctggactccgacggctccttcttcctctacagcaagctcaccgtggacaag
 P  P  V  L  D  S  D  G  S  F  F  L  Y  S  K  L  T  V  D  K
agcaggtggcagcaggggaacgtcttctcatgctccgtgatgcacgaggctctgcacaac
 S  R  W  Q  Q  G  N  V  F  S  C  S  V  M  H  E  A  L  H  N
cactacacgcagaagagcctctccctgtctccgggtaaa
 H  Y  T  Q  K  S  L  S  L  S  P  G  K
```

FIG. 20M

```
atggagagggggctgccgctcctctgcgccgtgctcgccctcgtcctcgccccggccggc
 M  E  R  G  L  P  L  L  C  A  V  L  A  L  V  L  A  P  A  G
gcttttcgcaacgataaatgtggggatactataaaaattgaaagccccgggtaccttaca
 A  F  R  N  D  K  C  G  D  T  I  K  I  E  S  P  G  Y  L  T
tctcctggttatcctcattcttatcacccaagtgaaaaatgcgaatggctgattcaggct
 S  P  G  Y  P  H  S  Y  H  P  S  E  K  C  E  W  L  I  Q  A
ccggacccataccagagaattatgatcaacttcaaccctcacttcgatttggaggacaga
 P  D  P  Y  Q  R  I  M  I  N  F  N  P  H  F  D  L  E  D  R
gactgcaagtatgactacgtggaagtcttcgatggagaaaatgaaaatggacattttagg
 D  C  K  Y  D  Y  V  E  V  F  D  G  E  N  E  N  G  H  F  R
ggaaagttctgtggaaagatagcccctcctcctgttgtgtcttcagggccatttcttttt
 G  K  F  C  G  K  I  A  P  P  P  V  V  S  S  G  P  F  L  F
atcaaatttgtctctgactacgaaacacatggtgcaggattttccatacgttatgaactt
 I  K  F  V  S  D  Y  E  T  H  G  A  G  F  S  I  R  Y  E  L
ttcaagagaggtcctgaatgttcccagaactacacaacacctagtggagtgataaagtcc
 F  K  R  G  P  E  C  S  Q  N  Y  T  T  P  S  G  V  I  K  S
cccggattccctgaaaaatatcccaacagccttgaatgcacttatattgtctttgcgcca
 P  G  F  P  E  K  Y  P  N  S  L  E  C  T  Y  I  V  F  A  P
aagatgtcagagattatcctggaatttgaaagctttgacctggagcctgactcaaatcct
 K  M  S  E  I  I  L  E  F  E  S  F  D  L  E  P  D  S  N  P
ccagggggggatgttctgtcgctacgaccggctagaaatctgggatggattccctgatgtt
 P  G  G  M  F  C  R  Y  D  R  L  E  I  W  D  G  F  P  D  V
ggccctcacattgggcgttactgtggacagaaaacaccaggtcgaatccgatcctcatcg
 G  P  H  I  G  R  Y  C  G  Q  K  T  P  G  R  I  R  S  S  S
ggcattctctccatggttttttacaccgacagcgcgatagcaaaagaaggtttctcagca
 G  I  L  S  M  V  F  Y  T  D  S  A  I  A  K  E  G  F  S  A
aactacagtgtcttgagatctgacaaaactcacacatgcccaccgtgcccagcacctgaa
 N  Y  S  V  L  R  S  D  K  T  H  T  C  P  P  C  P  A  P  E
ctcctggggggaccgtcagtcttcctcttccccccaaaacccaaggacaccctcatgatc
 L  L  G  G  P  S  V  F  L  F  P  P  K  P  K  D  T  L  M  I
tcccggacccctgaggtcacatgcgtggtggtggacgtgagccacgaagaccctgaggtc
 S  R  T  P  E  V  T  C  V  V  V  D  V  S  H  E  D  P  E  V
aagttcaactggtacgtggacggcgtggaggtgcataatgccaagacaaagccgcgggag
 K  F  N  W  Y  V  D  G  V  E  V  H  N  A  K  T  K  P  R  E
gagcagtacaacagcacgtaccgtgtggtcagcgtcctcaccgtcctgcaccaggactgg
 E  Q  Y  N  S  T  Y  R  V  V  S  V  L  T  V  L  H  Q  D  W
ctgaatggcaaggagtacaagtgcaaggtctccaacaaagccctcccagcccccatcgag
 L  N  G  K  E  Y  K  C  K  V  S  N  K  A  L  P  A  P  I  E
aaaaccatctccaaagccaaagggcagccccgagaaccacaggtgtacaccctgccccca
 K  T  I  S  K  A  K  G  Q  P  R  E  P  Q  V  Y  T  L  P  P
tcccgggaggagatgaccaagaaccaggtcagcctgacctgcctggtcaaaggcttctat
 S  R  E  E  M  T  K  N  Q  V  S  L  T  C  L  V  K  G  F  Y
cccagcgacatcgccgtggagtgggagagcaatgggcagccggagaacaactacaagacc
 P  S  D  I  A  V  E  W  E  S  N  G  Q  P  E  N  N  Y  K  T
acgcctcccgtgctggactccgacggctccttcttcctctacagcaagctcaccgtggac
 T  P  P  V  L  D  S  D  G  S  F  F  L  Y  S  K  L  T  V  D
aagagcaggtggcagcaggggaacgtcttctcatgctccgtgatgcacgaggctctgcac
 K  S  R  W  Q  Q  G  N  V  F  S  C  S  V  M  H  E  A  L  H
aaccactacacgcagaagagcctctccctgtctccgggtaaa
 N  H  Y  T  Q  K  S  L  S  L  S  P  G  K
```

FIG. 20N atggagaggggcctgccgctcctctgcgccgtgctcgccctcgtcctcgccccggccggc

M E R G L P L L C A V L A L V L A P A G gcttttcgcaacgataaatgtggcgatactataaaaattgaaagccccgggtaccttaca

A F R N D K C G D T I K I E S P G Y L T tctcctggttatcctaattcttatcacccaagtgaaaaatgcgaatggctgattcaggct

S P G Y P N S Y H P S E K C E W L I Q A ccggacccataccagagaattatgatcaacttcaaccctcacttcgatttggaggacaga

P D P Y Q R I M I N F N P H F D L E D R gactgcaagtatgactacgtggaagtcttcgatggagaaaatgaaaatggacattttagg

D C K Y D Y V E V F D G E N E N G H F R ggaaagttctgtggaaagatagcccctcctcctgttgtgtcttcagggccatttcttttt

G K F C G K I A P P P V V S S G P F L F atcaaatttgtctctgactacgaaacacatggtgcaggattttccatacgttatgaactt

I K F V S D Y E T H G A G F S I R Y E L ttcaagagaggtcctgaatgttcccagaactacacaacacctagtggagtgataaagtcc

F K R G P E C S Q N Y T T P S G V I K S cccggattccctgaaaaatatcccaacagccttgaatgcacttatattgtctttgcgcca

P G F P E K Y P N S L E C T Y I V F A P aagatgtcagagattatcctggaatttgaaagctttgacctggagcctgactcaaatcct

K M S E I I L E F E S F D L E P D S N P ccaggggggatgttctgtcgctacgaccggctagaaatctgggatggattccctgatgtt

P G G M F C R Y D R L E I W D G F P D V ggccctcacattgggcgttactgtggacagaaaacaccaggtcgaatccgatcctcatcg

G P H I G R Y C G Q K T P G R I R S S S ggcattctctccatggtttttacaccgacagcgcgatagcaaaagaaggtttctcagca

G I L S M V F Y T D S A I A K E G F S A aactacagtgtcttgcagagcagtgtctcagaagatttcaaatgtatggaagctctgggc

N Y S V L Q S S V S E D F K C M E A L G atggaatcaggagaaattcattctgaccagatcacagcttcttcccaggctagcaccaac

M E S G E I H S D Q I T A S S Q A S T N tggtctgcagagcgctcccgcctgaactaccccgagaatgggtggactcccggagaggat

W S A E R S R L N Y P E N G W T P G E D tcctaccgagagtggatacaggtagacttgggccttctgcgctttgtcacggctgtcggg

S Y R E W I Q V D L G L L R F V T A V G acacagggcgccatttcaaaagaaaccaagaagaaatattatgtcaagacttacaagatc

T Q G A I S K E T K K K Y Y V K T Y K I gacgttagctccaacggggaagactggatcaccataaaagaaggaaacaaacctgttctc

D V S S N G E D W I T I K E G N K P V L tttcagggaaacaccaaccccacagatgttgtggttgcagtattccccaaacccctgata

F Q G N T N P T D V V V A V F P K P L I actcgatttgtccgaatcaagcctgcaacttgggaaactggcatatctatgagatttgaa

T R F V R I K P A T W E T G I S M R F E gtatatggttgcaagataacagattatccttgctctggaatgttgggtatggtgtctgga

V Y G C K I T D Y P C S G M L G M V S G cttatttctgactcccagatcacatcatccaaccaaggggacagaaactggatgcctgaa

L I S D S Q I T S S N Q G D R N W M P E aacatccgcctggtaaccagtcgctctggctgggcacttccacccgcacctcattcctac

N I R L V T S R S G W A L P P A P H S Y atcaatgagtggctccaaatagacctgggggaggagaagatcgtgaggggcatcatcatt

I N E W L Q I D L G E E K I V R G I I I cagggtgggaagcaccgagagaacaaggtgttcatgaggaagttcaagatcgggtacagc

Q G G K H R E N K V F M R K F K I G Y S aacaacggctcggactggaagatgatcatggatgacagcaaacgcaaggcgaagtctttt

N N G S D W K M I M D D S K R K A K S F

FIG. 20O

```
gagggcaacaacaactatgatacacctgagctgcggactttttccagctctctccacgcga
 E  G  N  N  N  Y  D  T  P  E  L  R  T  F  P  A  L  S  T  R
ttcatcaggatctaccccgagagagccactcatggcggactggggctcagaatggagctg
 F  I  R  I  Y  P  E  R  A  T  H  G  G  L  G  L  R  M  E  L
ctgggctgtgaagtggaagcccctacagctggaccgaccactcccaacgggaacttggtg
 L  G  C  E  V  E  A  P  T  A  G  P  T  T  P  N  G  N  L  V
gatgaatgtgatgacgaccaggccaactgccacagtggaacaggtgatgacttccagctc
 D  E  C  D  D  D  Q  A  N  C  H  S  G  T  G  D  D  F  Q  L
acaggtggcaccactgtgctggccacagaaaagcccacggtcatagacagcaccatacaa
 T  G  G  T  T  V  L  A  T  E  K  P  T  V  I  D  S  T  I  Q
tcagagtttccaacatatggttttaactgtgaatttggctggggctctcacaagaccttc
 S  E  F  P  T  Y  G  F  N  C  E  F  G  W  G  S  H  K  T  F
tgccactgggaacatgacaatcacgtgcagctcaagtggagtgtgttgaccagcaagacg
 C  H  W  E  H  D  N  H  V  Q  L  K  W  S  V  L  T  S  K  T
ggacccattcaggatcacacaggagatggcaacttcatctattcccaagctgacgaaaat
 G  P  I  Q  D  H  T  G  D  G  N  F  I  Y  S  Q  A  D  E  N
cagaagggcaaagtggctcgcctggtgagccctgtggtttattcccagaactctgcccac
 Q  K  G  K  V  A  R  L  V  S  P  V  V  Y  S  Q  N  S  A  H
tgcatgaccttctggtatcacatgtctgggtcccacgtcggcacactcagggtcaaactg
 C  M  T  F  W  Y  H  M  S  G  S  H  V  G  T  L  R  V  K  L
cgctaccagaagccagaggagtacgatcagctggtctggatggccattggacaccaaggt
 R  Y  Q  K  P  E  E  Y  D  Q  L  V  W  M  A  I  G  H  Q  G
gaccactggaaggaagggcgtgtcttgctccacaagtctctgaaactttatcaggtgatt
 D  H  W  K  E  G  R  V  L  L  H  K  S  L  K  L  Y  Q  V  I
ttcgagggcgaaatcggaaaaggaaaccttggtgggattgctgtggatgacattagtatt
 F  E  G  E  I  G  K  G  N  L  G  G  I  A  V  D  D  I  S  I
aataaccacatttcacaggaagattgtgcaaaaccagcagacctggataaaaagaaccca
 N  N  H  I  S  Q  E  D  C  A  K  P  A  D  L  D  K  K  N  P
gaaattaaaattgatgaaacagggagcacgccaggatacgaaggtgaaggagaaggtgac
 E  I  K  I  D  E  T  G  S  T  P  G  Y  E  G  E  G  E  G  D
aagaacatctccaggaagccaggcaatgtgttgaagaccttagaccccagatctgacaaa
 K  N  I  S  R  K  P  G  N  V  L  K  T  L  D  P  R  S  D  K
actcacacatgcccaccgtgcccagcacctgaactcctggggggaccgtcagtcttcctc
 T  H  T  C  P  P  C  P  A  P  E  L  L  G  G  P  S  V  F  L
ttccccccaaaacccaaggacaccctcatgatctcccggacccctgaggtcacatgcgtg
 F  P  P  K  P  K  D  T  L  M  I  S  R  T  P  E  V  T  C  V
gtggtggacgtgagccacgaagaccctgaggtcaagttcaactggtacgtggacggcgtg
 V  V  D  V  S  H  E  D  P  E  V  K  F  N  W  Y  V  D  G  V
gaggtgcataatgccaagacaaagccgcgggaggagcagtacaacagcacgtaccgtgtg
 E  V  H  N  A  K  T  K  P  R  E  E  Q  Y  N  S  T  Y  R  V
gtcagcgtcctcaccgtcctgcaccaggactggctgaatggcaaggagtacaagtgcaag
 V  S  V  L  T  V  L  H  Q  D  W  L  N  G  K  E  Y  K  C  K
gtctccaacaaagccctcccagcccccatcgagaaaaccatctccaaagccaaagggcag
 V  S  N  K  A  L  P  A  P  I  E  K  T  I  S  K  A  K  G  Q
ccccgagaaccacaggtgtacaccctgcccccatcccgggaggagatgaccaagaaccag
 P  R  E  P  Q  V  Y  T  L  P  P  S  R  E  E  M  T  K  N  Q
gtcagcctgacctgcctggtcaaaggcttctatcccagcgacatcgccgtggagtgggag
 V  S  L  T  C  L  V  K  G  F  Y  P  S  D  I  A  V  E  W  E
agcaatgggcagccggagaacaactacaagaccacgcctcccgtgctggactccgacggc
 S  N  G  Q  P  E  N  N  Y  K  T  T  P  P  V  L  D  S  D  G
tccttcttcctctacagcaagctcaccgtggacaagagcaggtggcagcaggggaacgtc
 S  F  F  L  Y  S  K  L  T  V  D  K  S  R  W  Q  Q  G  N  V
ttctcatgctccgtgatgcacgaggctctgcacaaccactacacgcagaagagcctctcc
 F  S  C  S  V  M  H  E  A  L  H  N  H  Y  T  Q  K  S  L  S
ctgtctccgggtaaa
 L  S  P  G  K
```

FIG. 20P

MERGLPLLCAVLALVLAPAGAFRNDKCGDTIKIESPGYLTSPGYPHSYHPSEKCEWLIQAP
DPYQRIMINFNPHFDLEDRDCKYDYVEVFDGENENGHFRGKFCGKIAPPPVVSSGPFLFIK
FVSDYETHGAGFSIRYELFKRGPECSQNYTTPSGVIKSPGFPEKYPNSLECTYIVFAPKMS
EIILEFESFDLEPDSNPPGGMFCRYDRLEIWDGFPDVGPHIGRYCGQKTPGRIRSSSGILS
MVFYTDSAIAKEGFSANYSVLQSSVSEDFKCMEALGMESGEIHSDQITASSQASTNWSAE
RSRLNYPENGWTPGEDSYREWIQVDLGLLRFVTAVGTQGAISKETKKKYYVKTYKIDVSS
NGEDWITIKEGNKPVLFQGNTNPTDVVVAVFPKPLITRFVRIKPATWETGISMRFEVYGCKI
TDYPCSGMLGMVSGLISDSQITSSNQGDRNWMPENIRLVTSRSGWALPPAPHSYINEWL
QIDLGEEKIVRGIIIQGGKHRENKVFMRKFKIGYSNNGSDWKMIMDDSKRKAKSFEGNNNY
DTPELRTFPALSTRFIRIYPERATHGGLGLRMELLGCZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZDKTHTCPPCPAPELL
GGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVDK
SRWQQGNVFSCSVMHEALHNHYTQKSLSLSPGK

FIG. 20Q

ATGGAGAGGGGGCTGCCGCTCCTCTGCGCCGTGCTCGCCCTCGTCCTCGCCCCGGCCGGCGCTTTTCGCAACGA
TAAATGTGGCGATACTATAAAAATTGAAAGCCCCGGGTACCTTACATCTCCTGGTTATCCTCATTCTTATCACC
CAAGTGAAAAATGCGAATGGCTGATTCAGGCTCCGGACCCATACCAGAGAATTATGATCAACTTCAACCCTCAC
TTCGATTTGGAGGACAGAGACTGCAAGTATGACTACGTGGAAGTCTTCGATGGAGAAAATGAAAATGGACATTT
TAGGGGAAAGTTCTGTGGAAAGATAGCCCCTCCTCCTGTTGTGTCTTCAGGGCCATTTCTTTTTATCAAATTTG
TCTCTGACTACGAAACACATGGTGCAGGATTTTCCATACGTTATGAACTTTTCAAGAGAGGTCCTGAATGTTCC
CAGAACTACACAACACCTAGTGGAGTGATAAAGTCCCCCGGATTCCCTGAAAAATATCCCAACAGCCTTGAATG
CACTTATATTGTCTTTGCGCCAAAGATGTCAGAGATTATCCTGGAATTTGAAAGCTTTGACCTGGAGCCTGACT
CAAATCCTCCAGGGGGGATGTTCTGTCGCTACGACCGGCTAGAAATCTGGGATGGATTCCCTGATGTTGGCCCT
CACATTGGGCGTTACTGTGGACAGAAAACACCAGGTCGAATCCGATCCTCATCGGGCATTCTCTCCATGGTTTT
TTACACCGACAGCGCGATAGCAAAAGAAGGTTTCTCAGCAAACTACAGTGTCTTGCAGAGCAGTGTCTCAGAAG
ATTTCAAATGTATGGAAGCTCTGGGCATGGAATCAGGAGAAATTCATTCTGACCAGATCACAGCTTCTTCCCAG
GCTAGCACCAACTGGTCTGCAGAGCGCTCCCGCCTGAACTACCCTGAGAATGGGTGGACTCCCGGAGAGGATTC
CTACCGAGAGTGGATACAGGTAGACTTGGGCCTTCTGCGCTTTGTCACGGCTGTCGGGACACAGGGCGCCATTT
CAAAAGAAACCAAGAAGAAATATTATGTCAAGACTTACAAGATCGACGTTAGCTCCAACGGGGAAGACTGGATC
ACCATAAAAGAAGGAAACAAACCTGTTCTCTTTCAGGGAAACACCAACCCTACAGATGTTGTGGTTGCAGTATT
CCCCAAACCACTGATAACTCGATTTGTCCGAATCAAGCCTGCAACTTGGGAAACTGGCATATCTATGAGATTTG
AAGTATATGGTTGCAAGATAACAGATTATCCTTGCTCTGGAATGTTGGGTATGGTGTCTGGACTTATTTCTGAC
TCCCAGATCACATCATCCAACCAAGGGGACAGAAACTGGATGCCTGAAAACATCCGCCTGGTAACCAGTCGCTC
TGGCTGGGCACTTCCACCCGCACCTCATTCCTACATCAATGAGTGGCTCCAAATAGACCTGGGGGAGGAGAAGA
TCGTGAGGGGCATCATCATTCAGGGTGGGAAGCACCGAGAGAACAAGGTGTTCATGAGGAAGTTCAAGATCGGG
TACAGCAACAACGGCTCGGACTGGAAGATGATCATGGATGACAGCAAACGCAAGGCGAAGTCTTTTGAGGGCAA
CAACAACTATGATACACCTGAGCTGCGGACTTTTCCAGCTCTCTCCACGCGATTCATCAGGATCTACCCCGAGA
GAGCCACTCATGGCGGACTGGGGCTCAGAATGGAGCTGCTGGGCTGTNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNGACAAAACTCACACAT
GCCCACCGTGCCCAGCACCTGAACTCCTGGGGGGACCGTCAGTCTTCCTCTTCCCCCCAAAACCCAAGGACACC
CTCATGATCTCCCGGACCCCTGAGGTCACATGCGTGGTGGTGGACGTGAGCCACGAAGACCCTGAGGTCAAGTT
CAACTGGTACGTGGACGGCGTGGAGGTGCATAATGCCAAGACAAAGCCGCGGGAGGAGCAGTACAACAGCACGT
ACCGTGTGGTCAGCGTCCTCACCGTCCTGCACCAGGACTGGCTGAATGGCAAGGAGTACAAGTGCAAGGTCTCC
AACAAAGCCCTCCCAGCCCCCATCGAGAAAACCATCTCCAAAGCCAAAGGGCAGCCCCGAGAACCACAGGTGTA
CACCCTGCCCCCATCCCGGGAGGAGATGACCAAGAACCAGGTCAGCCTGACCTGCCTGGTCAAAGGCTTCTATC
CCAGCGACATCGCCGTGGAGTGGGAGAGCAATGGGCAGCCGGAGAACAACTACAAGACCACGCCTCCCGTGCTG
GACTCCGACGGCTCCTTCTTCCTCTACAGCAAGCTCACCGTGGACAAGAGCAGGTGGCAGCAGGGGAACGTCTT
CTCATGCTCCGTGATGCACGAGGCTCTGCACAACCACTACACGCAGAAGAGCCTCTCCCTGTCTCCGGGTAAA

FIG. 20R

MKRGLFLLCAVLALVLAPAGAFRNDKCGDTIKIESPGYLTSPGYPHSYHPSEKCEWLIQA
PDPYQRIMINFNPHFDLEDRDCKYDYVEVFDGENENGHFRGKFCGKIAPPPVVSSGPFLF
IKFVSDYETHGAGFSIRYELFKRGPECSQNYTTPSGVIKSPGFPEKYPNSLECTYIVFAP
KMSEIILEFESFDLEPDSNPPGGMFCRYDRLEIWDGFPDVGPHIGRYCGQKTPGRIRSSS
GILSMVFYTDSAIAKEGFSANYSVLQSSVSEDFKCMEALGMESGEIHSDQITASSQASTN
WSAERSRLNYPENGWTPGEDSYREWIQVDLGLLRFVTAVGTQGAISKETKKKYYVKTYKI
DVSSNGEDWITIKEGNKPVLFQGNTNPTDVVVAVFPKPLITRFVRIKPATWETGISMRFE
VYGCZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZ
ZZZZZZZZZZZZZZZZZZDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEYKCK
VSNKALPAPIEKTISKAKGQPREPQVYTLPPSRKEMTKNQVSLTCLVKGFYPSDIAVEWE
SNGQPENNYKTTPPVLDSDGSFFLYSKLTVDKSRWQQGNVFSCSVMHEALHNHYTQKSLS
LSPGK

FIG. 20S

ATGGAGAGGGGGCTGCCGCTCCTCTGCGCCGTGCTCGCCCTCGTCCTCGCCCCGGCCGGCGCTTTTC
GCAACGATAAATGTGGCCGATACTATAAAAATTGAAAGCCCCGGGTACCTTACATCTCCTGGTTATCC
TCATTCTTATCACCCAAGTGAAAAATGCGAATGGCTGATTCAGGCTCCGGACCCATACCAGAGAATT
ATGATCAACTTCAACCCTCACTTCGATTTGGAGGACAGAGACTGCAAGTATGACTACGTGGAAGTCT
TCGATGGAGAAAATGAAAATGGACATTTTAGGGGAAAGTTCTGTGGAAAGATAGCCCCTCCTCCTGT
TGTGTCTTCAGGGCCATTTCTTTTTATCAAATTTGTCTCTGACTACGAAACACATGGTGCAGGATTT
TCCATACGTTATGAACTTTTCAAGAGAGGTCCTGAATGTTCCCAGAACTACACAACACCTAGTGGAG
TGATAAAGTCCCCCGGATTCCCTGAAAAATATCCCAACAGCCTTGAATGCACTTATATTGTCTTTGC
GCCAAAGATGTCAGAGATTATCCTGGAATTTGAAAGCTTTGACCTGGAGCCTGACTCAAATCCTCCA
GGGGGGATGTTCTGTCGCTACGACCGGCTAGAAATCTGGGATGGATTCCCTGATGTTGGCCCTCACA
TTGGGCGTTACTGTGGACAGAAAACACCAGGTCGAATCCGATCCTCATCGGGCATTCTCTCCATGGT
TTTTTACACCGACAGCGCGATAGCAAAAGAAGGTTTCTCAGCAAACTACAGTGTCTTGCAGAGCAGT
GTCTCAGAAGATTTCAAATGTATGGAAGCTCTGGGCATGGAATCAGGAGAAATTCATTCTGACCAGA
TCACAGCTTCTTCCCAGGCTAGCACCAACTGGTCTGCAGAGCGCTCCCGCCTGAACTACCCTGAGAA
TGGGTGGACTCCCGGCAGAGGATTCCTACCGAGAGTGGATACAGGTAGACTTGGGCCTTCTGCGCTTT
GTCACGGCTGTCGGGACACAGGGCGCCATTTCAAAAGAAACCAAGAAGAAATATTATGTCAAGACTT
ACAAGATCGACGTTAGCTCCAACGGGGAAGACTGGATCACCATAAAAGAAGGAAACAAACCTGTTCT
CTTTCAGGGAAACACCAACCCTACAGATGTTGTGGTTGCAGTATTCCCCAAACCACTGATAACTCGA
TTTGTCCGAATCAAGCCTGCAACTTGGGAAACTGGCATATCTATGAGATTTGAAGTATATGGTTGCN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNGACAAAACTCACACATGCCCACCGTGCCCAGCACCTGAA
CTCCTGGGGGGACCGTCAGTCTTCCTCTTCCCCCCAAAACCCAAGGACACCCTCATGATCTCCCGGA
CCCCTGAGGTCACATGCGTGGTGGTGGACGTGAGCCACGAAGACCCTGAGGTCAAGTTCAACTGGTA
CGTGGACGGCGTGGAGGTGCATAATGCCAAGACAAAGCCGCGGGAGGAGCAGTACAACAGCACGTAC
CGTGTGGTCAGCGTCCTCACCGTCCTGCACCAGGACTGGCTGAATGGCAAGGAGTACAAGTGCAAGG
TCTCCAACAAAGCCCTCCCAGCCCCCATCGAGAAAACCATCTCCAAAGCCAAAGGGCAGCCCCGAGA
ACCACAGGTGTACACCCTGCCCCCATCCCGGGAGGAGATGACCAAGAACCAGGTCAGCCTGACCTGC
CTGGTCAAAGGCTTCTATCCCAGCGACATCGCCGTGGAGTGGGAGAGCAATGGGCAGCCGGAGAACA
ACTACAAGACCACGCCTCCCGTGCTGGACTCCGACGGCTCCTTCTTCCTCTACAGCAAGCTCACCGT
GGACAAGAGCAGGTGGCAGCAGGGGAACGTCTTCTCATGCTCCGTGATGCACGAGGCTCTGCACAAC
CACTACACGCAGAAGAGCCTCTCCCTGTCTCCGGGTAAA

FIG. 20T

```
atggagagggggctgccgctcctctgcgccgtgctcgccctcgtcctcgccccggccggc
 M  E  R  G  L  P  L  L  C  A  V  L  A  L  V  L  A  P  A  G
gcttttcgcaacgataaatgtggcgatactataaaaattgaaagccccgggtaccttaca
 A  F  R  N  D  K  C  G  D  T  I  K  I  E  S  P  G  Y  L  T
tctcctggttatcctcattcttatcacccaagtgaaaaatgcgaatggctgattcaggct
 S  P  G  Y  P  H  S  Y  H  P  S  E  K  C  E  W  L  I  Q  A
ccggacccataccagagaattatgatcaacttcaacccccacttcgatttggaggacaga
 P  D  P  Y  Q  R  I  M  I  N  F  N  P  H  F  D  L  E  D  R
gactgcaagtatgactacgtggaagtcttcgatggagaaaatgaaaatggacattttagg
 D  C  K  Y  D  Y  V  E  V  F  D  G  E  N  E  N  G  H  F  R
ggaaagttctgtggaaagatagcccctcctcctgttgtgtcttcagggccatttcttttt
 G  K  F  C  G  K  I  A  P  P  P  V  V  S  S  G  P  F  L  F
atcaaatttgtctctgactacgaaacacatggtgcaggattttccatacgttatgaactt
 I  K  F  V  S  D  Y  E  T  H  G  A  G  F  S  I  R  Y  E  L
ttcaagagaggtcctgaatgttcccagaactacacaacacctagtggagtgataaagtcc
 F  K  R  G  P  E  C  S  Q  N  Y  T  T  P  S  G  V  I  K  S
cccggattccctgaaaaatatcccaacagccttgaatgcacttatattgtctttgcgcca
 P  G  F  P  E  K  Y  P  N  S  L  E  C  T  Y  I  V  F  A  P
aagatgtcagagattatcctggaatttgaaagctttgacctggagcctgactcaaatcct
 K  M  S  E  I  I  L  E  F  E  S  F  D  L  E  P  D  S  N  P
ccaggggggatgttctgtcgctacgaccggctagaaatctgggatggattccctgatgtt
 P  G  G  M  F  C  R  Y  D  R  L  E  I  W  D  G  F  P  D  V
ggccctcacattgggcgttactgtggacagaaaacaccaggtcgaatccgatcctcatcg
 G  P  H  I  G  R  Y  C  G  Q  K  T  P  G  R  I  R  S  S  S
ggcattctctccatggttttttacaccgacagcgcgatagcaaaagaaggtttctcagca
 G  I  L  S  M  V  F  Y  T  D  S  A  I  A  K  E  G  F  S  A
aactacagtgtcttgcagagcagtgtctcagaagatttcaaatgtatggaagctctgggc
 N  Y  S  V  L  Q  S  S  V  S  E  D  F  K  C  M  E  A  L  G
atggaatcaggagaaattcattctgaccagatcacagcttcttcccaggctagcaccaac
 M  E  S  G  E  I  H  S  D  Q  I  T  A  S  S  Q  A  S  T  N
tggtctgcagagcgctcccgcctgaactaccctgagaatgggtggactcccggagaggat
 W  S  A  E  R  S  R  L  N  Y  P  E  N  G  W  T  P  G  E  D
tcctaccgagagtggatacaggtagacttgggccttctgcgctttgtcacggctgtcggg
 S  Y  R  E  W  I  Q  V  D  L  G  L  L  R  F  V  T  A  V  G
acacagggcgccatttcaaaagaaaccaagaagaaatattatgtcaagacttacaagatc
 T  Q  G  A  I  S  K  E  T  K  K  K  Y  Y  V  K  T  Y  K  I
gacgttagctccaacggggaagactggatcaccataaaagaaggaaacaaacctgttctc
 D  V  S  S  N  G  E  D  W  I  T  I  K  E  G  N  K  P  V  L
tttcagggaaacaccaaccccacagatgttgtggttgcagtattccccaaaccactgata
 F  Q  G  N  T  N  P  T  D  V  V  V  A  V  F  P  K  P  L  I
actcgatttgtccgaatcaagcctgcaacttgggaaactggcatatctatgagatttgaa
 T  R  F  V  R  I  K  P  A  T  W  E  T  G  I  S  M  R  F  E
gtatatggttgcaagataacagattatccttgctctggaatgttgggtatggtgtctgga
 V  Y  G  C  K  I  T  D  Y  P  C  S  G  M  L  G  M  V  S  G
cttatttctgactcccagatcacatcatccaaccaaggggacagaaactggatgcctgaa
 L  I  S  D  S  Q  I  T  S  S  N  Q  G  D  R  N  W  M  P  E
aacatccgcctggtaaccagtcgctctggctgggcacttccacccgcacctcattcctac
 N  I  R  L  V  T  S  R  S  G  W  A  L  P  P  A  P  H  S  Y
atcaatgagtggctccaaatagacctgggggaggagaagatcgtgaggggcatcatcatt
 I  N  E  W  L  Q  I  D  L  G  E  E  K  I  V  R  G  I  I  I
cagggtgggaagcaccgagagaacaaggtgttcatgaggaagttcaagatcgggtacagc
 Q  G  G  K  H  R  E  N  K  V  F  M  R  K  F  K  I  G  Y  S
```

FIG. 20U

```
aacaacggctcggactggaagatgatcatggatgacagcaaacgcaaggcgaagtctttt
 N  N  G  S  D  W  K  M  I  M  D  D  S  K  R  K  A  K  S  F
gagggcaacaacaactatgatacacctgagctgcggacttttccagctctctccacgcga
 E  G  N  N  N  Y  D  T  P  E  L  R  T  F  P  A  L  S  T  R
ttcatcaggatctaccccgagagagccactcatggcggactggggctcagaatggagctg
 F  I  R  I  Y  P  E  R  A  T  H  G  G  L  G  L  R  M  E  L
ctgggctgtagatctgacaaaactcacacatgcccaccgtgcccagcacctgaactcctg
 L  G  C  R  S  D  K  T  H  T  C  P  P  C  P  A  P  E  L  L
gggggaccgtcagtcttcctcttccccccaaaacccaaggacaccctcatgatctcccgg
 G  G  P  S  V  F  L  F  P  P  K  P  K  D  T  L  M  I  S  R
acccctgaggtcacatgcgtggtggtggacgtgagccacgaagaccctgaggtcaagttc
 T  P  E  V  T  C  V  V  V  D  V  S  H  E  D  P  E  V  K  F
aactggtacgtggacggcgtggaggtgcataatgccaagacaaagccgcgggaggagcag
 N  W  Y  V  D  G  V  E  V  H  N  A  K  T  K  P  R  E  E  Q
tacaacagcacgtaccgtgtggtcagcgtcctcaccgtcctgcaccaggactggctgaat
 Y  N  S  T  Y  R  V  V  S  V  L  T  V  L  H  Q  D  W  L  N
ggcaaggagtacaagtgcaaggtctccaacaaagccctcccagcccccatcgagaaaacc
 G  K  E  Y  K  C  K  V  S  N  K  A  L  P  A  P  I  E  K  T
atctccaaagccaaagggcagccccgagaaccacaggtgtacaccctgcccccatcccgg
 I  S  K  A  K  G  Q  P  R  E  P  Q  V  Y  T  L  P  P  S  R
gaggagatgaccaagaaccaggtcagcctgacctgcctggtcaaaggcttctatcccagc
 E  E  M  T  K  N  Q  V  S  L  T  C  L  V  K  G  F  Y  P  S
gacatcgccgtggagtgggagagcaatgggcagccggagaacaactacaagaccacgcct
 D  I  A  V  E  W  E  S  N  G  Q  P  E  N  N  Y  K  T  T  P
cccgtgctggactccgacggctccttcttcctctacagcaagctcaccgtggacaagagc
 P  V  L  D  S  D  G  S  F  F  L  Y  S  K  L  T  V  D  K  S
aggtggcagcaggggaacgtcttctcatgctccgtgatgcacgaggctctgcacaaccac
 R  W  Q  Q  G  N  V  F  S  C  S  V  M  H  E  A  L  H  N  H
tacacgcagaagagcctctccctgtctccgggtaaa
 Y  T  Q  K  S  L  S  L  S  P  G  K
```

FIG. 20V

```
tggagaggggctgccgctcctctgcgccgtgctcgccctcgtcctcgccccggccggc
 M  E  R  G  L  P  L  L  C  A  V  L  A  L  V  L  A  P  A  G
gctttccgcaacgataaatgtggcgatactataaaaattgaaagccccgggtaccttaca
 A  F  R  N  D  K  C  G  D  T  I  K  I  E  S  P  G  Y  L  T
tctcctggttatcctcattcttatcacccaagtgaaaaatgcgaatggctgattcaggct
 S  P  G  Y  P  H  S  Y  H  P  S  E  K  C  E  W  L  I  Q  A
ccggacccataccagagaattatgatcaacttcaaccctcacttcgatttggaggacaga
 P  D  P  Y  Q  R  I  M  I  N  F  N  P  H  F  D  L  E  D  R
gactgcaagtatgactacgtggaagtcttcgatggagaaaatgaaaatggacattttagg
 D  C  K  Y  D  Y  V  E  V  F  D  G  E  N  E  N  G  H  F  R
ggaaagttctgtggaaagatagcccctcctcctgttgtgtcttcagggccatttcttttt
 G  K  F  C  G  K  I  A  P  P  P  V  V  S  S  G  P  F  L  F
atcaaatttgtctctgactacgaaacacatggtgcaggattttccatacgttatgaactt
 I  K  F  V  S  D  Y  E  T  H  G  A  G  F  S  I  R  Y  E  L
ttcaagagaggtcctgaatgttcccagaactacacaacacctagtggagtgataaagtcc
 F  K  R  G  P  E  C  S  Q  N  Y  T  T  P  S  G  V  I  K  S
cccggattccctgaaaaatatcccaacagccttgaatgcacttatattgtctttgcgcca
 P  G  F  P  E  K  Y  P  N  S  L  E  C  T  Y  I  V  F  A  P
aagatgtcagagattatcctggaatttgaaagctttgacctggagcctgactcaaatcct
 K  M  S  E  I  I  L  E  F  E  S  F  D  L  E  P  D  S  N  P
ccaggggggatgttctgtcgctacgaccggctagaaatctgggatggattccctgatgtt
 P  G  G  M  F  C  R  Y  D  R  L  E  I  W  D  G  F  P  D  V
ggccctcacattgggcgttactgtggacagaaaacaccaggtcgaatccgatcctcatcg
 G  P  H  I  G  R  Y  C  G  Q  K  T  P  G  R  I  R  S  S  S
ggcattctctccatggttttttacaccgacagcgcgatagcaaaagaaggtttctcagca
 G  I  L  S  M  V  F  Y  T  D  S  A  I  A  K  E  G  F  S  A
aactacagtgtcttgcagagcagtgtctcagaagatttcaaatgtatggaagctctgggc
 N  Y  S  V  L  Q  S  S  V  S  E  D  F  K  C  M  E  A  L  G
atggaatcaggagaaattcattctgaccagatcacagcttcttcccaggctagcaccaac
 M  E  S  G  E  I  H  S  D  Q  I  T  A  S  S  Q  A  S  T  N
tggtctgcagagcgctcccgcctgaactaccctgagaatgggtggactcccggagaggat
 W  S  A  E  R  S  R  L  N  Y  P  E  N  G  W  T  P  G  E  D
tcctaccgagagtggatacaggtagacttgggccttctgcgctttgtcacggctgtcggg
 S  Y  R  E  W  I  Q  V  D  L  G  L  L  R  F  V  T  A  V  G
acacagggcgccatttcaaaagaaaccaagaagaaatattatgtcaagacttacaagatc
 T  Q  G  A  I  S  K  E  T  K  K  K  Y  Y  V  K  T  Y  K  I
gacgttagctccaacggggaagactggatcaccataaaagaaggaaacaaacctgttctc
 D  V  S  S  N  G  E  D  W  I  T  I  K  E  G  N  K  P  V  L
tttcagggaaacaccaaccctacagatgttgtggttgcagtattccccaaaccactgata
 F  Q  G  N  T  N  P  T  D  V  V  V  A  V  F  P  K  P  L  I
actcgatttgtccgaatcaagcctgcaacttgggaaactggcatatctatgagatttgaa
 T  R  F  V  R  I  K  P  A  T  W  E  T  G  I  S  M  R  F  E
gtatatggttgcagatctgacaaaactcacacatgcccaccgtgcccagcacctgaactc
 V  Y  G  C  R  S  D  K  T  H  T  C  P  P  C  P  A  P  E  L
ctggggggaccgtcagtcttcctcttccccccaaaacccaaggacaccctcatgatctcc
 L  G  G  P  S  V  F  L  F  P  P  K  P  K  D  T  L  M  I  S
cggacccctgaggtcacatgcgtggtggtggacgtgagccacgaagaccctgaggtcaag
 R  T  P  E  V  T  C  V  V  V  D  V  S  H  E  D  P  E  V  K
ttcaactggtacgtggacggcgtggaggtgcataatgccaagacaaagccgcgggaggag
 F  N  W  Y  V  D  G  V  E  V  H  N  A  K  T  K  P  R  E  E
cagtacaacagcacgtaccgtgtggtcagcgtcctcaccgtcctgcaccaggactggctg
 Q  Y  N  S  T  Y  R  V  V  S  V  L  T  V  L  H  Q  D  W  L
```

FIG. 20W

```
aatggcaaggagtacaagtgcaaggtctccaacaaagccctcccagcccccatcgagaaa
 N  G  K  E  Y  K  C  K  V  S  N  K  A  L  P  A  P  I  E  K
accatctccaaagccaaagggcagccccgagaaccacaggtgtacaccctgcccccatcc
 T  I  S  K  A  K  G  Q  P  R  E  P  Q  V  Y  T  L  P  P  S
cgggaggagatgaccaagaaccaggtcagcctgacctgcctggtcaaaggcttctatccc
 R  E  E  M  T  K  N  Q  V  S  L  T  C  L  V  K  G  F  Y  P
agcgacatcgccgtggagtgggagagcaatgggcagccggagaacaactacaagaccacg
 S  D  I  A  V  E  W  E  S  N  G  Q  P  E  N  N  Y  K  T  T
cctcccgtgctggactccgacggctccttcttcctctacagcaagctcaccgtggacaag
 P  P  V  L  D  S  D  G  S  F  F  L  Y  S  K  L  T  V  D  K
agcaggtggcagcaggggaacgtcttctcatgctccgtgatgcacgaggctctgcacaac
 S  R  W  Q  Q  G  N  V  F  S  C  S  V  M  H  E  A  L  H  N
cactacacgcagaagagcctctccctgtctccgggtaaa
 H  Y  T  Q  K  S  L  S  L  S  P  G  K
```

FIG. 20X

```
atggagaggggggctgccgttgctgtgcgccacgctcgcccttgccctcgccctggcgggc
 M  E  R  G  L  P  L  L  C  A  T  L  A  L  A  L  A  L  A  G
gctttccgcagcgacaaatgtggcgggaccataaaaatcgaaaacccagggtacctcaca
 A  F  R  S  D  K  C  G  G  T  I  K  I  E  N  P  G  Y  L  T
tctcccggttaccctcattcttaccatccaagtgagaagtgtgaatggctaatccaagct
 S  P  G  Y  P  H  S  Y  H  P  S  E  K  C  E  W  L  I  Q  A
ccggaaccctaccagagaatcatgatcaacttcaacccacatttcgatttggaggacaga
 P  E  P  Y  Q  R  I  M  I  N  F  N  P  H  F  D  L  E  D  R
gactgcaagtatgactacgtggaagtaatcgatggggagaatgaaggcggccgcctgtgg
 D  C  K  Y  D  Y  V  E  V  I  D  G  E  N  E  G  G  R  L  W
gggaagttctgtgggaagattgcaccttctcctgtggtgtcttcagggccctttctcttc
 G  K  F  C  G  K  I  A  P  S  P  V  V  S  S  G  P  F  L  F
atcaaatttgtctctgactatgagacacatggggcagggttttccatccgctatgaaatc
 I  K  F  V  S  D  Y  E  T  H  G  A  G  F  S  I  R  Y  E  I
ttcaagagagggcccgaatgttctcagaactatacagcacctactggagtgataaagtcc
 F  K  R  G  P  E  C  S  Q  N  Y  T  A  P  T  G  V  I  K  S
cctgggttccctgaaaaataccccaacagcttggagtgcacctacatcatctttgcacca
 P  G  F  P  E  K  Y  P  N  S  L  E  C  T  Y  I  I  F  A  P
aagatgtctgagataatcctggagtttgaaagttttgacctggagcaagactcgaatcct
 K  M  S  E  I  I  L  E  F  E  S  F  D  L  E  Q  D  S  N  P
cccggaggaatgttctgtcgctatgaccggctggagatctgggatggattccctgaagtt
 P  G  G  M  F  C  R  Y  D  R  L  E  I  W  D  G  F  P  E  V
ggccctcacattgggcgttattgtgggcagaaaactcctggccggatccgctcctcttca
 G  P  H  I  G  R  Y  C  G  Q  K  T  P  G  R  I  R  S  S  S
ggcgttctatccatggtcttttacactgacagcgcaatagcaaaagaaggtttctcagcc
 G  V  L  S  M  V  F  Y  T  D  S  A  I  A  K  E  G  F  S  A
aactacagtgtgctacagagcagcatctctgaagattttaagtgtatggaggctctgggc
 N  Y  S  V  L  Q  S  S  I  S  E  D  F  K  C  M  E  A  L  G
atggaatctggagagatccattctgatcagatcactgcatcttcacagtatggtaccaac
 M  E  S  G  E  I  H  S  D  Q  I  T  A  S  S  Q  Y  G  T  N
tggtctgtagagcgctcccgcctgaactaccctgaaaatgggtggactccaggagaagac
 W  S  V  E  R  S  R  L  N  Y  P  E  N  G  W  T  P  G  E  D
tcctacaaggagtggatccaggtggacttgggcctcctgcgattcgttactgctgtaggg
 S  Y  K  E  W  I  Q  V  D  L  G  L  L  R  F  V  T  A  V  G
acacagggtgccatttccaaggaaaccaagaagaaatattatgtcaagacttacagagta
 T  Q  G  A  I  S  K  E  T  K  K  K  Y  Y  V  K  T  Y  R  V
gacatcagctccaacggagaggactggatctccctgaaagagggaaataaagccattatc
 D  I  S  S  N  G  E  D  W  I  S  L  K  E  G  N  K  A  I  I
tttcagggaaacaccaaccccacagatgttgtcttaggagttttctccaaaccactgata
 F  Q  G  N  T  N  P  T  D  V  V  L  G  V  F  S  K  P  L  I
actcgatttgtccgaatcaaacctgtatcctgggaaactggtatatctatgagatttgaa
 T  R  F  V  R  I  K  P  V  S  W  E  T  G  I  S  M  R  F  E
gtttatggctgcaagataacagattatccttgctctggaatgttgggcatggtgtctgga
 V  Y  G  C  K  I  T  D  Y  P  C  S  G  M  L  G  M  V  S  G
cttatttcagactcccagattacagcatccaatcaagccgacaggaattggatgccagaa
 L  I  S  D  S  Q  I  T  A  S  N  Q  A  D  R  N  W  M  P  E
aacatccgtctggtgaccagtcgtaccggctgggcactgccaccctcaccccacccctac
 N  I  R  L  V  T  S  R  T  G  W  A  L  P  P  S  P  H  P  Y
accaatgaatggctccaagtggacctgggagatgagaagatagtaagaggtgtcatcatt
 T  N  E  W  L  Q  V  D  L  G  D  E  K  I  V  R  G  V  I  I
cagggtgggaagcaccgagaaaacaaggtgttcatgaggaagttcaagatcgcctatagt
 Q  G  G  K  H  R  E  N  K  V  F  M  R  K  F  K  I  A  Y  S
aacaatggctctgactggaaaactatcatggatgacagcaagcgcaaggctaagtcgttc
 N  N  G  S  D  W  K  T  I  M  D  D  S  K  R  K  A  K  S  F
gaaggcaacaacaactatgacacacctgagcttcggacgttttcacctctctccacaagg
 E  G  N  N  N  Y  D  T  P  E  L  R  T  F  S  P  L  S  T  R
```

FIG. 20Y ttcatcaggatctaccctgagagagccacacacagtgggcttgggctgaggatggagcta
F I R I Y P E R A T H S G L G L R M E L
ctgggctgtgaagtggaagcacctacagctggacccaccacacccaatgggaacccagtg
L G C E V E A P T A G P T T P N G N P V
gatgagtgtgacgacgaccaggccaactgccacagtggcacaggtgatgacttccagctc
D E C D D D Q A N C H S G T G D D F Q L
acaggaggcaccactgtcctggccacagagaagcccaccattatagacagcaccatccaa
T G G T T V L A T E K P T I I D S T I Q
tcagagttcccgacatacggttttaactgcgagtttggctggggctctcacaagacattc
S E F P T Y G F N C E F G W G S H K T F
tgccactgggagcatgacagccatgcacagctcaggtggagtgtgctgaccagcaagaca
C H W E H D S H A Q L R W S V L T S K T
gggccgattcaggaccatacaggagatggcaacttcatctattcccaagctgatgaaaat
G P I Q D H T G D G N F I Y S Q A D E N
cagaaaggcaaagtagcccgcctggtgagccctgtggtctattcccagagctctgcccac
Q K G K V A R L V S P V V Y S Q S S A H
tgtatgaccttctggtatcacatgtccggctctcatgtgggtacactgagggtcaaacta
C M T F W Y H M S G S H V G T L R V K L
cgctaccagaagccagaggaatatgatcaactggtctggatggtggttgggcaccaagga
R Y Q K P E E Y D Q L V W M V V G H Q G
gaccactggaaagaaggacgtgtcttgctgcacaaatctctgaaactatatcaggttatt
D H W K E G R V L L H K S L K L Y Q V I
tttgaaggtgaaatcggaaaaggaaaccttggtggaattgctgtggatgatatcagtatt
F E G E I G K G N L G G I A V D D I S I
aacaaccatatttctcaggaagactgtgcaaaaccaacagacctagataaaaagaacaca
N N H I S Q E D C A K P T D L D K K N T
gaaattaaaattgatgaaacagggagcactccaggatatgaaggagaaggggaaggtgac
E I K I D E T G S T P G Y E G E G E G D
aagaacatctccaggaagccaggcaatgtgcttaagaccctggatcccgtctcgagcacc
K N I S R K P G N V L K T L D P V S S T
atggttagatctggttgtaagccttgcatatgtacagtcccagaagtatcatctgtcttc
M V R S G C K P C I C T V P E V S S V F
atcttccccccaaagcccaaggatgtgctcaccattactctgactcctaaggtcacgtgt
I F P P K P K D V L T I T L T P K V T C
gttgtggtagacatcagcaaggatgatcccgaggtccagttcagctggtttgtagatgat
V V V D I S K D D P E V Q F S W F V D D
gtggaggtgcacacagctcagacgcaaccccgggaggagcagttcaacagcactttccgc
V E V H T A Q T Q P R E E Q F N S T F R
tcagtcagtgaacttcccatcatgcaccaggactggctcaatggcaaggagttcaaatgc
S V S E L P I M H Q D W L N G K E F K C
agggtcaacagtgcagctttccctgcccccatcgagaaaaccatctccaaaaccaaaggc
R V N S A A F P A P I E K T I S K T K G
agaccgaaggctccacaggtgtacaccattccacctcccaaggagcagatggccaaggat
R P K A P Q V Y T I P P P K E Q M A K D
aaagtcagtctgacctgcatgataacagacttcttccctgaagacattactgtggagtgg
K V S L T C M I T D F F P E D I T V E W
cagtggaatgggcagccagcggagaactacaagaacactcagcccatcatggacacagat
Q W N G Q P A E N Y K N T Q P I M D T D
ggctcttacttcgtctacagcaagctcaatgtgcagaagagcaactgggaggcaggaaat
G S Y F V Y S K L N V Q K S N W E A G N
actttcacctgctctgtgttacatgagggcctgcacaaccaccatactgagaagagcctc
T F T C S V L H E G L H N H H T E K S L
tcccactctcctggtaaatga
S H S P G K -

FIG. 20Z atggagagggggctgccgttgctgtgcgccacgctcgcccttgccctcgccctggcgggc
M E R G L P L L C A T L A L A L A L A G
gctttccgcagcgacaaatgtggcgggaccataaaaatcgaaaacccagggtacctcaca
A F R S D K C G G T I K I E N P G Y L T
tctcccggttacccccattcttaccatcccagtgagaagtgtgaatggctaatccaagct
S P G Y P H S Y H P S E K C E W L I Q A
ccggaaccctaccagagaatcatgatcaacttcaaccccacatttgatttggaggacaga
P E P Y Q R I M I N F N P H F D L E D R
gactgcaagtatgactacgtggaagtaatcgatggggagaatgaaggcggccgcctgtgg
D C K Y D Y V E V I D G E N E G G R L W
gggaagttctgtgggaagattgcaccttctcctgtggtgtcttcagggccctttctcttc
G K F C G K I A P S P V V S S G P F L F
atcaaatttgtctctgactatgagacacatggggcagggttttccatccgctatgaaatc
I K F V S D Y E T H G A G F S I R Y E I
ttcaagagagggcccgaatgttctcagaactatacagcacctactggagtgataaagtcc
F K R G P E C S Q N Y T A P T G V I K S
cctgggttccctgaaaaataccccaacagcttggagtgcacctacatcatctttgcacca
P G F P E K Y P N S L E C T Y I I F A P
aagatgtctgagataatcctggagtttgaaagttttgacctggagcaagactcgaatcct
K M S E I I L E F E S F D L E Q D S N P
cccggaggaatgttctgtcgctatgaccggctggagatctgggatggattccctgaagtt
P G G M F C R Y D R L E I W D G F P E V
ggccctcacattgggcgttattgtgggcagaaaactcctggccggatccgatcctcttca
G P H I G R Y C G Q K T P G R I R S S S
ggcgttctatccatggtcttttacactgacagcgcaatagcaaaagaaggtttctcagcc
G V L S M V F Y T D S A I A K E G F S A
aactacagtgtgctacagagcagcatctctgaagattttaagtgtatggaggctctgggc
N Y S V L Q S S I S E D F K C M E A L G
atggaatctggagagatccattctgatcagatcactgcatcttcacagtatggtaccaac
M E S G E I H S D Q I T A S S Q Y G T N
tggtctgtagagcgctcccgcctgaactaccctgaaaatgggtggactccaggagaagac
W S V E R S R L N Y P E N G W T P G E D
tcctacaaggagtggatccaggtggacttgggccttctgcgattcgttactgctgtaggg
S Y K E W I Q V D L G L L R F V T A V G
acacagggtgccatttccaaggaaaccaagaagaaatattatgtcaagacttacagagta
T Q G A I S K E T K K K Y Y V K T Y R V
gacatcagctccaacggagaggactggatctccctgaaagagggaaataaagccattatc
D I S S N G E D W I S L K E G N K A I I
tttcagggaaacaccaaccccacagatgttgtcttaggagttttctccaaaccactgata
F Q G N T N P T D V V L G V F S K P L I
actcgatttgtccgaatcaaacctgtatcctgggaaactggtatatctatgagatttgaa
T R F V R I K P V S W E T G I S M R F E
gtttatggctgcaagataacagattatccttgctctggaatgttgggcatggtgtctgga
V Y G C K I T D Y P C S G M L G M V S G
cttatttcagactcccagattacagcatccaatcaagccgacaggaattggatgccagaa
L I S D S Q I T A S N Q A D R N W M P E
aacatccgtctggtgaccagtcgtaccggctgggcactgccaccctcaccccacccatac
N I R L V T S R T G W A L P P S P H P Y
accaatgaatggctccaagtggacctgggagatgagaagatagtaagaggtgtcatcatt
T N E W L Q V D L G D E K I V R G V I I
cagggtgggaagcaccgagaaaacaaggtgttcatgaggaagttcaagatcgcctatagt
Q G G K H R E N K V F M R K F K I A Y S
aacaatggctctgactggaaaactatcatggatgacagcaagcgcaaggctaagtcgttc
N N G S D W K T I M D D S K R K A K S F
gaaggcaacaacaactatgacacacctgagcttcggacgttttcacctctctccacaagg
E G N N N Y D T P E L R T F S P L S T R

FIG. 20AA

```
ttcatcaggatctaccctgagagagccacacacagtgggcttgggctgaggatggagcta
 F  I  R  I  Y  P  E  R  A  T  H  S  G  L  G  L  R  M  E  L
ctgggctgtgtctcgagcaccatggttagatctggttgtaagccttgcatatgtacagtc
 L  G  C  V  S  S  T  M  V  R  S  G  C  K  P  C  I  C  T  V
ccagaagtatcatctgtcttcatcttccccccaaagcccaaggatgtgctcaccattact
 P  E  V  S  S  V  F  I  F  P  P  K  P  K  D  V  L  T  I  T
ctgactcctaaggtcacgtgtgttgtggtagacatcagcaaggatgatcccgaggtccag
 L  T  P  K  V  T  C  V  V  V  D  I  S  K  D  D  P  E  V  Q
ttcagctggtttgtagatgatgtggaggtgcacacagctcagacgcaaccccgggaggag
 F  S  W  F  V  D  D  V  E  V  H  T  A  Q  T  Q  P  R  E  E
cagttcaacagcactttccgctcagtcagtgaacttcccatcatgcaccaggactggctc
 Q  F  N  S  T  F  R  S  V  S  E  L  P  I  M  H  Q  D  W  L
aatggcaaggagttcaaatgcagggtcaacagtgcagctttccctgcccccatcgagaaa
 N  G  K  E  F  K  C  R  V  N  S  A  A  F  P  A  P  I  E  K
accatctccaaaaccaaaggcagaccgaaggctccacaggtgtacaccattccacctccc
 T  I  S  K  T  K  G  R  P  K  A  P  Q  V  Y  T  I  P  P  P
aaggagcagatggccaaggataaagtcagtctgacctgcatgataacagacttcttccct
 K  E  Q  M  A  K  D  K  V  S  L  T  C  M  I  T  D  F  F  P
gaagacattactgtggagtggcagtggaatgggcagccagcggagaactacaagaacact
 E  D  I  T  V  E  W  Q  W  N  G  Q  P  A  E  N  Y  K  N  T
cagcccatcatggacacagatggctcttacttcgtctacagcaagctcaatgtgcagaag
 Q  P  I  M  D  T  D  G  S  Y  F  V  Y  S  K  L  N  V  Q  K
agcaactgggaggcaggaaatactttcacctgctctgtgttacatgagggcctgcacaac
 S  N  W  E  A  G  N  T  F  T  C  S  V  L  H  E  G  L  H  N
caccatactgagaagagcctctcccactctcctggtaaatga
 H  H  T  E  K  S  L  S  H  S  P  G  K  -
```

FIG. 20BB atggagagggggctgccgttgctgtgcgccacgctcgcccttgccctcgccctggcgggc
M E R G L P L L C A T L A L A L A L A G
gctttccgcagcgacaaatgtggcgggaccataaaaatcgaaaacccagggtacctcaca
A F R S D K C G G T I K I E N P G Y L T
tctcccggttaccctcattcttaccatccaagtgagaagtgtgaatggctaatccaagct
S P G Y P H S Y H P S E K C E W L I Q A
ccggaaccctaccagagaatcatgatcaacttcaacccacatttcgatttggaggacaga
P E P Y Q R I M I N F N P H F D L E D R
gactgcaagtatgactacgtggaagtaatcgatggggagaatgaaggcggccgcctgtgg
D C K Y D Y V E V I D G E N E G G R L W
gggaagttctgtgggaagattgcaccttctcctgtggtgtcttcagggccctttctcttc
G K F C G K I A P S P V V S S G P F L F
atcaaatttgtctctgactatgagacacatggggcagggttttccatccgctatgaaatc
I K F V S D Y E T H G A G F S I R Y E I
ttcaagagagggcccgaatgttctcagaactatacagcacctactggagtgataaagtcc
F K R G P E C S Q N Y T A P T G V I K S
cctgggttccctgaaaaatacccaaacagcttggagtgcacctacatcatctttgcacca
P G F P E K Y P N S L E C T Y I I F A P
aagatgtctgagataatcctggagtttgaaagttttgacctggagcaagactcgaatcct
K M S E I I L E F E S F D L E Q D S N P
cccggaggaatgttctgtcgctatgaccggctggagatctgggatggattccctgaagtt
P G G M F C R Y D R L E I W D G F P E V
ggccctcacattgggcgttattgtgggcagaaaactcctggccggatccgctcctcttca
G P H I G R Y C G Q K T P G R I R S S S
ggcgttctatccatggtcttttacactgacagcgcaatagcaaaagaaggtttctcagcc
G V L S M V F Y T D S A I A K E G F S A
aactacagtgtgctacagagcagcatctctgaagattttaagtgtatggaggctctgggc
N Y S V L Q S S I S E D F K C M E A L G
atggaatctggagagatccattctgatcagatcactgcatcttcacagtatggtaccaac
M E S G E I H S D Q I T A S S Q Y G T N
tggtctgtagagcgctcccgcctgaactaccctgaaaatgggtggactccaggagaagac
W S V E R S R L N Y P E N G W T P G E D
tcctacaaggagtggatccaggtggacttgggcctcctgcgattcgttactgctgtaggg
S Y K E W I Q V D L G L L R F V T A V G
acacagggtgccatttccaaggaaaccaagaagaaatattatgtcaagacttacagagta
T Q G A I S K E T K K K Y Y V K T Y R V
gacatcagctccaacggagaggactggatctccctgaaagagggaaataaagccattatc
D I S S N G E D W I S L K E G N K A I I
tttcagggaaacaccaaccccacagatgttgtcttaggagttttctccaaaccactgata
F Q G N T N P T D V V L G V F S K P L I
actcgatttgtccgaatcaaacctgtatcctgggaaactggtatatctatgagatttgaa
T R F V R I K P V S W E T G I S M R F E
gtttatggctgcgtctcgagcaccatggttagatctggttgtaagccttgcatatgtaca
V Y G C V S S T M V R S G C K P C I C T
gtcccagaagtatcatctgtcttcatcttccccccaaagcccaaggatgtgctcaccatt
V P E V S S V F I F P P K P K D V L T I
actctgactcctaaggtcacgtgtgttgtggtagacatcagcaaggatgatcccgaggtc
T L T P K V T C V V V D I S K D D P E V
cagttcagctggtttgtagatgatgtggaggtgcacacagctcagacgcaaccccgggag
Q F S W F V D D V E V H T A Q T Q P R E
gagcagttcaacagcactttccgctcagtcagtgaacttcccatcatgcaccaggactgg
E Q F N S T F R S V S E L P I M H Q D W
ctcaatggcaaggagttcaaatgcagggtcaacagtgcagctttccctgcccccatcgag
L N G K E F K C R V N S A A F P A P I E

FIG. 20CC

```
aaaaccatctccaaaaccaaaggcagaccgaaggctccacaggtgtacaccattccacct
 K  T  I  S  K  T  K  G  R  P  K  A  P  Q  V  Y  T  I  P  P
cccaaggagcagatggccaaggataaagtcagtctgacctgcatgataacagacttcttc
 P  K  E  Q  M  A  K  D  K  V  S  L  T  C  M  I  T  D  F  F
cctgaagacattactgtggagtggcagtggaatgggcagccagcggagaactacaagaac
 P  E  D  I  T  V  E  W  Q  W  N  G  Q  P  A  E  N  Y  K  N
actcagcccatcatggacacagatggctcttacttcgtctacagcaagctcaatgtgcag
 T  Q  P  I  M  D  T  D  G  S  Y  F  V  Y  S  K  L  N  V  Q
aagagcaactgggaggcaggaaatactttcacctgctctgtgttacatgagggcctgcac
 K  S  N  W  E  A  G  N  T  F  T  C  S  V  L  H  E  G  L  H
aaccaccatactgagaagagcctctcccactctcctggtaaatga
 N  H  H  T  E  K  S  L  S  H  S  P  G  K  -
```

FIG. 21

```
         10         20         30         40         50         60
MGWLIRIVCL FWGVLLTARA NYQNGKNNVP RLKLSYKEML ESNNVITFNG LANSSSYHTF
         70         80         90        100        110        120
LLDEERSKLY VGAKDHIFSF DLVNIKDFQK IVWPVSYTRR DECKWAGKDI LKECANFIKV
        130        140        150        160        170        180
LKAYNQTHLY ACGTGAFHPI CTYIEIGHHP EDNIFKLENS HFENGRGKSP YDPKLLTASL
        190        200        210        220        230        240
LIDGELYSGT AADFMGRDFA IFRTLGHHHP IRTEQHDSRW LNDPKFISAH LISESDNPED
        250        260        270        280        290        300
DKVYFFFREN AIDGEHSGKA THARIGQICK NDFGGHRSLV NKWTTFLKAR LICSVPGPNG
        310        320        330        340        350        360
IDTHFDELQD VFLMNFKDPK NPVVYGVFTT SSNIFKGSAV CMYSMSDVRR VFLGPYAHRD
        370        380        390        400        410        420
GPNYQWVPYQ GRVPYPRPGT CPSKTFGGFD STKDLPDDVI TFARSHPAMY NPVFPMNNRP
        430        440        450        460        470        480
IVIKTDVNYQ FTQIVVDRVD AEDGQYDVMF IGTDVGTVLK VVSIPKETWY DLEEVLLEEM
        490        500        510        520        530        540
TVFREPTAIS AMELSTKQQQ LYIGSTAGVA QLPLHRCDIY GKACAECCLA RDPYCAWDGS
        550        560        570        580        590        600
ACSRYFPTAK RRTRRQDIRN GDPLTHCSDL HHDNHHGHSP EERIIYGVEN SSTFLECSPK
        610        620        630        640        650        660
SQRALVYWQF QRRNEERKEE IRVDDHIIRT DQGLLLRSLQ QKDSGNYLCH AVEHGFIQTL
        670        680        690        700        710        720
LKVTLEVIDT EHLEELLHKD DDGDGSKTKE MSNSMTPSQK VWYRDFMQLI NHPNLNTMDE
        730        740        750        760        770
FCEQVWKRDR KQRRQRPGHT PGNSNKWKHL QENKKGRNRR THEFERAPRS V
```

FIG. 22

```
1   merglpllca vlalvlapag afrndkcgdt ikiespgylt spgypHsyhp sekcewliqa   a1
 61 pdpyqrimin fnphfdledr dckydyvevf dgenenghfr gkfcgkiapp pvvssgpflf
121 ikfvsdyeth gagfsiryei fkrgpecsqn yttpsgviks pgfpekypns lectyivfap
181 kmseiilefe sfdlepdsnp pggmfcrydr leiwdgfpdv gphigrycgq ktpgrirsss   a2
241 gilsmvfytd saiakegfsa nysvlqssvs edfkcmealg mesgeihsdq itassqystn
301 wsaersrlny pengwtpged syrewiqvdl gllrfvtavg tqgaisketk kkyyvktyki   b1
361 dvssngedwi tikegnkpvl fqgntnptdv vvavfpkpli trfvrikpat wetgismrfe
421 vygckitdyp csgmlgmvsg lisdsqitss nqgdrnwmpe nirlvtsrsg walppaphsy   b2
481 inewlqidlg eekivrgiii qggkhrenkv fmrkfkigys nngsdwkmim ddskrkaksf
541 egnnnydtpe lrtfpalstr firiyperat hgglglrmel lgcevegqtt vlatekptvi   c
601 dstiqsgik
```

FIG. 26A

```
             ┌──── Signal ────┬── a1
                     10         20         30         40         50         60         70
Rat          MERGLPLLCA TLALALALAG AFRSDKCGGT IKIENPGYLT SPGYPHSYHP SEKCEWLIQA PEPYQRIMIN
Human        MERGLPLLCA VLALVLAPAG AFRNDKCGDT IKIESPGYLT SPGYPHSYHP SEKCEWLIQA PDPYQRIMIN
Mouse        MERGLPLLCA TLALALALAG AFRSDKCGGT IKIENPGYLT SPGYPHSYHP SEKCEWLIQA PEPYQRIMIN
Consensus    MERGLPLLCA .LAL.LA.AG AFR.DKCG.T IKIE.PGYLT SPGYPHSYHP SEKCEWLIQA P.PYQRIMIN

                     80         90        100        110        120        130        140
Rat          FNPHFDLEDR DCKYDYVEVI DGENEGGRLW GKFCGKIAPS PVVSSGPFLF IKFVSDYETH GAGFSIRYEI
Human        FNPHFDLEDR DCKYDYVEVF DGENENGHFR GKFCGKIAPP PVVSSGPFLF IKFVSDYETH GAGFSIRYEI
Mouse        FNPHFDLEDR DCKYDYVEVI DGENEGGRLW GKFCGKIAPS PVVSSGPFLF IKFVSDYETH GAGFSIRYEI
Consensus    FNPHFDLEDR DCKYDYVEV. DGENE.G... GKFCGKIAP. PVVSSGPFLF IKFVSDYETH GAGFSIRYEI

                ─┬─ a2
                 └150       160        170        180        190        200        210
Rat          FKRGPECSQN YTAPTGVIKS PGFPEKYPNS LECTYIIFAP KMSEIILEFE SFDLEQDSNP PGGVFCRYDR
Human        FKRGPECSQN YTTPSGVIKS PGFPEKYPNS LECTYIVFAP KMSEIILEFE SFDLEPDSNP PGGMFCRYDR
Mouse        FKRGPECSQN YTAPTGVIKS PGFPEKYPNS LECTYIIFAP KMSEIILEFE SFDLEQDSNP PGGMFCRYDR
Consensus    FKRGPECSQN YT.P.GVIKS PGFPEKYPNS LECTYI.FAP KMSEIILEFE SFDLE.DSNP PGG.FCRYDR

                                                                                  ─┬─ b1
                    220        230        240        250        260        270        280
Rat          LEIWDGFPEV GPHIGRYCGQ KTPGRIRSSS GILSMVFYTD SAIAKEGFSA NYSVLQSSIS EDFKCMEALG
Human        LEIWDGFPDV GPHIGRYCGQ KTPGRIRSSS GILSMVFYTD SAIAKEGFSA NYSVLQSSVS EDFKCMEALG
Mouse        LEIWDGFPEV GPHIGRYCGQ KTPGRIRSSS GVLSMVFYTD SAIAKEGFSA NYSVLQSSIS EDFKCMEALG
Consensus    LEIWDGFP.V GPHIGRYCGQ KTPGRIRSSS G.LSMVFYTD SAIAKEGFSA NYSVLQSS.S EDFKCMEALG

                    290        300        310        320        330        340        350
Rat          MESGEIHSDQ ITASSQYGTN WSVERSRLNY PENGWTPGED SYREWIQVDL GLLRFVTAVG TQGAISKETK
Human        MESGEIHSDQ ITASSQYSTN WSAERSRLNY PENGWTPGED SYREWIQVDL GLLRFVTAVG TQGAISKETK
Mouse        MESGEIHSDQ ITASSQYGTN WSVERSRLNY PENGWTPGED SYREWIQVDL GLLRFVTAVG TQGAISKETK
Consensus    MESGEIHSDQ ITASSQY.TN WS.ERSRLNY PENGWTPGED SY.EWIQVDL GLLRFVTAVG TQGAISKETK

                    360        370        380        390        400        410        420
Rat          KKYYVKTYRV DISSNGEDWI TLKEGNKAII FQGNTNPTDV VFGVFPKPLI TRFVRIKPAS WETGISMRFE
Human        KKYYVKTYKI DVSSNGEDWI TIKEGNKPVL FQGNTNPTDV VVAVFPKPLI TRFVRIKPAT WETGISMRFE
Mouse        KKYYVKTYRV DISSNGEDWI SLKEGNKAII FQGNTNPTDV VLGVFPKPLI TRFVRIKPVS WETGISMRFE
Consensus    KKYYVKTY.. D.SSNGEDWI ..KEGNK... FQGNTNPTDV V..VFPKPLI TRFVRIKP.. WETGISMRFE

                ─┬─ b2
                    430        440        450        460        470        480        490
Rat          VYGCKITDYP CSGMLGMVSG LISDSQITAS NQGDRNWMPE NIRLVTSRTG WALPPSPHPY INEWLQVDLG
Human        VYGCKITDYP CSGMLGMVSG LISDSQITSS NQGDRNWMPE NIRLVTSRSG WALPPAPHSY INEWLQIDLG
Mouse        VYGCKITDYP CSGMLGMVSG LISDSQITAS NQADRNWMPE NIRLVTSRTG WALPPSPHPY INEWLQVDLG
Consensus    VYGCKITDYP CSGMLGMVSG LISDSQIT.S NQ.DRNWMPE NIRLVTSR.G WALPP.PH.Y INEWLQ.DLG

                    500        510        520        530        540        550        560
Rat          EEKIVRGVII QGGKHRENKV FMRKFKIAYS NNGSDWKMIM DDSKRKAKSF EGNNNYDTPE LRAFTPLSTR
Human        EEKIVRGIII QGGKHRENKV FMRKFKIGYS NNGSDWKMIM DDSKRKAKSF EGNNNYDTPE LRTFPALSTR
Mouse        EEKIVRGVII QGGKHRENKV FMRKFKIAYS NNGSDWKTIM DDSKRKAKSF EGNNNYDTPE LRTFSPLSTR
Consensus    EEKIVRG.II QGGKHRENKV FMRKFKI.YS NNGSDWK.IM DDSKRKAKSF EGNNNYDTPE LR.F..LSTR

                                     ─┬─ C
                    570        580        590        600        610        620        630
Rat          FIRIYPERAT HSGLGLRMEL LGCEVEVPTA GPTTPNGNPV DECDDDQANC HSGTGDDFQL TGGTTVLATE
Human        FIRIYPERAT HGGLGLRMEL LGCEVEAPTA GPTTPNGNLV DECDDDQANC HSGTGDDFQL TGGTTVLATE
Mouse        FIRIYPERAT HSGLGLRMEL LGCEVEAPTA GPTTPNGNPV DECDDDQANC HSGTGDDFQL TGGTTVLATE
Consensus    FIRIYPERAT H.GLGLRMEL LGCEVE.PTA GPTTPNGN.V DECDDDQANC HSGTGDDFQL TGGTTVLATE

                    640        650        660        670        680        690        700
Rat          KPTIIDSTIQ SEFPTYGFNC EFGWGSHKTF CHWEHDSHAQ LRWSVLTSKT GPIQDHTGDG NFIYSQADEN
Human        KPTVIDSTIQ SEFPTYGFNC EFGWGSHKTF CHWEHDNHVQ LKWSVLTSKT GPIQDHTGDG NFIYSQADEN
Mouse        KPTIIDSTIQ SEFPTYGFNC EFGWGSHKTF CHWEHDSHAQ LRWSVLTSKT GPIQDHTGDG NFIYSQADEN
Consensus    KPT.IDSTIQ SEFPTYGFNC EFGWGSHKTF CHWEHD.H.Q L.W.VLTSKT GPIQDHTGDG NFIYSQADEN
```

FIG. 27A

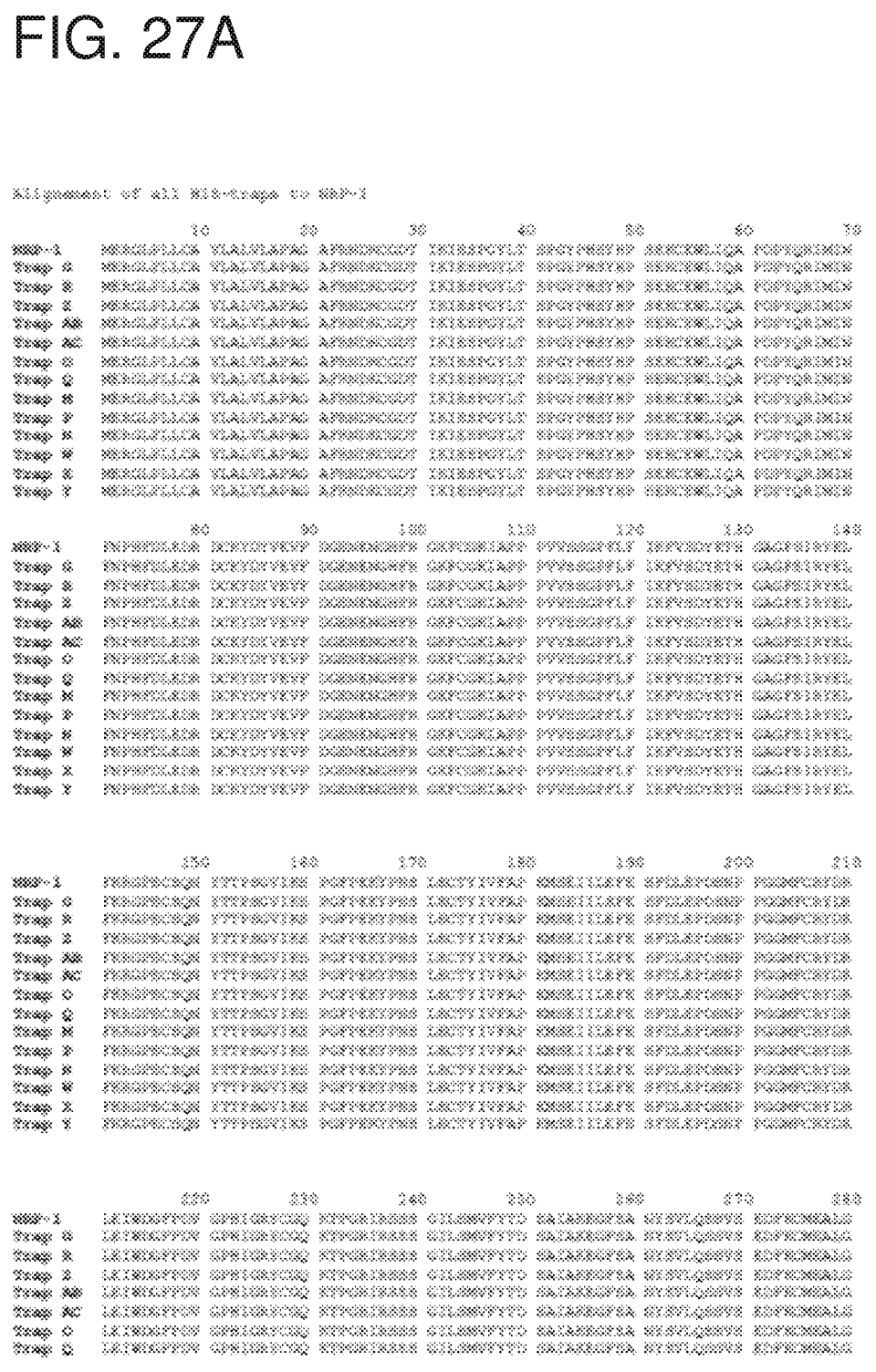

[illegible]

FIG. 27C

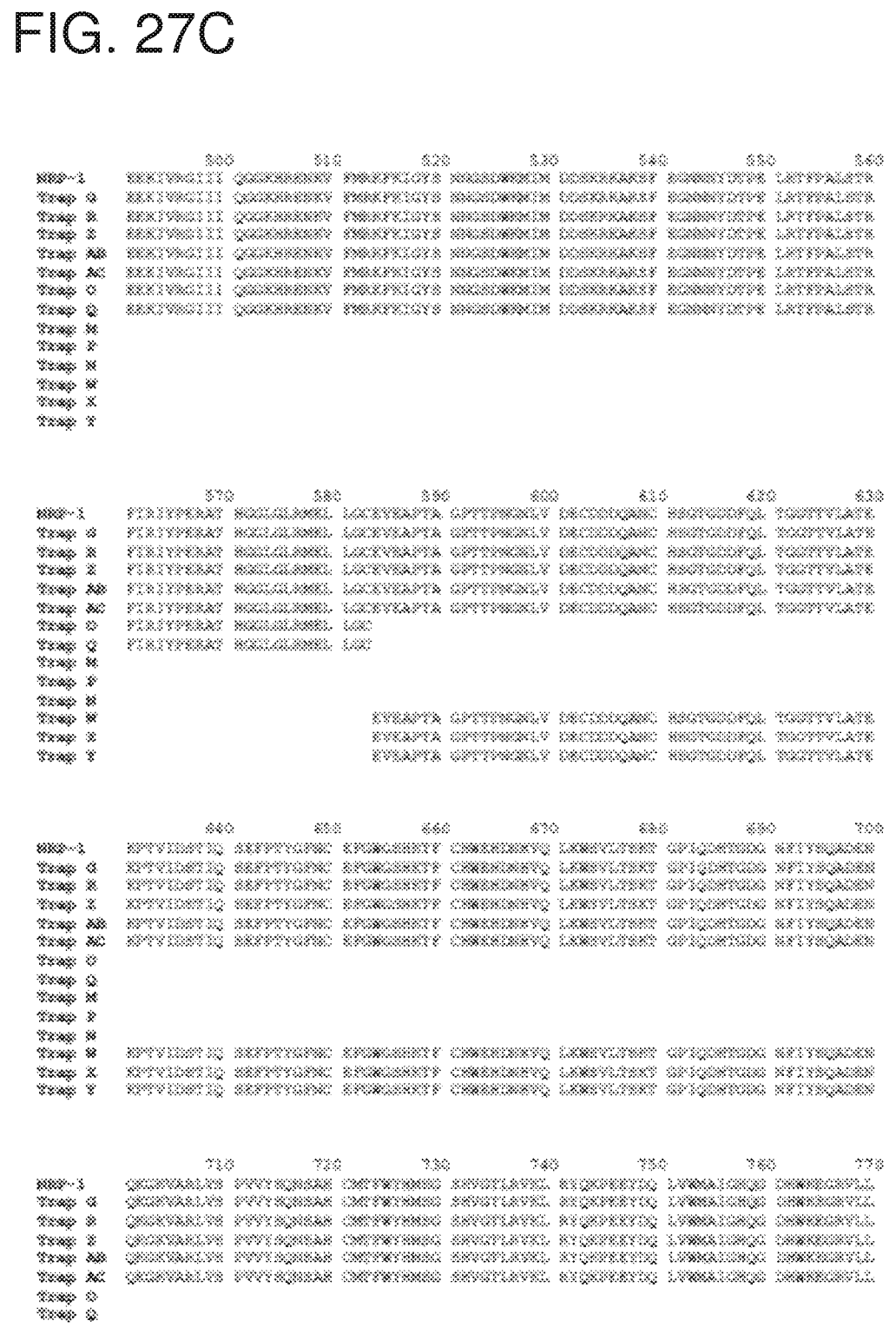

[illegible]

FIG. 27D

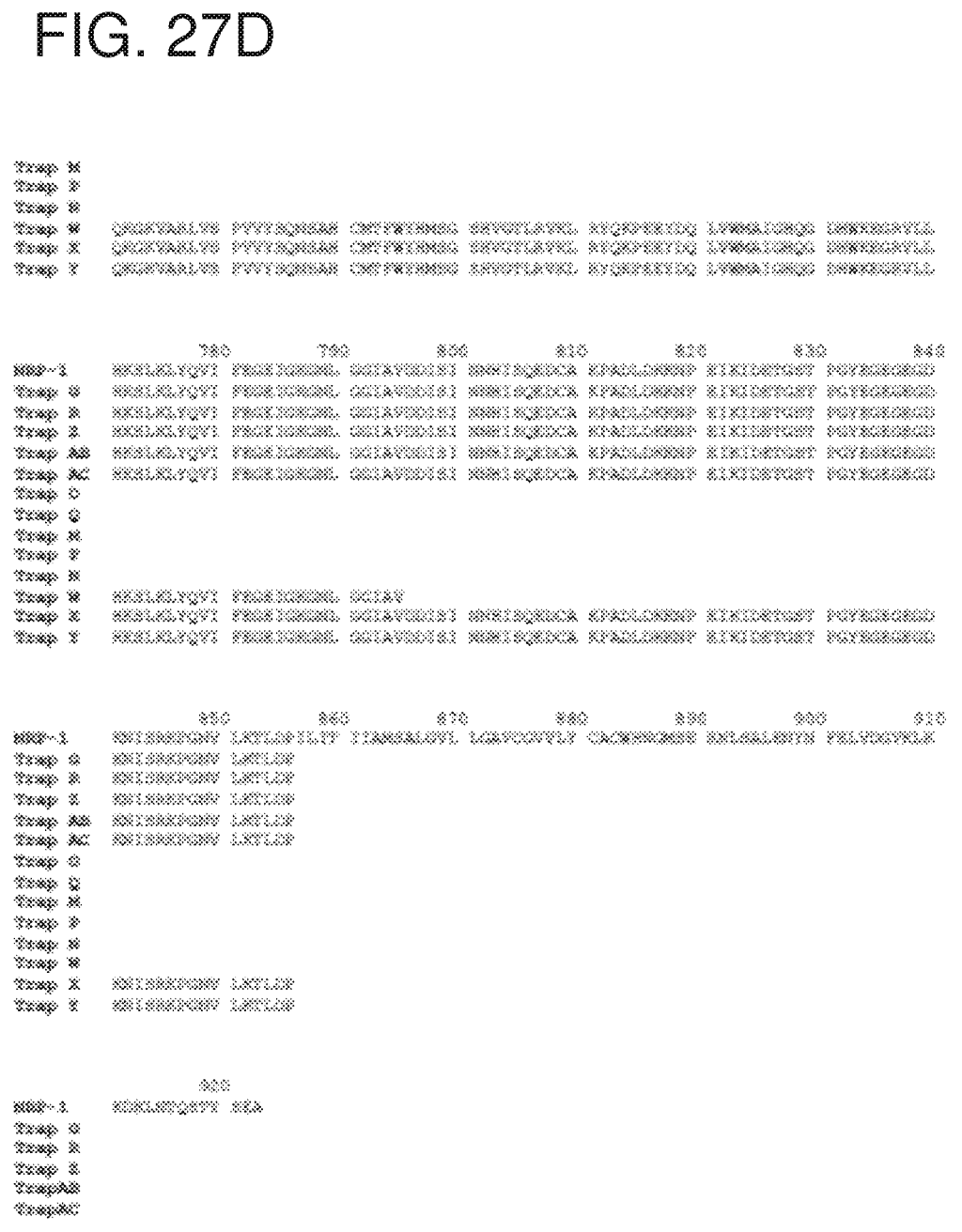

```
Trap M
Trap P
Trap R
Trap W   QKDKVAALVS PVVYSQHEAK CNTFWINMRG SRVDTLAVKL KYQKPEKYDQ LVRKAIQKQS DRKKEGAVLL
Trap X   QKDKVAALVS PVVYSQHEAK CNTFWINMRG SRVDTLAVKL KYQKPEKYDQ LVRKAIQKQS DRKKEGAVLL
Trap Y   QKDKVAALVS PVVYSQHEAK CNTFWINMRG SRVDTLAVKL KYQKPEKYDQ LVRKAIQKQS DRKKEGAVLL

                780        790        800        810        820        830        840
MSP-1    KKSLKLYQVI FRSEIKNRNL GGIAVKDIEI NNKIAQKDCA KPAOLQKKKP EIKIDETQKT PGYKGRKGKD
Trap G   KKSLKLYQVI FRSEIKNRNL GGIAVKDIEI NNKIAQKDCA KPAOLQKKKP EIKIDETQKT PGYKGRKGKD
Trap H   KKSLKLYQVI FRSEIKNRNL GGIAVKDIEI NNKIAQKDCA KPAOLQKKKP EIKIDETQKT PGYKGRKGKD
Trap I   KKSLKLYQVI FRSEIKNRNL GGIAVKDIEI NNKIAQKDCA KPAOLQKKKP EIKIDETQKT PGYKGRKGKD
Trap AB  KKSLKLYQVI FRSEIKNRNL GGIAVKDIEI NNKIAQKDCA KPAOLQKKKP EIKIDETQKT PGYKGRKGKD
Trap AC  KKSLKLYQVI FRSEIKNRNL GGIAVKDIEI NNKIAQKDCA KPAOLQKKKP EIKIDETQKT PGYKGRKGKD
Trap O
Trap Q
Trap M
Trap P
Trap R
Trap W   KKSLKLYQVI FRSEIKNRNL GGIAV
Trap X   KKSLKLYQVI FRSEIKNRNL GGIAVKDIEI NNKIAQKDCA KPAOLQKKKP EIKIDETQKT PGYKGRKGKD
Trap Y   KKSLKLYQVI FRSEIKNRNL GGIAVKDIEI NNKIAQKDCA KPAOLQKKKP EIKIDETQKT PGYKGRKGKD

                850        860        870        880        890        900        910
MSP-1    KNIEKKPQNV LKTLDPILTF IIAKKALDVL LGAVCGVVLY CACRRKKKEE KKLAKALEYS PELVDKYKLK
Trap G   KNIEKKPQNV LKTLDP
Trap H   KNIEKKPQNV LKTLDP
Trap I   KNIEKKPQNV LKTLDP
Trap AB  KNIEKKPQNV LKTLDP
Trap AC  KNIEKKPQNV LKTLDP
Trap O
Trap Q
Trap M
Trap P
Trap R
Trap W
Trap X   KNIEKKPQNV LKTLDP
Trap Y   KNIEKKPQNV LKTLDP

                920
MSP-1    KDKLKTQKTE KEA
Trap G
Trap H
Trap I
TrapAB
TrapAC
```

FIG. 27E

FC-traps to NRP-1

```
                   10         20         30         40         50         60         70
NRP-1      MERGLPLLCA VLALVLAPAG AFRNDKCGDT IKIESPGYLT SPGYPHSYHP SEKCEWLIQA PDPYQRIMIN
Trap A     MERGLPLLCA VLALVLAPAG AFRNDKCGDT IKIESPGYLT SPGYPHSYHP SEKCEWLIQA PDPYQRIMIN
Trap J     MERGLPLLCA VLALVLAPAG AFRNDKCGDT IKIESPGYLT SPGYPHSYHP SEKCEWLIQA PDPYQRIMIN
Trap I     MERGLPLLCA VLALVLAPAG AFRNDKCGDT IKIESPGYLT SPGYPHSYHP SEKCEWLIQA PDPYQRIMIN
Trap L     MERGLPLLCA VLALVLAPAG AFRNDKCGDT IKIESPGYLT SPGYPHSYHP SEKCEWLIQA PDPYQRIMIN
Trap D     MERGLPLLCA VLALVLAPAG AFRNDKCGDT IKIESPGYLT SPGYPHSYHP SEKCEWLIQA PDPYQRIMIN
Trap K     MERGLPLLCA VLALVLAPAG AFRNDKCGDT IKIESPGYLT SPGYPHSYHP SEKCEWLIQA PDPYQRIMIN
Trap C     MERGLPLLCA VLALVLAPAG AFRNDKCGDT IKIESPGYLT SPGYPHSYHP SEKCEWLIQA PDPYQRIMIN
Trap S     MERGLPLLCA VLALVLAPAG AFRNDKCGDT IKIESPGYLT SPGYPHSYHP SEKCEWLIQA PDPYQRIMIN
Trap U     MERGLPLLCA VLALVLAPAG AFRNDKCGDT IKIESPGYLT SPGYPHSYHP SEKCEWLIQA PDPYQRIMIN
Trap V     MERGLPLLCA VLALVLAPAG AFRNDKCGDT IKIESPGYLT SPGYPHSYHP SEKCEWLIQA PDPYQRIMIN

                   80         90        100        110        120        130        140
NRP-1      FNPHFDLEDR DCKYDYVEVF DGENENGHFR GKFCGKIAPP PVVSSGPFLF IKFVSDYETH GAGFSIRYEI
Trap A     FNPHFDLEDR DCKYDYVEVF DGENENGHFR GKFCGKIAPP PVVSSGPFLF IKFVSDYETH GAGFSIRYEI
Trap J     FNPHFDLEDR DCKYDYVEVF DGENENGHFR GKFCGKIAPP PVVSSGPFLF IKFVSDYETH GAGFSIRYEI
Trap I     FNPHFDLEDR DCKYDYVEVF DGENENGHFR GKFCGKIAPP PVVSSGPFLF IKFVSDYETH GAGFSIRYEI
Trap L     FNPHFDLEDR DCKYDYVEVF DGENENGHFR GKFCGKIAPP PVVSSGPFLF IKFVSDYETH GAGFSIRYEI
Trap D     FNPHFDLEDR DCKYDYVEVF DGENENGHFR GKFCGKIAPP PVVSSGPFLF IKFVSDYETH GAGFSIRYEI
Trap K     FNPHFDLEDR DCKYDYVEVF DGENENGHFR GKFCGKIAPP PVVSSGPFLF IKFVSDYETH GAGFSIRYEI
Trap C     FNPHFDLEDR DCKYDYVEVF DGENENGHFR GKFCGKIAPP PVVSSGPFLF IKFVSDYETH GAGFSIRYEI
Trap S     FNPHFDLEDR DCKYDYVEVF DGENENGHFR GKFCGKIAPP PVVSSGPFLF IKFVSDYETH GAGFSIRYEI
Trap U     FNPHFDLEDR DCKYDYVEVF DGENENGHFR GKFCGKIAPP PVVSSGPFLF IKFVSDYETH GAGFSIRYEI
Trap V     FNPHFDLEDR DCKYDYVEVF DGENENGHFR GKFCGKIAPP PVVSSGPFLF IKFVSDYETH GAGFSIRYEI

                  150        160        170        180        190        200        210
NRP-1      FKRGPECSQN YTTPSGVIKS PGFPEKYPNS LECTYIVFAP KMSEIILEFE SFDLEPDSNP PGGMFCRYDR
Trap A     FKRGPECSQN YTTPSGVIKS PGFPEKYPNS LECTYIVFAP KMSEIILEFE SFDLEPDSNP PGGMFCRYDR
Trap J     FKRGPECSQN YTTPSGVIKS PGFPEKYPNS LECTYIVFAP KMSEIILEFE SFDLEPDSNP PGGMFCRYDR
Trap I     FKRGPECSQN YTTPSGVIKS PGFPEKYPNS LECTYIVFAP KMSEIILEFE SFDLEPDSNP PGGMFCRYDR
Trap L     FKRGPECSQN YTTPSGVIKS PGFPEKYPNS LECTYIVFAP KMSEIILEFE SFDLEPDSNP PGGMFCRYDR
Trap D     FKRGPECSQN YTTPSGVIKS PGFPEKYPNS LECTYIVFAP KMSEIILEFE SFDLEPDSNP PGGMFCRYDR
Trap K     FKRGPECSQN YTTPSGVIKS PGFPEKYPNS LECTYIVFAP KMSEIILEFE SFDLEPDSNP PGGMFCRYDR
Trap C     FKRGPECSQN YTTPSGVIKS PGFPEKYPNS LECTYIVFAP KMSEIILEFE SFDLEPDSNP PGGMFCRYDR
Trap S     FKRGPECSQN YTTPSGVIKS PGFPEKYPNS LECTYIVFAP KMSEIILEFE SFDLEPDSNP PGGMFCRYDR
Trap U     FKRGPECSQN YTTPSGVIKS PGFPEKYPNS LECTYIVFAP KMSEIILEFE SFDLEPDSNP PGGMFCRYDR
Trap V     FKRGPECSQN YTTPSGVIKS PGFPEKYPNS LECTYIVFAP KMSEIILEFE SFDLEPDSNP PGGMFCRYDR

                  220        230        240        250        260        270        280
NRP-1      LEIWDGFPDV GPHIGRYCGQ KTPGRIRSSS GILSMVFYTD SAIAKEGFSA NYSVLQSSVS EDFKCMEALG
Trap A     LEIWDGFPDV GPHIGRYCGQ KTPGRIRSSS GILSMVFYTD SAIAKEGFSA NYSVLQSSVS EDFKCMEALG
Trap J     LEIWDGFPDV GPHIGRYCGQ KTPGRIRSSS GILSMVFYTD SAIAKEGFSA NYSVLQSSVS EDFKCMEALG
Trap I     LEIWDGFPDV GPHIGRYCGQ KTPGRIRSSS GILSMVFYTD SAIAKEGFSA NYSVLQSSVS EDFKCMEALG
Trap L     LEIWDGFPDV GPHIGRYCGQ KTPGRIRSSS GILSMVFYTD SAIAKEGFSA NYSVLQSSVS EDFKCMEALG
Trap D     LEIWDGFPDV GPHIGRYCGQ KTPGRIRSSS GILSMVFYTD SAIAKEGFSA NYSVLQSSVS EDFKCMEALG
Trap K     LEIWDGFPDV GPHIGRYCGQ KTPGRIRSSS GILSMVFYTD SAIAKEGFSA NYSVLQSSVS EDFKCMEALG
Trap C     LEIWDGFPDV GPHIGRYCGQ KTPGRIRSSS GILSMVFYTD SAIAKEGFSA NYSVL
Trap S     LEIWDGFPDV GPHIGRYCGQ KTPGRIRSSS GILSMVFYTD SAIAKEGFSA NYSVLQSSVS EDFKCMEALG
Trap U     LEIWDGFPDV GPHIGRYCGQ KTPGRIRSSS GILSMVFYTD SAIAKEGFSA NYSVLQSSVS EDFKCMEALG
Trap V     LEIWDGFPDV GPHIGRYCGQ KTPGRIRSSS GILSMVFYTD SAIAKEGFSA NYSVLQSSVS EDFK
```

FIG. 27F

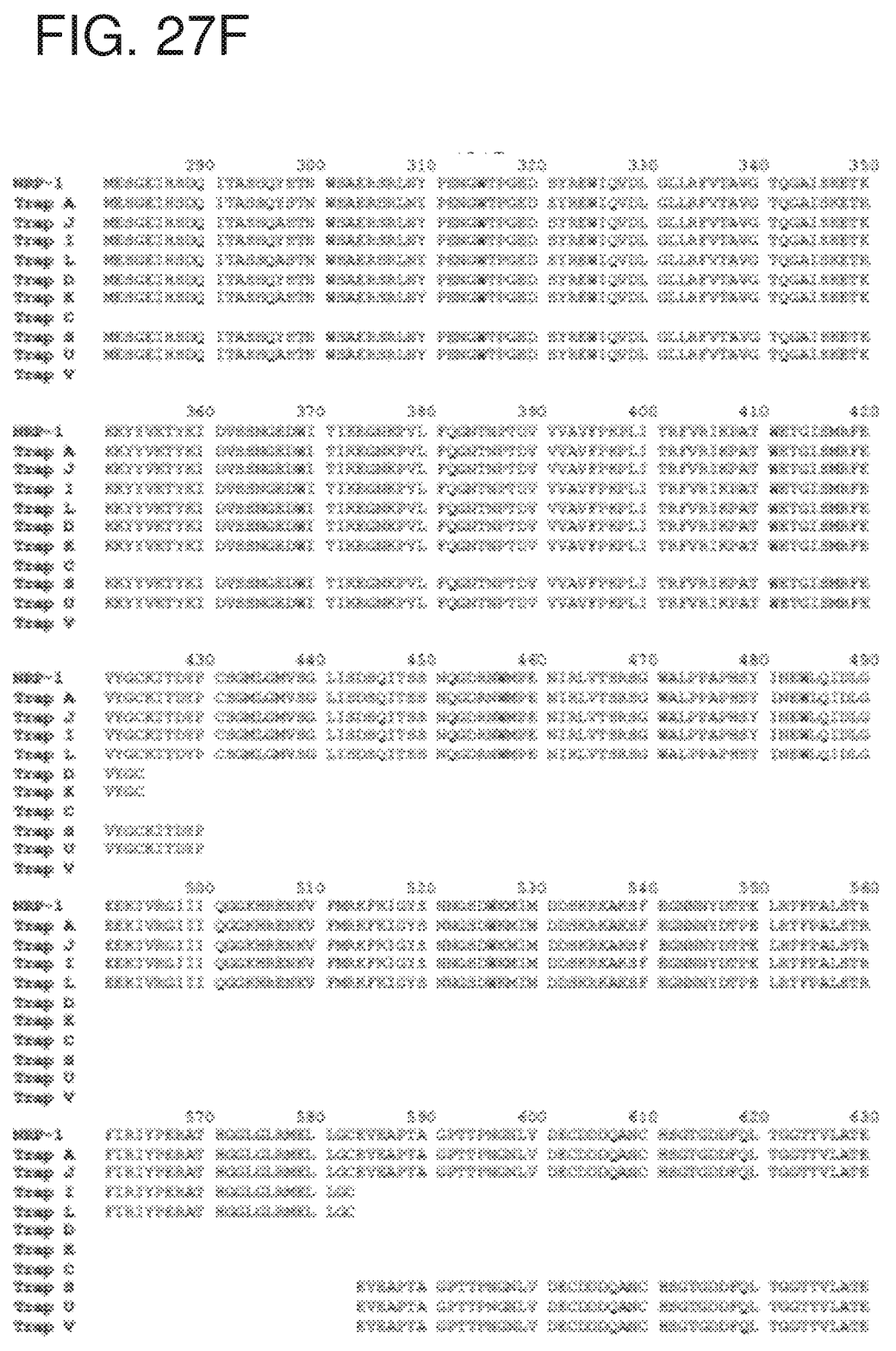

| | 290 | 300 | 310 | 320 | 330 | 340 | 350 |
|---|---|---|---|---|---|---|---|
| MBP-1 | [illegible] | [illegible] | [illegible] | [illegible] | [illegible] | [illegible] | [illegible] |
| Trap A | [illegible] | [illegible] | [illegible] | [illegible] | [illegible] | [illegible] | [illegible] |
| Trap J | [illegible] | [illegible] | [illegible] | [illegible] | [illegible] | [illegible] | [illegible] |
| Trap I | [illegible] | [illegible] | [illegible] | [illegible] | [illegible] | [illegible] | [illegible] |
| Trap L | [illegible] | [illegible] | [illegible] | [illegible] | [illegible] | [illegible] | [illegible] |
| Trap D | [illegible] | [illegible] | [illegible] | [illegible] | [illegible] | [illegible] | [illegible] |
| Trap K | [illegible] | [illegible] | [illegible] | [illegible] | [illegible] | [illegible] | [illegible] |
| Trap C | | | | | | | |
| Trap S | [illegible] | [illegible] | [illegible] | [illegible] | [illegible] | [illegible] | [illegible] |
| Trap U | [illegible] | [illegible] | [illegible] | [illegible] | [illegible] | [illegible] | [illegible] |
| Trap V | | | | | | | |

| | 360 | 370 | 380 | 390 | 400 | 410 | 420 |
|---|---|---|---|---|---|---|---|
| MBP-1 | [illegible] | [illegible] | [illegible] | [illegible] | [illegible] | [illegible] | [illegible] |
| Trap A | [illegible] | [illegible] | [illegible] | [illegible] | [illegible] | [illegible] | [illegible] |
| Trap J | [illegible] | [illegible] | [illegible] | [illegible] | [illegible] | [illegible] | [illegible] |
| Trap I | [illegible] | [illegible] | [illegible] | [illegible] | [illegible] | [illegible] | [illegible] |
| Trap L | [illegible] | [illegible] | [illegible] | [illegible] | [illegible] | [illegible] | [illegible] |
| Trap D | [illegible] | [illegible] | [illegible] | [illegible] | [illegible] | [illegible] | [illegible] |
| Trap K | [illegible] | [illegible] | [illegible] | [illegible] | [illegible] | [illegible] | [illegible] |
| Trap C | | | | | | | |
| Trap S | [illegible] | [illegible] | [illegible] | [illegible] | [illegible] | [illegible] | [illegible] |
| Trap U | [illegible] | [illegible] | [illegible] | [illegible] | [illegible] | [illegible] | [illegible] |
| Trap V | | | | | | | |

| | 430 | 440 | 450 | 460 | 470 | 480 | 490 |
|---|---|---|---|---|---|---|---|
| MBP-1 | [illegible] | [illegible] | [illegible] | [illegible] | [illegible] | [illegible] | [illegible] |
| Trap A | [illegible] | [illegible] | [illegible] | [illegible] | [illegible] | [illegible] | [illegible] |
| Trap J | [illegible] | [illegible] | [illegible] | [illegible] | [illegible] | [illegible] | [illegible] |
| Trap I | [illegible] | [illegible] | [illegible] | [illegible] | [illegible] | [illegible] | [illegible] |
| Trap L | [illegible] | [illegible] | [illegible] | [illegible] | [illegible] | [illegible] | [illegible] |
| Trap D | [illegible] | | | | | | |
| Trap K | [illegible] | | | | | | |
| Trap C | | | | | | | |
| Trap S | [illegible] | | | | | | |
| Trap U | [illegible] | | | | | | |
| Trap V | | | | | | | |

| | 500 | 510 | 520 | 530 | 540 | 550 | 560 |
|---|---|---|---|---|---|---|---|
| MBP-1 | [illegible] | [illegible] | [illegible] | [illegible] | [illegible] | [illegible] | [illegible] |
| Trap A | [illegible] | [illegible] | [illegible] | [illegible] | [illegible] | [illegible] | [illegible] |
| Trap J | [illegible] | [illegible] | [illegible] | [illegible] | [illegible] | [illegible] | [illegible] |
| Trap I | [illegible] | [illegible] | [illegible] | [illegible] | [illegible] | [illegible] | [illegible] |
| Trap L | [illegible] | [illegible] | [illegible] | [illegible] | [illegible] | [illegible] | [illegible] |
| Trap D | | | | | | | |
| Trap K | | | | | | | |
| Trap C | | | | | | | |
| Trap S | | | | | | | |
| Trap U | | | | | | | |
| Trap V | | | | | | | |

| | 570 | 580 | 590 | 600 | 610 | 620 | 630 |
|---|---|---|---|---|---|---|---|
| MBP-1 | [illegible] | [illegible] | [illegible] | [illegible] | [illegible] | [illegible] | [illegible] |
| Trap A | [illegible] | [illegible] | [illegible] | [illegible] | [illegible] | [illegible] | [illegible] |
| Trap J | [illegible] | [illegible] | [illegible] | [illegible] | [illegible] | [illegible] | [illegible] |
| Trap I | [illegible] | [illegible] | [illegible] | | | | |
| Trap L | [illegible] | [illegible] | [illegible] | | | | |
| Trap D | | | | | | | |
| Trap K | | | | | | | |
| Trap C | | | | | | | |
| Trap S | | | [illegible] | [illegible] | [illegible] | [illegible] | [illegible] |
| Trap U | | | [illegible] | [illegible] | [illegible] | [illegible] | [illegible] |
| Trap V | | | [illegible] | [illegible] | [illegible] | [illegible] | [illegible] |

FIG. 27G

| | 640 | 650 | 660 | 670 | 680 | 690 | 700 |
|---|---|---|---|---|---|---|---|
| NBP-1 | KPTVIDRFIQ | EKFFTYGPKC | KPGKQERKTF | CRRKKDRKVQ | LKKEVLTEKT | GFIQDKTGDG | NFIYRQADKN |
| Trap A | KPTVIDRFIQ | EKFFTYGPKC | KPGKQERKTF | CRRKKDRKVQ | LKKEVLTEKT | GFIQDKTGDG | NFIYRQADKN |
| Trap J | KPTVIDRFIQ | EKFFTYGPKC | KPGKQERKTF | CRRKKDRKVQ | LKKEVLTEKT | GFIQDKTGDG | NFIYRQADKN |
| Trap I | | | | | | | |
| Trap L | | | | | | | |
| Trap G | | | | | | | |
| Trap E | | | | | | | |
| Trap C | | | | | | | |
| Trap B | KPTVIDRFIQ | EKFFTYGPKC | KPGKQERKTF | CRRKKDRKVQ | LKKEVLTEKT | GFIQDKTGDG | NFIYRQADKN |
| Trap U | KPTVIDRFIQ | EKFFTYGPKC | KPGKQERKTF | CRRKKDRKVQ | LKKEVLTEKT | GFIQDKTGDG | NFIYRQADKN |
| Trap V | KPTVIDRFIQ | EKFFTYGPKC | KPGKQERKTF | CRRKKDRKVQ | LKKEVLTEKT | GFIQDKTGDG | NFIYRQADKN |

| | 710 | 720 | 730 | 740 | 750 | 760 | 770 |
|---|---|---|---|---|---|---|---|
| NBP-1 | QKEEVARLVE | PVVYRQNEAK | CKTFKTRKEG | KKVGTLAVKL | KYQKPEKYDQ | LVKKAIGKQG | DKKKKDKVLL |
| Trap A | QKEEVARLVE | PVVYRQNEAK | CKTFKTRKEG | KKVGTLAVKL | KYQKPEKYDQ | LVKKAIGKQG | DKKKKDKVLL |
| Trap J | QKEEVARLVE | PVVYRQNEAK | CKTFKTRKEG | KKVGTLAVKL | KYQKPEKYDQ | LVKKAIGKQG | DKKKKDKVLL |
| Trap I | | | | | | | |
| Trap L | | | | | | | |
| Trap D | | | | | | | |
| Trap E | | | | | | | |
| Trap C | | | | | | | |
| Trap B | QKEEVARLVE | PVVYRQNEAK | CKTFKTRKEG | KKVGTLAVKL | KYQKPEKYDQ | LVKKAIGKQG | DKKKKDKVLL |
| Trap U | QKEEVARLVE | PVVYRQNEAK | CKTFKTRKEG | KKVGTLAVKL | KYQKPEKYDQ | LVKKAIGKQG | DKKKKDKVLL |
| Trap V | QKEEVARLVE | PVVYRQNEAK | CKTFKTRKEG | KKVGTLAVKL | KYQKPEKYDQ | LVKKAIGKQG | DKKKKDKVLL |

| | 780 | 790 | 800 | 810 | 820 | 830 | 840 |
|---|---|---|---|---|---|---|---|
| NBP-1 | KKELKLYQVI | FKEKIDKKKL | GKIAVDKIKI | KKKIAQEKCA | KPAELDKKKP | KIKIDKTGKT | PGYKEKGKGD |
| Trap A | KKELKLYQVI | FKEKIDKKKL | GKIAVDKIKI | KKKIAQEKCA | KPAELDKKKP | KIKIDKTGKT | PGYKEKGKGD |
| Trap J | KKELKLYQVI | FKEKIDKKKL | GKIAVDKIKI | KKKIAQEKCA | KPAELDKKKP | KIKIDKTGKT | PGYKEKGKGD |
| Trap I | | | | | | | |
| Trap L | | | | | | | |
| Trap D | | | | | | | |
| Trap E | | | | | | | |
| Trap C | | | | | | | |
| Trap B | KKELKLYQVI | FKEKIDKKKL | GKIAVDKIKI | KKKIAQEKCA | KPAELDKKKP | KIKIDKTGKT | PGYKEKGKGD |
| Trap U | KKELKLYQVI | FKEKIDKKKL | GKIAVDKIKI | KKKITQEKCA | KPAELDKKKP | KIKIDKTGKT | PGYKEKGKGD |
| Trap V | KKELKLYQVI | FKEKIDKKKL | GKIAVDKIKI | KKKIAQEKCA | KPAELDKKKP | KIKIDKTGKT | PGYKEKGKGD |

| | 850 | 860 | 870 | 880 | 890 | 900 | 910 |
|---|---|---|---|---|---|---|---|
| NBP-1 | KKIEKKPGKV | LKTLDFILIY | IIAKKALGVL | LGKVCGVVLY | CKCKKKKKKK | KKLKAALKKK | FKLVDCVKLK |
| Trap A | KKIEKKPGKV | LKTLDF | | | | | |
| Trap J | KKIEKKPGKV | LKTLDF | | | | | |
| Trap I | | | | | | | |
| Trap L | | | | | | | |
| Trap D | | | | | | | |
| Trap E | | | | | | | |
| Trap C | | | | | | | |
| Trap B | KKIEKKPGKV | LKTLDF | | | | | |
| Trap U | KKIEKKPGKV | LKTLDF | | | | | |
| Trap V | KKIEKKPGKV | LKTLDF | | | | | |

FIG. 27H

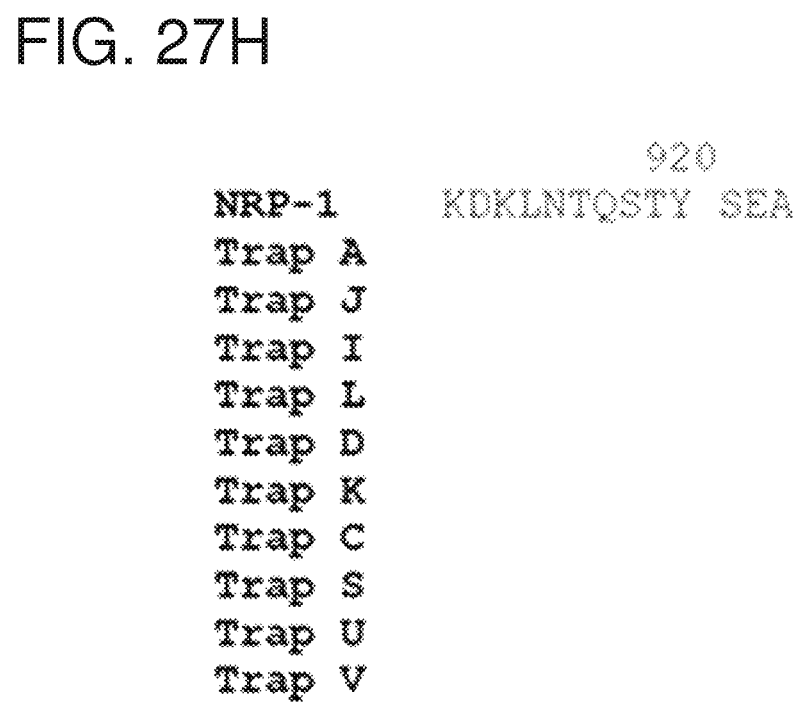

| | 920 |
|---|---|
| NRP-1 | KDKLNTQSTY SEA |
| Trap A | |
| Trap J | |
| Trap I | |
| Trap L | |
| Trap D | |
| Trap K | |
| Trap C | |
| Trap S | |
| Trap U | |
| Trap V | |

SEQUENCE LISTING

```
Sequence total quantity: 128
SEQ ID NO: 1            moltype = AA  length = 1064
FEATURE                 Location/Qualifiers
REGION                  1..1064
                        note = Synthetic polypeptide
source                  1..1064
                        mol_type = protein
                        organism = synthetic construct
SEQUENCE: 1
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLQSSVSE DFKCMEALGM ESGEIHSDQI TASSQYSTNW SAERSRLNYP ENGWTPGEDS  300
YREWIQVDLG LLRFVTAVGT QGAISKETKK KYYVKTYKID VSSNGEDWIT IKEGNKPVLF  360
QGNTNPTDVV VAVFPKPLIT RFVRIKPATW ETGISMRFEV YGCKITDYPC SGMLGMVSGL  420
ISDSQITSSN QGDRNWMPEN IRLVTSRSGW ALPPAPHSYI NEWLQIDLGE EKIVRGIIIQ  480
GGKHRENKVF MRKFKIGYSN NGSDWKMIMD DSKRKAKSFE GNNNYDTPEL RTFPALSTRF  540
IRIYPERATH GGLGLRMELL GCEVEAPTAG PTTPNGNLVD ECDDDQANCH SGTGDDFQLT  600
```

```
GGTTVLATEK PTVIDSTIQS EFPTYGFNCE FGWGSHKTFC HWEHDNHVQL KWSVLTSKTG  660
PIQDHTGDGN FIYSQADENQ KGKVARLVSP VVYSQNSAHC MTFWYHMSGS HVGTLRVKLR  720
YQKPEEYDQL VWMAIGHQGD HWKEGRVLLH KSLKLYQVIF EGEIGKGNLG GIAVDDISIN  780
NHISQEDCAK PADLDKKNPE IKIDETGSTP GYEGEGEGDK NISRKPGNVL KTLDPRSDKT  840
HTCPPCPAPE LLGGPSVFLF PPKPKDTLMI SRTPEVTCVV VDVSHEDPEV KFNWYVDGVE  900
VHNAKTKPRE EQYNSTYRVV SVLTVLHQDW LNGKEYKCKV SNKALPAPIE KTISKAKGQP  960
REPQVYTLPP SREEMTKNQV SLTCLVKGFY PSDIAVEWES NGQPENNYKT TPPVLDSDGS  1020
FFLYSKLTVD KSRWQQGNVF SCSVMHEALH NHYTQKSLSL SPGK                  1064

SEQ ID NO: 2           moltype = DNA  length = 3255
FEATURE                Location/Qualifiers
misc_feature           1..3255
                       note = Synthetic polynucleotide
source                 1..3255
                       mol_type = other DNA
                       organism = synthetic construct
SEQUENCE: 2
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccaggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgcagag cagtgtctca gaagatttca aatgtatgga agctctgggc  840
atggaatcag gagaaattca ttctgaccag atcacagctt cttcccagta tagcaccaac  900
tggtctgcag agcgctcccg cctgaactac cctgagaatg ggtggactcc cggagaggat  960
tcctaccgag agtggataca ggtagacttg ggccttctgc gctttgtcac ggctgtcggg  1020
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
actcgatttg tccgaatcaa gcctgcaact tgggaaactg gcatatctat gagatttgaa  1260
gtatatggtt gcaagataac agattatcct tgctctggaa tgttgggtat ggtgtctgga  1320
cttatttctg actcccagat cacatcatcc aaccaagggg acagaaactg gatgcctgaa  1380
aacatccgcc tggtaaccag tcgctctggc tgggcacttc caccccgcacc tcattcctac  1440
atcaatgagt ggctccaaat agacctgggg gaggagaaga tcgtgagggg catcatcatt  1500
cagggtggga agcaccgaga gaacaaggtg ttcatgagga agttcaagat cgggtacagc  1560
aacaacggct cggactggaa gatgatcatg gatgacagca aacgcaaggc gaagtctttt  1620
gagggcaaca acaactatga tacacctgag ctgcggactt ttccagctct ctccacgcga  1680
ttcatcagga tctaccccga gagagccact catggcggac tggggctcag aatggagctg  1740
ctgggctgtg aagtggaagc ccctacagct ggaccgacca ctcccaacgg gaacttggtg  1800
gatgaatgtg atgacgacca ggccaactgc cacagtggaa caggtgatga cttccagctc  1860
acaggtggca ccactgtgct ggccacagaa aagcccacgg tcatagacag caccatacaa  1920
tcagagtttc caacatatgg ttttaactgt gaatttggct ggggctctca caagaccttc  1980
tgccactggg aacatgacaa tcacgtgcag ctcaagtgga gtgtgttgac cagcaagacg  2040
ggacccattc aggatcacac aggagatggc aacttcatct attcccaagc tgacgaaaat  2100
cagaagggca aagtggctcg cctggtgagc cctgtggttt attcccagaa ctctgcccac  2160
tgcatgacct tctggtatca catgtctggg tcccacgtcg gcacactcag ggtcaaactg  2220
cgctaccaga agccagagga gtacgatcag ctggtctgga tggccattgg acaccaaggt  2280
gaccactgga aggaagggcg tgtcttgctc cacaagtctc tgaaacttta tcaggtgatt  2340
ttcgagggcg aaatcggaaa aggaaacctt ggtgggattg ctgtggatga cattagtatt  2400
aataaccaca tttcacaaga agattgtgca aaaccagcag acctggataa aaagaaccca  2460
gaaattaaaa ttgatgaaac agggagcacg ccaggatacg aaggtgaagg agaaggtgac  2520
aagaacatct ccaggaagcc aggcaatgtg ttgaagacct tagaccccag atctgacaaa  2580
actcacacat gcccaccgtg cccagcacct gaactcctgg ggggaccgtc agtcttcctc  2640
ttccccccaa aacccaagga caccctcatg atctcccgga cccctgaggt cacatgcgtg  2700
gtggtggacg tgagccacga agaccctgag gtcaagttca actggtacgt ggacggcgtg  2760
gaggtgcata atgccaagac aaagccgcgg gaggagcagt acaacagcac gtaccgtgtg  2820
gtcagcgtcc tcaccgtcct gcaccaggac tggctgaatg gcaaggagta caagtgcaag  2880
gtctccaaca aagccctccc agcccccatc gagaaaacca tctccaaagc caaagggcag  2940
ccccgagaac cacaggtgta caccctgccc ccatcccggg aggagatgac caagaaccag  3000
gtcagcctga cctgcctggt caaaggcttc tatcccagcg acatcgccgt ggagtgggag  3060
agcaatgggc agccggagaa caactacaag accacgcctc ccgtgctgga ctccgacggc  3120
tccttcttcc tctacagcaa gctcaccgtg gacaagagca ggtggcagca ggggaacgtc  3180
ttctcatgct ccgtgatgca cgaggctctg cacaaccact acacgcagaa gagcctctcc  3240
ctgtctccgg gtaaa                                                  3255

SEQ ID NO: 3           moltype = AA  length = 1064
FEATURE                Location/Qualifiers
REGION                 1..1064
                       note = Synthetic polypeptide
REGION                 563..837
                       note = misc_feature - Xaa can be any naturally occurring
```

```
                         amino acid
source                  1..1064
                        mol_type = protein
                        organism = synthetic construct
SEQUENCE: 3
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLQSSVSE DFKCMEALGM ESGEIHSDQI TASSQYSTNW SAERSRLNYP ENGWTPGEDS  300
YREWIQVDLG LLRFVTAVGT QGAISKETKK KYYVKTYKID VSSNGEDWIT IKEGNKPVLF  360
QGNTNPTDVV VAVFPKPLIT RFVRIKPATW ETGISMRFEV YGCKITDYPC SGMLGMVSGL  420
ISDSQITSSN QGDRNWMPEN IRLVTSRSGW ALPPAPHSYI NEWLQIDLGE EKIVRGIIIQ  480
GGKHRENKVF MRKFKIGYSN NGSDWKMIMD DSKRKAKSFE GNNNYDTPEL RTFPALSTRF  540
IRIYPERATH GGLGLRMELL GCXXXXXXXX XXXXXXXXXX XXXXXXXXXX XXXXXXXXXX  600
XXXXXXXXXX XXXXXXXXXX XXXXXXXXXX XXXXXXXXXX XXXXXXXXXX XXXXXXXXXX  660
XXXXXXXXXX XXXXXXXXXX XXXXXXXXXX XXXXXXXXXX XXXXXXXXXX XXXXXXXXXX  720
XXXXXXXXXX XXXXXXXXXX XXXXXXXXXX XXXXXXXXXX XXXXXXXXXX XXXXXXXXXX  780
XXXXXXXXXX XXXXXXXXXX XXXXXXXXXX XXXXXXXXXX XXXXXXXXXX XXXXXXXDKT  840
HTCPPCPAPE LLGGPSVFLF PPKPKDTLMI SRTPEVTCVV VDVSHEDPEV KFNWYVDGVE  900
VHNAKTKPRE EQYNSTYRVV SVLTVLHQDW LNGKEYKCKV SNKALPAPIE KTISKAKGQP  960
REPQVYTLPP SREEMTKNQV SLTCLVKGFY PSDIAVEWES NGQPENNYKT TPPVLDSDGS  1020
FFLYSKLTVD KSRWQQGNVF SCSVMHEALH NHYTQKSLSL SPGK                  1064

SEQ ID NO: 4            moltype = DNA  length = 3255
FEATURE                 Location/Qualifiers
misc_feature            1..3255
                        note = Synthetic polynucleotide
misc_feature            1750..2574
                        note = n is a, c, g, or t
source                  1..3255
                        mol_type = other DNA
                        organism = synthetic construct
SEQUENCE: 4
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccagggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgcagag cagtgtctca gaagatttca aatgtatgga agctctgggc  840
atggaatcag gagaaattca ttctgaccag atcacagctt cttcccagta tagcaccaac  900
tggtctgcag agcgctcccg cctgaactac cctgagaatg ggtggactcc cggagaggat  960
tcctaccgag agtggataca ggtagacttg ggccttctgc gctttgtcac ggctgtcggg  1020
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
actcgatttg tccgaatcaa gcctgcaact tgggaaactg gcatatctat gagatttgaa  1260
gtatatggtt gcaagataac agattatcct tgctctggaa tgttgggtat ggtgtctgga  1320
cttatttctg actcccagat cacatcatcc aaccaagggg acagaaactg gatgcctgaa  1380
aacatccgcc tggtaaccag tcgctctggc tgggcacttc cacccgcacc tcattcctac  1440
atcaatgagt ggctccaaat agacctgggg gaggagaaga tcgtgagggg catcatcatt  1500
cagggtggga agcaccgaga gaacaaggtg ttcatgagga agttcaagat cgggtacagc  1560
aacaacggct cggactggaa gatgatcatg gatgacagca aacgcaaggc gaagtctttt  1620
gagggcaaca acaactatga tacacctgag ctgcggactt ttccagctct ctccacgcga  1680
ttcatcagga tctaccccga gagagccact catggcggac tggggctcag aatggagctg  1740
ctgggctgtn nnnnnnnnnn nnnnnnnnnn nnnnnnnnnn nnnnnnnnnn nnnnnnnnnn  1800
nnnnnnnnnn nnnnnnnnnn nnnnnnnnnn nnnnnnnnnn nnnnnnnnnn nnnnnnnnnn  1860
nnnnnnnnnn nnnnnnnnnn nnnnnnnnnn nnnnnnnnnn nnnnnnnnnn nnnnnnnnnn  1920
nnnnnnnnnn nnnnnnnnnn nnnnnnnnnn nnnnnnnnnn nnnnnnnnnn nnnnnnnnnn  1980
nnnnnnnnnn nnnnnnnnnn nnnnnnnnnn nnnnnnnnnn nnnnnnnnnn nnnnnnnnnn  2040
nnnnnnnnnn nnnnnnnnnn nnnnnnnnnn nnnnnnnnnn nnnnnnnnnn nnnnnnnnnn  2100
nnnnnnnnnn nnnnnnnnnn nnnnnnnnnn nnnnnnnnnn nnnnnnnnnn nnnnnnnnnn  2160
nnnnnnnnnn nnnnnnnnnn nnnnnnnnnn nnnnnnnnnn nnnnnnnnnn nnnnnnnnnn  2220
nnnnnnnnnn nnnnnnnnnn nnnnnnnnnn nnnnnnnnnn nnnnnnnnnn nnnnnnnnnn  2280
nnnnnnnnnn nnnnnnnnnn nnnnnnnnnn nnnnnnnnnn nnnnnnnnnn nnnnnnnnnn  2340
nnnnnnnnnn nnnnnnnnnn nnnnnnnnnn nnnnnnnnnn nnnnnnnnnn nnnnnnnnnn  2400
nnnnnnnnnn nnnnnnnnnn nnnnnnnnnn nnnnnnnnnn nnnnnnnnnn nnnnnnnnnn  2460
nnnnnnnnnn nnnnnnnnnn nnnnnnnnnn nnnnnnnnnn nnnnnnnnnn nnnnnnnnnn  2520
nnnnnnnnnn nnnnnnnnnn nnnnnnnnnn nnnnnnnnnn nnnnnnnnnn nnnngacaaa  2580
actcacacat gcccaccgtg cccagcacct gaactcctgg ggggaccgtc agtcttcctc  2640
ttccccccaa aacccaagga caccctcatg atctcccgga cccctgaggt cacatgcgtg  2700
```

```
gtggtggacg tgagccacga agaccctgag gtcaagttca actggtacgt ggacggcgtg  2760
gaggtgcata atgccaagac aaagccgcgg gaggagcagt acaacagcac gtaccgtgtg  2820
gtcagcgtcc tcaccgtcct gcaccaggac tggctgaatg gcaaggagta caagtgcaag  2880
gtctccaaca aagccctccc agcccccatc gagaaaacca tctccaaagc caaagggcag  2940
ccccgagaac cacaggtgta caccctgccc ccatcccggg aggagatgac caagaaccag  3000
gtcagcctga cctgcctggt caaaggcttc tatcccagcg acatcgccgt ggagtgggag  3060
agcaatgggc agccggagaa caactacaag accacgcctc ccgtgctgga ctccgacggc  3120
tccttcttcc tctacagcaa gctcaccgtg gacaagagca ggtggcagca ggggaacgtc  3180
ttctcatgct ccgtgatgca cgaggctctg cacaaccact acacgcagaa gagcctctcc  3240
ctgtctccgg gtaaa                                                   3255

SEQ ID NO: 5            moltype = AA  length = 1064
FEATURE                 Location/Qualifiers
REGION                  1..1064
                        note = Synthetic polypeptide
REGION                  404..837
                        note = misc_feature - Xaa can be any naturally occurring
                         amino acid
source                  1..1064
                        mol_type = protein
                        organism = synthetic construct
SEQUENCE: 5
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLQSSVSE DFKCMEALGM ESGEIHSDQI TASSQYSTNW SAERSRLNYP ENGWTPGEDS  300
YREWIQVDLG LLRFVTAVGT QGAISKETKK KYYVKTYKID VSSNGEDWIT IKEGNKPVLF  360
QGNTNPTDVV VAVFPKPLIT RFVRIKPATW ETGISMRFEV YGCXXXXXXX XXXXXXXXXX  420
XXXXXXXXXX XXXXXXXXXX XXXXXXXXXX XXXXXXXXXX XXXXXXXXXX XXXXXXXXXX  480
XXXXXXXXXX XXXXXXXXXX XXXXXXXXXX XXXXXXXXXX XXXXXXXXXX XXXXXXXXXX  540
XXXXXXXXXX XXXXXXXXXX XXXXXXXXXX XXXXXXXXXX XXXXXXXXXX XXXXXXXXXX  600
XXXXXXXXXX XXXXXXXXXX XXXXXXXXXX XXXXXXXXXX XXXXXXXXXX XXXXXXXXXX  660
XXXXXXXXXX XXXXXXXXXX XXXXXXXXXX XXXXXXXXXX XXXXXXXXXX XXXXXXXXXX  720
XXXXXXXXXX XXXXXXXXXX XXXXXXXXXX XXXXXXXXXX XXXXXXXXXX XXXXXXXXXX  780
XXXXXXXXXX XXXXXXXXXX XXXXXXXXXX XXXXXXXXXX XXXXXXXXXX XXXXXXXDKT  840
HTCPPCPAPE LLGGPSVFLF PPKPKDTLMI SRTPEVTCVV VDVSHEDPEV KFNWYVDGVE  900
VHNAKTKPRE EQYNSTYRVV SVLTVLHQDW LNGKEYKCKV SNKALPAPIE KTISKAKGQP  960
REPQVYTLPP SREEMTKNQV SLTCLVKGFY PSDIAVEWES NGQPENNYKT TPPVLDSDGS  1020
FFLYSKLTVD KSRWQQGNVF SCSVMHEALH NHYTQKSLSL SPGK                  1064

SEQ ID NO: 6            moltype = DNA  length = 3255
FEATURE                 Location/Qualifiers
misc_feature            1..3255
                        note = Synthetic polynucleotide
misc_feature            1273..2574
                        note = n is a, c, g, or t
source                  1..3255
                        mol_type = other DNA
                        organism = synthetic construct
SEQUENCE: 6
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccagggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgcagag cagtgtctca gaagatttca aatgtatgga agctctgggc  840
atggaatcag gagaaattca ttctgaccag atcacagctt cttcccagta tagcaccaac  900
tggtctgcag agcgctcccg cctgaactac cctgagaatg ggtggactcc cggagaggat  960
tcctaccgag agtggataca ggtagacttg ggccttctgc gctttgtcac ggctgtcggg  1020
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
actcgatttg tccgaatcaa gcctgcaact tgggaaactg gcatatctat gagatttgaa  1260
gtatatggtt gcnnnnnnnn nnnnnnnnnn nnnnnnnnnn nnnnnnnnnn nnnnnnnnnn  1320
nnnnnnnnnn nnnnnnnnnn nnnnnnnnnn nnnnnnnnnn nnnnnnnnnn nnnnnnnnnn  1380
nnnnnnnnnn nnnnnnnnnn nnnnnnnnnn nnnnnnnnnn nnnnnnnnnn nnnnnnnnnn  1440
nnnnnnnnnn nnnnnnnnnn nnnnnnnnnn nnnnnnnnnn nnnnnnnnnn nnnnnnnnnn  1500
nnnnnnnnnn nnnnnnnnnn nnnnnnnnnn nnnnnnnnnn nnnnnnnnnn nnnnnnnnnn  1560
nnnnnnnnnn nnnnnnnnnn nnnnnnnnnn nnnnnnnnnn nnnnnnnnnn nnnnnnnnnn  1620
nnnnnnnnnn nnnnnnnnnn nnnnnnnnnn nnnnnnnnnn nnnnnnnnnn nnnnnnnnnn  1680
```

```
nnnnnnnnnn nnnnnnnnnn nnnnnnnnnn nnnnnnnnnn nnnnnnnnnn nnnnnnnnnn  1740
nnnnnnnnnn nnnnnnnnnn nnnnnnnnnn nnnnnnnnnn nnnnnnnnnn nnnnnnnnnn  1800
nnnnnnnnnn nnnnnnnnnn nnnnnnnnnn nnnnnnnnnn nnnnnnnnnn nnnnnnnnnn  1860
nnnnnnnnnn nnnnnnnnnn nnnnnnnnnn nnnnnnnnnn nnnnnnnnnn nnnnnnnnnn  1920
nnnnnnnnnn nnnnnnnnnn nnnnnnnnnn nnnnnnnnnn nnnnnnnnnn nnnnnnnnnn  1980
nnnnnnnnnn nnnnnnnnnn nnnnnnnnnn nnnnnnnnnn nnnnnnnnnn nnnnnnnnnn  2040
nnnnnnnnnn nnnnnnnnnn nnnnnnnnnn nnnnnnnnnn nnnnnnnnnn nnnnnnnnnn  2100
nnnnnnnnnn nnnnnnnnnn nnnnnnnnnn nnnnnnnnnn nnnnnnnnnn nnnnnnnnnn  2160
nnnnnnnnnn nnnnnnnnnn nnnnnnnnnn nnnnnnnnnn nnnnnnnnnn nnnnnnnnnn  2220
nnnnnnnnnn nnnnnnnnnn nnnnnnnnnn nnnnnnnnnn nnnnnnnnnn nnnnnnnnnn  2280
nnnnnnnnnn nnnnnnnnnn nnnnnnnnnn nnnnnnnnnn nnnnnnnnnn nnnnnnnnnn  2340
nnnnnnnnnn nnnnnnnnnn nnnnnnnnnn nnnnnnnnnn nnnnnnnnnn nnnnnnnnnn  2400
nnnnnnnnnn nnnnnnnnnn nnnnnnnnnn nnnnnnnnnn nnnnnnnnnn nnnnnnnnnn  2460
nnnnnnnnnn nnnnnnnnnn nnnnnnnnnn nnnnnnnnnn nnnnnnnnnn nnnnnnnnnn  2520
nnnnnnnnnn nnnnnnnnnn nnnnnnnnnn nnnnnnnnnn nnnnnnnnnn nnnngacaaa  2580
actcacacat gcccaccgtg cccagcacct gaactcctgg ggggaccgtc agtcttcctc  2640
ttccccccaa aacccaagga caccctcatg atctcccgga cccctgaggt cacatgcgtg  2700
gtggtggacg tgagccacga agaccctgag gtcaagttca actggtacgt ggacggcgtg  2760
gaggtgcata atgccaagac aaagccgcgg gaggagcagt acaacagcac gtaccgtgtg  2820
gtcagcgtcc tcaccgtcct gcaccaggac tggctgaatg gcaaggagta caagtgcaag  2880
gtctccaaca aagccctccc agcccccatc gagaaaacca tctccaaagc caaagggcag  2940
ccccgagaac cacaggtgta caccctgccc ccatcccggg aggagatgac caagaaccag  3000
gtcagcctga cctgcctggt caaaggcttc tatcccagcg acatcgccgt ggagtgggag  3060
agcaatgggc agccggagaa caactacaag accacgcctc ccgtgctgga ctccgacggc  3120
tccttcttcc tctacagcaa gctcaccgtg gacaagagca ggtggcagca ggggaacgtc  3180
ttctcatgct ccgtgatgca cgaggctctg cacaaccact acacgcagaa gagcctctcc  3240
ctgtctccgg gtaaa                                                   3255

SEQ ID NO: 7           moltype = AA  length = 1064
FEATURE                Location/Qualifiers
REGION                 1..1064
                       note = Synthetic polypeptide
REGION                 245..837
                       note = misc_feature - Xaa can be any naturally occurring
                        amino acid
source                 1..1064
                       mol_type = protein
                       organism = synthetic construct
SEQUENCE: 7
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLXXXXXX XXXXXXXXXX XXXXXXXXXX XXXXXXXXXX XXXXXXXXXX XXXXXXXXXX  300
XXXXXXXXXX XXXXXXXXXX XXXXXXXXXX XXXXXXXXXX XXXXXXXXXX XXXXXXXXXX  360
XXXXXXXXXX XXXXXXXXXX XXXXXXXXXX XXXXXXXXXX XXXXXXXXXX XXXXXXXXXX  420
XXXXXXXXXX XXXXXXXXXX XXXXXXXXXX XXXXXXXXXX XXXXXXXXXX XXXXXXXXXX  480
XXXXXXXXXX XXXXXXXXXX XXXXXXXXXX XXXXXXXXXX XXXXXXXXXX XXXXXXXXXX  540
XXXXXXXXXX XXXXXXXXXX XXXXXXXXXX XXXXXXXXXX XXXXXXXXXX XXXXXXXXXX  600
XXXXXXXXXX XXXXXXXXXX XXXXXXXXXX XXXXXXXXXX XXXXXXXXXX XXXXXXXXXX  660
XXXXXXXXXX XXXXXXXXXX XXXXXXXXXX XXXXXXXXXX XXXXXXXXXX XXXXXXXXXX  720
XXXXXXXXXX XXXXXXXXXX XXXXXXXXXX XXXXXXXXXX XXXXXXXXXX XXXXXXXXXX  780
XXXXXXXXXX XXXXXXXXXX XXXXXXXXXX XXXXXXXXXX XXXXXXXXXX XXXXXXXDKT  840
HTCPPCPAPE LLGGPSVFLF PPKPKDTLMI SRTPEVTCVV VDVSHEDPEV KFNWYVDGVE  900
VHNAKTKPRE EQYNSTYRVV SVLTVLHQDW LNGKEYKCKV SNKALPAPIE KTISKAKGQP  960
REPQVYTLPP SREEMTKNQV SLTCLVKGFY PSDIAVEWES NGQPENNYKT TPPVLDSDGS  1020
FFLYSKLTVD KSRWQQGNVF SCSVMHEALH NHYTQKSLSL SPGK                  1064

SEQ ID NO: 8           moltype = DNA  length = 3255
FEATURE                Location/Qualifiers
misc_feature           1..3255
                       note = Synthetic polynucleotide
misc_feature           796..2574
                       note = n is a, c, g, or t
source                 1..3255
                       mol_type = other DNA
                       organism = synthetic construct
SEQUENCE: 8
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccagggggga tgttctgtcg ctacgaccgg ctagaaatct gggatggatt ccctgatgtt  660
```

```
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgnnnnn nnnnnnnnnn nnnnnnnnnn nnnnnnnnnn nnnnnnnnnn  840
nnnnnnnnnn nnnnnnnnnn nnnnnnnnnn nnnnnnnnnn nnnnnnnnnn nnnnnnnnnn  900
nnnnnnnnnn nnnnnnnnnn nnnnnnnnnn nnnnnnnnnn nnnnnnnnnn nnnnnnnnnn  960
nnnnnnnnnn nnnnnnnnnn nnnnnnnnnn nnnnnnnnnn nnnnnnnnnn nnnnnnnnnn  1020
nnnnnnnnnn nnnnnnnnnn nnnnnnnnnn nnnnnnnnnn nnnnnnnnnn nnnnnnnnnn  1080
nnnnnnnnnn nnnnnnnnnn nnnnnnnnnn nnnnnnnnnn nnnnnnnnnn nnnnnnnnnn  1140
nnnnnnnnnn nnnnnnnnnn nnnnnnnnnn nnnnnnnnnn nnnnnnnnnn nnnnnnnnnn  1200
nnnnnnnnnn nnnnnnnnnn nnnnnnnnnn nnnnnnnnnn nnnnnnnnnn nnnnnnnnnn  1260
nnnnnnnnnn nnnnnnnnnn nnnnnnnnnn nnnnnnnnnn nnnnnnnnnn nnnnnnnnnn  1320
nnnnnnnnnn nnnnnnnnnn nnnnnnnnnn nnnnnnnnnn nnnnnnnnnn nnnnnnnnnn  1380
nnnnnnnnnn nnnnnnnnnn nnnnnnnnnn nnnnnnnnnn nnnnnnnnnn nnnnnnnnnn  1440
nnnnnnnnnn nnnnnnnnnn nnnnnnnnnn nnnnnnnnnn nnnnnnnnnn nnnnnnnnnn  1500
nnnnnnnnnn nnnnnnnnnn nnnnnnnnnn nnnnnnnnnn nnnnnnnnnn nnnnnnnnnn  1560
nnnnnnnnnn nnnnnnnnnn nnnnnnnnnn nnnnnnnnnn nnnnnnnnnn nnnnnnnnnn  1620
nnnnnnnnnn nnnnnnnnnn nnnnnnnnnn nnnnnnnnnn nnnnnnnnnn nnnnnnnnnn  1680
nnnnnnnnnn nnnnnnnnnn nnnnnnnnnn nnnnnnnnnn nnnnnnnnnn nnnnnnnnnn  1740
nnnnnnnnnn nnnnnnnnnn nnnnnnnnnn nnnnnnnnnn nnnnnnnnnn nnnnnnnnnn  1800
nnnnnnnnnn nnnnnnnnnn nnnnnnnnnn nnnnnnnnnn nnnnnnnnnn nnnnnnnnnn  1860
nnnnnnnnnn nnnnnnnnnn nnnnnnnnnn nnnnnnnnnn nnnnnnnnnn nnnnnnnnnn  1920
nnnnnnnnnn nnnnnnnnnn nnnnnnnnnn nnnnnnnnnn nnnnnnnnnn nnnnnnnnnn  1980
nnnnnnnnnn nnnnnnnnnn nnnnnnnnnn nnnnnnnnnn nnnnnnnnnn nnnnnnnnnn  2040
nnnnnnnnnn nnnnnnnnnn nnnnnnnnnn nnnnnnnnnn nnnnnnnnnn nnnnnnnnnn  2100
nnnnnnnnnn nnnnnnnnnn nnnnnnnnnn nnnnnnnnnn nnnnnnnnnn nnnnnnnnnn  2160
nnnnnnnnnn nnnnnnnnnn nnnnnnnnnn nnnnnnnnnn nnnnnnnnnn nnnnnnnnnn  2220
nnnnnnnnnn nnnnnnnnnn nnnnnnnnnn nnnnnnnnnn nnnnnnnnnn nnnnnnnnnn  2280
nnnnnnnnnn nnnnnnnnnn nnnnnnnnnn nnnnnnnnnn nnnnnnnnnn nnnnnnnnnn  2340
nnnnnnnnnn nnnnnnnnnn nnnnnnnnnn nnnnnnnnnn nnnnnnnnnn nnnnnnnnnn  2400
nnnnnnnnnn nnnnnnnnnn nnnnnnnnnn nnnnnnnnnn nnnnnnnnnn nnnnnnnnnn  2460
nnnnnnnnnn nnnnnnnnnn nnnnnnnnnn nnnnnnnnnn nnnnnnnnnn nnnnnnnnnn  2520
nnnnnnnnnn nnnnnnnnnn nnnnnnnnnn nnnnnnnnnn nnnnnnnnnn nnnngacaaa  2580
actcacacat gcccaccgtg cccagcacct gaactcctgg ggggaccgtc agtcttcctc  2640
ttccccccaa aacccaagga caccctcatg atctcccgga cccctgaggt cacatgcgtg  2700
gtggtggacg tgagccacga agaccctgag gtcaagttca actggtacgt ggacggcgtg  2760
gaggtgcata atgccaagac aaagccgcgg gaggagcagt acaacagcac gtaccgtgtg  2820
gtcagcgtcc tcaccgtcct gcaccaggac tggctgaatg gcaaggagta caagtgcaag  2880
gtctccaaca aagccctccc agcccccatc gagaaaacca tctccaaagc caaagggcag  2940
ccccgagaac cacaggtgta caccctgccc ccatcccggg aggagatgac caagaaccag  3000
gtcagcctga cctgcctggt caaaggcttc tatcccagcg acatcgccgt ggagtgggag  3060
agcaatgggc agccggagaa caactacaag accacgcctc ccgtgctgga ctccgacggc  3120
tccttcttcc tctacagcaa gctcaccgtg gacaagagca ggtggcagca ggggaacgtc  3180
ttctcatgct ccgtgatgca cgaggctctg cacaaccact acacgcagaa gagcctctcc  3240
ctgtctccgg gtaaa                                                   3255

SEQ ID NO: 9          moltype = AA  length = 791
FEATURE               Location/Qualifiers
REGION                1..791
                      note = Synthetic polypeptide
source                1..791
                      mol_type = protein
                      organism = synthetic construct
SEQUENCE: 9
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLQSSVSE DFKCMEALGM ESGEIHSDQI TASSQYSTNW SAERSRLNYP ENGWTPGEDS  300
YREWIQVDLG LLRFVTAVGT QGAISKETKK KYYVKTYKID VSSNGEDWIT IKEGNKPVLF  360
QGNTNPTDVV VAVFPKPLIT RFVRIKPATW ETGISMRFEV YGCKITDYPC SGMLGMVSGL  420
ISDSQITSSN QGDRNWMPEN IRLVTSRSGW ALPPAPHSYI NEWLQIDLGE EKIVRGIIIQ  480
GGKHRENKVF MRKFKIGYSN NGSDWKMIMD DSKRKAKSFE GNNNYDTPEL RTFPALSTRF  540
IRIYPERATH GGLGLRMELL GCRSDKTHTC PPCPAPELLG GPSVFLFPPK PKDTLMISRT  600
PEVTCVVVDV SHEDPEVKFN WYVDGVEVHN AKTKPREEQY NSTYRVVSVL TVLHQDWLNG  660
KEYKCKVSNK ALPAPIEKTI SKAKGQPREP QVYTLPPSRE EMTKNQVSLT CLVKGFYPSD  720
IAVEWESNGQ PENNYKTTPP VLDSDGSFFL YSKLTVDKSR WQQGNVFSCS VMHEALHNHY  780
TQKSLSLSPG K                                                       791

SEQ ID NO: 10         moltype = DNA  length = 2436
FEATURE               Location/Qualifiers
misc_feature          1..2436
                      note = Synthetic polynucleotide
source                1..2436
                      mol_type = other DNA
                      organism = synthetic construct
SEQUENCE: 10
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
```

```
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccaggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgcagag cagtgtctca gaagatttca aatgtatgga agctctgggc  840
atggaatcag gagaaattca ttctgaccag atcacagctt cttcccagta tagcaccaac  900
tggtctgcag agcgctcccg cctgaactac cctgagaatg ggtggactcc cggagaggat  960
tcctaccgag agtggataca ggtagacttg ggccttctgc gctttgtcac ggctgtcggg  1020
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
actcgatttg tccgaatcaa gcctgcaact tgggaaactg gcatatctat gagatttgaa  1260
gtatatggtt gcaagataac agattatcct tgctctggaa tgttgggtat ggtgtctgga  1320
cttatttctg actcccagat cacatcatcc aaccaagggg acagaaactg gatgcctgaa  1380
aacatccgcc tggtaaccag tcgctctggc tgggcacttc cacccgcacc tcattcctac  1440
atcaatgagt ggctccaaat agacctgggg gaggagaaga tcgtgagggg catcatcatt  1500
cagggtggga agcaccgaga gaacaaggtg ttcatgagga agttcaagat cgggtacagc  1560
aacaacggct cggactggaa gatgatcatg gatgacagca aacgcaaggc gaagtctttt  1620
gagggcaaca acaactatga tacacctgag ctgcggactt ttccagctct ctccacgcga  1680
ttcatcagga tctaccccga gagagccact catggcggac tggggctcag aatggagctg  1740
ctgggctgta gatctgacaa aactcacaca tgcccaccgt gcccagcacc tgaactcctg  1800
gggggaccgt cagtcttcct cttcccccca aaacccaagg acaccctcat gatctcccgg  1860
acccctgagg tcacatgcgt ggtggtggac gtgagccacg aagaccctga ggtcaagttc  1920
aactggtacg tggacggcgt ggaggtgcat aatgccaaga caaagccgcg ggaggagcag  1980
tacaacagca cgtaccgtgt ggtcagcgtc ctcaccgtcc tgcaccagga ctggctgaat  2040
ggcaaggagt acaagtgcaa ggtctccaac aaagccctcc cagcccccat cgagaaaacc  2100
atctccaaag ccaaagggca gccccgagaa ccacaggtgt acaccctgcc cccatcccgg  2160
gaggagatga ccaagaacca ggtcagcctg acctgcctgg tcaaaggctt ctatcccagc  2220
gacatcgccg tggagtggga gagcaatggg cagccggaga acaactacaa gaccacgcct  2280
cccgtgctgg actccgacgg ctccttcttc ctctacagca agctcaccgt ggacaagagc  2340
aggtggcagc aggggaacgt cttctcatgc tccgtgatgc acgaggctct gcacaaccac  2400
tacacgcaga agagcctctc cctgtctccg ggtaaa                            2436
```

```
SEQ ID NO: 11          moltype = AA  length = 632
FEATURE                Location/Qualifiers
REGION                 1..632
                       note = Synthetic polypeptide
source                 1..632
                       mol_type = protein
                       organism = synthetic construct
SEQUENCE: 11
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLQSSVSE DFKCMEALGM ESGEIHSDQI TASSQYSTNW SAERSRLNYP ENGWTPGEDS  300
YREWIQVDLG LLRFVTAVGT QGAISKETKK KYYVKTYKID VSSNGEDWIT IKEGNKPVLF  360
QGNTNPTDVV VAVFPKPLIT RFVRIKPATW ETGISMRFEV YGCRSDKTHT CPPCPAPELL  420
GGPSVFLFPP KPKDTLMISR TPEVTCVVVD VSHEDPEVKF NWYVDGVEVH NAKTKPREEQ  480
YNSTYRVVSV LTVLHQDWLN GKEYKCKVSN KALPAPIEKT ISKAKGQPRE PQVYTLPPSR  540
EEMTKNQVSL TCLVKGFYPS DIAVEWESNG QPENNYKTTP PVLDSDGSFF LYSKLTVDKS  600
RWQQGNVFSC SVMHEALHNH YTQKSLSLSP GK                                632
```

```
SEQ ID NO: 12          moltype = DNA  length = 1959
FEATURE                Location/Qualifiers
misc_feature           1..1959
                       note = Synthetic polynucleotide
source                 1..1959
                       mol_type = other DNA
                       organism = synthetic construct
SEQUENCE: 12
atggagaggg ggctgccgct cctctgcgcc gtgctcgccc tcgtcctcgc ccccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccaggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
```

```
ggcattctct ccatggtttt ttacaccgac agcgcgatag caaaagaagg tttctcagca  780
aactacagtg tcttgcagag cagtgtctca gaagatttca aatgtatgga agctctgggc  840
atggaatcag gagaaattca ttctgaccag atcacagctt cttcccagta tagcaccaac  900
tggtctgcag agcgctcccg cctgaactac cctgagaatg ggtggactcc cggagaggat  960
tcctaccgag agtggataca ggtagacttg ggccttctgc gctttgtcac ggctgtcggg  1020
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
actcgatttg tccgaatcaa gcctgcaact tgggaaactg gcatatctat gagatttgaa  1260
gtatatggtt gcagatctga caaaactcac acatgcccac cgtgcccagc acctgaactc  1320
ctggggggac cgtcagtctt cctcttcccc ccaaaaccca aggacaccct catgatctcc  1380
cggacccctg aggtcacatg cgtggtggtg gacgtgagcc acgaagaccc tgaggtcaag  1440
ttcaactggt acgtggacgg cgtggaggtg cataatgcca agacaaagcc gcgggaggag  1500
cagtacaaca gcacgtaccg tgtggtcagc gtcctcaccg tcctgcacca ggactggctg  1560
aatggcaagg agtacaagtg caaggtctcc aacaaagccc tcccagcccc catcgagaaa  1620
accatctcca aagccaaagg gcagccccga gaaccacagg tgtacaccct gcccccatcc  1680
cgggaggaga tgaccaagaa ccaggtcagc ctgacctgcc tggtcaaagg cttctatccc  1740
agcgacatcg ccgtggagtg ggagagcaat gggcagccgg agaacaacta caagaccacg  1800
cctcccgtgc tggactccga cggctccttc ttcctctaca gcaagctcac cgtggacaag  1860
agcaggtggc agcaggggaa cgtcttctca tgctccgtga tgcacgaggc tctgcacaac  1920
cactacacgc agaagagcct ctccctgtct ccgggtaaa                         1959

SEQ ID NO: 13          moltype = AA  length = 473
FEATURE                Location/Qualifiers
REGION                 1..473
                       note = Synthetic polypeptide
source                 1..473
                       mol_type = protein
                       organism = synthetic construct
SEQUENCE: 13
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLRSDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS REEMTKNQVS LTCLVKGFYP SDIAVEWESN GQPENNYKTT  420
PPVLDSDGSF FLYSKLTVDK SRWQQGNVFS CSVMHEALHN HYTQKSLSLS PGK         473

SEQ ID NO: 14          moltype = DNA  length = 1482
FEATURE                Location/Qualifiers
misc_feature           1..1482
                       note = Synthetic polynucleotide
source                 1..1482
                       mol_type = other DNA
                       organism = synthetic construct
SEQUENCE: 14
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccagggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgagatc tgacaaaact cacacatgcc caccgtgccc agcacctgaa  840
ctcctggggg gaccgtcagt cttcctcttc cccccaaaac ccaaggacac cctcatgatc  900
tcccggaccc ctgaggtcac atgcgtggtg gtggacgtga gccacgaaga ccctgaggtc  960
aagttcaact ggtacgtgga cggcgtggag gtgcataatg ccaagacaaa gccgcgggag  1020
gagcagtaca acagcacgta ccgtgtggtc agcgtcctca ccgtcctgca ccaggactgg  1080
ctgaatggca aggagtacaa gtgcaaggtc tccaacaaag ccctcccagc ccccatcgag  1140
aaaaccatct ccaaagccaa agggcagccc cgagaaccac aggtgtacac cctgccccca  1200
tcccgggagg agatgaccaa gaaccaggtc agcctgacct gcctggtcaa aggcttctat  1260
cccagcgaca tcgccgtgga gtgggagagc aatgggcagc cggagaacaa ctacaagacc  1320
acgcctcccg tgctggactc cgacggctcc ttcttcctct acagcaagct caccgtggac  1380
aagagcaggt ggcagcaggg gaacgtcttc tcatgctccg tgatgcacga ggctctgcac  1440
aaccactaca cgcagaagag cctctccctg tctccgggta aa                     1482

SEQ ID NO: 15          moltype = AA  length = 1064
FEATURE                Location/Qualifiers
REGION                 1..1064
                       note = Synthetic polypeptide
source                 1..1064
                       mol_type = protein
```

```
                        organism = synthetic construct
SEQUENCE: 15
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLQSSVSE DFKCMEALGM ESGEIHSDQI TASSQASTNW SAERSRLNYP ENGWTPGEDS  300
YREWIQVDLG LLRFVTAVGT QGAISKETKK KYYVKTYKID VSSNGEDWIT IKEGNKPVLF  360
QGNTNPTDVV VAVFPKPLIT RFVRIKPATW ETGISMRFEV YGCKITDYPC SGMLGMVSGL  420
ISDSQITSSN QGDRNWMPEN IRLVTSRSGW ALPPAPHSYI NEWLQIDLGE EKIVRGIIIQ  480
GGKHRENKVF MRKFKIGYSN NGSDWKMIMD DSKRKAKSFE GNNNYDTPEL RTFPALSTRF  540
IRIYPERATH GGLGLRMELL GCEVEAPTAG PTTPNGNLVD ECDDDQANCH SGTGDDFQLT  600
GGTTVLATEK PTVIDSTIQS EFPTYGFNCE FGWGSHKTFC HWEHDNHVQL KWSVLTSKTG  660
PIQDHTGDGN FIYSQADENQ KGKVARLVSP VVYSQNSAHC MTFWYHMSGS HVGTLRVKLR  720
YQKPEEYDQL VWMAIGHQGD HWKEGRVLLH KSLKLYQVIF EGEIGKGNLG GIAVDDISIN  780
NHISQEDCAK PADLDKKNPE IKIDETGSTP GYEGEGEGDK NISRKPGNVL KTLDPRSDKT  840
HTCPPCPAPE LLGGPSVFLF PPKPKDTLMI SRTPEVTCVV VDVSHEDPEV KFNWYVDGVE  900
VHNAKTKPRE EQYNSTYRVV SVLTVLHQDW LNGKEYKCKV SNKALPAPIE KTISKAKGQP  960
REPQVYTLPP SREEMTKNQV SLTCLVKGFY PSDIAVEWES NGQPENNYKT TPPVLDSDGS  1020
FFLYSKLTVD KSRWQQGNVF SCSVMHEALH NHYTQKSLSL SPGK                  1064

SEQ ID NO: 16           moltype = DNA  length = 3255
FEATURE                 Location/Qualifiers
misc_feature            1..3255
                        note = Synthetic polynucleotide
source                  1..3255
                        mol_type = other DNA
                        organism = synthetic construct
SEQUENCE: 16
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccagggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgcagag cagtgtctca gaagatttca aatgtatgga agctctgggc  840
atggaatcag gagaaattca ttctgaccag atcacagctt cttcccaggc tagcaccaac  900
tggtctgcag agcgctcccg cctgaactac cctgagaatg ggtggactcc cggagaggat  960
tcctaccgag agtggataca ggtagacttg ggccttctgc gctttgtcac ggctgtcggg  1020
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
actcgatttg tccgaatcaa gcctgcaact tgggaaactg gcatatctat gagatttgaa  1260
gtatatggtt gcaagataac agattatcct tgctctggaa tgttgggtat ggtgtctgga  1320
cttatttctg actcccagat cacatcatcc aaccaagggg acagaaactg gatgcctgaa  1380
aacatccgcc tggtaaccag tcgctctggc tgggcacttc cacccgcacc tcattcctac  1440
atcaatgagt ggctccaaat agacctgggg gaggagaaga tcgtgagggg catcatcatt  1500
cagggtggga agcaccgaga gaacaaggtg ttcatgagga agttcaagat cgggtacagc  1560
aacaacggct cggactggaa gatgatcatg gatgacagca aacgcaaggc gaagtctttt  1620
gagggcaaca acaactatga tacacctgag ctgcggactt ttccagctct ctccacgcga  1680
ttcatcagga tctaccccga gagagccact catggcggac tggggctcag aatggagctg  1740
ctgggctgtg aagtggaagc ccctacagct ggaccgacca ctcccaacgg gaacttggtg  1800
gatgaatgtg atgacgacca ggccaactgc cacagtggaa caggtgatga cttccagctc  1860
acaggtggca ccactgtgct ggccacagaa aagcccacgg tcatagacag caccatacaa  1920
tcagagtttc caacatatgg ttttaactgt gaatttggct ggggctctca caagaccttc  1980
tgccactggg aacatgacaa tcacgtgcag ctcaagtgga gtgtgttgac cagcaagacg  2040
ggacccattc aggatcacac aggagatggc aacttcatct attcccaagc tgacgaaaat  2100
cagaagggca aagtggctcg cctggtgagc cctgtggttt attcccagaa ctctgcccac  2160
tgcatgacct tctggtatca catgtctggg tcccacgtcg gcacactcag ggtcaaactg  2220
cgctaccaga agccagagga gtacgatcag ctggtctgga tggccattgg acaccaaggt  2280
gaccactgga aggaagggcg tgtcttgctc cacaagtctc tgaaacttta tcaggtgatt  2340
ttcgagggcg aaatcggaaa aggaaacctt ggtgggattg ctgtggatga cattagtatt  2400
aataaccaca tttcacaaga agattgtgca aaaccagcag acctggataa aaagaaccca  2460
gaaattaaaa ttgatgaaac agggagcacg ccaggatacg aaggtgaagg agaaggtgac  2520
aagaacatct ccaggaagcc aggcaatgtg ttgaagacct tagaccccag atctgacaaa  2580
actcacacat gcccaccgtg cccagcacct gaactcctgg ggggaccgtc agtcttcctc  2640
ttccccccaa aacccaagga caccctcatg atctcccgga cccctgaggt cacatgcgtg  2700
gtggtggacg tgagccacga agaccctgag gtcaagttca actggtacgt ggacggcgtg  2760
gaggtgcata atgccaagac aaagccgcgg gaggagcagt acaacagcac gtaccgtgtg  2820
gtcagcgtcc tcaccgtcct gcaccaggac tggctgaatg gcaaggagta caagtgcaag  2880
gtctccaaca aagccctccc agcccccatc gagaaaacca tctccaaagc caaagggcag  2940
ccccgagaac cacaggtgta caccctgccc ccatcccggg aggagatgac caagaaccag  3000
```

```
gtcagcctga cctgcctggt caaaggcttc tatcccagcg acatcgccgt ggagtgggag  3060
agcaatgggc agccggagaa caactacaag accacgcctc ccgtgctgga ctccgacggc  3120
tccttcttcc tctacagcaa gctcaccgtg gacaagagca ggtggcagca ggggaacgtc  3180
ttctcatgct ccgtgatgca cgaggctctg cacaaccact acacgcagaa gagcctctcc  3240
ctgtctccgg gtaaa                                                   3255

SEQ ID NO: 17           moltype = AA  length = 1064
FEATURE                 Location/Qualifiers
REGION                  1..1064
                        note = Synthetic polypeptide
REGION                  563..837
                        note = misc_feature - Xaa can be any naturally occurring
                         amino acid
source                  1..1064
                        mol_type = protein
                        organism = synthetic construct
SEQUENCE: 17
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLQSSVSE DFKCMEALGM ESGEIHSDQI TASSQASTNW SAERSRLNYP ENGWTPGEDS  300
YREWIQVDLG LLRFVTAVGT QGAISKETKK KYYVKTYKID VSSNGEDWIT IKEGNKPVLF  360
QGNTNPTDVV VAVFPKPLIT RFVRIKPATW ETGISMRFEV YGCKITDYPC SGMLGMVSGL  420
ISDSQITSSN QGDRNWMPEN IRLVTSRSGW ALPPAPHSYI NEWLQIDLGE EKIVRGIIIQ  480
GGKHRENKVF MRKFKIGYSN NGSDWKMIMD DSKRKAKSFE GNNNYDTPEL RTFPALSTRF  540
IRIYPERATH GGLGLRMELL GCXXXXXXXX XXXXXXXXXX XXXXXXXXXX XXXXXXXXXX  600
XXXXXXXXXX XXXXXXXXXX XXXXXXXXXX XXXXXXXXXX XXXXXXXXXX XXXXXXXXXX  660
XXXXXXXXXX XXXXXXXXXX XXXXXXXXXX XXXXXXXXXX XXXXXXXXXX XXXXXXXXXX  720
XXXXXXXXXX XXXXXXXXXX XXXXXXXXXX XXXXXXXXXX XXXXXXXXXX XXXXXXXXXX  780
XXXXXXXXXX XXXXXXXXXX XXXXXXXXXX XXXXXXXXXX XXXXXXXXXX XXXXXXXDKT  840
HTCPPCPAPE LLGGPSVFLF PPKPKDTLMI SRTPEVTCVV VDVSHEDPEV KFNWYVDGVE  900
VHNAKTKPRE EQYNSTYRVV SVLTVLHQDW LNGKEYKCKV SNKALPAPIE KTISKAKGQP  960
REPQVYTLPP SREEMTKNQV SLTCLVKGFY PSDIAVEWES NGQPENNYKT TPPVLDSDGS  1020
FFLYSKLTVD KSRWQQGNVF SCSVMHEALH NHYTQKSLSL SPGK                  1064

SEQ ID NO: 18           moltype = DNA  length = 3255
FEATURE                 Location/Qualifiers
misc_feature            1..3255
                        note = Synthetic polynucleotide
misc_feature            1750..2574
                        note = n is a, c, g, or t
source                  1..3255
                        mol_type = other DNA
                        organism = synthetic construct
SEQUENCE: 18
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccagggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgcagag cagtgtctca gaagatttca aatgtatgga agctctgggc  840
atggaatcag gagaaattca ttctgaccag atcacagctt cttcccaggc tagcaccaac  900
tggtctgcag agcgctcccg cctgaactac cctgagaatg ggtggactcc cggagaggat  960
tcctaccgag agtggataca ggtagacttg ggccttctgc gctttgtcac ggctgtcggg  1020
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
actcgatttg tccgaatcaa gcctgcaact tgggaaactg gcatatctat gagatttgaa  1260
gtatatggtt gcaagataac agattatcct tgctctggaa tgttgggtat ggtgtctgga  1320
cttatttctg actcccagat cacatcatcc aaccaagggg acagaaactg gatgcctgaa  1380
aacatccgcc tggtaaccag tcgctctggc tgggcacttc caccccgcacc tcattcctac  1440
atcaatgagt ggctccaaat agacctgggg gaggagaaga tcgtgagggg catcatcatt  1500
cagggtggga agcaccgaga gaacaaggtg ttcatgagga agttcaagat cgggtacagc  1560
aacaacggct cggactggaa gatgatcatg gatgacagca aacgcaaggc gaagtctttt  1620
gagggcaaca acaactatga tacacctgag ctgcggactt ttccagctct ctccacgcga  1680
ttcatcagga tctaccccga gagagccact catggcggac tggggctcag aatggagctg  1740
ctgggctgtn nnnnnnnnnn nnnnnnnnnn nnnnnnnnnn nnnnnnnnnn nnnnnnnnnn  1800
nnnnnnnnnn nnnnnnnnnn nnnnnnnnnn nnnnnnnnnn nnnnnnnnnn nnnnnnnnnn  1860
nnnnnnnnnn nnnnnnnnnn nnnnnnnnnn nnnnnnnnnn nnnnnnnnnn nnnnnnnnnn  1920
nnnnnnnnnn nnnnnnnnnn nnnnnnnnnn nnnnnnnnnn nnnnnnnnnn nnnnnnnnnn  1980
```

```
nnnnnnnnnn nnnnnnnnnn nnnnnnnnnn nnnnnnnnnn nnnnnnnnnn nnnnnnnnnn  2040
nnnnnnnnnn nnnnnnnnnn nnnnnnnnnn nnnnnnnnnn nnnnnnnnnn nnnnnnnnnn  2100
nnnnnnnnnn nnnnnnnnnn nnnnnnnnnn nnnnnnnnnn nnnnnnnnnn nnnnnnnnnn  2160
nnnnnnnnnn nnnnnnnnnn nnnnnnnnnn nnnnnnnnnn nnnnnnnnnn nnnnnnnnnn  2220
nnnnnnnnnn nnnnnnnnnn nnnnnnnnnn nnnnnnnnnn nnnnnnnnnn nnnnnnnnnn  2280
nnnnnnnnnn nnnnnnnnnn nnnnnnnnnn nnnnnnnnnn nnnnnnnnnn nnnnnnnnnn  2340
nnnnnnnnnn nnnnnnnnnn nnnnnnnnnn nnnnnnnnnn nnnnnnnnnn nnnnnnnnnn  2400
nnnnnnnnnn nnnnnnnnnn nnnnnnnnnn nnnnnnnnnn nnnnnnnnnn nnnnnnnnnn  2460
nnnnnnnnnn nnnnnnnnnn nnnnnnnnnn nnnnnnnnnn nnnnnnnnnn nnnnnnnnnn  2520
nnnnnnnnnn nnnnnnnnnn nnnnnnnnnn nnnnnnnnnn nnnnnnnnnn nnnngacaaa  2580
actcacacat gcccaccgtg cccagcacct gaactcctgg ggggaccgtc agtcttcctc  2640
ttccccccaa aacccaagga caccctcatg atctcccgga cccctgaggt cacatgcgtg  2700
gtggtggacg tgagccacga agaccctgag gtcaagttca actggtacgt ggacggcgtg  2760
gaggtgcata atgccaagac aaagccgcgg gaggagcagt acaacagcac gtaccgtgtg  2820
gtcagcgtcc tcaccgtcct gcaccaggac tggctgaatg gcaaggagta caagtgcaag  2880
gtctccaaca aagccctccc agcccccatc gagaaaacca tctccaaagc caaagggcag  2940
ccccgagaac cacaggtgta caccctgccc ccatcccggg aggagatgac caagaaccag  3000
gtcagcctga cctgcctggt caaaggcttc tatcccagcg acatcgccgt ggagtgggag  3060
agcaatgggc agccggagaa caactacaag accacgcctc ccgtgctgga ctccgacggc  3120
tccttcttcc tctacagcaa gctcaccgtg gacaagagca ggtggcagca ggggaacgtc  3180
ttctcatgct ccgtgatgca cgaggctctg cacaaccact acacgcagaa gagcctctcc  3240
ctgtctccgg gtaaa                                                   3255

SEQ ID NO: 19          moltype = AA  length = 1064
FEATURE                Location/Qualifiers
REGION                 1..1064
                       note = Synthetic polypeptide
REGION                 404..837
                       note = misc_feature - Xaa can be any naturally occurring
                        amino acid
source                 1..1064
                       mol_type = protein
                       organism = synthetic construct
SEQUENCE: 19
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLQSSVSE DFKCMEALGM ESGEIHSDQI TASSQASTNW SAERSRLNYP ENGWTPGEDS  300
YREWIQVDLG LLRFVTAVGT QGAISKETKK KYYVKTYKID VSSNGEDWIT IKEGNKPVLF  360
QGNTNPTDVV VAVFPKPLIT RFVRIKPATW ETGISMRFEV YGCXXXXXXX XXXXXXXXXX  420
XXXXXXXXXX XXXXXXXXXX XXXXXXXXXX XXXXXXXXXX XXXXXXXXXX XXXXXXXXXX  480
XXXXXXXXXX XXXXXXXXXX XXXXXXXXXX XXXXXXXXXX XXXXXXXXXX XXXXXXXXXX  540
XXXXXXXXXX XXXXXXXXXX XXXXXXXXXX XXXXXXXXXX XXXXXXXXXX XXXXXXXXXX  600
XXXXXXXXXX XXXXXXXXXX XXXXXXXXXX XXXXXXXXXX XXXXXXXXXX XXXXXXXXXX  660
XXXXXXXXXX XXXXXXXXXX XXXXXXXXXX XXXXXXXXXX XXXXXXXXXX XXXXXXXXXX  720
XXXXXXXXXX XXXXXXXXXX XXXXXXXXXX XXXXXXXXXX XXXXXXXXXX XXXXXXXXXX  780
XXXXXXXXXX XXXXXXXXXX XXXXXXXXXX XXXXXXXXXX XXXXXXXXXX XXXXXXXDKT  840
HTCPPCPAPE LLGGPSVFLF PPKPKDTLMI SRTPEVTCVV VDVSHEDPEV KFNWYVDGVE  900
VHNAKTKPRE EQYNSTYRVV SVLTVLHQDW LNGKEYKCKV SNKALPAPIE KTISKAKGQP  960
REPQVYTLPP SREEMTKNQV SLTCLVKGFY PSDIAVEWES NGQPENNYKT TPPVLDSDGS  1020
FFLYSKLTVD KSRWQQGNVF SCSVMHEALH NHYTQKSLSL SPGK                  1064

SEQ ID NO: 20          moltype = DNA  length = 3255
FEATURE                Location/Qualifiers
misc_feature           1..3255
                       note = Synthetic polynucleotide
misc_feature           1273..2574
                       note = n is a, c, g, or t
source                 1..3255
                       mol_type = other DNA
                       organism = synthetic construct
SEQUENCE: 20
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttctttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccagggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgcagag cagtgtctca gaagatttca aatgtatgga agctctgggc  840
atggaatcag gagaaattca ttctgaccag atcacagctt cttcccaggc tagcaccaac  900
tggtctgcag agcgctcccg cctgaactac cctgagaatg ggtggactcc cggagaggat  960
```

```
tcctaccgag agtggataca ggtagacttg ggccttctgc gctttgtcac ggctgtcggg  1020
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
actcgatttg tccgaatcaa gcctgcaact tgggaaactg gcatatctat gagatttgaa  1260
gtatatggtt gcnnnnnnnn nnnnnnnnnn nnnnnnnnnn nnnnnnnnnn nnnnnnnnnn  1320
nnnnnnnnnn nnnnnnnnnn nnnnnnnnnn nnnnnnnnnn nnnnnnnnnn nnnnnnnnnn  1380
nnnnnnnnnn nnnnnnnnnn nnnnnnnnnn nnnnnnnnnn nnnnnnnnnn nnnnnnnnnn  1440
nnnnnnnnnn nnnnnnnnnn nnnnnnnnnn nnnnnnnnnn nnnnnnnnnn nnnnnnnnnn  1500
nnnnnnnnnn nnnnnnnnnn nnnnnnnnnn nnnnnnnnnn nnnnnnnnnn nnnnnnnnnn  1560
nnnnnnnnnn nnnnnnnnnn nnnnnnnnnn nnnnnnnnnn nnnnnnnnnn nnnnnnnnnn  1620
nnnnnnnnnn nnnnnnnnnn nnnnnnnnnn nnnnnnnnnn nnnnnnnnnn nnnnnnnnnn  1680
nnnnnnnnnn nnnnnnnnnn nnnnnnnnnn nnnnnnnnnn nnnnnnnnnn nnnnnnnnnn  1740
nnnnnnnnnn nnnnnnnnnn nnnnnnnnnn nnnnnnnnnn nnnnnnnnnn nnnnnnnnnn  1800
nnnnnnnnnn nnnnnnnnnn nnnnnnnnnn nnnnnnnnnn nnnnnnnnnn nnnnnnnnnn  1860
nnnnnnnnnn nnnnnnnnnn nnnnnnnnnn nnnnnnnnnn nnnnnnnnnn nnnnnnnnnn  1920
nnnnnnnnnn nnnnnnnnnn nnnnnnnnnn nnnnnnnnnn nnnnnnnnnn nnnnnnnnnn  1980
nnnnnnnnnn nnnnnnnnnn nnnnnnnnnn nnnnnnnnnn nnnnnnnnnn nnnnnnnnnn  2040
nnnnnnnnnn nnnnnnnnnn nnnnnnnnnn nnnnnnnnnn nnnnnnnnnn nnnnnnnnnn  2100
nnnnnnnnnn nnnnnnnnnn nnnnnnnnnn nnnnnnnnnn nnnnnnnnnn nnnnnnnnnn  2160
nnnnnnnnnn nnnnnnnnnn nnnnnnnnnn nnnnnnnnnn nnnnnnnnnn nnnnnnnnnn  2220
nnnnnnnnnn nnnnnnnnnn nnnnnnnnnn nnnnnnnnnn nnnnnnnnnn nnnnnnnnnn  2280
nnnnnnnnnn nnnnnnnnnn nnnnnnnnnn nnnnnnnnnn nnnnnnnnnn nnnnnnnnnn  2340
nnnnnnnnnn nnnnnnnnnn nnnnnnnnnn nnnnnnnnnn nnnnnnnnnn nnnnnnnnnn  2400
nnnnnnnnnn nnnnnnnnnn nnnnnnnnnn nnnnnnnnnn nnnnnnnnnn nnnnnnnnnn  2460
nnnnnnnnnn nnnnnnnnnn nnnnnnnnnn nnnnnnnnnn nnnnnnnnnn nnnnnnnnnn  2520
nnnnnnnnnn nnnnnnnnnn nnnnnnnnnn nnnnnnnnnn nnnnnnnnnn nnnngacaaa  2580
actcacacat gcccaccgtg cccagcacct gaactcctgg ggggaccgtc agtcttcctc  2640
ttccccccaa aacccaagga caccctcatg atctcccgga cccctgaggt cacatgcgtg  2700
gtggtggacg tgagccacga agaccctgag gtcaagttca actggtacgt ggacggcgtg  2760
gaggtgcata atgccaagac aaagccgcgg gaggagcagt acaacagcac gtaccgtgtg  2820
gtcagcgtcc tcaccgtcct gcaccaggac tggctgaatg gcaaggagta caagtgcaag  2880
gtctccaaca aagccctccc agcccccatc gagaaaacca tctccaaagc caaagggcag  2940
ccccgagaac cacaggtgta caccctgccc ccatcccggg aggagatgac caagaaccag  3000
gtcagcctga cctgcctggt caaaggcttc tatcccagcg acatcgccgt ggagtgggag  3060
agcaatgggc agccggagaa caactacaag accacgcctc ccgtgctgga ctccgacggc  3120
tccttcttcc tctacagcaa gctcaccgtg gacaagagca ggtggcagca ggggaacgtc  3180
ttctcatgct ccgtgatgca cgaggctctg cacaaccact acacgcagaa gagcctctcc  3240
ctgtctccgg gtaaa                                                   3255

SEQ ID NO: 21           moltype = AA  length = 791
FEATURE                 Location/Qualifiers
REGION                  1..791
                        note = Synthetic polypeptide
source                  1..791
                        mol_type = protein
                        organism = synthetic construct
SEQUENCE: 21
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLQSSVSE DFKCMEALGM ESGEIHSDQI TASSQASTNW SAERSRLNYP ENGWTPGEDS  300
YREWIQVDLG LLRFVTAVGT QGAISKETKK KYYVKTYKID VSSNGEDWIT IKEGNKPVLF  360
QGNTNPTDVV VAVFPKPLIT RFVRIKPATW ETGISMRFEV YGCKITDYPC SGMLGMVSGL  420
ISDSQITSSN QGDRNWMPEN IRLVTSRSGW ALPPAPHSYI NEWLQIDLGE EKIVRGIIIQ  480
GGKHRENKVF MRKFKIGYSN NGSDWKMIMD DSKRKAKSFE GNNNYDTPEL RTFPALSTRF  540
IRIYPERATH GGLGLRMELL GCRSDKTHTC PPCPAPELLG GPSVFLFPPK PKDTLMISRT  600
PEVTCVVVDV SHEDPEVKFN WYVDGVEVHN AKTKPREEQY NSTYRVVSVL TVLHQDWLNG  660
KEYKCKVSNK ALPAPIEKTI SKAKGQPREP QVYTLPPSRE EMTKNQVSLT CLVKGFYPSD  720
IAVEWESNGQ PENNYKTTPP VLDSDGSFFL YSKLTVDKSR WQQGNVFSCS VMHEALHNHY  780
TQKSLSLSPG K                                                       791

SEQ ID NO: 22           moltype = DNA  length = 2436
FEATURE                 Location/Qualifiers
misc_feature            1..2436
                        note = Synthetic polynucleotide
source                  1..2436
                        mol_type = other DNA
                        organism = synthetic construct
SEQUENCE: 22
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
```

```
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccaggggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgcagag cagtgtctca gaagatttca aatgtatgga agctctgggc  840
atggaatcag gagaaattca ttctgaccag atcacagctt cttcccaggc tagcaccaac  900
tggtctgcag agcgctcccg cctgaactac cctgagaatg ggtggactcc cggagaggat  960
tcctaccgag agtggataca ggtagacttg ggccttctgc gctttgtcac ggctgtcggg  1020
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
actcgatttg tccgaatcaa gcctgcaact tgggaaactg gcatatctat gagatttgaa  1260
gtatatggtt gcaagataac agattatcct tgctctggaa tgttgggtat ggtgtctgga  1320
cttatttctg actcccagat cacatcatcc aaccaagggg acagaaactg gatgcctgaa  1380
aacatccgcc tggtaaccag tcgctctggc tgggcacttc cacccgcacc tcattcctac  1440
atcaatgagt ggctccaaat agacctgggg gaggagaaga tcgtgagggg catcatcatt  1500
cagggtggga agcaccgaga gaacaaggtg ttcatgagga agttcaagat cgggtacagc  1560
aacaacggct cggactggaa gatgatcatg gatgacagca aacgcaaggc gaagtctttt  1620
gagggcaaca acaactatga tacacctgag ctgcggactt ttccagctct ctccacgcga  1680
ttcatcagga tctaccccga gagagccact catggcggac tggggctcag aatggagctg  1740
ctgggctgta gatctgacaa aactcacaca tgcccaccgt gcccagcacc tgaactcctg  1800
gggggaccgt cagtcttcct cttcccccca aaacccaagg acaccctcat gatctcccgg  1860
acccctgagg tcacatgcgt ggtggtggac gtgagccacg aagaccctga ggtcaagttc  1920
aactggtacg tggacggcgt ggaggtgcat aatgccaaga caaagccgcg ggaggagcag  1980
tacaacagca cgtaccgtgt ggtcagcgtc ctcaccgtcc tgcaccagga ctggctgaat  2040
ggcaaggagt acaagtgcaa ggtctccaac aaagccctcc cagcccccat cgagaaaacc  2100
atctccaaag ccaaagggca gccccgagaa ccacaggtgt acaccctgcc cccatcccgg  2160
gaggagatga ccaagaacca ggtcagcctg acctgcctgg tcaaaggctt ctatcccagc  2220
gacatcgccg tggagtggga gagcaatggg cagccggaga acaactacaa gaccacgcct  2280
cccgtgctgg actccgacgg ctccttcttc ctctacagca agctcaccgt ggacaagagc  2340
aggtggcagc aggggaacgt cttctcatgc tccgtgatgc acgaggctct gcacaaccac  2400
tacacgcaga agagcctctc cctgtctccg ggtaaa                            2436

SEQ ID NO: 23          moltype = AA  length = 632
FEATURE                Location/Qualifiers
REGION                 1..632
                       note = Synthetic polypeptide
source                 1..632
                       mol_type = protein
                       organism = synthetic construct
SEQUENCE: 23
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLQSSVSE DFKCMEALGM ESGEIHSDQI TASSQASTNW SAERSRLNYP ENGWTPGEDS  300
YREWIQVDLG LLRFVTAVGT QGAISKETKK KYYVKTYKID VSSNGEDWIT IKEGNKPVLF  360
QGNTNPTDVV VAVFPKPLIT RFVRIKPATW ETGISMRFEV YGCRSDKTHT CPPCPAPELL  420
GGPSVFLFPP KPKDTLMISR TPEVTCVVVD VSHEDPEVKF NWYVDGVEVH NAKTKPREEQ  480
YNSTYRVVSV LTVLHQDWLN GKEYKCKVSN KALPAPIEKT ISKAKGQPRE PQVYTLPPSR  540
EEMTKNQVSL TCLVKGFYPS DIAVEWESNG QPENNYKTTP PVLDSDGSFF LYSKLTVDKS  600
RWQQGNVFSC SVMHEALHNH YTQKSLSLSP GK                                632

SEQ ID NO: 24          moltype = DNA  length = 1962
FEATURE                Location/Qualifiers
misc_feature           1..1962
                       note = Synthetic polynucleotide
source                 1..1962
                       mol_type = other DNA
                       organism = synthetic construct
SEQUENCE: 24
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccaggggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgcagag cagtgtctca gaagatttca aatgtatgga agctctgggc  840
atggaatcag gagaaattca ttctgaccag atcacagctt cttcccaggc tagcaccaac  900
tggtctgcag agcgctcccg cctgaactac cctgagaatg ggtggactcc cggagaggat  960
tcctaccgag agtggataca ggtagacttg ggccttctgc gctttgtcac ggctgtcggg  1020
```

```
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
actcgatttg tccgaatcaa gcctgcaact tgggaaactg gcatatctat gagatttgaa  1260
gtatatggtt gcagatctga caaaactcac acatgcccac cgtgcccagc acctgaactc  1320
ctggggggac cgtcagtctt cctcttcccc ccaaaaccca aggacaccct catgatctcc  1380
cggacccctg aggtcacatg cgtggtggtg gacgtgagcc acgaagaccc tgaggtcaag  1440
ttcaactggt acgtggacgg cgtggaggtg cataatgcca agacaaagcc gcgggaggag  1500
cagtacaaca gcacgtaccg tgtggtcagc gtcctcaccg tcctgcacca ggactggctg  1560
aatggcaagg agtacaagtg caaggtctcc aacaaagccc tcccagcccc catcgagaaa  1620
accatctcca aagccaaagg gcagccccga gaaccacagg tgtacaccct gcccccatcc  1680
cgggaggaga tgaccaagaa ccaggtcagc ctgacctgcc tggtcaaagg cttctatccc  1740
agcgacatcg ccgtggagtg ggagagcaat gggcagccgg agaacaacta caagaccacg  1800
cctcccgtgc tggactccga cggctccttc ttcctctaca gcaagctcac cgtggacaag  1860
agcaggtggc agcaggggaa cgtcttctca tgctccgtga tgcacgaggc tctgcacaac  1920
cactacacgc agaagagcct ctccctgtct ccgggtaaat ga                      1962
```

```
SEQ ID NO: 25          moltype = AA  length = 1065
FEATURE                Location/Qualifiers
REGION                 1..1065
                       note = Synthetic polypeptide
source                 1..1065
                       mol_type = protein
                       organism = synthetic construct
SEQUENCE: 25
FRSDKCGGTI KIENPGYLTS PGYPHSYHPS EKCEWLIQAP EPYQRIMINF NPHFDLEDRD  60
CKYDYVEVID GENEGGRLWG KFCGKIAPSP VVSSGPFLFI KFVSDYETHG AGFSIRYEIF  120
KRGPECSQNY TAPTGVIKSP GFPEKYPNSL ECTYIIFAPK MSEIILEFES FDLEQDSNPP  180
GGMFCRYDRL EIWDGFPEVG PHIGRYCGQK TPGRIRSSSG VLSMVFYTDS AIAKEGFSAN  240
YSVLQSSISE DFKCMEALGM ESGEIHSDQI TASSQYGTNW SVERSRLNYP ENGWTPGEDS  300
YKEWIQVDLG LLRFVTAVGT QGAISKETKK KYYVKTYRVD ISSNGEDWIS LKEGNKAIIF  360
QGNTNPTDVV LGVFSKPLIT RFVRIKPVSW ETGISMRFEV YGCKITDYPC SGMLGMVSGL  420
ISDSQITASN QADRNWMPEN IRLVTSRTGW ALPPSPHPYT NEWLQVDLGD EKIVRGVIIQ  480
GGKHRENKVF MRKFKIAYSN NGSDWKTIMD DSKRKAKSFE GNNNYDTPEL RTFSPLSTRF  540
IRIYPERATH SGLGLRMELL GCEVEAPTAG PTTPNGNPVD ECDDDQANCH SGTGDDFQLT  600
GGTTVLATEK PTIIDSTIQS EFPTYGFNCE FGWGSHKTFC HWEHDSHAQL RWSVLTSKTG  660
PIQDHTGDGN FIYSQADENQ KGKVARLVSP VVYSQSSAHC MTFWYHMSGS HVGTLRVKLR  720
YQKPEEYDQL VWMVVGHQGD HWKEGRVLLH KSLKLYQVIF EGEIGKGNLG GIAVDDISIN  780
NHISQEDCAK PTDLDKKNTE IKIDETGSTP GYEGEGEGDK NISRKPGNVL KTLDPVSSTM  840
VRSGCKPCIC TVPEVSSVFI FPPKPKDVLT ITLTPKVTCV VVDISKDDPE VQFSWFVDDV  900
EVHTAQTQPR EEQFNSTFRS VSELPIMHQD WLNGKEFKCR VNSAAFPAPI EKTISKTKGR  960
PKAPQVYTIP PPKEQMAKDK VSLTCMITDF FPEDITVEWQ WNGQPAENYK NTQPIMDTDG  1020
SYFVYSKLNV QKSNWEAGNT FTCSVLHEGL HNHHTEKSLS HSPGK                  1065
```

```
SEQ ID NO: 26          moltype = DNA  length = 3261
FEATURE                Location/Qualifiers
misc_feature           1..3261
                       note = Synthetic polynucleotide
source                 1..3261
                       mol_type = other DNA
                       organism = synthetic construct
SEQUENCE: 26
atggagaggg ggctgccgtt gctgtgcgcc acgctcgccc ttgccctcgc cctggcgggc  60
gctttccgca gcgacaaatg tggcgggacc ataaaaatcg aaaacccagg gtacctcaca  120
tctcccggtt accctcattc ttaccatcca agtgagaagt gtgaatggct aatccaagct  180
ccggaaccct accagagaat catgatcaac ttcaacccac atttcgattt ggaggacaga  240
gactgcaagt atgactacgt ggaagtaatc gatggggaga atgaaggcgg ccgcctgtgg  300
gggaagttct gtgggaagat tgcaccttct cctgtggtgt cttcagggcc ctttctcttc  360
atcaaatttg tctctgacta tgagacacat ggggcagggt tttccatccg ctatgaaatc  420
ttcaagagag ggcccgaatg ttctcagaac tatacagcac ctactggagt gataaagtcc  480
cctgggttcc ctgaaaaata ccccaacagc ttggagtgca cctacatcat ctttgcacca  540
aagatgtctg agataatcct ggagtttgaa agttttgacc tggagcaaga ctcgaatcct  600
cccggaggaa tgttctgtcg ctatgaccgg ctggagatct gggatggatt ccctgaagtt  660
ggccctcaca ttgggcgtta ttgtgggcag aaaactcctg gccggatccg ctcctcttca  720
ggcgttctat ccatggtctt ttacactgac agcgcaatag caaaagaagg tttctcagcc  780
aactacagtg tgctacagag cagcatctct gaagatttta agtgtatgga ggctctgggc  840
atggaatctg gagagatcca ttctgatcag atcactgcat cttcacagta tggtaccaac  900
tggtctgtag agcgctcccg cctgaactac cctgaaaatg ggtggactcc aggagaagac  960
tcctacaagg agtggatcca ggtggacttg ggcctcctgc gattcgttac tgctgtaggg  1020
acacagggtg ccatttccaa ggaaaccaag aagaaatatt atgtcaagac ttacagagta  1080
gacatcagct ccaacggaga ggactggatc tccctgaaag agggaaataa agccattatc  1140
tttcagggaa acaccaaccc cacagatgtt gtcttaggag ttttctccaa accactgata  1200
actcgatttg tccgaatcaa acctgtatcc tgggaaactg gtatatctat gagatttgaa  1260
gtttatggct gcaagataac agattatcct tgctctggaa tgttgggcat ggtgtctgga  1320
cttatttcag actcccagat tacagcatcc aatcaagccg acaggaattg gatgccagaa  1380
aacatccgtc tggtgaccag tcgtaccggc tgggcactgc caccctcacc ccacccatac  1440
accaatgaat ggctccaagt ggacctggga gatgagaaga tagtaagagg tgtcatcatt  1500
cagggtggga agcaccgaga aaacaaggtg ttcatgagga agttcaagat cgcctatagt  1560
aacaatggct ctgactggaa aactatcatg gatgacagca agcgcaaggc taagtcgttc  1620
```

```
gaaggcaaca acaactatga cacacctgag cttcggacgt tttcacctct ctccacaagg  1680
ttcatcagga tctaccctga gagagccaca cacagtgggc ttgggctgag gatggagcta  1740
ctgggctgtg aagtggaagc acctacagct ggaccaacca cacccaatgg gaacccagtg  1800
gatgagtgtg acgacgacca ggccaactgc cacagtggca caggtgatga cttccagctc  1860
acaggaggca ccactgtcct ggccacagag aagccaacca ttatagacag caccatccaa  1920
tcagagttcc cgacatacgg ttttaactgc gagtttggct ggggctctca caagacattc  1980
tgccactggg agcatgacag ccatgcacag ctcaggtgga gtgtgctgac cagcaagaca  2040
gggccgattc aggaccatac aggagatggc aacttcatct attcccaagc tgatgaaaat  2100
cagaaaggca aagtagcccg cctggtgagc cctgtggtct attcccagag ctctgcccac  2160
tgtatgacct tctggtatca catgtccggc tctcatgtgg gtacactgag ggtcaaacta  2220
cgctaccaga agccagagga atatgatcaa ctggtctgga tggtggttgg gcaccaagga  2280
gaccactgga aagaaggacg tgtcttgctg cacaaatctc tgaaactata tcaggttatt  2340
tttgaaggtg aaatcggaaa aggaaacctt ggtggaattg ctgtggatga tatcagtatt  2400
aacaaccata tttctcagga agactgtgca aaaccaacag acctagataa aaagaacaca  2460
gaaattaaaa ttgatgaaac agggagcact ccaggatatg aaggagaagg ggaaggtgac  2520
aagaacatct ccaggaagcc aggcaatgtg cttaagaccc tggatcccgt ctcgagcacc  2580
atggttagat ctggttgtaa gccttgcata tgtacagtcc cagaagtatc atctgtcttc  2640
atcttccccc caaagcccaa ggatgtgctc accattactc tgactcctaa ggtcacgtgt  2700
gttgtggtag acatcagcaa ggatgatccc gaggtccagt tcagctggtt tgtagatgat  2760
gtggaggtgc acacagctca gacgcaaccc cgggaggagc agttcaacag cactttccgc  2820
tcagtcagtg aacttcccat catgcaccag gactggctca atggcaagga gttcaaatgc  2880
agggtcaaca gtgcagcttt ccctgccccc atcgagaaaa ccatctccaa aaccaaaggc  2940
agaccgaagg ctccacaggt gtacaccatt ccacctccca aggagcagat ggccaaggat  3000
aaagtcagtc tgacctgcat gataacagac ttcttccctg aagacattac tgtggagtgg  3060
cagtggaatg ggcagccagc ggagaactac aagaacactc agcccatcat ggacacagat  3120
ggctcttact tcgtctacag caagctcaat gtgcagaaga gcaactggga ggcaggaaat  3180
actttcacct gctctgtgtt acatgagggc ctgcacaacc accatactga gaagagcctc  3240
tcccactctc ctggtaaatg a                                            3261

SEQ ID NO: 27          moltype = AA  length = 813
FEATURE                Location/Qualifiers
REGION                 1..813
                       note = Synthetic polypeptide
source                 1..813
                       mol_type = protein
                       organism = synthetic construct
SEQUENCE: 27
MERGLPLLCA TLALALALAG AFRSDKCGGT IKIENPGYLT SPGYPHSYHP SEKCEWLIQA  60
PEPYQRIMIN FNPHFDLEDR DCKYDYVEVI DGENEGGRLW GKFCGKIAPS PVVSSGPFLF  120
IKFVSDYETH GAGFSIRYEI FKRGPECSQN YTAPTGVIKS PGFPEKYPNS LECTYIIFAP  180
KMSEIILEFE SFDLEQDSNP PGGMFCRYDR LEIWDGFPEV GPHIGRYCGQ KTPGRIRSSS  240
GVLSMVFYTD SAIAKEGFSA NYSVLQSSIS EDFKCMEALG MESGEIHSDQ ITASSQYGTN  300
WSVERSRLNY PENGWTPGED SYKEWIQVDL GLLRFVTAVG TQGAISKETK KKYYVKTYRV  360
DISSNGEDWI SLKEGNKAII FQGNTNPTDV VLGVFSKPLI TRFVRIKPVS WETGISMRFE  420
VYGCKITDYP CSGMLGMVSG LISDSQITAS NQADRNWMPE NIRLVTSRTG WALPPSPHPY  480
TNEWLQVDLG DEKIVRGVII QGGKHRENKV FMRKFKIAYS NNGSDWKTIM DDSKRKAKSF  540
EGNNNYDTPE LRTFSPLSTR FIRIYPERAT HSGLGLRMEL LGCVSSTMVR SGCKPCICTV  600
PEVSSVFIFP PKPKDVLTIT LTPKVTCVVV DISKDDPEVQ FSWFVDDVEV HTAQTQPREE  660
QFNSTFRSVS ELPIMHQDWL NGKEFKCRVN SAAFPAPIEK TISKTKGRPK APQVYTIPPP  720
KEQMAKDKVS LTCMITDFFP EDITVEWQWN GQPAENYKNT QPIMDTDGSY FVYSKLNVQK  780
SNWEAGNTFT CSVLHEGLHN HHTEKSLSHS PGK                                813

SEQ ID NO: 28          moltype = DNA  length = 2442
FEATURE                Location/Qualifiers
misc_feature           1..2442
                       note = Synthetic polynucleotide
source                 1..2442
                       mol_type = other DNA
                       organism = synthetic construct
SEQUENCE: 28
atggagaggg ggctgccgtt gctgtgcgcc acgctcgccc ttgccctcgc cctggcgggc  60
gctttccgca gcgacaaatg tggcgggacc ataaaaatcg aaaacccagg gtacctcaca  120
tctcccggtt accctcattc ttaccatcca agtgagaagt gtgaatggct aatccaagct  180
ccggaaccct accagagaat catgatcaac ttcaacccac atttcgattt ggaggacaga  240
gactgcaagt atgactacgt ggaagtaatc gatggggaga atgaaggcgg ccgcctgtgg  300
gggaagttct gtgggaagat tgcaccttct cctgtggtgt cttcagggcc ctttctcttc  360
atcaaatttg tctctgacta tgagacacat ggggcagggt tttccatccg ctatgaaatc  420
ttcaagagag ggcccgaatg ttctcagaac tatacagcac ctactggagt gataaagtcc  480
cctgggttcc ctgaaaaata ccccaacagc ttggagtgca cctacatcat ctttgcacca  540
aagatgtctg agataatcct ggagtttgaa agttttgacc tggagcaaga ctcgaatcct  600
cccggaggaa tgttctgtcg ctatgaccgg ctggagatct gggatggatt ccctgaagtt  660
ggccctcaca ttgggcgtta ttgtgggcag aaaactcctg gccggatccg ctcctcttca  720
ggcgttctat ccatggtctt ttacactgac agcgcaatag caaaagaagg tttctcagcc  780
aactacagtg tgctacagag cagcatctct gaagatttta agtgtatgga ggctctgggc  840
atggaatctg gagagatcca ttctgatcag atcactgcat cttcacagta tggtaccaac  900
tggtctgtag agcgctcccg cctgaactac cctgaaaatg ggtggactcc aggagaagac  960
tcctacaagg agtggatcca ggtggacttg ggcctcctgc gattcgttac tgctgtaggg  1020
acacagggtg ccatttccaa ggaaaccaag aagaaatatt atgtcaagac ttacagagta  1080
gacatcagct ccaacggaga ggactggatc tccctgaaag agggaaataa agccattatc  1140
```

```
tttcagggaa acaccaaccc cacagatgtt gtcttaggag ttttctccaa accactgata  1200
actcgatttg tccgaatcaa acctgtatcc tgggaaactg gtatatctat gagatttgaa  1260
gtttatggct gcaagataac agattatcct tgctctggaa tgttgggcat ggtgtctgga  1320
cttatttcag actcccagat tacagcatcc aatcaagccg acaggaattg gatgccagaa  1380
aacatccgtc tggtgaccag tcgtaccggc tgggcactgc caccctcacc ccacccatac  1440
accaatgaat ggctccaagt ggacctggga gatgagaaga tagtaagagg tgtcatcatt  1500
cagggtggga agcaccgaga aaacaaggtg ttcatgagga agttcaagat cgcctatagt  1560
aacaatggct ctgactggaa aactatcatg gatgacagca agcgcaaggc taagtcgttc  1620
gaaggcaaca acaactatga cacacctgag cttcggacgt tttcacctct ctccacaagg  1680
ttcatcagga tctaccctga gagagccaca cacagtgggc ttgggctgag gatggagcta  1740
ctgggctgtg tctcgagcac catggttaga tctggttgta agccttgcat atgtacagtc  1800
ccagaagtat catctgtctt catcttcccc ccaaagccca aggatgtgct caccattact  1860
ctgactccta aggtcacgtg tgttgtggta gacatcagca aggatgatcc cgaggtccag  1920
ttcagctggt ttgtagatga tgtggaggtg cacacagctc agacgcaacc ccgggaggag  1980
cagttcaaca gcactttccg ctcagtcagt gaacttccca tcatgcacca ggactggctc  2040
aatggcaagg agttcaaatg cagggtcaac agtgcagctt tccctgcccc catcgagaaa  2100
accatctcca aaaccaaagg cagaccgaag gctccacagg tgtacaccat tccacctccc  2160
aaggagcaga tggccaagga taaagtcagt ctgacctgca tgataacaga cttcttccct  2220
gaagacatta ctgtggagtg gcagtggaat gggcagccag cggagaacta caagaacact  2280
cagcccatca tggacacaga tggctcttac ttcgtctaca gcaagctcaa tgtgcagaag  2340
agcaactggg aggcaggaaa tactttcacc tgctctgtgt tacatgaggg cctgcacaac  2400
caccatactg agaagagcct ctcccactct cctggtaaat ga                     2442

SEQ ID NO: 29          moltype = AA  length = 633
FEATURE                Location/Qualifiers
REGION                 1..633
                       note = Synthetic polypeptide
source                 1..633
                       mol_type = protein
                       organism = synthetic construct
SEQUENCE: 29
FRSDKCGGTI KIENPGYLTS PGYPHSYHPS EKCEWLIQAP EPYQRIMINF NPHFDLEDRD  60
CKYDYVEVID GENEGGRLWG KFCGKIAPSP VVSSGPFLFI KFVSDYETHG AGFSIRYEIF  120
KRGPECSQNY TAPTGVIKSP GFPEKYPNSL ECTYIIFAPK MSEIILEFES FDLEQDSNPP  180
GGMFCRYDRL EIWDGFPEVG PHIGRYCGQK TPGRIRSSSG VLSMVFYTDS AIAKEGFSAN  240
YSVLQSSISE DFKCMEALGM ESGEIHSDQI TASSQYGTNW SVERSRLNYP ENGWTPGEDS  300
YKEWIQVDLG LLRFVTAVGT QGAISKETKK KYYVKTYRVD ISSNGEDWIS LKEGNKAIIF  360
QGNTNPTDVV LGVFSKPLIT RFVRIKPVSW ETGISMRFEV YGCVSSTMVR SGCKPCICTV  420
PEVSSVFIFP PKPKDVLTIT LTPKVTCVVV DISKDDPEVQ FSWFVDDVEV HTAQTQPREE  480
QFNSTFRSVS ELPIMHQDWL NGKEFKCRVN SAAFPAPIEK TISKTKGRPK APQVYTIPPP  540
KEQMAKDKVS LTCMITDFFP EDITVEWQWN GQPAENYKNT QPIMDTDGSY FVYSKLNVQK  600
SNWEAGNTFT CSVLHEGLHN HHTEKSLSHS PGK                                633

SEQ ID NO: 30          moltype = DNA  length = 1965
FEATURE                Location/Qualifiers
misc_feature           1..1965
                       note = Synthetic polynucleotide
source                 1..1965
                       mol_type = other DNA
                       organism = synthetic construct
SEQUENCE: 30
atggagaggg ggctgccgtt gctgtgcgcc acgctcgccc ttgccctcgc cctggcgggc  60
gctttccgca gcgacaaatg tggcgggacc ataaaaatcg aaaacccagg gtacctcaca  120
tctcccggtt accctcattc ttaccatcca agtgagaagt gtgaatggct aatccaagct  180
ccggaaccct accagagaat catgatcaac ttcaacccac atttcgattt ggaggacaga  240
gactgcaagt atgactacgt ggaagtaatc gatggggaga atgaaggcgg ccgcctgtgg  300
gggaagttct gtgggaagat tgcaccttct cctgtggtgt cttcagggcc ctttctcttc  360
atcaaatttg tctctgacta tgagacacat ggggcagggt tttccatccg ctatgaaatc  420
ttcaagagag ggcccgaatg ttctcagaac tatacagcac ctactggagt gataaagtcc  480
cctgggttcc ctgaaaaata ccccaacagc ttggagtgca cctacatcat ctttgcacca  540
aagatgtctg agataatcct ggagtttgaa agttttgacc tggagcaaga ctcgaatcct  600
cccggaggaa tgttctgtcg ctatgaccgg ctggagatct gggatggatt ccctgaagtt  660
ggccctcaca ttgggcgtta ttgtgggcag aaaactcctg gccggatccg ctcctcttca  720
ggcgttctat ccatggtctt ttacactgac agcgcaatag caaaagaagg tttctcagcc  780
aactacagtg tgctacagag cagcatctct gaagatttta agtgtatgga ggctctgggc  840
atggaatctg gagagatcca ttctgatcag atcactgcat cttcacagta tggtaccaac  900
tggtctgtag agcgctcccg cctgaactac cctgaaaatg ggtggactcc aggagaagac  960
tcctacaagg agtggatcca ggtggacttg ggcctcctgc gattcgttac tgctgtaggg  1020
acacagggtg ccatttccaa ggaaaccaag aagaaatatt atgtcaagac ttacagagta  1080
gacatcagct ccaacggaga ggactggatc tccctgaaag agggaaataa agccattatc  1140
tttcagggaa acaccaaccc cacagatgtt gtcttaggag ttttctccaa accactgata  1200
actcgatttg tccgaatcaa acctgtatcc tgggaaactg gtatatctat gagatttgaa  1260
gtttatggct gcgtctcgag caccatggtt agatctggtt gtaagccttg catatgtaca  1320
gtcccagaag tatcatctgt cttcatcttc cccccaaagc ccaaggatgt gctcaccatt  1380
actctgactc ctaaggtcac gtgtgttgtg gtagacatca gcaaggatga tcccgaggtc  1440
cagttcagct ggtttgtaga tgatgtggag gtgcacacag ctcagacgca accccgggag  1500
gagcagttca acagcacttt ccgctcagtc agtgaacttc ccatcatgca ccaggactgg  1560
ctcaatggca aggagttcaa atgcagggtc aacagtgcag ctttccctgc ccccatcgag  1620
aaaaccatct ccaaaaccaa aggcagaccg aaggctccac aggtgtacac cattccacct  1680
```

```
cccaaggagc agatggccaa ggataaagtc agtctgacct gcatgataac agacttcttc  1740
cctgaagaca ttactgtgga gtggcagtgg aatgggcagc cagcggagaa ctacaagaac  1800
actcagccca tcatggacac agatggctct tacttcgtct acagcaagct caatgtgcag  1860
aagagcaact gggaggcagg aaatactttc acctgctctg tgttacatga gggcctgcac  1920
aaccaccata ctgagaagag cctctcccac tctcctggta aatga                  1965

SEQ ID NO: 31          moltype = AA  length = 911
FEATURE                Location/Qualifiers
REGION                 1..911
                       note = Synthetic polypeptide
source                 1..911
                       mol_type = protein
                       organism = synthetic construct
SEQUENCE: 31
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLQSSVSE DFKCMEALGM ESGEIHSDQI TASSQYSTNW SAERSRLNYP ENGWTPGEDS  300
YREWIQVDLG LLRFVTAVGT QGAISKETKK KYYVKTYKID VSSNGEDWIT IKEGNKPVLF  360
QGNTNPTDVV VAVFPKPLIT RFVRIKPATW ETGISMRFEV YGCKITDYPE VEAPTAGPTT  420
PNGNLVDECD DDQANCHSGT GDDFQLTGGT TVLATEKPTV IDSTIQSEFP TYGFNCEFGW  480
GSHKTFCHWE HDNHVQLKWS VLTSKTGPIQ DHTGDGNFIY SQADENQKGK VARLVSPVVY  540
SQNSAHCMTF WYHMSGSHVG TLRVKLRYQK PEEYDQLVWM AIGHQGDHWK EGRVLLHKSL  600
KLYQVIFEGE IGKGNLGGIA VDDISINNHI SQEDCAKPAD LDKKNPEIKI DETGSTPGYE  660
GEGEGDKNIS RKPGNVLKTL DPRSDKTHTC PPCPAPELLG GPSVFLFPPK PKDTLMISRT  720
PEVTCVVVDV SHEDPEVKFN WYVDGVEVHN AKTKPREEQY NSTYRVVSVL TVLHQDWLNG  780
KEYKCKVSNK ALPAPIEKTI SKAKGQPREP QVYTLPPSRE EMTKNQVSLT CLVKGFYPSD  840
IAVEWESNGQ PENNYKTTPP VLDSDGSFFL YSKLTVDKSR WQQGNVFSCS VMHEALHNHY  900
TQKSLSLSPG K                                                       911

SEQ ID NO: 32          moltype = DNA  length = 2799
FEATURE                Location/Qualifiers
misc_feature           1..2799
                       note = Synthetic polynucleotide
source                 1..2799
                       mol_type = other DNA
                       organism = synthetic construct
SEQUENCE: 32
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccagggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgcagag cagtgtctca gaagatttca aatgtatgga agctctgggc  840
atggaatcag gagaaattca ttctgaccag atcacagctt cttcccagta tagcaccaac  900
tggtctgcag agcgctcccg cctgaactac cctgagaatg ggtggactcc cggagaggat  960
tcctaccgag agtggataca ggtagacttg ggccttctgc gctttgtcac ggctgtcggg  1020
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
actcgatttg tccgaatcaa gcctgcaact tgggaaactg gcatatctat gagatttgaa  1260
gtatatggtt gcaagataac agattatcct gaagtggaag cccctacagc tggaccgacc  1320
actcccaacg ggaacttggt ggatgaatgt gatgacgacc aggccaactg ccacagtgga  1380
acaggtgatg acttccagct cacaggtggc accactgtgc tggccacaga aaagcccacg  1440
gtcatagaca gcaccataca atcagagttt ccaacatatg gttttaactg tgaatttggc  1500
tggggctctc acaagacctt ctgccactgg gaacatgaca atcacgtgca gctcaagtgg  1560
agtgtgttga ccagcaagac gggacccatt caggatcaca caggagatgg caacttcatc  1620
tattcccaag ctgacgaaaa tcagaagggc aaagtggctc gcctggtgag ccctgtggtt  1680
tattcccaga actctgccca ctgcatgacc ttctggtatc acatgtctgg gtcccacgtc  1740
ggcacactca gggtcaaact gcgctaccag aagccagagg agtacgatca gctggtctgg  1800
atggccattg gacaccaagg tgaccactgg aaggaagggc gtgtcttgct ccacaagtct  1860
ctgaaacttt atcaggtgat tttcgagggc gaaatcggaa aaggaaacct tggtgggatt  1920
gctgtggatg acattagtat taataaccac atttcacaag aagattgtgc aaaaccagca  1980
gacctggata aaaagaaccc agaaattaaa attgatgaaa cagggagcac gccaggatac  2040
gaaggtgaag gagaaggtga caagaacatc tccaggaagc caggcaatgt gttgaagacc  2100
ttagacccca gatctgacaa aactcacaca tgcccaccgt gcccagcacc tgaactcctg  2160
gggggaccgt cagtcttcct cttcccccca aaacccaagg acaccctcat gatctcccgg  2220
acccctgagg tcacatgcgt ggtggtggac gtgagccacg aagaccctga ggtcaagttc  2280
aactggtacg tggacggcgt ggaggtgcat aatgccaaga caaagccgcg ggaggagcag  2340
tacaacagca cgtaccgtgt ggtcagcgtc ctcaccgtcc tgcaccagga ctggctgaat  2400
```

```
ggcaaggagt acaagtgcaa ggtctccaac aaagccctcc cagcccccat cgagaaaacc  2460
atctccaaag ccaaagggca gccccgagaa ccacaggtgt acaccctgcc cccatcccgg  2520
gaggagatga ccaagaacca ggtcagcctg acctgcctgg tcaaaggctt ctatcccagc  2580
gacatcgccg tggagtggga gagcaatggg cagccggaga acaactacaa gaccacgcct  2640
cccgtgctgg actccgacgg ctccttcttc ctctacagca agctcaccgt ggacaagagc  2700
aggtggcagc aggggaacgt cttctcatgc tccgtgatgc acgaggctct gcacaaccac  2760
tacacgcaga agagcctctc cctgtctccg ggtaaatga                        2799

SEQ ID NO: 33          moltype = AA  length = 911
FEATURE                Location/Qualifiers
REGION                 1..911
                       note = Synthetic polypeptide
source                 1..911
                       mol_type = protein
                       organism = synthetic construct
SEQUENCE: 33
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLQSSVSE DFKCMEALGM ESGEIHSDQI TASSQASTNW SAERSRLNYP ENGWTPGEDS  300
YREWIQVDLG LLRFVTAVGT QGAISKETKK KYYVKTYKID VSSNGEDWIT IKEGNKPVLF  360
QGNTNPTDVV VAVFPKPLIT RFVRIKPATW ETGISMRFEV YGCKITDYPE VEAPTAGPTT  420
PNGNLVDECD DDQANCHSGT GDDFQLTGGT TVLATEKPTV IDSTIQSEFP TYGFNCEFGW  480
GSHKTFCHWE HDNHVQLKWS VLTSKTGPIQ DHTGDGNFIY SQADENQKGK VARLVSPVVY  540
SQNSAHCMTF WYHMSGSHVG TLRVKLRYQK PEEYDQLVWM AIGHQGDHWK EGRVLLHKSL  600
KLYQVIFEGE IGKGNLGGIA VDDISINNHI SQEDCAKPAD LDKKNPEIKI DETGSTPGYE  660
GEGEGDKNIS RKPGNVLKTL DPRSDKTHTC PPCPAPELLG GPSVFLFPPK PKDTLMISRT  720
PEVTCVVVDV SHEDPEVKFN WYVDGVEVHN AKTKPREEQY NSTYRVVSVL TVLHQDWLNG  780
KEYKCKVSNK ALPAPIEKTI SKAKGQPREP QVYTLPPSRE EMTKNQVSLT CLVKGFYPSD  840
IAVEWESNGQ PENNYKTTPP VLDSDGSFFL YSKLTVDKSR WQQGNVFSCS VMHEALHNHY  900
TQKSLSLSPG K                                                       911

SEQ ID NO: 34          moltype = DNA  length = 2799
FEATURE                Location/Qualifiers
misc_feature           1..2799
                       note = Synthetic polynucleotide
source                 1..2799
                       mol_type = other DNA
                       organism = synthetic construct
SEQUENCE: 34
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccagggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgcagag cagtgtctca gaagatttca aatgtatgga agctctgggc  840
atggaatcag gagaaattca ttctgaccag atcacagctt cttcccaggc tagcaccaac  900
tggtctgcag agcgctcccg cctgaactac cctgagaatg ggtggactcc cggagaggat  960
tcctaccgag agtggataca ggtagacttg ggccttctgc gctttgtcac ggctgtcggg  1020
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
actcgatttg tccgaatcaa gcctgcaact tgggaaactg gcatatctat gagatttgaa  1260
gtatatggtt gcaagataac agattatcct gaagtggaag cccctacagc tggaccgacc  1320
actcccaacg ggaacttggt ggatgaatgt gatgacgacc aggccaactg ccacagtgga  1380
acaggtgatg acttccagct cacaggtggc accactgtgc tggccacaga aaagcccacg  1440
gtcatagaca gcaccataca atcagagttt ccaacatatg gttttaactg tgaatttggc  1500
tggggctctc acaagacctt ctgccactgg gaacatgaca atcacgtgca gctcaagtgg  1560
agtgtgttga ccagcaagac gggacccatt caggatcaca caggagatgg caacttcatc  1620
tattcccaag ctgacgaaaa tcagaagggc aaagtggctc gcctggtgag ccctgtggtt  1680
tattcccaga actctgccca ctgcatgacc ttctggtatc acatgtctgg gtcccacgtc  1740
ggcacactca gggtcaaact gcgctaccag aagccagagg agtacgatca gctggtctgg  1800
atggccattg gacaccaagg tgaccactgg aaggaagggc gtgtcttgct ccacaagtct  1860
ctgaaacttt atcaggtgat tttcgagggc gaaatcggaa aaggaaacct tggtgggatt  1920
gctgtggatg acattagtat taataaccac atttcacaag aagattgtgc aaaaccagca  1980
gacctggata aaaagaaccc agaaattaaa attgatgaaa cagggagcac gccaggatac  2040
gaaggtgaag gagaaggtga caagaacatc tccaggaagc caggcaatgt gttgaagacc  2100
ttagacccca gatctgacaa aactcacaca tgcccaccgt gcccagcacc tgaactcctg  2160
gggggaccgt cagtcttcct cttcccccca aaacccaagg acaccctcat gatctcccgg  2220
acccctgagg tcacatgcgt ggtggtggac gtgagccacg aagaccctga ggtcaagttc  2280
```

```
aactggtacg tggacggcgt ggaggtgcat aatgccaaga caaagccgcg ggaggagcag  2340
tacaacagca cgtaccgtgt ggtcagcgtc ctcaccgtcc tgcaccagga ctggctgaat  2400
ggcaaggagt acaagtgcaa ggtctccaac aaagccctcc cagcccccat cgagaaaacc  2460
atctccaaag ccaaagggca gccccgagaa ccacaggtgt acaccctgcc cccatcccgg  2520
gaggagatga ccaagaacca ggtcagcctg acctgcctgg tcaaaggctt ctatcccagc  2580
gacatcgccg tggagtggga gagcaatggg cagccggaga acaactacaa gaccacgcct  2640
cccgtgctgg actccgacgg ctccttcttc ctctacagca agctcaccgt ggacaagagc  2700
aggtggcagc aggggaacgt cttctcatgc tccgtgatgc acgaggctct gcacaaccac  2760
tacacgcaga agagcctctc cctgtctccg ggtaaatga                          2799

SEQ ID NO: 35          moltype = AA  length = 755
FEATURE                Location/Qualifiers
REGION                 1..755
                       note = Synthetic polypeptide
source                 1..755
                       mol_type = protein
                       organism = synthetic construct
SEQUENCE: 35
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLQSSVSE DFKEVEAPTA GPTTPNGNLV DECDDDQANC HSGTGDDFQL TGGTTVLATE  300
KPTVIDSTIQ SEFPTYGFNC EFGWGSHKTF CHWEHDNHVQ LKWSVLTSKT GPIQDHTGDG  360
NFIYSQADEN QKGKVARLVS PVVYSQNSAH CMTFWYHMSG SHVGTLRVKL RYQKPEEYDQ  420
LVWMAIGHQG DHWKEGRVLL HKSLKLYQVI FEGEIGKGNL GGIAVDDISI NNHISQEDCA  480
KPADLDKKNP EIKIDETGST PGYEGEGEGD KNISRKPGNV LKTLDPRSDK THTCPPCPAP  540
ELLGGPSVFL FPPKPKDTLM ISRTPEVTCV VVDVSHEDPE VKFNWYVDGV EVHNAKTKPR  600
EEQYNSTYRV VSVLTVLHQD WLNGKEYKCK VSNKALPAPI EKTISKAKGQ PREPQVYTLP  660
PSREEMTKNQ VSLTCLVKGF YPSDIAVEWE SNGQPENNYK TTPPVLDSDG SFFLYSKLTV  720
DKSRWQQGNV FSCSVMHEAL HNHYTQKSLS LSPGK                             755

SEQ ID NO: 36          moltype = DNA  length = 2331
FEATURE                Location/Qualifiers
misc_feature           1..2331
                       note = Synthetic polynucleotide
source                 1..2331
                       mol_type = other DNA
                       organism = synthetic construct
SEQUENCE: 36
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccagggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgcagag cagtgtctca gaagatttca aagaagtgga agcccctaca  840
gctggaccga ccactcccaa cgggaacttg gtggatgaat gtgatgacga ccaggccaac  900
tgccacagtg gaacaggtga tgacttccag ctcacaggtg gcaccactgt gctggccaca  960
gaaaagccca cggtcataga cagcaccata caatcagagt ttccaacata tggttttaac  1020
tgtgaatttg gctggggctc tcacaagacc ttctgccact gggaacatga caatcacgtg  1080
cagctcaagt ggagtgtgtt gaccagcaag acgggaccca ttcaggatca cacaggagat  1140
ggcaacttca tctattccca agctgacgaa aatcagaagg gcaaagtggc tcgcctggtg  1200
agccctgtgg tttattccca gaactctgcc cactgcatga ccttctggta tcacatgtct  1260
gggtcccacg tcggcacact cagggtcaaa ctgcgctacc agaagccaga ggagtacgat  1320
cagctggtct ggatggccat tggacaccaa ggtgaccact ggaaggaagg gcgtgtcttg  1380
ctccacaagt ctctgaaact ttatcaggtg attttcgagg gcgaaatcgg aaaaggaaac  1440
cttggtggga ttgctgtgga tgacattagt attaataacc acatttcaca agaagattgt  1500
gcaaaaccag cagacctgga taaaaagaac ccagaaatta aaattgatga aacagggagc  1560
acgccaggat acgaaggtga aggagaaggt gacaagaaca tctccaggaa gccaggcaat  1620
gtgttgaaga ccttagaccc cagatctgac aaaactcaca catgcccacc gtgcccagca  1680
cctgaactcc tggggggacc gtcagtcttc ctcttccccc caaaacccaa ggacaccctc  1740
atgatctccc ggacccctga ggtcacatgc gtggtggtgg acgtgagcca cgaagaccct  1800
gaggtcaagt tcaactggta cgtggacggc gtggaggtgc ataatgccaa gacaaagccg  1860
cgggaggagc agtacaacag cacgtaccgt gtggtcagcg tcctcaccgt cctgcaccag  1920
gactggctga atggcaagga gtacaagtgc aaggtctcca acaaagccct cccagccccc  1980
atcgagaaaa ccatctccaa agccaaaggg cagccccgag aaccacaggt gtacaccctg  2040
cccccatccc gggaggagat gaccaagaac caggtcagcc tgacctgcct ggtcaaaggc  2100
ttctatccca gcgacatcgc cgtggagtgg gagagcaatg ggcagccgga gaacaactac  2160
aagaccacgc ctcccgtgct ggactccgac ggctccttct tcctctacag caagctcacc  2220
gtggacaaga gcaggtggca gcaggggaac gtcttctcat gctccgtgat gcacgaggct  2280
ctgcacaacc actacacgca gaagagcctc tccctgtctc cgggtaaatg a            2331
```

```
SEQ ID NO: 37          moltype = AA  length = 227
FEATURE                Location/Qualifiers
REGION                 1..227
                       note = Synthetic polypeptide
source                 1..227
                       mol_type = protein
                       organism = synthetic construct
SEQUENCE: 37
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK               227

SEQ ID NO: 38          moltype = AA  length = 853
FEATURE                Location/Qualifiers
REGION                 1..853
                       note = Synthetic polypeptide
source                 1..853
                       mol_type = protein
                       organism = synthetic construct
SEQUENCE: 38
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLQSSVSE DFKCMEALGM ESGEIHSDQI TASSQYSTNW SAERSRLNYP ENGWTPGEDS  300
YREWIQVDLG LLRFVTAVGT QGAISKETKK KYYVKTYKID VSSNGEDWIT IKEGNKPVLF  360
QGNTNPTDVV VAVFPKPLIT RFVRIKPATW ETGISMRFEV YGCKITDYPC SGMLGMVSGL  420
ISDSQITSSN QGDRNWMPEN IRLVTSRSGW ALPPAPHSYI NEWLQIDLGE EKIVRGIIIQ  480
GGKHRENKVF MRKFKIGYSN NGSDWKMIMD DSKRKAKSFE GNNNYDTPEL RTFPALSTRF  540
IRIYPERATH GGLGLRMELL GCEVEAPTAG PTTPNGNLVD ECDDDQANCH SGTGDDFQLT  600
GGTTVLATEK PTVIDSTIQS EFPTYGFNCE FGWGSHKTFC HWEHDNHVQL KWSVLTSKTG  660
PIQDHTGDGN FIYSQADENQ KGKVARLVSP VVYSQNSAHC MTFWYHMSGS HVGTLRVKLR  720
YQKPEEYDQL VWMAIGHQGD HWKEGRVLLH KSLKLYQVIF EGEIGKGNLG GIAVDDISIN  780
NHISQEDCAK PADLDKKNPE IKIDETGSTP GYEGEGEGDK NISRKPGNVL KTLDPRSGSK  840
ENLYFQGHHH HHH                                                     853

SEQ ID NO: 39          moltype = DNA  length = 2625
FEATURE                Location/Qualifiers
misc_feature           1..2625
                       note = Synthetic polynucleotide
source                 1..2625
                       mol_type = other DNA
                       organism = synthetic construct
SEQUENCE: 39
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccagggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgcagag cagtgtctca gaagatttca aatgtatgga agctctgggc  840
atggaatcag gagaaattca ttctgaccag atcacagctt cttcccagta tagcaccaac  900
tggtctgcag agcgctcccg cctgaactac cctgagaatg ggtggactcc cggagaggat  960
tcctaccgag agtggataca ggtagacttg ggccttctgc gctttgtcac ggctgtcggg  1020
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
actcgatttg tccgaatcaa gcctgcaact tgggaaactg gcatatctat gagatttgaa  1260
gtatatggtt gcaagataac agattatcct tgctctggaa tgttgggtat ggtgtctgga  1320
cttatttctg actcccagat cacatcatcc aaccaagggg acagaaactg gatgcctgaa  1380
aacatccgcc tggtaaccag tcgctctggc tgggcacttc caccccgcacc tcattcctac  1440
atcaatgagt ggctccaaat agacctgggg gaggagaaga tcgtgagggg catcatcatt  1500
cagggtggga agcaccgaga gaacaaggtg ttcatgagga agttcaagat cgggtacagc  1560
aacaacggct cggactggaa gatgatcatg gatgacagca aacgcaaggc gaagtctttt  1620
gagggcaaca acaactatga tacacctgag ctgcggactt ttccagctct ctccacgcga  1680
ttcatcagga tctaccccga gagagccact catggcggac tggggctcag aatggagctg  1740
ctgggctgtg aagtggaagc cccctacagct ggaccgacca ctcccaacgg gaacttggtg  1800
gatgaatgtg atgacgacca ggccaactgc cacagtggaa caggtgatga cttccagctc  1860
acaggtggca ccactgtgct ggccacagaa aagcccacgg tcatagacag caccatacaa  1920
tcagagtttc caacatatgg ttttaactgt gaatttggct ggggctctca caagaccttc  1980
```

```
tgccactggg aacatgacaa tcacgtgcag ctcaagtgga gtgtgttgac cagcaagacg  2040
ggacccattc aggatcacac aggagatggc aacttcatct attcccaagc tgacgaaaat  2100
cagaagggca aagtggctcg cctggtgagc cctgtggttt attcccagaa ctctgcccac  2160
tgcatgacct tctggtatca catgtctggg tcccacgtcg gcacactcag ggtcaaactg  2220
cgctaccaga agccagagga gtacgatcag ctggtctgga tggccattgg acaccaaggt  2280
gaccactgga aggaagggcg tgtcttgctc cacaagtctc tgaaacttta tcaggtgatt  2340
ttcgagggcg aaatcggaaa aggaaacctt ggtgggattg ctgtggatga cattagtatt  2400
aataaccaca tttcacaaga agattgtgca aaaccagcag acctggataa aaagaaccca  2460
gaaattaaaa ttgatgaaac agggagcacg ccaggatacg aaggtgaagg agaaggtgac  2520
aagaacatct ccaggaagcc aggcaatgtg ttgaagacct tagaccccag atctggatcc  2580
aaggaaaact tgtatttcca gggccatcat catcatcatc attga                   2625
```

```
SEQ ID NO: 40          moltype = AA  length = 580
FEATURE                Location/Qualifiers
REGION                 1..580
                       note = Synthetic polypeptide
source                 1..580
                       mol_type = protein
                       organism = synthetic construct
SEQUENCE: 40
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLQSSVSE DFKCMEALGM ESGEIHSDQI TASSQYSTNW SAERSRLNYP ENGWTPGEDS  300
YREWIQVDLG LLRFVTAVGT QGAISKETKK KYYVKTYKID VSSNGEDWIT IKEGNKPVLF  360
QGNTNPTDVV VAVFPKPLIT RFVRIKPATW ETGISMRFEV YGCKITDYPC SGMLGMVSGL  420
ISDSQITSSN QGDRNWMPEN IRLVTSRSGW ALPPAPHSYI NEWLQIDLGE EKIVRGIIIQ  480
GGKHRENKVF MRKFKIGYSN NGSDWKMIMD DSKRKAKSFE GNNNYDTPEL RTFPALSTRF  540
IRIYPERATH GGLGLRMELL GCRSGSKENL YFQGHHHHHH                     580
```

```
SEQ ID NO: 41          moltype = DNA  length = 1806
FEATURE                Location/Qualifiers
misc_feature           1..1806
                       note = Synthetic polynucleotide
source                 1..1806
                       mol_type = other DNA
                       organism = synthetic construct
SEQUENCE: 41
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat ttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccaggggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgcagag cagtgtctca gaagatttca aatgtatgga agctctgggc  840
atggaatcag gagaaattca ttctgaccag atcacagctt cttcccagta tagcaccaac  900
tggtctgcag agcgctcccg cctgaactac cctgagaatg ggtggactcc cggagaggat  960
tcctaccgag agtggataca ggtagacttg ggccttctgc gctttgtcac ggctgtcggg  1020
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
actcgatttg tccgaatcaa gcctgcaact tgggaaactg gcatatctat gagatttgaa  1260
gtatatggtt gcaagataac agattatcct tgctctggaa tgttgggtat ggtgtctgga  1320
cttatttctg actcccagat cacatcatcc aaccaagggg acagaaactg gatgcctgaa  1380
aacatccgcc tggtaaccag tcgctctggc tgggcacttc cacccgcacc tcattcctac  1440
atcaatgagt ggctccaaat agacctgggg gaggagaaga tcgtgagggg catcatcatt  1500
cagggtggga agcaccgaga gaacaaggtg ttcatgagga agttcaagat cgggtacagc  1560
aacaacggct cggactggaa gatgatcatg gatgacagca aacgcaaggc gaagtctttt  1620
gagggcaaca acaactatga tacacctgag ctgcggactt ttccagctct ctccacgcga  1680
ttcatcagga tctaccccga gagagccact catggcggac tggggctcag aatggagctg  1740
ctgggctgta gatctggatc caaggaaaac ttgtatttcc agggccatca tcatcatcat  1800
cattga                                                             1806
```

```
SEQ ID NO: 42          moltype = AA  length = 421
FEATURE                Location/Qualifiers
REGION                 1..421
                       note = Synthetic polypeptide
source                 1..421
                       mol_type = protein
                       organism = synthetic construct
SEQUENCE: 42
```

-continued

```
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLQSSVSE DFKCMEALGM ESGEIHSDQI TASSQYSTNW SAERSRLNYP ENGWTPGEDS  300
YREWIQVDLG LLRFVTAVGT QGAISKETKK KYYVKTYKID VSSNGEDWIT IKEGNKPVLF  360
QGNTNPTDVV VAVFPKPLIT RFVRIKPATW ETGISMRFEV YGCRSGSKEN LYFQGHHHHH  420
H                                                                 421

SEQ ID NO: 43          moltype = DNA  length = 1329
FEATURE                Location/Qualifiers
misc_feature           1..1329
                       note = Synthetic polynucleotide
source                 1..1329
                       mol_type = other DNA
                       organism = synthetic construct
SEQUENCE: 43
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccaggggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgcagag cagtgtctca gaagatttca aatgtatgga agctctgggc  840
atggaatcag gagaaattca ttctgaccag atcacagctt cttcccagta tagcaccaac  900
tggtctgcag agcgctcccg cctgaactac cctgagaatg ggtggactcc cggagaggat  960
tcctaccgag agtggataca ggtagacttg ggccttctgc gctttgtcac ggctgtcggg  1020
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
actcgatttg tccgaatcaa gcctgcaact tgggaaactg gcatatctat gagatttgaa  1260
gtatatggtt gcagatctgg atccaaggaa aacttgtatt tccagggcca tcatcatcat  1320
catcattga                                                         1329

SEQ ID NO: 44          moltype = AA  length = 262
FEATURE                Location/Qualifiers
REGION                 1..262
                       note = Synthetic polypeptide
source                 1..262
                       mol_type = protein
                       organism = synthetic construct
SEQUENCE: 44
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLRSGSKE NLYFQGHHHH HH                                          262

SEQ ID NO: 45          moltype = DNA  length = 852
FEATURE                Location/Qualifiers
misc_feature           1..852
                       note = Synthetic polynucleotide
source                 1..852
                       mol_type = other DNA
                       organism = synthetic construct
SEQUENCE: 45
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccaggggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgagatc tggatccaag gaaaacttgt atttccaggg ccatcatcat  840
catcatcatt ga                                                     852
```

```
SEQ ID NO: 46          moltype = AA  length = 853
FEATURE                Location/Qualifiers
REGION                 1..853
                       note = Synthetic polypeptide
source                 1..853
                       mol_type = protein
                       organism = synthetic construct
SEQUENCE: 46
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLQSSVSE DFKCMEALGM ESGEIHSDQI TASSQASTNW SAERSRLNYP ENGWTPGEDS  300
YREWIQVDLG LLRFVTAVGT QGAISKETKK KYYVKTYKID VSSNGEDWIT IKEGNKPVLF  360
QGNTNPTDVV VAVFPKPLIT RFVRIKPATW ETGISMRFEV YGCKITDYPC SGMLGMVSGL  420
ISDSQITSSN QGDRNWMPEN IRLVTSRSGW ALPPAPHSYI NEWLQIDLGE EKIVRGIIIQ  480
GGKHRENKVF MRKFKIGYSN NGSDWKMIMD DSKRKAKSFE GNNNYDTPEL RTFPALSTRF  540
IRIYPERATH GGLGLRMELL GCEVEAPTAG PTTPNGNLVD ECDDDQANCH SGTGDDFQLT  600
GGTTVLATEK PTVIDSTIQS EFPTYGFNCE FGWGSHKTFC HWEHDNHVQL KWSVLTSKTG  660
PIQDHTGDGN FIYSQADENQ KGKVARLVSP VVYSQNSAHC MTFWYHMSGS HVGTLRVKLR  720
YQKPEEYDQL VWMAIGHQGD HWKEGRVLLH KSLKLYQVIF EGEIGKGNLG GIAVDDISIN  780
NHISQEDCAK PADLDKKNPE IKIDETGSTP GYEGEGEGDK NISRKPGNVL KTLDPRSGSK  840
ENLYFQGHHH HHH                                                    853

SEQ ID NO: 47          moltype = DNA  length = 2625
FEATURE                Location/Qualifiers
misc_feature           1..2625
                       note = Synthetic polynucleotide
source                 1..2625
                       mol_type = other DNA
                       organism = synthetic construct
SEQUENCE: 47
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccagggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgcagag cagtgtctca gaagatttca aatgtatgga agctctgggc  840
atggaatcag gagaaattca ttctgaccag atcacagctt cttcccaggc tagcaccaac  900
tggtctgcag agcgctcccg cctgaactac cctgagaatg ggtggactcc cggagaggat  960
tcctaccgag agtggataca ggtagacttg ggccttctgc gctttgtcac ggctgtcggg  1020
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
actcgatttg tccgaatcaa gcctgcaact tgggaaactg gcatatctat gagatttgaa  1260
gtatatggtt gcaagataac agattatcct tgctctggaa tgttgggtat ggtgtctgga  1320
cttatttctg actcccagat cacatcatcc aaccaagggg acagaaactg gatgcctgaa  1380
aacatccgcc tggtaaccag tcgctctggc tgggcacttc caccccgcacc tcattcctac  1440
atcaatgagt ggctccaaat agacctgggg gaggagaaga tcgtgagggg catcatcatt  1500
cagggtggga agcaccgaga gaacaaggtg ttcatgagga agttcaagat cgggtacagc  1560
aacaacggct cggactggaa gatgatcatg gatgacagca aacgcaaggc gaagtctttt  1620
gagggcaaca acaactatga tacacctgag ctgcggactt ttccagctct ctccacgcga  1680
ttcatcagga tctaccccga gagagccact catggcggac tggggctcag aatggagctg  1740
ctgggctgtg aagtggaagc ccctacagct ggaccgacca ctcccaacgg gaacttggtg  1800
gatgaatgtg atgacgacca ggccaactgc cacagtggaa caggtgatga cttccagctc  1860
acaggtggca ccactgtgct ggccacagaa aagcccacgg tcatagacag caccatacaa  1920
tcagagtttc caacatatgg ttttaactgt gaatttggct ggggctctca caagaccttc  1980
tgccactggg aacatgacaa tcacgtgcag ctcaagtgga gtgtgttgac cagcaagacg  2040
ggacccattc aggatcacac aggagatggc aacttcatct attcccaagc tgacgaaaat  2100
cagaagggca aagtggctcg cctggtgagc cctgtggttt attcccagaa ctctgcccac  2160
tgcatgacct tctggtatca catgtctggg tcccacgtcg gcacactcag ggtcaaactg  2220
cgctaccaga agccagagga gtacgatcag ctggtctgga tggccattgg acaccaaggt  2280
gaccactgga aggaagggcg tgtcttgctc cacaagtctc tgaaacttta tcaggtgatt  2340
ttcgagggcg aaatcggaaa aggaaacctt ggtgggattg ctgtggatga cattagtatt  2400
aataaccaca tttcacaaga agattgtgca aaaccagcag acctggataa aaagaaccca  2460
gaaattaaaa ttgatgaaac agggagcacg ccaggatacg aaggtgaagg agaaggtgac  2520
aagaacatct ccaggaagcc aggcaatgtg ttgaagacct tagaccccag atctggatcc  2580
aaggaaaact tgtatttcca gggccatcat catcatcatc attga                 2625

SEQ ID NO: 48          moltype = AA  length = 580
FEATURE                Location/Qualifiers
```

```
REGION                  1..580
                        note = Synthetic polypeptide
source                  1..580
                        mol_type = protein
                        organism = synthetic construct
SEQUENCE: 48
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLQSSVSE DFKCMEALGM ESGEIHSDQI TASSQASTNW SAERSRLNYP ENGWTPGEDS  300
YREWIQVDLG LLRFVTAVGT QGAISKETKK KYYVKTYKID VSSNGEDWIT IKEGNKPVLF  360
QGNTNPTDVV VAVFPKPLIT RFVRIKPATW ETGISMRFEV YGCKITDYPC SGMLGMVSGL  420
ISDSQITSSN QGDRNWMPEN IRLVTSRSGW ALPPAPHSYI NEWLQIDLGE EKIVRGIIIQ  480
GGKHRENKVF MRKFKIGYSN NGSDWKMIMD DSKRKAKSFE GNNNYDTPEL RTFPALSTRF  540
IRIYPERATH GGLGLRMELL GCRSGSKENL YFQGHHHHHH                        580

SEQ ID NO: 49           moltype = DNA  length = 1806
FEATURE                 Location/Qualifiers
misc_feature            1..1806
                        note = Synthetic polynucleotide
source                  1..1806
                        mol_type = other DNA
                        organism = synthetic construct
SEQUENCE: 49
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccagggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgcagag cagtgtctca gaagatttca aatgtatgga agctctgggc  840
atggaatcag gagaaattca ttctgaccag atcacagctt cttcccaggc tagcaccaac  900
tggtctgcag agcgctcccg cctgaactac cctgagaatg ggtggactcc cggagaggat  960
tcctaccgag agtggataca ggtagacttg ggccttctgc gctttgtcac ggctgtcggg  1020
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
actcgatttg tccgaatcaa gcctgcaact tgggaaactg gcatatctat gagatttgaa  1260
gtatatggtt gcaagataac agattatcct tgctctggaa tgttgggtat ggtgtctgga  1320
cttatttctg actcccagat cacatcatcc aaccaagggg acagaaactg gatgcctgaa  1380
aacatccgcc tggtaaccag tcgctctggc tgggcacttc caccccgcacc tcattcctac  1440
atcaatgagt ggctccaaat agacctgggg gaggagaaga tcgtgagggg catcatcatt  1500
cagggtggga agcaccgaga gaacaaggtg ttcatgagga agttcaagat cgggtacagc  1560
aacaacggct cggactggaa gatgatcatg gatgacagca aacgcaaggc gaagtctttt  1620
gagggcaaca acaactatga tacacctgag ctgcggactt ttccagctct ctccacgcga  1680
ttcatcagga tctaccccga gagagccact catggcggac tggggctcag aatggagctg  1740
ctgggctgta gatctggatc caaggaaaac ttgtatttcc agggccatca tcatcatcat  1800
cattga                                                             1806

SEQ ID NO: 50           moltype = AA  length = 421
FEATURE                 Location/Qualifiers
REGION                  1..421
                        note = Synthetic polypeptide
source                  1..421
                        mol_type = protein
                        organism = synthetic construct
SEQUENCE: 50
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLQSSVSE DFKCMEALGM ESGEIHSDQI TASSQASTNW SAERSRLNYP ENGWTPGEDS  300
YREWIQVDLG LLRFVTAVGT QGAISKETKK KYYVKTYKID VSSNGEDWIT IKEGNKPVLF  360
QGNTNPTDVV VAVFPKPLIT RFVRIKPATW ETGISMRFEV YGCRSGSKEN LYFQGHHHHH  420
H                                                                  421

SEQ ID NO: 51           moltype = DNA  length = 1329
FEATURE                 Location/Qualifiers
misc_feature            1..1329
                        note = Synthetic polynucleotide
source                  1..1329
```

```
                        mol_type = other DNA
                        organism = synthetic construct
SEQUENCE: 51
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccagggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgcagag cagtgtctca gaagatttca aatgtatgga agctctgggc  840
atggaatcag gagaaattca ttctgaccag atcacagctt cttcccaggc tagcaccaac  900
tggtctgcag agcgctcccg cctgaactac cctgagaatg ggtggactcc cggagaggat  960
tcctaccgag agtggataca ggtagacttg ggccttctgc gctttgtcac ggctgtcggg  1020
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
actcgatttg tccgaatcaa gcctgcaact tgggaaactg gcatatctat gagatttgaa  1260
gtatatggtt gcagatctgg atccaaggaa aacttgtatt tccagggcca tcatcatcat  1320
catcattga                                                          1329

SEQ ID NO: 52           moltype = AA  length = 700
FEATURE                 Location/Qualifiers
REGION                  1..700
                        note = Synthetic polypeptide
source                  1..700
                        mol_type = protein
                        organism = synthetic construct
SEQUENCE: 52
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLQSSVSE DFKCMEALGM ESGEIHSDQI TASSQYSTNW SAERSRLNYP ENGWTPGEDS  300
YREWIQVDLG LLRFVTAVGT QGAISKETKK KYYVKTYKID VSSNGEDWIT IKEGNKPVLF  360
QGNTNPTDVV VAVFPKPLIT RFVRIKPATW ETGISMRFEV YGCKITDYPE VEAPTAGPTT  420
PNGNLVDECD DDQANCHSGT GDDFQLTGGT TVLATEKPTV IDSTIQSEFP TYGFNCEFGW  480
GSHKTFCHWE HDNHVQLKWS VLTSKTGPIQ DHTGDGNFIY SQADENQKGK VARLVSPVVY  540
SQNSAHCMTF WYHMSGSHVG TLRVKLRYQK PEEYDQLVWM AIGHQGDHWK EGRVLLHKSL  600
KLYQVIFEGE IGKGNLGGIA VDDISINNHI SQEDCAKPAD LDKKNPEIKI DETGSTPGYE  660
GEGEGDKNIS RKPGNVLKTL DPRSGSKENL YFQGHHHHHH                        700

SEQ ID NO: 53           moltype = DNA  length = 2166
FEATURE                 Location/Qualifiers
misc_feature            1..2166
                        note = Synthetic polynucleotide
source                  1..2166
                        mol_type = other DNA
                        organism = synthetic construct
SEQUENCE: 53
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccagggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgcagag cagtgtctca gaagatttca aatgtatgga agctctgggc  840
atggaatcag gagaaattca ttctgaccag atcacagctt cttcccagta tagcaccaac  900
tggtctgcag agcgctcccg cctgaactac cctgagaatg ggtggactcc cggagaggat  960
tcctaccgag agtggataca ggtagacttg ggccttctgc gctttgtcac ggctgtcggg  1020
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
actcgatttg tccgaatcaa gcctgcaact tgggaaactg gcatatctat gagatttgaa  1260
gtatatggtt gcaagataac agattatcct gaagtggaag cccctacagc tggaccgacc  1320
actcccaacg ggaacttggt ggatgaatgt gatgacgacc aggccaactg ccacagtgga  1380
```

```
acaggtgatg acttccagct cacaggtggc accactgtgc tggccacaga aaagcccacg  1440
gtcatagaca gcaccataca atcagagttt ccaacatatg gttttaactg tgaatttggc  1500
tggggctctc acaagacctt ctgccactgg gaacatgaca atcacgtgca gctcaagtgg  1560
agtgtgttga ccagcaagac gggacccatt caggatcaca caggagatgg caacttcatc  1620
tattcccaag ctgacgaaaa tcagaagggc aaagtggctc gcctggtgag ccctgtggtt  1680
tattcccaga actctgccca ctgcatgacc ttctggtatc acatgtctgg gtcccacgtc  1740
ggcacactca gggtcaaact gcgctaccag aagccagagg agtacgatca gctggtctgg  1800
atggccattg gacaccaagg tgaccactgg aaggaagggc gtgtcttgct ccacaagtct  1860
ctgaaacttt atcaggtgat tttcgagggc gaaatcggaa aaggaaacct tggtgggatt  1920
gctgtggatg acattagtat taataaccac atttcacaag aagattgtgc aaaaccagca  1980
gacctggata aaaagaaccc agaaattaaa attgatgaaa cagggagcac gccaggatac  2040
gaaggtgaag gagaaggtga caagaacatc tccaggaagc caggcaatgt gttgaagacc  2100
ttagacccca gatctggatc caaggaaaac ttgtatttcc agggccatca tcatcatcat  2160
cattga                                                             2166

SEQ ID NO: 54          moltype = AA  length = 700
FEATURE                Location/Qualifiers
REGION                 1..700
                       note = Synthetic polypeptide
source                 1..700
                       mol_type = protein
                       organism = synthetic construct
SEQUENCE: 54
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLQSSVSE DFKCMEALGM ESGEIHSDQI TASSQASTNW SAERSRLNYP ENGWTPGEDS  300
YREWIQVDLG LLRFVTAVGT QGAISKETKK KYYVKTYKID VSSNGEDWIT IKEGNKPVLF  360
QGNTNPTDVV VAVFPKPLIT RFVRIKPATW ETGISMRFEV YGCKITDYPE VEAPTAGPTT  420
PNGNLVDECD DDQANCHSGT GDDFQLTGGT TVLATEKPTV IDSTIQSEFP TYGFNCEFGW  480
GSHKTFCHWE HDNHVQLKWS VLTSKTGPIQ DHTGDGNFIY SQADENQKGK VARLVSPVVY  540
SQNSAHCMTF WYHMSGSHVG TLRVKLRYQK PEEYDQLVWM AIGHQGDHWK EGRVLLHKSL  600
KLYQVIFEGE IGKGNLGGIA VDDISINNHI SQEDCAKPAD LDKKNPEIKI DETGSTPGYE  660
GEGEGDKNIS RKPGNVLKTL DPRSGSKENL YFQGHHHHHH                          700

SEQ ID NO: 55          moltype = DNA  length = 2166
FEATURE                Location/Qualifiers
misc_feature           1..2166
                       note = Synthetic polynucleotide
source                 1..2166
                       mol_type = other DNA
                       organism = synthetic construct
SEQUENCE: 55
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccaggggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgcagag cagtgtctca gaagatttca aatgtatgga agctctgggc  840
atggaatcag gagaaattca ttctgaccag atcacagctt cttcccaggc tagcaccaac  900
tggtctgcag agcgctcccg cctgaactac cctgagaatg ggtggactcc cggagaggat  960
tcctaccgag agtggataca ggtagacttg ggccttctgc gctttgtcac ggctgtcggg  1020
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
actcgatttg tccgaatcaa gcctgcaact tgggaaactg gcatatctat gagatttgaa  1260
gtatatggtt gcaagataac agattatcct gaagtggaag cccctacagc tggaccgacc  1320
actcccaacg ggaacttggt ggatgaatgt gatgacgacc aggccaactg ccacagtgga  1380
acaggtgatg acttccagct cacaggtggc accactgtgc tggccacaga aaagcccacg  1440
gtcatagaca gcaccataca atcagagttt ccaacatatg gttttaactg tgaatttggc  1500
tggggctctc acaagacctt ctgccactgg gaacatgaca atcacgtgca gctcaagtgg  1560
agtgtgttga ccagcaagac gggacccatt caggatcaca caggagatgg caacttcatc  1620
tattcccaag ctgacgaaaa tcagaagggc aaagtggctc gcctggtgag ccctgtggtt  1680
tattcccaga actctgccca ctgcatgacc ttctggtatc acatgtctgg gtcccacgtc  1740
ggcacactca gggtcaaact gcgctaccag aagccagagg agtacgatca gctggtctgg  1800
atggccattg gacaccaagg tgaccactgg aaggaagggc gtgtcttgct ccacaagtct  1860
ctgaaacttt atcaggtgat tttcgagggc gaaatcggaa aaggaaacct tggtgggatt  1920
gctgtggatg acattagtat taataaccac atttcacaag aagattgtgc aaaaccagca  1980
gacctggata aaaagaaccc agaaattaaa attgatgaaa cagggagcac gccaggatac  2040
gaaggtgaag gagaaggtga caagaacatc tccaggaagc caggcaatgt gttgaagacc  2100
```

```
ttagacccca gatctggatc caaggaaaac ttgtatttcc agggccatca tcatcatcat  2160
cattga                                                              2166

SEQ ID NO: 56          moltype = AA  length = 544
FEATURE                Location/Qualifiers
REGION                 1..544
                       note = Synthetic polypeptide
source                 1..544
                       mol_type = protein
                       organism = synthetic construct
SEQUENCE: 56
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLQSSVSE DFKEVEAPTA GPTTPNGNLV DECDDDQANC HSGTGDDFQL TGGTTVLATE  300
KPTVIDSTIQ SEFPTYGFNC EFGWGSHKTF CHWEHDNHVQ LKWSVLTSKT GPIQDHTGDG  360
NFIYSQADEN QKGKVARLVS PVVYSQNSAH CMTFWYHMSG SHVGTLRVKL RYQKPEEYDQ  420
LVWMAIGHQG DHWKEGRVLL HKSLKLYQVI FEGEIGKGNL GGIAVDDISI NNHISQEDCA  480
KPADLDKKNP EIKIDETGST PGYEGEGEGD KNISRKPGNV LKTLDPRSGS KENLYFQGHH  540
HHHH                                                                544

SEQ ID NO: 57          moltype = DNA  length = 1698
FEATURE                Location/Qualifiers
misc_feature           1..1698
                       note = Synthetic polynucleotide
source                 1..1698
                       mol_type = other DNA
                       organism = synthetic construct
SEQUENCE: 57
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccagggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgcagag cagtgtctca gaagatttca aagaagtgga agcccctaca  840
gctggaccga ccactcccaa cgggaacttg gtggatgaat gtgatgacga ccaggccaac  900
tgccacagtg gaacaggtga tgacttccag ctcacaggtg gcaccactgt gctggccaca  960
gaaaagccca cggtcataga cagcaccata caatcagagt ttccaacata tggttttaac  1020
tgtgaatttg gctggggctc tcacaagacc ttctgccact gggaacatga caatcacgtg  1080
cagctcaagt ggagtgtgtt gaccagcaag acgggaccca ttcaggatca cacaggagat  1140
ggcaacttca tctattccca agctgacgaa aatcagaagg gcaaagtggc tcgcctggtg  1200
agccctgtgg tttattccca gaactctgcc cactgcatga ccttctggta tcacatgtct  1260
gggtcccacg tcggcacact cagggtcaaa ctgcgctacc agaagccaga ggagtacgat  1320
cagctggtct ggatggccat tggacaccaa ggtgaccact ggaaggaagg gcgtgtcttg  1380
ctccacaagt ctctgaaact ttatcaggtg attttcgagg gcgaaatcgg aaaaggaaac  1440
cttggtggga ttgctgtgga tgacattagt attaataacc acatttcaca agaagattgt  1500
gcaaaaccag cagacctgga taaaaagaac ccagaaatta aaattgatga aacagggagc  1560
acgccaggat acgaaggtga aggagaaggt gacaagaaca tctccaggaa gccaggcaat  1620
gtgttgaaga ccttagaccc cagatctgga tccaaggaaa acttgtattt ccagggccat  1680
catcatcatc atcattga                                                 1698

SEQ ID NO: 58          moltype = AA  length = 853
FEATURE                Location/Qualifiers
REGION                 1..853
                       note = Synthetic polypeptide
source                 1..853
                       mol_type = protein
                       organism = synthetic construct
SEQUENCE: 58
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLQSSVSE DFKCMEALGM ESGEIHSDQI TASSQYSTNW SAERSRLNYP ENGWTPGEDS  300
YREWIQVDLG LLRFVTAVGT QGAIAKKTKK KYYVKTYKID VSSNGEDWIT IKEGNKPVLF  360
QGNTNPTDVV VAVFPKPLIT RFVRIKPATW ETGISMRFEV YGCKITDYPC SGMLGMVSGL  420
ISDSQITSSN QGDRNWMPEN IRLVTSRSGW ALPPAPHSYI NEWLQIDLGE EKIVRGIIIQ  480
GGKHRENKVF MRKFKIGYSN NGSDWKMIMD DSKRKAKSFE GNNNYDTPEL RTFPALSTRF  540
IRIYPERATH GGLGLRMELL GCEVEAPTAG PTTPNGNLVD ECDDDQANCH SGTGDDFQLT  600
GGTTVLATEK PTVIDSTIQS EFPTYGFNCE FGWGSHKTFC HWEHDNHVQL KWSVLTSKTG  660
```

```
PIQDHTGDGN FIYSQADENQ KGKVARLVSP VVYSQNSAHC MTFWYHMSGS HVGTLRVKLR  720
YQKPEEYDQL VWMAIGHQGD HWKEGRVLLH KSLKLYQVIF EGEIGKGNLG GIAVDDISIN  780
NHISQEDCAK PADLDKKNPE IKIDETGSTP GYEGEGEGDK NISRKPGNVL KTLDPRSGSK  840
ENLYFQGHHH HHH                                                     853

SEQ ID NO: 59           moltype = DNA  length = 2625
FEATURE                 Location/Qualifiers
misc_feature            1..2625
                        note = Synthetic polynucleotide
source                  1..2625
                        mol_type = other DNA
                        organism = synthetic construct
SEQUENCE: 59
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccaggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgcagag cagtgtctca gaagatttca aatgtatgga agctctgggc  840
atggaatcag gagaaattca ttctgaccag atcacagctt cttcccagta tagcaccaac  900
tggtctgcag agcgctcccg cctgaactac cctgagaatg ggtggactcc cggagaggat  960
tcctaccgag agtggataca ggtagacttg ggccttctgc gctttgtcac ggctgtcggg  1020
acacagggcg ccattgccaa aaagaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
actcgatttg tccgaatcaa gcctgcaact tgggaaactg gcatatctat gagatttgaa  1260
gtatatggtt gcaagataac agattatcct tgctctggaa tgttgggtat ggtgtctgga  1320
cttatttctg actcccagat cacatcatcc aaccaagggg acagaaactg gatgcctgaa  1380
aacatccgcc tggtaaccag tcgctctggc tgggcacttc cacccgcacc tcattcctac  1440
atcaatgagt ggctccaaat agacctgggg gaggagaaga tcgtgagggg catcatcatt  1500
cagggtggga agcaccgaga gaacaaggtg ttcatgagga agttcaagat cgggtacagc  1560
aacaacggct cggactggaa gatgatcatg gatgacagca aacgcaaggc gaagtctttt  1620
gagggcaaca acaactatga tacacctgag ctgcggactt ttccagctct ctccacgcga  1680
ttcatcagga tctaccccga gagagccact catggcggac tggggctcag aatggagctg  1740
ctgggctgtg aagtggaagc cctacagct ggaccgacca ctcccaacgg gaacttggtg  1800
gatgaatgtg atgacgacca ggccaactgc cacagtggaa caggtgatga cttccagctc  1860
acaggtggca ccactgtgct ggccacagaa aagcccacgg tcatagacag caccatacaa  1920
tcagagtttc caacatatgg ttttaactgt gaatttggct ggggctctca caagaccttc  1980
tgccactggg aacatgacaa tcacgtgcag ctcaagtgga gtgtgttgac cagcaagacg  2040
ggacccattc aggatcacac aggagatggc aacttcatct attcccaagc tgacgaaaat  2100
cagaagggca aagtggctcg cctggtgagc cctgtggttt attcccagaa ctctgcccac  2160
tgcatgacct tctggtatca catgtctggg tcccacgtcg gcacactcag ggtcaaactg  2220
cgctaccaga agccagagga gtacgatcag ctggtctgga tggccattgg acaccaaggt  2280
gaccactgga aggaagggcg tgtcttgctc cacaagtctc tgaaacttta tcaggtgatt  2340
ttcgagggcg aaatcggaaa aggaaacctt ggtgggattg ctgtggatga cattagtatt  2400
aataaccaca tttcacaaga agattgtgca aaaccagcag acctggataa aaagaaccca  2460
gaaattaaaa ttgatgaaac agggagcacg ccaggatacg aaggtgaagg agaaggtgac  2520
aagaacatct ccaggaagcc aggcaatgtg ttgaagacct tagaccccag atctggatcc  2580
aaggaaaact tgtatttcca gggccatcat catcatcatc attga                  2625

SEQ ID NO: 60           moltype = AA  length = 853
FEATURE                 Location/Qualifiers
REGION                  1..853
                        note = Synthetic polypeptide
source                  1..853
                        mol_type = protein
                        organism = synthetic construct
SEQUENCE: 60
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLQSSVSE DFKCMEALGM ESGEIHSDQI TASSQYSTNW SAERSRLNYP ENGWTPGEKS  300
YREWIQVDLG LLRFVTAVGT QGAISKETKK KYYVKTYKID VSSNGEDWIT IKEGNKPVLF  360
QGNTNPTDVV VAVFPKPLIT RFVRIKPATW ETGISMRFEV YGCKITDYPC SGMLGMVSGL  420
ISDSQITSSN QGDRNWMPEN IRLVTSRSGW ALPPAPHSYI NEWLQIDLGE EKIVRGIIIQ  480
GGKHRENKVF MRKFKIGYSN NGSDWKMIMD DSKRKAKSFE GNNNYDTPEL RTFPALSTRF  540
IRIYPERATH GGLGLRMELL GCEVEAPTAG PTTPNGNLVD ECDDDQANCH SGTGDDFQLT  600
GGTTVLATEK PTVIDSTIQS EFPTYGFNCE FGWGSHKTFC HWEHDNHVQL KWSVLTSKTG  660
PIQDHTGDGN FIYSQADENQ KGKVARLVSP VVYSQNSAHC MTFWYHMSGS HVGTLRVKLR  720
YQKPEEYDQL VWMAIGHQGD HWKEGRVLLH KSLKLYQVIF EGEIGKGNLG GIAVDDISIN  780
```

```
NHISQEDCAK PADLDKKNPE IKIDETGSTP GYEGEGEGDK NISRKPGNVL KTLDPRSGSK  840
ENLYFQGHHH HHH                                                     853

SEQ ID NO: 61          moltype = DNA  length = 2625
FEATURE                Location/Qualifiers
misc_feature           1..2625
                       note = Synthetic polynucleotide
source                 1..2625
                       mol_type = other DNA
                       organism = synthetic construct
SEQUENCE: 61
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccagggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgcagag cagtgtctca gaagatttca aatgtatgga agctctgggc  840
atggaatcag gagaaattca ttctgaccag atcacagctt cttcccagta tagcaccaac  900
tggtctgcag agcgctcccg cctgaactac cctgagaatg ggtggactcc cggagagaag  960
tcctaccgag agtggataca ggtagacttg ggccttctgc gctttgtcac ggctgtcggg  1020
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
actcgatttg tccgaatcaa gcctgcaact tgggaaactg gcatatctat gagatttgaa  1260
gtatatggtt gcaagataac agattatcct tgctctggaa tgttgggtat ggtgtctgga  1320
cttatttctg actcccagat cacatcatcc aaccaagggg acagaaactg gatgcctgaa  1380
aacatccgcc tggtaaccag tcgctctggc tgggcacttc caccccgcacc tcattcctac  1440
atcaatgagt ggctccaaat agacctgggg gaggagaaga tcgtgagggg catcatcatt  1500
cagggtggga agcaccgaga gaacaaggtg ttcatgagga agttcaagat cgggtacagc  1560
aacaacggct cggactggaa gatgatcatg gatgacagca aacgcaaggc gaagtctttt  1620
gagggcaaca acaactatga tacacctgag ctgcggactt ttccagctct ctccacgcga  1680
ttcatcagga tctaccccga gagagccact catggcggac tggggctcag aatggagctg  1740
ctgggctgtg aagtggaagc ccctacagct ggaccgacca ctcccaacgg gaacttggtg  1800
gatgaatgtg atgacgacca ggccaactgc cacagtggaa caggtgatga cttccagctc  1860
acaggtggca ccactgtgct ggccacagaa aagcccacgg tcatagacag caccatacaa  1920
tcagagtttc caacatatgg ttttaactgt gaatttggct ggggctctca caagaccttc  1980
tgccactggg aacatgacaa tcacgtgcag ctcaagtgga gtgtgttgac cagcaagacg  2040
ggacccattc aggatcacac aggagatggc aacttcatct attcccaagc tgacgaaaat  2100
cagaagggca aagtggctcg cctggtgagc cctgtggttt attcccagaa ctctgcccac  2160
tgcatgacct tctggtatca catgtctggg tcccacgtcg gcacactcag ggtcaaactg  2220
cgctaccaga agccagagga gtacgatcag ctggtctgga tggccattgg acaccaaggt  2280
gaccactgga aggaagggcg tgtcttgctc cacaagtctc tgaaacttta tcaggtgatt  2340
ttcgagggcg aaatcggaaa aggaaacctt ggtgggattg ctgtggatga cattagtatt  2400
aataaccaca tttcacaaga agattgtgca aaaccagcag acctggataa aaagaaccca  2460
gaaattaaaa ttgatgaaac agggagcacg ccaggatacg aaggtgaagg agaaggtgac  2520
aagaacatct ccaggaagcc aggcaatgtg ttgaagacct tagaccccag atctggatcc  2580
aaggaaaact tgtatttcca gggccatcat catcatcatc attga                  2625

SEQ ID NO: 62          moltype = AA  length = 853
FEATURE                Location/Qualifiers
REGION                 1..853
                       note = Synthetic polypeptide
source                 1..853
                       mol_type = protein
                       organism = synthetic construct
SEQUENCE: 62
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECSQNY TTPSGVIKSP GFPEKYPNSL ECTYIVFAPK MSEIILEFES FDLEPDSNPP  180
GGMFCRYDRL EIWDGFPDVG PHIGRYCGQK TPGRIRSSSG ILSMVFYTDS AIAKEGFSAN  240
YSVLQSSVSE DFKCMEALGM ESGEIHSDQI TASSQYSTNW SAERSRLNYP ENGWTPGKKS  300
YREWIQVDLG LLRFVTAVGT QGAISKETKK KYYVKTYKID VSSNGEDWIT IKEGNKPVLF  360
QGNTNPTDVV VAVFPKPLIT RFVRIKPATW ETGISMRFEV YGCKITDYPC SGMLGMVSGL  420
ISDSQITSSN QGDRNWMPEN IRLVTSRSGW ALPPAPHSYI NEWLQIDLGE EKIVRGIIIQ  480
GGKHRENKVF MRKFKIGYSN NGSDWKMIMD DSKRKAKSFE GNNNYDTPEL RTFPALSTRF  540
IRIYPERATH GGLGLRMELL GCEVEAPTAG PTTPNGNLVD ECDDDQANCH SGTGDDFQLT  600
GGTTVLATEK PTVIDSTIQS EFPTYGFNCE FGWGSHKTFC HWEHDNHVQL KWSVLTSKTG  660
PIQDHTGDGN FIYSQADENQ KGKVARLVSP VVYSQNSAHC MTFWYHMSGS HVGTLRVKLR  720
YQKPEEYDQL VWMAIGHQGD HWKEGRVLLH KSLKLYQVIF EGEIGKGNLG GIAVDDISIN  780
NHISQEDCAK PADLDKKNPE IKIDETGSTP GYEGEGEGDK NISRKPGNVL KTLDPRSGSK  840
ENLYFQGHHH HHH                                                     853
```

```
SEQ ID NO: 63          moltype = DNA  length = 2625
FEATURE                Location/Qualifiers
misc_feature           1..2625
                       note = Synthetic polynucleotide
source                 1..2625
                       mol_type = other DNA
                       organism = synthetic construct
SEQUENCE: 63
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccagggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgcagag cagtgtctca gaagatttca aatgtatgga agctctgggc  840
atggaatcag gagaaattca ttctgaccag atcacagctt cttcccagta tagcaccaac  900
tggtctgcag agcgctcccg cctgaactac cctgagaatg ggtggactcc cggaaagaag  960
tcctaccgag agtggataca ggtagacttg ggccttctgc gctttgtcac ggctgtcggg  1020
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
actcgatttg tccgaatcaa gcctgcaact tgggaaactg gcatatctat gagatttgaa  1260
gtatatggtt gcaagataac agattatcct tgctctggaa tgttgggtat ggtgtctgga  1320
cttatttctg actcccagat cacatcatcc aaccaagggg acagaaactg gatgcctgaa  1380
aacatccgcc tggtaaccag tcgctctggc tgggcacttc cacccgcacc tcattcctac  1440
atcaatgagt ggctccaaat agacctgggg gaggagaaga tcgtgagggg catcatcatt  1500
cagggtggga agcaccgaga gaacaaggtg ttcatgagga agttcaagat cgggtacagc  1560
aacaacggct cggactggaa gatgatcatg gatgacagca aacgcaaggc gaagtctttt  1620
gagggcaaca acaactatga tacacctgag ctgcggactt ttccagctct ctccacgcga  1680
ttcatcagga tctaccccga gagagccact catggcggac tggggctcag aatggagctg  1740
ctgggctgtg aagtggaagc ccctacagct ggaccgacca ctcccaacgg gaacttggtg  1800
gatgaatgtg atgacgacca ggccaactgc cacagtggaa caggtgatga cttccagctc  1860
acaggtggca ccactgtgct ggccacagaa aagcccacgg tcatagacag caccatacaa  1920
tcagagtttc caacatatgg ttttaactgt gaatttggct ggggctctca caagaccttc  1980
tgccactggg aacatgacaa tcacgtgcag ctcaagtgga gtgtgttgac cagcaagacg  2040
ggacccattc aggatcacac aggagatggc aacttcatct attcccaagc tgacgaaaat  2100
cagaagggca aagtggctcg cctggtgagc cctgtggttt attcccagaa ctctgcccac  2160
tgcatgacct tctggtatca catgtctggg tcccacgtcg gcacactcag ggtcaaactg  2220
cgctaccaga agccagagga gtacgatcag ctggtctgga tggccattgg acaccaaggt  2280
gaccactgga aggaagggcg tgtcttgctc cacaagtctc tgaaacttta tcaggtgatt  2340
ttcgagggcg aaatcggaaa aggaaacctt ggtgggattg ctgtggatga cattagtatt  2400
aataaccaca tttcacaaga agattgtgca aaaccagcag acctggataa aaagaaccca  2460
gaaattaaaa ttgatgaaac agggagcacg ccaggatacg aaggtgaagg agaaggtgac  2520
aagaacatct ccaggaagcc aggcaatgtg ttgaagacct tagaccccag atctggatcc  2580
aaggaaaact tgtatttcca gggccatcat catcatcatc attga                 2625

SEQ ID NO: 64          moltype = AA  length = 771
FEATURE                Location/Qualifiers
source                 1..771
                       mol_type = protein
                       organism = Homo sapiens
SEQUENCE: 64
MGWLTRIVCL FWGVLLTARA NYQNGKNNVP RLKLSYKEML ESNNVITFNG LANSSSYHTF  60
LLDEERSRLY VGAKDHIFSF DLVNIKDFQK IVWPVSYTRR DECKWAGKDI LKECANFIKV  120
LKAYNQTHLY ACGTGAFHPI CTYIEIGHHP EDNIFKLENS HFENGRGKSP YDPKLLTASL  180
LIDGELYSGT AADFMGRDFA IFRTLGHHHP IRTEQHDSRW LNDPKFISAH LISESDNPED  240
DKVYFFFREN AIDGEHSGKA THARIGQICK NDFGGHRSLV NKWTTFLKAR LICSVPGPNG  300
IDTHFDELQD VFLMNFKDPK NPVVYGVFTT SSNIFKGSAV CMYSMSDVRR VFLGPYAHRD  360
GPNYQWVPYQ GRVPYPRPGT CPSKTFGGFD STKDLPDDVI TFARSHPAMY NPVFPMNNRP  420
IVIKTDVNYQ FTQIVVDRVD AEDGQYDVMF IGTDVGTVLK VVSIPKETWY DLEEVLLEEM  480
TVFREPTAIS AMELSTKQQQ LYIGSTAGVA QLPLHRCDIY GKACAECCLA RDPYCAWDGS  540
ACSRYFPTAK RRTRRQDIRN GDPLTHCSDL HHDNHHGHSP EERIIYGVEN SSTFLECSPK  600
SQRALVYWQF QRRNEERKEE IRVDDHIIRT DQGLLLRSLQ QKDSGNYLCH AVEHGFIQTL  660
LKVTLEVIDT EHLEELLHKD DDGDGSKTKE MSNSMTPSQK VWYRDFMQLI NHPNLNTMDE  720
FCEQVWKRDR KQRRQRPGHT PGNSNKWKHL QENKKGRNRR THEFERAPRS V           771

SEQ ID NO: 65          moltype = AA  length = 609
FEATURE                Location/Qualifiers
source                 1..609
                       mol_type = protein
                       organism = Homo sapiens
```

```
SEQUENCE: 65
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEI FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVLQSSVS EDFKCMEALG MESGEIHSDQ ITASSQYSTN  300
WSAERSRLNY PENGWTPGED SYREWIQVDL GLLRFVTAVG TQGAISKETK KKYYVKTYKI  360
DVSSNGEDWI TIKEGNKPVL FQGNTNPTDV VVAVFPKPLI TRFVRIKPAT WETGISMRFE  420
VYGCKITDYP CSGMLGMVSG LISDSQITSS NQGDRNWMPE NIRLVTSRSG WALPPAPHSY  480
INEWLQIDLG EEKIVRGIII QGGKHRENKV FMRKFKIGYS NNGSDWKMIM DDSKRKAKSF  540
EGNNNYDTPE LRTFPALSTR FIRIYPERAT HGGLGLRMEL LGCEVEGGTT VLATEKPTVI  600
DSTIQSGIK                                                         609

SEQ ID NO: 66          moltype = AA  length = 923
FEATURE                Location/Qualifiers
source                 1..923
                       mol_type = protein
                       organism = Homo sapiens
SEQUENCE: 66
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVLQSSVS EDFKCMEALG MESGEIHSDQ ITASSQYSTN  300
WSAERSRLNY PENGWTPGED SYREWIQVDL GLLRFVTAVG TQGAISKETK KKYYVKTYKI  360
DVSSNGEDWI TIKEGNKPVL FQGNTNPTDV VVAVFPKPLI TRFVRIKPAT WETGISMRFE  420
VYGCKITDYP CSGMLGMVSG LISDSQITSS NQGDRNWMPE NIRLVTSRSG WALPPAPHSY  480
INEWLQIDLG EEKIVRGIII QGGKHRENKV FMRKFKIGYS NNGSDWKMIM DDSKRKAKSF  540
EGNNNYDTPE LRTFPALSTR FIRIYPERAT HGGLGLRMEL LGCEVEAPTA GPTTPNGNLV  600
DECDDDQANC HSGTGDDFQL TGGTTVLATE KPTVIDSTIQ SEFPTYGFNC EFGWGSHKTF  660
CHWEHDNHVQ LKWSVLTSKT GPIQDHTGDG NFIYSQADEN QKGKVARLVS PVVYSQNSAH  720
CMTFWYHMSG SHVGTLRVKL RYQKPEEYDQ LVWMAIGHQG DHWKEGRVLL HKSLKLYQVI  780
FEGEIGKGNL GGIAVDDISI NNHISQEDCA KPADLDKKNP EIKIDETGST PGYEGEGEGD  840
KNISRKPGNV LKTLDPILIT IIAMSALGVL LGAVCGVVLY CACWHNGMSE RNLSALENYN  900
FELVDGVKLK KDKLNTQSTY SEA                                         923

SEQ ID NO: 67          moltype = AA  length = 923
FEATURE                Location/Qualifiers
source                 1..923
                       mol_type = protein
                       organism = Mus musculus
SEQUENCE: 67
MERGLPLLCA TLALALALAG AFRSDKCGGT IKIENPGYLT SPGYPHSYHP SEKCEWLIQA  60
PEPYQRIMIN FNPHFDLEDR DCKYDYVEVI DGENEGGRLW GKFCGKIAPS PVVSSGPFLF  120
IKFVSDYETH GAGFSIRYEI FKRGPECSQN YTAPTGVIKS PGFPEKYPNS LECTYIIFAP  180
KMSEIILEFE SFDLEQDSNP PGGMFCRYDR LEIWDGFPEV GPHIGRYCGQ KTPGRIRSSS  240
GVLSMVFYTD SAIAKEGFSA NYSVLQSSIS EDFKCMEALG MESGEIHSDQ ITASSQYGTN  300
WSVERSRLNY PENGWTPGED SYKEWIQVDL GLLRFVTAVG TQGAISKETK KKYYVKTYRV  360
DISSNGEDWI SLKEGNKAII FQGNTNPTDV VLGVFSKPLI TRFVRIKPVS WETGISMRFE  420
VYGCKITDYP CSGMLGMVSG LISDSQITAS NQADRNWMPE NIRLVTSRTG WALPPSPHPY  480
TNEWLQVDLG DEKIVRGVII QGGKHRENKV FMRKFKIAYS NNGSDWKTIM DDSKRKAKSF  540
EGNNNYDTPE LRTFSPLSTR FIRIYPERAT HSGLGLRMEL LGCEVEAPTA GPTTPNGNPV  600
DECDDDQANC HSGTGDDFQL TGGTTVLATE KPTIIDSTIQ SEFPTYGFNC EFGWGSHKTF  660
CHWEHDSHAQ LRWSVLTSKT GPIQDHTGDG NFIYSQADEN QKGKVARLVS PVVYSQSSAH  720
CMTFWYHMSG SHVGTLRVKL RYQKPEEYDQ LVWMVVGHQG DHWKEGRVLL HKSLKLYQVI  780
FEGEIGKGNL GGIAVDDISI NNHISQEDCA KPTDLDKKNT EIKIDETGST PGYEGEGEGD  840
KNISRKPGNV LKTLDPILIT IIAMSALGVL LGAVCGVVLY CACWHNGMSE RNLSALENYN  900
FELVDGVKLK KDKLNPQSNY SEA                                         923

SEQ ID NO: 68          moltype = AA  length = 923
FEATURE                Location/Qualifiers
source                 1..923
                       mol_type = protein
                       organism = Rattus norvegicus
SEQUENCE: 68
MERGLPLLCA TLALALALAG AFRSDKCGGT IKIENPGYLT SPGYPHSYHP SEKCEWLIQA  60
PEPYQRIMIN FNPHFDLEDR DCKYDYVEVI DGENEGGRLW GKFCGKIAPS PVVSSGPFLF  120
IKFVSDYETH GAGFSIRYEI FKRGPECSQN YTAPTGVIKS PGFPEKYPNS LECTYIIFAP  180
KMSEIILEFE SFDLEQDSNP PGGVFCRYDR LEIWDGFPEV GPHIGRYCGQ KTPGRIRSSS  240
GILSMVFYTD SAIAKEGFSA NYSVLQSSIS EDFKCMEALG MESGEIHSDQ ITASSQYGTN  300
WSVERSRLNY PENGWTPGED SYREWIQVDL GLLRFVTAVG TQGAISKETK KKYYVKTYRV  360
DISSNGEDWI TLKEGNKAII FQGNTNPTDV VFGVFPKPLI TRFVRIKPAS WETGISMRFE  420
VYGCKITDYP CSGMLGMVSG LISDSQITAS NQGDRNWMPE NIRLVTSRTG WALPPSPHPY  480
INEWLQVDLG DEKIVRGVII QGGKHRENKV FMRKFKIAYS NNGSDWKMIM DDSKRKAKSF  540
EGNNNYDTPE LRAFTPLSTR FIRIYPERAT HSGLGLRMEL LGCEVEVPTA GPTTPNGNPV  600
DECDDDQANC HSGTGDDFQL TGGTTVLATE KPTIIDSTIQ SEFPTYGFNC EFGWGSHKTF  660
CHWEHDSHAQ LRWRVLTSKT GPIQDHTGDG NFIYSQADEN QKGKVARLVS PVVYSQSSAH  720
CMTFWYHMSG SHVGTLRVKL HYQKPEEYDQ LVWMVVGHQG DHWKEGRVLL HKSLKLYQVI  780
FEGEIGKGNL GGIAVDDISI NNHIPQEDCA KPTDLDKKNT EIKIDETGST PGYEEEGKGD  840
```

```
KNISRKPGNV LKTLDPILIT IIAMSALGVL LGAVCGVVLY CACWHNGMSE RNLSALENYN  900
FELVDGVKLK KDKLNPQSNY SEA                                          923

SEQ ID NO: 69            moltype = AA  length = 923
FEATURE                  Location/Qualifiers
REGION                   1..923
                         note = Synthetic polypeptide
SITE                     11
                         note = misc_feature - Xaa can be any naturally occurring
                          amino acid
SITE                     15
                         note = misc_feature - Xaa can be any naturally occurring
                          amino acid
SITE                     18
                         note = misc_feature - Xaa can be any naturally occurring
                          amino acid
SITE                     24
                         note = misc_feature - Xaa can be any naturally occurring
                          amino acid
SITE                     29
                         note = misc_feature - Xaa can be any naturally occurring
                          amino acid
SITE                     35
                         note = misc_feature - Xaa can be any naturally occurring
                          amino acid
SITE                     62
                         note = misc_feature - Xaa can be any naturally occurring
                          amino acid
SITE                     90
                         note = misc_feature - Xaa can be any naturally occurring
                          amino acid
SITE                     96
                         note = misc_feature - Xaa can be any naturally occurring
                          amino acid
REGION                   98..100
                         note = misc_feature - Xaa can be any naturally occurring
                          amino acid
SITE                     110
                         note = misc_feature - Xaa can be any naturally occurring
                          amino acid
SITE                     140
                         note = misc_feature - Xaa can be any naturally occurring
                          amino acid
SITE                     153
                         note = misc_feature - Xaa can be any naturally occurring
                          amino acid
SITE                     155
                         note = misc_feature - Xaa can be any naturally occurring
                          amino acid
SITE                     177
                         note = misc_feature - Xaa can be any naturally occurring
                          amino acid
SITE                     196
                         note = misc_feature - Xaa can be any naturally occurring
                          amino acid
SITE                     204
                         note = misc_feature - Xaa can be any naturally occurring
                          amino acid
SITE                     219
                         note = misc_feature - Xaa can be any naturally occurring
                          amino acid
SITE                     242
                         note = misc_feature - Xaa can be any naturally occurring
                          amino acid
SITE                     269
                         note = misc_feature - Xaa can be any naturally occurring
                          amino acid
SITE                     298
                         note = misc_feature - Xaa can be any naturally occurring
                          amino acid
SITE                     303
                         note = misc_feature - Xaa can be any naturally occurring
                          amino acid
SITE                     323
                         note = misc_feature - Xaa can be any naturally occurring
                          amino acid
REGION                   359..360
                         note = misc_feature - Xaa can be any naturally occurring
                          amino acid
```

| | |
|---|---|
| SITE | 362<br>note = misc_feature - Xaa can be any naturally occurring amino acid |
| REGION | 371..372<br>note = misc_feature - Xaa can be any naturally occurring amino acid |
| REGION | 378..380<br>note = misc_feature - Xaa can be any naturally occurring amino acid |
| REGION | 392..393<br>note = misc_feature - Xaa can be any naturally occurring amino acid |
| SITE | 396<br>note = misc_feature - Xaa can be any naturally occurring amino acid |
| REGION | 409..410<br>note = misc_feature - Xaa can be any naturally occurring amino acid |
| SITE | 449<br>note = misc_feature - Xaa can be any naturally occurring amino acid |
| SITE | 453<br>note = misc_feature - Xaa can be any naturally occurring amino acid |
| SITE | 469<br>note = misc_feature - Xaa can be any naturally occurring amino acid |
| SITE | 476<br>note = misc_feature - Xaa can be any naturally occurring amino acid |
| SITE | 479<br>note = misc_feature - Xaa can be any naturally occurring amino acid |
| SITE | 481<br>note = misc_feature - Xaa can be any naturally occurring amino acid |
| SITE | 487<br>note = misc_feature - Xaa can be any naturally occurring amino acid |
| SITE | 491<br>note = misc_feature - Xaa can be any naturally occurring amino acid |
| SITE | 498<br>note = misc_feature - Xaa can be any naturally occurring amino acid |
| SITE | 518<br>note = misc_feature - Xaa can be any naturally occurring amino acid |
| SITE | 528<br>note = misc_feature - Xaa can be any naturally occurring amino acid |
| SITE | 553<br>note = misc_feature - Xaa can be any naturally occurring amino acid |
| REGION | 555..556<br>note = misc_feature - Xaa can be any naturally occurring amino acid |
| SITE | 572<br>note = misc_feature - Xaa can be any naturally occurring amino acid |
| SITE | 587<br>note = misc_feature - Xaa can be any naturally occurring amino acid |
| SITE | 599<br>note = misc_feature - Xaa can be any naturally occurring amino acid |
| SITE | 634<br>note = misc_feature - Xaa can be any naturally occurring amino acid |
| SITE | 667<br>note = misc_feature - Xaa can be any naturally occurring amino acid |
| SITE | 669<br>note = misc_feature - Xaa can be any naturally occurring amino acid |
| SITE | 672<br>note = misc_feature - Xaa can be any naturally occurring amino acid |
| SITE | 674 |

```
                     note = misc_feature - Xaa can be any naturally occurring
                      amino acid
SITE                 717
                     note = misc_feature - Xaa can be any naturally occurring
                      amino acid
SITE                 741
                     note = misc_feature - Xaa can be any naturally occurring
                      amino acid
REGION               755..756
                     note = misc_feature - Xaa can be any naturally occurring
                      amino acid
SITE                 805
                     note = misc_feature - Xaa can be any naturally occurring
                      amino acid
SITE                 812
                     note = misc_feature - Xaa can be any naturally occurring
                      amino acid
REGION               819..820
                     note = misc_feature - Xaa can be any naturally occurring
                      amino acid
SITE                 835
                     note = misc_feature - Xaa can be any naturally occurring
                      amino acid
SITE                 838
                     note = misc_feature - Xaa can be any naturally occurring
                      amino acid
SITE                 916
                     note = misc_feature - Xaa can be any naturally occurring
                      amino acid
SITE                 919
                     note = misc_feature - Xaa can be any naturally occurring
                      amino acid
source               1..923
                     mol_type = protein
                     organism = synthetic construct
SEQUENCE: 69
MERGLPLLCA XLALXLAXAG AFRXDKCGXT IKIEXPGYLT SPGYPHSYHP SEKCEWLIQA  60
PXPYQRIMIN FNPHFDLEDR DCKYDYVEVX DGENEXGXXX GKFCGKIAPX PVVSSGPFLF  120
IKFVSDYETH GAGFSIRYEX FKRGPECSQN YTXPXGVIKS PGFPEKYPNS LECTYIXFAP  180
KMSEIILEFE SFDLEXDSNP PGGXFCRYDR LEIWDGFPXV GPHIGRYCGQ KTPGRIRSSS  240
GXLSMVFYTD SAIAKEGFSA NYSVLQSSXS EDFKCMEALG MESGEIHSDQ ITASSQYXTN  300
WSXERSRLNY PENGWTPGED SYXEWIQVDL GLLRFVTAVG TQGAISKETK KKYYVKTYXX  360
DXSSNGEDWI XXKEGNKXXX FQGNTNPTDV VXXVFXKPLI TRFVRIKPXX WETGISMRFE  420
VYGCKITDYP CSGMLGMVSG LISDSQITXS NQXDRNWMPE NIRLVTSRXG WALPPXPHXY  480
XNEWLQXDLG XEKIVRGXII QGGKHRENKV FMRKFKIXYS NNGSDWKXIM DDSKRKAKSF  540
EGNNNYDTPE LRXFXXLSTR FIRIYPERAT HXGLGLRMEL LGCEVEXPTA GPTTPNGNXV  600
DECDDDQANC HSGTGDDFQL TGGTTVLATE KPTXIDSTIQ SEFPTYGFNC EFGWGSHKTF  660
CHWEHDXHXQ LXWXVLTSKT GPIQDHTGDG NFIYSQADEN QKGKVARLVS PVVYSQXSAH  720
CMTFWYHMSG SHVGTLRVKL XYQKPEEYDQ LVWMXXGHQG DHWKEGRVLL HKSLKLYQVI  780
FEGEIGKGNL GGIAVDDISI NNHIXQEDCA KXDLDKKNXX EIKIDETGST PGYEXEGXGD  840
KNISRKPGNV LKTLDPILIT IIAMSALGVL LGAVCGVVLY CACWHNGMSE RNLSALENYN  900
FELVDGVKLK KDKLNXQSXY SEA                                          923

SEQ ID NO: 70        moltype = AA  length = 21
FEATURE              Location/Qualifiers
source               1..21
                     mol_type = protein
                     organism = Homo sapiens
SEQUENCE: 70
MERGLPLLCA VLALVLAPAG A                                            21

SEQ ID NO: 71        moltype = AA  length = 115
FEATURE              Location/Qualifiers
source               1..115
                     mol_type = protein
                     organism = Homo sapiens
SEQUENCE: 71
CGDTIKIESP GYLTSPGYPH SYHPSEKCEW LIQAPDPYQR IMINFNPHFD LEDRDCKYDY  60
VEVFDGENEN GHFRGKFCGK IAPPPVVSSG PFLFIKFVSD YETHGAGFSI RYELF       115

SEQ ID NO: 72        moltype = AA  length = 119
FEATURE              Location/Qualifiers
source               1..119
                     mol_type = protein
                     organism = Homo sapiens
SEQUENCE: 72
CSQNYTTPSG VIKSPGFPEK YPNSLECTYI VFAPKMSEII LEFESFDLEP DSNPPGGMFC  60
RYDRLEIWDG FPDVGPHIGR YCGQKTPGRI RSSSGILSMV FYTDSAIAKE GFSANYSVL   119
```

```
SEQ ID NO: 73          moltype = AA  length = 150
FEATURE                Location/Qualifiers
source                 1..150
                       mol_type = protein
                       organism = Homo sapiens
SEQUENCE: 73
CMEALGMESG EIHSDQITAS SQYSTNWSAE RSRLNYPENG WTPGEDSYRE WIQVDLGLLR  60
FVTAVGTQGA ISKETKKKYY VKTYKIDVSS NGEDWITIKE GNKPVLFQGN TNPTDVVVAV  120
FPKPLITRFV RIKPATWETG ISMRFEVYGC                                   150

SEQ ID NO: 74          moltype = AA  length = 153
FEATURE                Location/Qualifiers
source                 1..153
                       mol_type = protein
                       organism = Homo sapiens
SEQUENCE: 74
CSGMLGMVSG LISDSQITSS NQGDRNWMPE NIRLVTSRSG WALPPAPHSY INEWLQIDLG  60
EEKIVRGIII QGGKHRENKV FMRKFKIGYS NNGSDWKMIM DDSKRKAKSF EGNNNYDTPE  120
LRTFPALSTR FIRIYPERAT HGGLGLRMEL LGC                               153

SEQ ID NO: 75          moltype = AA  length = 167
FEATURE                Location/Qualifiers
source                 1..167
                       mol_type = protein
                       organism = Homo sapiens
SEQUENCE: 75
TYGFNCEFGW GSHKTFCHWE HDNHVQLKWS VLTSKTGPIQ DHTGDGNFIY SQADENQKGK  60
VARLVSPVVY SQNSAHCMTF WYHMSGSHVG TLRVKLRYQK PEEYDQLVWM AIGHQGDHWK  120
EGRVLLHKSL KLYQVIFEGE IGKGNLGGIA VDDISINNHI SQEDCAK                167

SEQ ID NO: 76          moltype = AA  length = 10
FEATURE                Location/Qualifiers
REGION                 1..10
                       note = Synthetic polypeptide
source                 1..10
                       mol_type = protein
                       organism = synthetic construct
SEQUENCE: 76
GSKENLYFQG                                                         10

SEQ ID NO: 77          moltype = AA  length = 40
FEATURE                Location/Qualifiers
source                 1..40
                       mol_type = protein
                       organism = Homo sapiens
SEQUENCE: 77
WHNGMSERNL SALENYNFEL VDGVKLKKDK LNTQSTYSEA                        40

SEQ ID NO: 78          moltype = AA  length = 127
FEATURE                Location/Qualifiers
source                 1..127
                       mol_type = protein
                       organism = Homo sapiens
SEQUENCE: 78
FRNDKCGDTI KIESPGYLTS PGYPHSYHPS EKCEWLIQAP DPYQRIMINF NPHFDLEDRD  60
CKYDYVEVFD GENENGHFRG KFCGKIAPPP VVSSGPFLFI KFVSDYETHG AGFSIRYELF  120
KRGPECS                                                            127

SEQ ID NO: 79          moltype = AA  length = 127
FEATURE                Location/Qualifiers
source                 1..127
                       mol_type = protein
                       organism = Homo sapiens
SEQUENCE: 79
QNYTTPSGVI KSPGFPEKYP NSLECTYIVF APKMSEIILE FESFDLEPDS NPPGGMFCRY  60
DRLEIWDGFP DVGPHIGRYC GQKTPGRIRS SSGILSMVFY TDSAIAKEGF SANYSVLQSS  120
VSEDFKC                                                            127

SEQ ID NO: 80          moltype = AA  length = 153
FEATURE                Location/Qualifiers
source                 1..153
                       mol_type = protein
                       organism = Homo sapiens
SEQUENCE: 80
MEALGMESGE IHSDQITASS QYSTNWSAER SRLNYPENGW TPGEDSYREW IQVDLGLLRF  60
VTAVGTQGAI SKETKKKYYV KTYKIDVSSN GEDWITIKEG NKPVLFQGNT NPTDVVVAVF  120
PKPLITRFVR IKPATWETGI SMRFEVYGCK ITD                               153

SEQ ID NO: 81          moltype = AA  length = 161
```

```
FEATURE                Location/Qualifiers
source                 1..161
                       mol_type = protein
                       organism = Homo sapiens
SEQUENCE: 81
YPCSGMLGMV SGLISDSQIT SSNQGDRNWM PENIRLVTSR SGWALPPAPH SYINEWLQID  60
LGEEKIVRGI IIQGGKHREN KVFMRKFKIG YSNNGSDWKM IMDDSKRKAK SFEGNNNYDT  120
PELRTFPALS TRFIRIYPER ATHGGLGLRM ELLGCEVEAP T                     161

SEQ ID NO: 82          moltype = AA  length = 270
FEATURE                Location/Qualifiers
source                 1..270
                       mol_type = protein
                       organism = Homo sapiens
SEQUENCE: 82
AGPTTPNGNL VDECDDDQAN CHSGTGDDFQ LTGGTTVLAT EKPTVIDSTI QSEFPTYGFN  60
CEFGWGSHKT FCHWEHDNHV QLKWSVLTSK TGPIQDHTGD GNFIYSQADE NQKGKVARLV  120
SPVVYSQNSA HCMTFWYHMS GSHVGTLRVK LRYQKPEEYD QLVWMAIGHQ GDHWKEGRVL  180
LHKSLKLYQV IFEGEIGKGN LGGIAVDDIS INNHISQEDC AKPADLDKKN PEIKIDETGS  240
TPGYEGEGEG DKNISRKPGN VLKTLDPILI                                  270

SEQ ID NO: 83          moltype = AA  length = 834
FEATURE                Location/Qualifiers
REGION                 1..834
                       note = Synthetic polypeptide
source                 1..834
                       mol_type = protein
                       organism = synthetic construct
SEQUENCE: 83
RNDKCGDTIK IESPGYLTSP GYPHSYHPSE KCEWLIQAPD PYQRIMINFN PHFDLEDRDC  60
KYDYVEVFDG ENENGHFRGK FCGKIAPPPV VSSGPFLFIK FVSDYETHGA GFSIRYELFK  120
RGPECSQNYT TPSGVIKSPG FPEKYPNSLE CTYIVFAPKM SEIILEFESF DLEPDSNPPG  180
GMFCRYDRLE IWDGFPDVGP HIGRYCGQKT PGRIRSSSGI LSMVFYTDSA IAKEGFSANY  240
SVLQSSVSED FKCMEALGME SGEIHSDQIT ASSQYSTNWS AERSRLNYPE NGWTPGEDSY  300
REWIQVDLGL LRFVTAVGTQ GAISKETKKK YYVKTYKIDV SSNGEDWITI KEGNKPVLFQ  360
GNTNPTDVVV AVFPKPLITR FVRIKPATWE TGISMRFEVY GCKITDYPCS GMLGMVSGLI  420
SDSQITSSNQ GDRNWMPENI RLVTSRSGWA LPPAPHSYIN EWLQIDLGEE KIVRGIIIQG  480
GKHRENKVFM RKFKIGYSNN GSDWKMIMDD SKRKAKSFEG NNNYDTPELR TFPALSTRFI  540
RIYPERATHG GLGLRMELLG CEVEAPTAGP TTPNGNLVDE CDDDQANCHS GTGDDFQLTG  600
GTTVLATEKP TVIDSTIQSE FPTYGFNCEF GWGSHKTFCH WEHDNHVQLK WSVLTSKTGP  660
IQDHTGDGNF IYSQADENQK GKVARLVSPV VYSQNSAHCM TFWYHMSGSH VGTLRVKLRY  720
QKPEEYDQLV WMAIGHQGDH WKEGRVLLHK SLKLYQVIFE GEIGKGNLGG IAVDDISINN  780
HISQEDCAKP ADLDKKNPEI KIDETGSTPG YEGEGEGDKN ISRKPGNVLK TLDP        834

SEQ ID NO: 84          moltype = DNA  length = 2571
FEATURE                Location/Qualifiers
misc_feature           1..2571
                       note = Synthetic polynucleotide
source                 1..2571
                       mol_type = other DNA
                       organism = synthetic construct
SEQUENCE: 84
atggagaggg ggctgccgct cctctgcgcc gtgctcgccc tcgtcctcgc cccggccggc  60
gcttttcgca acgataaatg tggcgatact ataaaaattg aaagccccgg gtaccttaca  120
tctcctggtt atcctcattc ttatcaccca agtgaaaaat gcgaatggct gattcaggct  180
ccggacccat accagagaat tatgatcaac ttcaaccctc acttcgattt ggaggacaga  240
gactgcaagt atgactacgt ggaagtcttc gatggagaaa atgaaaatgg acattttagg  300
ggaaagttct gtggaaagat agcccctcct cctgttgtgt cttcagggcc atttcttttt  360
atcaaatttg tctctgacta cgaaacacat ggtgcaggat tttccatacg ttatgaactt  420
ttcaagagag gtcctgaatg ttcccagaac tacacaacac ctagtggagt gataaagtcc  480
cccggattcc ctgaaaaata tcccaacagc cttgaatgca cttatattgt ctttgcgcca  540
aagatgtcag agattatcct ggaatttgaa agctttgacc tggagcctga ctcaaatcct  600
ccagggggga tgttctgtcg ctacgaccgg ctagaaatct gggatggatt ccctgatgtt  660
ggccctcaca ttgggcgtta ctgtggacag aaaacaccag gtcgaatccg atcctcatcg  720
ggcattctct ccatggtttt ttacaccgac agcgcgatag caaaagaagg tttctcagca  780
aactacagtg tcttgcagag cagtgtctca gaagatttca aatgtatgga agctctgggc  840
atggaatcag gagaaattca ttctgaccag atcacagctt cttcccagta tagcaccaac  900
tggtctgcag agcgctcccg cctgaactac cctgagaatg ggtggactcc cggagaggat  960
tcctaccgag agtggataca ggtagacttg ggccttctgc gctttgtcac ggctgtcggg  1020
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
actcgatttg tccgaatcaa gcctgcaact tgggaaactg gcatatctat gagatttgaa  1260
gtatatggtt gcaagataac agattatcct tgctctggaa tgttgggtat ggtgtctgga  1320
cttatttctg actcccagat cacatcatcc aaccaagggg acagaaactg gatgcctgaa  1380
aacatccgcc tggtaaccag tcgctctggc tgggcacttc caccccgcacc tcattcctac  1440
atcaatgagt ggctccaaat agacctgggg gaggagaaga tcgtgagggg catcatcatt  1500
cagggtggga agcaccgaga gaacaaggtg ttcatgagga agttcaagat cgggtacagc  1560
aacaacggct cggactggaa gatgatcatg gatgacagca aacgcaaggc gaagtctttt  1620
```

```
gagggcaaca acaactatga tacacctgag ctgcggactt ttccagctct ctccacgcga  1680
ttcatcagga tctaccccga gagagccact catggcggac tggggctcag aatggagctg  1740
ctgggctgtg aagtggaagc ccctacagct ggaccgacca ctcccaacgg gaacttggtg  1800
gatgaatgtg atgacgacca ggccaactgc cacagtggaa caggtgatga cttccagctc  1860
acaggtggca ccactgtgct ggccacagaa aagcccacgg tcatagacag caccatacaa  1920
tcagagtttc caacatatgg ttttaactgt gaatttggct ggggctctca caagaccttc  1980
tgccactggg aacatgacaa tcacgtgcag ctcaagtgga gtgtgttgac cagcaagacg  2040
ggacccattc aggatcacac aggagatggc aacttcatct attcccaagc tgacgaaaat  2100
cagaagggca aagtggctcg cctggtgagc cctgtggttt attcccagaa ctctgcccac  2160
tgcatgacct tctggtatca catgtctggg tcccacgtcg gcacactcag ggtcaaactg  2220
cgctaccaga agccagagga gtacgatcag ctggtctgga tggccattgg acaccaaggt  2280
gaccactgga aggaagggcg tgtcttgctc cacaagtctc tgaaacttta tcaggtgatt  2340
ttcgagggcg aaatcggaaa aggaaacctt ggtgggattg ctgtggatga cattagtatt  2400
aataaccaca tttcacaaga agattgtgca aaaccagcag acctggataa aaagaaccca  2460
gaaattaaaa ttgatgaaac agggagcacg ccaggatacg aaggtgaagg agaaggtgac  2520
aagaacatct ccaggaagcc aggcaatgtg ttgaagacct tagacccctg a           2571

SEQ ID NO: 85          moltype = DNA  length = 22
FEATURE                Location/Qualifiers
misc_feature           1..22
                       note = Synthetic oligonucleotide
source                 1..22
                       mol_type = other DNA
                       organism = synthetic construct
SEQUENCE: 85
gacggccagg tcatcactat tg                                          22

SEQ ID NO: 86          moltype = DNA  length = 22
FEATURE                Location/Qualifiers
misc_feature           1..22
                       note = Synthetic oligonucleotide
source                 1..22
                       mol_type = other DNA
                       organism = synthetic construct
SEQUENCE: 86
ccacaggatt ccatacccaa ga                                          22

SEQ ID NO: 87          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 87
gctcctgctc cgtagcctgc                                             20

SEQ ID NO: 88          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 88
tcggcgttgc tttcggtccc                                             20

SEQ ID NO: 89          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 89
gccctgagtc aagaggacag                                             20

SEQ ID NO: 90          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 90
ctcctaggcc cctcagaagt                                             20

SEQ ID NO: 91          moltype = DNA  length = 23
FEATURE                Location/Qualifiers
```

```
misc_feature           1..23
                       note = Synthetic oligonucleotide
source                 1..23
                       mol_type = other DNA
                       organism = synthetic construct
SEQUENCE: 91
ccctcacact cagatcatct tct                                          23

SEQ ID NO: 92          moltype = DNA  length = 19
FEATURE                Location/Qualifiers
misc_feature           1..19
                       note = Synthetic oligonucleotide
source                 1..19
                       mol_type = other DNA
                       organism = synthetic construct
SEQUENCE: 92
gctacgacgt gggctacag                                               19

SEQ ID NO: 93          moltype = DNA  length = 21
FEATURE                Location/Qualifiers
misc_feature           1..21
                       note = Synthetic polynucleotide
source                 1..21
                       mol_type = other DNA
                       organism = synthetic construct
SEQUENCE: 93
ctggtacatc aggacctcac a                                            21

SEQ ID NO: 94          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 94
gagctcctta acatgccctg                                              20

SEQ ID NO: 95          moltype = DNA  length = 25
FEATURE                Location/Qualifiers
misc_feature           1..25
                       note = Synthetic oligonucleotide
source                 1..25
                       mol_type = other DNA
                       organism = synthetic construct
SEQUENCE: 95
agacaaagcc agagtccttc agaga                                        25

SEQ ID NO: 96          moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 96
gccactcctt ctgtgactcg agc                                          23

SEQ ID NO: 97          moltype = AA  length = 40
FEATURE                Location/Qualifiers
source                 1..40
                       mol_type = protein
                       organism = Homo sapiens
SEQUENCE: 97
WHNGMSERNL SALENYNFEL VDGVKLKKDK LNTQSTYSEA                        40

SEQ ID NO: 98          moltype = AA  length = 64
FEATURE                Location/Qualifiers
source                 1..64
                       mol_type = protein
                       organism = Homo sapiens
SEQUENCE: 98
TIIAMSALGV LLGAVCGVVL YCACWHNGMS ERNLSALENY NFELVDGVKL KKDKLNTQST  60
YSEA                                                               64

SEQ ID NO: 99          moltype = AA  length = 19
FEATURE                Location/Qualifiers
source                 1..19
                       mol_type = protein
```

```
                        organism = Homo sapiens
SEQUENCE: 99
VLATEKPTVI DSTIQSGIK                                             19

SEQ ID NO: 100          moltype = AA  length = 856
FEATURE                 Location/Qualifiers
REGION                  1..856
                        note = Synthetic polynucleotide
source                  1..856
                        mol_type = protein
                        organism = synthetic construct
SEQUENCE: 100
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVLQSSVS EDFKCMEALG MESGEIHSDQ ITASSQYSTN  300
WSAERSRLNY PENGWTPGED SYREWIQVDL GLLRFVTAVG TQGAISKETK KKYYVKTYKI  360
DVSSNGEDWI TIKEGNKPVL FQGNTNPTDV VVAVFPKPLI TRFVRIKPAT WETGISMRFE  420
VYGCKITDYP CSGMLGMVSG LISDSQITSS NQGDRNWMPE NIRLVTSRSG WALPPAPHSY  480
INEWLQIDLG EEKIVRGIII QGGKHRENKV FMRKFKIGYS NNGSDWKMIM DDSKRKAKSF  540
EGNNNYDTPE LRTFPALSTR FIRIYPERAT HGGLGLRMEL LGCEVEAPTA GPTTPNGNLV  600
DECDDDQANC HSGTGDDFQL TGGTTVLATE KPTVIDSTIQ SEFPTYGFNC EFGWGSHKTF  660
CHWEHDNHVQ LKWSVLTSKT GPIQDHTGDG NFIYSQADEN QKGKVARLVS PVVYSQNSAH  720
CMTFWYHMSG SHVGTLRVKL RYQKPEEYDQ LVWMAIGHQG DHWKEGRVLL HKSLKLYQVI  780
FEGEIGKGNL GGIAVDDISI NNHISQEDCA KPADLDKKNP EIKIDETGST PGYEGEGEGD  840
KNISRKPGNV LKTLDP                                                856

SEQ ID NO: 101          moltype = AA  length = 856
FEATURE                 Location/Qualifiers
REGION                  1..856
                        note = Synthetic polynucleotide
source                  1..856
                        mol_type = protein
                        organism = synthetic construct
SEQUENCE: 101
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVLQSSVS EDFKCMEALG MESGEIHSDQ ITASSQASTN  300
WSAERSRLNY PENGWTPGED SYREWIQVDL GLLRFVTAVG TQGAISKETK KKYYVKTYKI  360
DVSSNGEDWI TIKEGNKPVL FQGNTNPTDV VVAVFPKPLI TRFVRIKPAT WETGISMRFE  420
VYGCKITDYP CSGMLGMVSG LISDSQITSS NQGDRNWMPE NIRLVTSRSG WALPPAPHSY  480
INEWLQIDLG EEKIVRGIII QGGKHRENKV FMRKFKIGYS NNGSDWKMIM DDSKRKAKSF  540
EGNNNYDTPE LRTFPALSTR FIRIYPERAT HGGLGLRMEL LGCEVEAPTA GPTTPNGNLV  600
DECDDDQANC HSGTGDDFQL TGGTTVLATE KPTVIDSTIQ SEFPTYGFNC EFGWGSHKTF  660
CHWEHDNHVQ LKWSVLTSKT GPIQDHTGDG NFIYSQADEN QKGKVARLVS PVVYSQNSAH  720
CMTFWYHMSG SHVGTLRVKL RYQKPEEYDQ LVWMAIGHQG DHWKEGRVLL HKSLKLYQVI  780
FEGEIGKGNL GGIAVDDISI NNHISQEDCA KPADLDKKNP EIKIDETGST PGYEGEGEGD  840
KNISRKPGNV LKTLDP                                                856

SEQ ID NO: 102          moltype = AA  length = 856
FEATURE                 Location/Qualifiers
REGION                  1..856
                        note = Synthetic polynucleotide
source                  1..856
                        mol_type = protein
                        organism = synthetic construct
SEQUENCE: 102
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVLQSSVS EDFKCMEALG MESGEIHSDQ ITASSQYSTN  300
WSAERSRLNY PENGWTPGKK SYREWIQVDL GLLRFVTAVG TQGAISKETK KKYYVKTYKI  360
DVSSNGEDWI TIKEGNKPVL FQGNTNPTDV VVAVFPKPLI TRFVRIKPAT WETGISMRFE  420
VYGCKITDYP CSGMLGMVSG LISDSQITSS NQGDRNWMPE NIRLVTSRSG WALPPAPHSY  480
INEWLQIDLG EEKIVRGIII QGGKHRENKV FMRKFKIGYS NNGSDWKMIM DDSKRKAKSF  540
EGNNNYDTPE LRTFPALSTR FIRIYPERAT HGGLGLRMEL LGCEVEAPTA GPTTPNGNLV  600
DECDDDQANC HSGTGDDFQL TGGTTVLATE KPTVIDSTIQ SEFPTYGFNC EFGWGSHKTF  660
CHWEHDNHVQ LKWSVLTSKT GPIQDHTGDG NFIYSQADEN QKGKVARLVS PVVYSQNSAH  720
CMTFWYHMSG SHVGTLRVKL RYQKPEEYDQ LVWMAIGHQG DHWKEGRVLL HKSLKLYQVI  780
FEGEIGKGNL GGIAVDDISI NNHISQEDCA KPADLDKKNP EIKIDETGST PGYEGEGEGD  840
KNISRKPGNV LKTLDP                                                856

SEQ ID NO: 103          moltype = AA  length = 856
FEATURE                 Location/Qualifiers
REGION                  1..856
```

```
                        note = Synthetic polynucleotide
source                  1..856
                        mol_type = protein
                        organism = synthetic construct
SEQUENCE: 103
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVLQSSVS EDFKCMEALG MESGEIHSDQ ITASSQYSTN  300
WSAERSRLNY PENGWTPGED SYREWIQVDL GLLRFVTAVG TQGAIAKKTK KKYYVKTYKI  360
DVSSNGEDWI TIKEGNKPVL FQGNTNPTDV VVAVFPKPLI TRFVRIKPAT WETGISMRFE  420
VYGCKITDYP CSGMLGMVSG LISDSQITSS NQGDRNWMPE NIRLVTSRSG WALPPAPHSY  480
INEWLQIDLG EEKIVRGIII QGGKHRENKV FMRKFKIGYS NNGSDWKMIM DDSKRKAKSF  540
EGNNNYDTPE LRTFPALSTR FIRIYPERAT HGGLGLRMEL LGCEVEAPTA GPTTPNGNLV  600
DECDDDQANC HSGTGDDFQL TGGTTVLATE KPTVIDSTIQ SEFPTYGFNC EFGWGSHKTF  660
CHWEHDNHVQ LKWSVLTSKT GPIQDHTGDG NFIYSQADEN QKGKVARLVS PVVYSQNSAH  720
CMTFWYHMSG SHVGTLRVKL RYQKPEEYDQ LVWMAIGHQG DHWKEGRVLL HKSLKLYQVI  780
FEGEIGKGNL GGIAVDDISI NNHISQEDCA KPADLDKKNP EIKIDETGST PGYEGEGEGD  840
KNISRKPGNV LKTLDP                                                 856

SEQ ID NO: 104          moltype = AA  length = 856
FEATURE                 Location/Qualifiers
REGION                  1..856
                        note = Synthetic polynucleotide
source                  1..856
                        mol_type = protein
                        organism = synthetic construct
SEQUENCE: 104
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVLQSSVS EDFKCMEALG MESGEIHSDQ ITASSQYSTN  300
WSAERSRLNY PENGWTPGEK SYREWIQVDL GLLRFVTAVG TQGAISKETK KKYYVKTYKI  360
DVSSNGEDWI TIKEGNKPVL FQGNTNPTDV VVAVFPKPLI TRFVRIKPAT WETGISMRFE  420
VYGCKITDYP CSGMLGMVSG LISDSQITSS NQGDRNWMPE NIRLVTSRSG WALPPAPHSY  480
INEWLQIDLG EEKIVRGIII QGGKHRENKV FMRKFKIGYS NNGSDWKMIM DDSKRKAKSF  540
EGNNNYDTPE LRTFPALSTR FIRIYPERAT HGGLGLRMEL LGCEVEAPTA GPTTPNGNLV  600
DECDDDQANC HSGTGDDFQL TGGTTVLATE KPTVIDSTIQ SEFPTYGFNC EFGWGSHKTF  660
CHWEHDNHVQ LKWSVLTSKT GPIQDHTGDG NFIYSQADEN QKGKVARLVS PVVYSQNSAH  720
CMTFWYHMSG SHVGTLRVKL RYQKPEEYDQ LVWMAIGHQG DHWKEGRVLL HKSLKLYQVI  780
FEGEIGKGNL GGIAVDDISI NNHISQEDCA KPADLDKKNP EIKIDETGST PGYEGEGEGD  840
KNISRKPGNV LKTLDP                                                 856

SEQ ID NO: 105          moltype = AA  length = 583
FEATURE                 Location/Qualifiers
REGION                  1..583
                        note = Synthetic polynucleotide
source                  1..583
                        mol_type = protein
                        organism = synthetic construct
SEQUENCE: 105
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVLQSSVS EDFKCMEALG MESGEIHSDQ ITASSQYSTN  300
WSAERSRLNY PENGWTPGED SYREWIQVDL GLLRFVTAVG TQGAISKETK KKYYVKTYKI  360
DVSSNGEDWI TIKEGNKPVL FQGNTNPTDV VVAVFPKPLI TRFVRIKPAT WETGISMRFE  420
VYGCKITDYP CSGMLGMVSG LISDSQITSS NQGDRNWMPE NIRLVTSRSG WALPPAPHSY  480
INEWLQIDLG EEKIVRGIII QGGKHRENKV FMRKFKIGYS NNGSDWKMIM DDSKRKAKSF  540
EGNNNYDTPE LRTFPALSTR FIRIYPERAT HGGLGLRMEL LGC                   583

SEQ ID NO: 106          moltype = AA  length = 583
FEATURE                 Location/Qualifiers
REGION                  1..583
                        note = Synthetic polynucleotide
source                  1..583
                        mol_type = protein
                        organism = synthetic construct
SEQUENCE: 106
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVLQSSVS EDFKCMEALG MESGEIHSDQ ITASSQASTN  300
WSAERSRLNY PENGWTPGED SYREWIQVDL GLLRFVTAVG TQGAISKETK KKYYVKTYKI  360
DVSSNGEDWI TIKEGNKPVL FQGNTNPTDV VVAVFPKPLI TRFVRIKPAT WETGISMRFE  420
```

```
VYGCKITDYP CSGMLGMVSG LISDSQITSS NQGDRNWMPE NIRLVTSRSG WALPPAPHSY  480
INEWLQIDLG EEKIVRGIII QGGKHRENKV FMRKFKIGYS NNGSDWKMIM DDSKRKAKSF  540
EGNNNYDTPE LRTFPALSTR FIRIYPERAT HGGLGLRMEL LGC                    583

SEQ ID NO: 107          moltype = AA  length = 424
FEATURE                 Location/Qualifiers
REGION                  1..424
                        note = Synthetic polynucleotide
source                  1..424
                        mol_type = protein
                        organism = synthetic construct
SEQUENCE: 107
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVLQSSVS EDFKCMEALG MESGEIHSDQ ITASSQYSTN  300
WSAERSRLNY PENGWTPGED SYREWIQVDL GLLRFVTAVG TQGAISKETK KKYYVKTYKI  360
DVSSNGEDWI TIKEGNKPVL FQGNTNPTDV VVAVFPKPLI TRFVRIKPAT WETGISMRFE  420
VYGC                                                               424

SEQ ID NO: 108          moltype = AA  length = 424
FEATURE                 Location/Qualifiers
REGION                  1..424
                        note = Synthetic polynucleotide
source                  1..424
                        mol_type = protein
                        organism = synthetic construct
SEQUENCE: 108
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVLQSSVS EDFKCMEALG MESGEIHSDQ ITASSQASTN  300
WSAERSRLNY PENGWTPGED SYREWIQVDL GLLRFVTAVG TQGAISKETK KKYYVKTYKI  360
DVSSNGEDWI TIKEGNKPVL FQGNTNPTDV VVAVFPKPLI TRFVRIKPAT WETGISMRFE  420
VYGC                                                               424

SEQ ID NO: 109          moltype = AA  length = 265
FEATURE                 Location/Qualifiers
REGION                  1..265
                        note = Synthetic polynucleotide
source                  1..265
                        mol_type = protein
                        organism = synthetic construct
SEQUENCE: 109
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVL                                        265

SEQ ID NO: 110          moltype = AA  length = 642
FEATURE                 Location/Qualifiers
REGION                  1..642
                        note = Synthetic polynucleotide
source                  1..642
                        mol_type = protein
                        organism = synthetic construct
SEQUENCE: 110
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVLQSSVS EDFKCMEALG MESGEIHSDQ ITASSQYSTN  300
WSAERSRLNY PENGWTPGED SYREWIQVDL GLLRFVTAVG TQGAISKETK KKYYVKTYKI  360
DVSSNGEDWI TIKEGNKPVL FQGNTNPTDV VVAVFPKPLI TRFVRIKPAT WETGISMRFE  420
VYGCKITDYP EVEAPTAGPT TPNGNLVDEC DDDQANCHSG TGDDFQLTGG TTVLATEKPT  480
VIDSTIQSEF PTYGFNCEFG WGSHKTFCHW EHDNHVQLKW SVLTSKTGPI QDHTGDGNFI  540
YSQADENQKG KVARLVSPVV YSQNSAHCMT FWYHMSGSHV GTLRVKLRYQ KPEEYDQLVW  600
MAIGHQGDHW KEGRVLLHKS LKLYQVIFEG EIGKGNLGGI AV                     642

SEQ ID NO: 111          moltype = AA  length = 703
FEATURE                 Location/Qualifiers
REGION                  1..703
                        note = Synthetic polynucleotide
source                  1..703
                        mol_type = protein
                        organism = synthetic construct
```

```
SEQUENCE: 111
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVLQSSVS EDFKCMEALG MESGEIHSDQ ITASSQASTN  300
WSAERSRLNY PENGWTPGED SYREWIQVDL GLLRFVTAVG TQGAISKETK KKYYVKTYKI  360
DVSSNGEDWI TIKEGNKPVL FQGNTNPTDV VVAVFPKPLI TRFVRIKPAT WETGISMRFE  420
VYGCKITDYP EVEAPTAGPT TPNGNLVDEC DDDQANCHSG TGDDFQLTGG TTVLATEKPT  480
VIDSTIQSEF PTYGFNCEFG WGSHKTFCHW EHDNHVQLKW SVLTSKTGPI QDHTGDGNFI  540
YSQADENQKG KVARLVSPVV YSQNSAHCMT FWYHMSGSHV GTLRVKLRYQ KPEEYDQLVW  600
MAIGHQGDHW KEGRVLLHKS LKLYQVIFEG EIGKGNLGGI AVDDISINNH ISQEDCAKPA  660
DLDKKNPEIK IDETGSTPGY EGEGEGDKNI SRKPGNVLKT LDP                   703

SEQ ID NO: 112         moltype = AA  length = 547
FEATURE                Location/Qualifiers
REGION                 1..547
                       note = Synthetic polynucleotide
source                 1..547
                       mol_type = protein
                       organism = synthetic construct
SEQUENCE: 112
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVLQSSVS EDFKEVEAPT AGPTTPNGNL VDECDDDQAN  300
CHSGTGDDFQ LTGGTTVLAT EKPTVIDSTI QSEFPTYGFN CEFGWGSHKT FCHWEHDNHV  360
QLKWSVLTSK TGPIQDHTGD GNFIYSQADE NQKGKVARLV SPVVYSQNSA HCMTFWYHMS  420
GSHVGTLRVK LRYQKPEEYD QLVWMAIGHQ GDHWKEGRVL LHKSLKLYQV IFEGEIGKGN  480
LGGIAVDDIS INNHISQEDC AKPADLDKKN PEIKIDETGS TPGYEGEGEG DKNISRKPGN  540
VLKTLDP                                                           547

SEQ ID NO: 113         moltype = AA  length = 703
FEATURE                Location/Qualifiers
REGION                 1..703
                       note = Synthetic polypeptide
source                 1..703
                       mol_type = protein
                       organism = synthetic construct
SEQUENCE: 113
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVLQSSVS EDFKCMEALG MESGEIHSDQ ITASSQYSTN  300
WSAERSRLNY PENGWTPGED SYREWIQVDL GLLRFVTAVG TQGAISKETK KKYYVKTYKI  360
DVSSNGEDWI TIKEGNKPVL FQGNTNPTDV VVAVFPKPLI TRFVRIKPAT WETGISMRFE  420
VYGCKITDYP EVEAPTAGPT TPNGNLVDEC DDDQANCHSG TGDDFQLTGG TTVLATEKPT  480
VIDSTIQSEF PTYGFNCEFG WGSHKTFCHW EHDNHVQLKW SVLTSKTGPI QDHTGDGNFI  540
YSQADENQKG KVARLVSPVV YSQNSAHCMT FWYHMSGSHV GTLRVKLRYQ KPEEYDQLVW  600
MAIGHQGDHW KEGRVLLHKS LKLYQVIFEG EIGKGNLGGI AVDDISINNH ISQEDCAKPA  660
DLDKKNPEIK IDETGSTPGY EGEGEGDKNI SRKPGNVLKT LDP                   703

SEQ ID NO: 114         moltype = AA  length = 1085
FEATURE                Location/Qualifiers
REGION                 1..1085
                       note = Synthetic polypeptide
source                 1..1085
                       mol_type = protein
                       organism = synthetic construct
SEQUENCE: 114
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVLQSSVS EDFKCMEALG MESGEIHSDQ ITASSQYSTN  300
WSAERSRLNY PENGWTPGED SYREWIQVDL GLLRFVTAVG TQGAISKETK KKYYVKTYKI  360
DVSSNGEDWI TIKEGNKPVL FQGNTNPTDV VVAVFPKPLI TRFVRIKPAT WETGISMRFE  420
VYGCKITDYP CSGMLGMVSG LISDSQITSS NQGDRNWMPE NIRLVTSRSG WALPPAPHSY  480
INEWLQIDLG EEKIVRGIII QGGKHRENKV FMRKFKIGYS NNGSDWKMIM DDSKRKAKSF  540
EGNNNYDTPE LRTFPALSTR FIRIYPERAT HGGLGLRMEL LGCEVEAPTA GPTTPNGNLV  600
DECDDDQANC HSGTGDDFQL TGGTTVLATE KPTVIDSTIQ SEFPTYGFNC EFGWGSHKTF  660
CHWEHDNHVQ LKWSVLTSKT GPIQDHTGDG NFIYSQADEN QKGKVARLVS PVVYSQNSAH  720
CMTFWYHMSG SHVGTLRVKL RYQKPEEYDQ LVWMAIGHQG DHWKEGRVLL HKSLKLYQVI  780
FEGEIGKGNL GGIAVDDISI NNHISQEDCA KPADLDKKNP EIKIDETGST PGYEGEGEGD  840
KNISRKPGNV LKTLDPRSDK THTCPPCPAP ELLGGPSVFL FPPKPKDTLM ISRTPEVTCV  900
VVDVSHEDPE VKFNWYVDGV EVHNAKTKPR EEQYNSTYRV VSVLTVLHQD WLNGKEYKCK  960
VSNKALPAPI EKTISKAKGQ PREPQVYTLP PSREEMTKNQ VSLTCLVKGF YPSDIAVEWE  1020
```

-continued

```
SNGQPENNYK TTPPVLDSDG SFFLYSKLTV DKSRWQQGNV FSCSVMHEAL HNHYTQKSLS  1080
LSPGK                                                              1085

SEQ ID NO: 115         moltype = AA  length = 1085
FEATURE                Location/Qualifiers
REGION                 1..1085
                       note = Synthetic polypeptide
REGION                 584..858
                       note = misc_feature - Xaa can be any naturally occurring
                        amino acid
source                 1..1085
                       mol_type = protein
                       organism = synthetic construct
SEQUENCE: 115
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVLQSSVS EDFKCMEALG MESGEIHSDQ ITASSQYSTN  300
WSAERSRLNY PENGWTPGED SYREWIQVDL GLLRFVTAVG TQGAISKETK KKYYVKTYKI  360
DVSSNGEDWI TIKEGNKPVL FQGNTNPTDV VVAVFPKPLI TRFVRIKPAT WETGISMRFE  420
VYGCKITDYP CSGMLGMVSG LISDSQITSS NQGDRNWMPE NIRLVTSRSG WALPPAPHSY  480
INEWLQIDLG EEKIVRGIII QGGKHRENKV FMRKFKIGYS NNGSDWKMIM DDSKRKAKSF  540
EGNNNYDTPE LRTFPALSTR FIRIYPERAT HGGLGLRMEL LGCXXXXXXX XXXXXXXXXX  600
XXXXXXXXXX XXXXXXXXXX XXXXXXXXXX XXXXXXXXXX XXXXXXXXXX XXXXXXXXXX  660
XXXXXXXXXX XXXXXXXXXX XXXXXXXXXX XXXXXXXXXX XXXXXXXXXX XXXXXXXXXX  720
XXXXXXXXXX XXXXXXXXXX XXXXXXXXXX XXXXXXXXXX XXXXXXXXXX XXXXXXXXXX  780
XXXXXXXXXX XXXXXXXXXX XXXXXXXXXX XXXXXXXXXX XXXXXXXXXX XXXXXXXXXX  840
XXXXXXXXXX XXXXXXXXDK THTCPPCPAP ELLGGPSVFL FPPKPKDTLM ISRTPEVTCV  900
VVDVSHEDPE VKFNWYVDGV EVHNAKTKPR EEQYNSTYRV VSVLTVLHQD WLNGKEYKCK  960
VSNKALPAPI EKTISKAKGQ PREPQVYTLP PSREEMTKNQ VSLTCLVKGF YPSDIAVEWE  1020
SNGQPENNYK TTPPVLDSDG SFFLYSKLTV DKSRWQQGNV FSCSVMHEAL HNHYTQKSLS  1080
LSPGK                                                              1085

SEQ ID NO: 116         moltype = AA  length = 1085
FEATURE                Location/Qualifiers
REGION                 1..1085
                       note = Synthetic polypeptide
REGION                 425..858
                       note = misc_feature - Xaa can be any naturally occurring
                        amino acid
source                 1..1085
                       mol_type = protein
                       organism = synthetic construct
SEQUENCE: 116
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVLQSSVS EDFKCMEALG MESGEIHSDQ ITASSQYSTN  300
WSAERSRLNY PENGWTPGED SYREWIQVDL GLLRFVTAVG TQGAISKETK KKYYVKTYKI  360
DVSSNGEDWI TIKEGNKPVL FQGNTNPTDV VVAVFPKPLI TRFVRIKPAT WETGISMRFE  420
VYGCXXXXXX XXXXXXXXXX XXXXXXXXXX XXXXXXXXXX XXXXXXXXXX XXXXXXXXXX  480
XXXXXXXXXX XXXXXXXXXX XXXXXXXXXX XXXXXXXXXX XXXXXXXXXX XXXXXXXXXX  540
XXXXXXXXXX XXXXXXXXXX XXXXXXXXXX XXXXXXXXXX XXXXXXXXXX XXXXXXXXXX  600
XXXXXXXXXX XXXXXXXXXX XXXXXXXXXX XXXXXXXXXX XXXXXXXXXX XXXXXXXXXX  660
XXXXXXXXXX XXXXXXXXXX XXXXXXXXXX XXXXXXXXXX XXXXXXXXXX XXXXXXXXXX  720
XXXXXXXXXX XXXXXXXXXX XXXXXXXXXX XXXXXXXXXX XXXXXXXXXX XXXXXXXXXX  780
XXXXXXXXXX XXXXXXXXXX XXXXXXXXXX XXXXXXXXXX XXXXXXXXXX XXXXXXXXXX  840
XXXXXXXXXX XXXXXXXXDK THTCPPCPAP ELLGGPSVFL FPPKPKDTLM ISRTPEVTCV  900
VVDVSHEDPE VKFNWYVDGV EVHNAKTKPR EEQYNSTYRV VSVLTVLHQD WLNGKEYKCK  960
VSNKALPAPI EKTISKAKGQ PREPQVYTLP PSREEMTKNQ VSLTCLVKGF YPSDIAVEWE  1020
SNGQPENNYK TTPPVLDSDG SFFLYSKLTV DKSRWQQGNV FSCSVMHEAL HNHYTQKSLS  1080
LSPGK                                                              1085

SEQ ID NO: 117         moltype = AA  length = 1085
FEATURE                Location/Qualifiers
REGION                 1..1085
                       note = Synthetic polypeptide
REGION                 266..858
                       note = misc_feature - Xaa can be any naturally occurring
                        amino acid
source                 1..1085
                       mol_type = protein
                       organism = synthetic construct
SEQUENCE: 117
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
```

```
KMSEIILEFE SFDLEPDSNP PGGMFCRYDR LEIWDGFPDV GPHIGRYCGQ KTPGRIRSSS  240
GILSMVFYTD SAIAKEGFSA NYSVLXXXXX XXXXXXXXXX XXXXXXXXXX XXXXXXXXXX  300
XXXXXXXXXX XXXXXXXXXX XXXXXXXXXX XXXXXXXXXX XXXXXXXXXX XXXXXXXXXX  360
XXXXXXXXXX XXXXXXXXXX XXXXXXXXXX XXXXXXXXXX XXXXXXXXXX XXXXXXXXXX  420
XXXXXXXXXX XXXXXXXXXX XXXXXXXXXX XXXXXXXXXX XXXXXXXXXX XXXXXXXXXX  480
XXXXXXXXXX XXXXXXXXXX XXXXXXXXXX XXXXXXXXXX XXXXXXXXXX XXXXXXXXXX  540
XXXXXXXXXX XXXXXXXXXX XXXXXXXXXX XXXXXXXXXX XXXXXXXXXX XXXXXXXXXX  600
XXXXXXXXXX XXXXXXXXXX XXXXXXXXXX XXXXXXXXXX XXXXXXXXXX XXXXXXXXXX  660
XXXXXXXXXX XXXXXXXXXX XXXXXXXXXX XXXXXXXXXX XXXXXXXXXX XXXXXXXXXX  720
XXXXXXXXXX XXXXXXXXXX XXXXXXXXXX XXXXXXXXXX XXXXXXXXXX XXXXXXXXXX  780
XXXXXXXXXX XXXXXXXXXX XXXXXXXXXX XXXXXXXXXX XXXXXXXXXX XXXXXXXXXX  840
XXXXXXXXXX XXXXXXXXDK THTCPPCPAP ELLGGPSVFL FPPKPKDTLM ISRTPEVTCV  900
VVDVSHEDPE VKFNWYVDGV EVHNAKTKPR EEQYNSTYRV VSVLTVLHQD WLNGKEYKCK  960
VSNKALPAPI EKTISKAKGQ PREPQVYTLP PSREEMTKNQ VSLTCLVKGF YPSDIAVEWE  1020
SNGQPENNYK TTPPVLDSDG SFFLYSKLTV DKSRWQQGNV FSCSVMHEAL HNHYTQKSLS  1080
LSPGK                                                              1085

SEQ ID NO: 118         moltype = AA  length = 812
FEATURE                Location/Qualifiers
REGION                 1..812
                       note = Synthetic polypeptide
source                 1..812
                       mol_type = protein
                       organism = synthetic construct
SEQUENCE: 118
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVLQSSVS EDFKCMEALG MESGEIHSDQ ITASSQYSTN  300
WSAERSRLNY PENGWTPGED SYREWIQVDL GLLRFVTAVG TQGAISKETK KKYYVKTYKI  360
DVSSNGEDWI TIKEGNKPVL FQGNTNPTDV VVAVFPKPLI TRFVRIKPAT WETGISMRFE  420
VYGCKITDYP CSGMLGMVSG LISDSQITSS NQGDRNWMPE NIRLVTSRSG WALPPAPHSY  480
INEWLQIDLG EEKIVRGIII QGGKHRENKV FMRKFKIGYS NNGSDWKMIM DDSKRKAKSF  540
EGNNNYDTPE LRTFPALSTR FIRIYPERAT HGGLGLRMEL LGCRSDKTHT CPPCPAPELL  600
GGPSVFLFPP KPKDTLMISR TPEVTCVVVD VSHEDPEVKF NWYVDGVEVH NAKTKPREEQ  660
YNSTYRVVSV LTVLHQDWLN GKEYKCKVSN KALPAPIEKT ISKAKGQPRE PQVYTLPPSR  720
EEMTKNQVSL TCLVKGFYPS DIAVEWESNG QPENNYKTTP PVLDSDGSFF LYSKLTVDKS  780
RWQQGNVFSC SVMHEALHNH YTQKSLSLSP GK                                812

SEQ ID NO: 119         moltype = AA  length = 653
FEATURE                Location/Qualifiers
REGION                 1..653
                       note = Synthetic polypeptide
source                 1..653
                       mol_type = protein
                       organism = synthetic construct
SEQUENCE: 119
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVLQSSVS EDFKCMEALG MESGEIHSDQ ITASSQYSTN  300
WSAERSRLNY PENGWTPGED SYREWIQVDL GLLRFVTAVG TQGAISKETK KKYYVKTYKI  360
DVSSNGEDWI TIKEGNKPVL FQGNTNPTDV VVAVFPKPLI TRFVRIKPAT WETGISMRFE  420
VYGCRSDKTH TCPPCPAPEL LGGPSVFLFP PKPKDTLMIS RTPEVTCVVV DVSHEDPEVK  480
FNWYVDGVEV HNAKTKPREE QYNSTYRVVS VLTVLHQDWL NGKEYKCKVS NKALPAPIEK  540
TISKAKGQPR EPQVYTLPPS REEMTKNQVS LTCLVKGFYP SDIAVEWESN GQPENNYKTT  600
PPVLDSDGSF FLYSKLTVDK SRWQQGNVFS CSVMHEALHN HYTQKSLSLS PGK         653

SEQ ID NO: 120         moltype = AA  length = 494
FEATURE                Location/Qualifiers
REGION                 1..494
                       note = Synthetic polypeptide
source                 1..494
                       mol_type = protein
                       organism = synthetic construct
SEQUENCE: 120
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVLRSDKT HTCPPCPAPE LLGGPSVFLF PPKPKDTLMI  300
SRTPEVTCVV VDVSHEDPEV KFNWYVDGVE VHNAKTKPRE EQYNSTYRVV SVLTVLHQDW  360
LNGKEYKCKV SNKALPAPIE KTISKAKGQP REPQVYTLPP SREEMTKNQV SLTCLVKGFY  420
PSDIAVEWES NGQPENNYKT TPPVLDSDGS FFLYSKLTVD KSRWQQGNVF SCSVMHEALH  480
NHYTQKSLSL SPGK                                                    494

SEQ ID NO: 121         moltype = AA  length = 1085
```

```
FEATURE                 Location/Qualifiers
REGION                  1..1085
                        note = Synthetic polypeptide
source                  1..1085
                        mol_type = protein
                        organism = synthetic construct
SEQUENCE: 121
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVLQSSVS EDFKCMEALG MESGEIHSDQ ITASSQASTN  300
WSAERSRLNY PENGWTPGED SYREWIQVDL GLLRFVTAVG TQGAISKETK KKYYVKTYKI  360
DVSSNGEDWI TIKEGNKPVL FQGNTNPTDV VVAVFPKPLI TRFVRIKPAT WETGISMRFE  420
VYGCKITDYP CSGMLGMVSG LISDSQITSS NQGDRNWMPE NIRLVTSRSG WALPPAPHSY  480
INEWLQIDLG EEKIVRGIII QGGKHRENKV FMRKFKIGYS NNGSDWKMIM DDSKRKAKSF  540
EGNNNYDTPE LRTFPALSTR FIRIYPERAT HGGLGLRMEL LGCEVEAPTA GPTTPNGNLV  600
DECDDDQANC HSGTGDDFQL TGGTTVLATE KPTVIDSTIQ SEFPTYGFNC EFGWGSHKTF  660
CHWEHDNHVQ LKWSVLTSKT GPIQDHTGDG NFIYSQADEN QKGKVARLVS PVVYSQNSAH  720
CMTFWYHMSG SHVGTLRVKL RYQKPEEYDQ LVWMAIGHQG DHWKEGRVLL HKSLKLYQVI  780
FEGEIGKGNL GGIAVDDISI NNHISQEDCA KPADLDKKNP EIKIDETGST PGYEGEGEGD  840
KNISRKPGNV LKTLDPRSDK THTCPPCPAP ELLGGPSVFL FPPKPKDTLM ISRTPEVTCV  900
VVDVSHEDPE VKFNWYVDGV EVHNAKTKPR EEQYNSTYRV VSVLTVLHQD WLNGKEYKCK  960
VSNKALPAPI EKTISKAKGQ PREPQVYTLP PSREEMTKNQ VSLTCLVKGF YPSDIAVEWE  1020
SNGQPENNYK TTPPVLDSDG SFFLYSKLTV DKSRWQQGNV FSCSVMHEAL HNHYTQKSLS  1080
LSPGK                                                             1085

SEQ ID NO: 122          moltype = AA  length = 1085
FEATURE                 Location/Qualifiers
REGION                  1..1085
                        note = Synthetic polypeptide
REGION                  584..858
                        note = misc_feature - Xaa can be any naturally occurring
                         amino acid
source                  1..1085
                        mol_type = protein
                        organism = synthetic construct
SEQUENCE: 122
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVLQSSVS EDFKCMEALG MESGEIHSDQ ITASSQASTN  300
WSAERSRLNY PENGWTPGED SYREWIQVDL GLLRFVTAVG TQGAISKETK KKYYVKTYKI  360
DVSSNGEDWI TIKEGNKPVL FQGNTNPTDV VVAVFPKPLI TRFVRIKPAT WETGISMRFE  420
VYGCKITDYP CSGMLGMVSG LISDSQITSS NQGDRNWMPE NIRLVTSRSG WALPPAPHSY  480
INEWLQIDLG EEKIVRGIII QGGKHRENKV FMRKFKIGYS NNGSDWKMIM DDSKRKAKSF  540
EGNNNYDTPE LRTFPALSTR FIRIYPERAT HGGLGLRMEL LGCXXXXXXX XXXXXXXXXX  600
XXXXXXXXXX XXXXXXXXXX XXXXXXXXXX XXXXXXXXXX XXXXXXXXXX XXXXXXXXXX  660
XXXXXXXXXX XXXXXXXXXX XXXXXXXXXX XXXXXXXXXX XXXXXXXXXX XXXXXXXXXX  720
XXXXXXXXXX XXXXXXXXXX XXXXXXXXXX XXXXXXXXXX XXXXXXXXXX XXXXXXXXXX  780
XXXXXXXXXX XXXXXXXXXX XXXXXXXXXX XXXXXXXXXX XXXXXXXXXX XXXXXXXXXX  840
XXXXXXXXXX XXXXXXXXDK THTCPPCPAP ELLGGPSVFL FPPKPKDTLM ISRTPEVTCV  900
VVDVSHEDPE VKFNWYVDGV EVHNAKTKPR EEQYNSTYRV VSVLTVLHQD WLNGKEYKCK  960
VSNKALPAPI EKTISKAKGQ PREPQVYTLP PSREEMTKNQ VSLTCLVKGF YPSDIAVEWE  1020
SNGQPENNYK TTPPVLDSDG SFFLYSKLTV DKSRWQQGNV FSCSVMHEAL HNHYTQKSLS  1080
LSPGK                                                             1085

SEQ ID NO: 123          moltype = AA  length = 1085
FEATURE                 Location/Qualifiers
REGION                  1..1085
                        note = Synthetic polypeptide
REGION                  425..858
                        note = misc_feature - Xaa can be any naturally occurring
                         amino acid
source                  1..1085
                        mol_type = protein
                        organism = synthetic construct
SEQUENCE: 123
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVLQSSVS EDFKCMEALG MESGEIHSDQ ITASSQASTN  300
WSAERSRLNY PENGWTPGED SYREWIQVDL GLLRFVTAVG TQGAISKETK KKYYVKTYKI  360
DVSSNGEDWI TIKEGNKPVL FQGNTNPTDV VVAVFPKPLI TRFVRIKPAT WETGISMRFE  420
VYGCXXXXXX XXXXXXXXXX XXXXXXXXXX XXXXXXXXXX XXXXXXXXXX XXXXXXXXXX  480
XXXXXXXXXX XXXXXXXXXX XXXXXXXXXX XXXXXXXXXX XXXXXXXXXX XXXXXXXXXX  540
XXXXXXXXXX XXXXXXXXXX XXXXXXXXXX XXXXXXXXXX XXXXXXXXXX XXXXXXXXXX  600
```

```
XXXXXXXXXX XXXXXXXXXX XXXXXXXXXX XXXXXXXXXX XXXXXXXXXX XXXXXXXXXX  660
XXXXXXXXXX XXXXXXXXXX XXXXXXXXXX XXXXXXXXXX XXXXXXXXXX XXXXXXXXXX  720
XXXXXXXXXX XXXXXXXXXX XXXXXXXXXX XXXXXXXXXX XXXXXXXXXX XXXXXXXXXX  780
XXXXXXXXXX XXXXXXXXXX XXXXXXXXXX XXXXXXXXXX XXXXXXXXXX XXXXXXXXXX  840
XXXXXXXXXX XXXXXXXXDK THTCPPCPAP ELLGGPSVFL FPPKPKDTLM ISRTPEVTCV  900
VVDVSHEDPE VKFNWYVDGV EVHNAKTKPR EEQYNSTYRV VSVLTVLHQD WLNGKEYKCK  960
VSNKALPAPI EKTISKAKGQ PREPQVYTLP PSREEMTKNQ VSLTCLVKGF YPSDIAVEWE  1020
SNGQPENNYK TTPPVLDSDG SFFLYSKLTV DKSRWQQGNV FSCSVMHEAL HNHYTQKSLS  1080
LSPGK                                                              1085

SEQ ID NO: 124          moltype = AA  length = 812
FEATURE                 Location/Qualifiers
REGION                  1..812
                        note = Synthetic polypeptide
source                  1..812
                        mol_type = protein
                        organism = synthetic construct
SEQUENCE: 124
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVLQSSVS EDFKCMEALG MESGEIHSDQ ITASSQASTN  300
WSAERSRLNY PENGWTPGED SYREWIQVDL GLLRFVTAVG TQGAISKETK KKYYVKTYKI  360
DVSSNGEDWI TIKEGNKPVL FQGNTNPTDV VVAVFPKPLI TRFVRIKPAT WETGISMRFE  420
VYGCKITDYP CSGMLGMVSG LISDSQITSS NQGDRNWMPE NIRLVTSRSG WALPPAPHSY  480
INEWLQIDLG EEKIVRGIII QGGKHRENKV FMRKFKIGYS NNGSDWKMIM DDSKRKAKSF  540
EGNNNYDTPE LRTFPALSTR FIRIYPERAT HGGLGLRMEL LGCRSDKTHT CPPCPAPELL  600
GGPSVFLFPP KPKDTLMISR TPEVTCVVVD VSHEDPEVKF NWYVDGVEVH NAKTKPREEQ  660
YNSTYRVVSV LTVLHQDWLN GKEYKCKVSN KALPAPIEKT ISKAKGQPRE PQVYTLPPSR  720
EEMTKNQVSL TCLVKGFYPS DIAVEWESNG QPENNYKTTP PVLDSDGSFF LYSKLTVDKS  780
RWQQGNVFSC SVMHEALHNH YTQKSLSLSP GK                                812

SEQ ID NO: 125          moltype = AA  length = 653
FEATURE                 Location/Qualifiers
REGION                  1..653
                        note = Synthetic polypeptide
source                  1..653
                        mol_type = protein
                        organism = synthetic construct
SEQUENCE: 125
MERGLPLLCA VLALVLAPAG AFRNDKCGDT IKIESPGYLT SPGYPHSYHP SEKCEWLIQA  60
PDPYQRIMIN FNPHFDLEDR DCKYDYVEVF DGENENGHFR GKFCGKIAPP PVVSSGPFLF  120
IKFVSDYETH GAGFSIRYEL FKRGPECSQN YTTPSGVIKS PGFPEKYPNS LECTYIVFAP  180
KMSEIILEFE SFDLEPDSNP PGGMFCRYDR LEIWDGFPDV GPHIGRYCGQ KTPGRIRSSS  240
GILSMVFYTD SAIAKEGFSA NYSVLQSSVS EDFKCMEALG MESGEIHSDQ ITASSQASTN  300
WSAERSRLNY PENGWTPGED SYREWIQVDL GLLRFVTAVG TQGAISKETK KKYYVKTYKI  360
DVSSNGEDWI TIKEGNKPVL FQGNTNPTDV VVAVFPKPLI TRFVRIKPAT WETGISMRFE  420
VYGCRSDKTH TCPPCPAPEL LGGPSVFLFP PKPKDTLMIS RTPEVTCVVV DVSHEDPEVK  480
FNWYVDGVEV HNAKTKPREE QYNSTYRVVS VLTVLHQDWL NGKEYKCKVS NKALPAPIEK  540
TISKAKGQPR EPQVYTLPPS REEMTKNQVS LTCLVKGFYP SDIAVEWESN GQPENNYKTT  600
PPVLDSDGSF FLYSKLTVDK SRWQQGNVFS CSVMHEALHN HYTQKSLSLS PGK         653

SEQ ID NO: 126          moltype = AA  length = 1086
FEATURE                 Location/Qualifiers
REGION                  1..1086
                        note = Synthetic polypeptide
source                  1..1086
                        mol_type = protein
                        organism = synthetic construct
SEQUENCE: 126
MERGLPLLCA VLALVLAPAG AFRSDKCGGT IKIENPGYLT SPGYPHSYHP SEKCEWLIQA  60
PEPYQRIMIN FNPHFDLEDR DCKYDYVEVI DGENEGGRLW GKFCGKIAPS PVVSSGPFLF  120
IKFVSDYETH GAGFSIRYEI FKRGPECSQN YTAPTGVIKS PGFPEKYPNS LECTYIIFAP  180
KMSEIILEFE SFDLEQDSNP PGGMFCRYDR LEIWDGFPEV GPHIGRYCGQ KTPGRIRSSS  240
GVLSMVFYTD SAIAKEGFSA NYSVLQSSIS EDFKCMEALG MESGEIHSDQ ITASSQYGTN  300
WSVERSRLNY PENGWTPGED SYKEWIQVDL GLLRFVTAVG TQGAISKETK KKYYVKTYRV  360
DISSNGEDWI SLKEGNKAII FQGNTNPTDV VLGVFSKPLI TRFVRIKPVS WETGISMRFE  420
VYGCKITDYP CSGMLGMVSG LISDSQITAS NQADRNWMPE NIRLVTSRTG WALPPSPHPY  480
TNEWLQVDLG DEKIVRGVII QGGKHRENKV FMRKFKIAYS NNGSDWKTIM DDSKRKAKSF  540
EGNNNYDTPE LRTFSPLSTR FIRIYPERAT HSGLGLRMEL LGCEVEAPTA GPTTPNGNPV  600
DECDDDQANC HSGTGDDFQL TGGTTVLATE KPTIIDSTIQ SEFPTYGFNC EFGWGSHKTF  660
CHWEHDSHAQ LRWSVLTSKT GPIQDHTGDG NFIYSQADEN QKGKVARLVS PVVYSQSSAH  720
CMTFWYHMSG SHVGTLRVKL RYQKPEEYDQ LVWMVVGHQG DHWKEGRVLL HKSLKLYQVI  780
FEGEIGKGNL GGIAVDDISI NNHISQEDCA KPTDLDKKNT EIKIDETGST PGYEGEGEGD  840
KNISRKPGNV LKTLDPVSST MVRSGCKPCI CTVPEVSSVF IFPPKPKDVL TITLTPKVTC  900
VVVDISKDDP EVQFSWFVDD VEVHTAQTQP REEQFNSTFR SVSELPIMHQ DWLNGKEFKC  960
RVNSAAFPAP IEKTISKTKG RPKAPQVYTI PPPKEQMAKD KVSLTCMITD FFPEDITVEW  1020
QWNGQPAENY KNTQPIMDTD GSYFVYSKLN VQKSNWEAGN TFTCSVLHEG LHNHHTEKSL  1080
```

-continued

```
SHSPGK                                                            1086

SEQ ID NO: 127          moltype = AA  length = 813
FEATURE                 Location/Qualifiers
REGION                  1..813
                        note = Synthetic polypeptide
source                  1..813
                        mol_type = protein
                        organism = synthetic construct
SEQUENCE: 127
MERGLPLLCA VLALVLAPAG AFRSDKCGGT IKIENPGYLT SPGYPHSYHP SEKCEWLIQA  60
PEPYQRIMIN FNPHFDLEDR DCKYDYVEVI DGENEGGRLW GKFCGKIAPS PVVSSGPFLF  120
IKFVSDYETH GAGFSIRYEI FKRGPECSQN YTAPTGVIKS PGFPEKYPNS LECTYIIFAP  180
KMSEIILEFE SFDLEQDSNP PGGMFCRYDR LEIWDGFPEV GPHIGRYCGQ KTPGRIRSSS  240
GVLSMVFYTD SAIAKEGFSA NYSVLQSSIS EDFKCMEALG MESGEIHSDQ ITASSQYGTN  300
WSVERSRLNY PENGWTPGED SYKEWIQVDL GLLRFVTAVG TQGAISKETK KKYYVKTYRV  360
DISSNGEDWI SLKEGNKAII FQGNTNPTDV VLGVFSKPLI TRFVRIKPVS WETGISMRFE  420
VYGCKITDYP CSGMLGMVSG LISDSQITAS NQADRNWMPE NIRLVTSRTG WALPPSPHPY  480
TNEWLQVDLG DEKIVRGVII QGGKHRENKV FMRKFKIAYS NNGSDWKTIM DDSKRKAKSF  540
EGNNNYDTPE LRTFSPLSTR FIRIYPERAT HSGLGLRMEL LGCVSSTMVR SGCKPCICTV  600
PEVSSVFIFP PKPKDVLTIT LTPKVTCVVV DISKDDPEVQ FSWFVDDVEV HTAQTQPREE  660
QFNSTFRSVS ELPIMHQDWL NGKEFKCRVN SAAFPAPIEK TISKTKGRPK APQVYTIPPP  720
KEQMAKDKVS LTCMITDFFP EDITVEWQWN GQPAENYKNT QPIMDTDGSY FVYSKLNVQK  780
SNWEAGNTFT CSVLHEGLHN HHTEKSLSHS PGK                              813

SEQ ID NO: 128          moltype = AA  length = 654
FEATURE                 Location/Qualifiers
REGION                  1..654
                        note = Synthetic polypeptide
source                  1..654
                        mol_type = protein
                        organism = synthetic construct
SEQUENCE: 128
MERGLPLLCA VLALVLAPAG AFRSDKCGGT IKIENPGYLT SPGYPHSYHP SEKCEWLIQA  60
PEPYQRIMIN FNPHFDLEDR DCKYDYVEVI DGENEGGRLW GKFCGKIAPS PVVSSGPFLF  120
IKFVSDYETH GAGFSIRYEI FKRGPECSQN YTAPTGVIKS PGFPEKYPNS LECTYIIFAP  180
KMSEIILEFE SFDLEQDSNP PGGMFCRYDR LEIWDGFPEV GPHIGRYCGQ KTPGRIRSSS  240
GVLSMVFYTD SAIAKEGFSA NYSVLQSSIS EDFKCMEALG MESGEIHSDQ ITASSQYGTN  300
WSVERSRLNY PENGWTPGED SYKEWIQVDL GLLRFVTAVG TQGAISKETK KKYYVKTYRV  360
DISSNGEDWI SLKEGNKAII FQGNTNPTDV VLGVFSKPLI TRFVRIKPVS WETGISMRFE  420
VYGCVSSTMV RSGCKPCICT VPEVSSVFIF PPKPKDVLTI TLTPKVTCVV VDISKDDPEV  480
QFSWFVDDVE VHTAQTQPRE EQFNSTFRSV SELPIMHQDW LNGKEFKCRV NSAAFPAPIE  540
KTISKTKGRP KAPQVYTIPP PKEQMAKDKV SLTCMITDFF PEDITVEWQW NGQPAENYKN  600
TQPIMDTDGS YFVYSKLNVQ KSNWEAGNTF TCSVLHEGLH NHHTEKSLSH SPGK        654
```

COMPOSITIONS AND METHODS FOR TREATING AND PREVENTING INFLAMMATION

CROSS REFERENCE TO RELATED APPLICATIONS

This is a continuation of U.S. application Ser. No. 16/983,185, filed Aug. 3, 2020, which is a continuation of U.S. application Ser. No. 16/422,273, filed May 24, 2019, issued as U.S. Pat. No. 10,766,964 on Sep. 8, 2020, which is a divisional of U.S. application Ser. No. 15/507,407, filed Feb. 28, 2017, issued as U.S. Pat. No. 10,738,122 on Aug. 11, 2020, which is the U.S. National Stage of International Patent Application No. PCT/CA2015/050862, filed Sep. 8, 2015, which was published in English under PCT Article 21(2), which in turn claims priority to U.S. Provisional Application No. U.S. 62/046,459, filed Sep. 5, 2014. The above-referenced applications are incorporated herein by reference in their entirety.

STATEMENT REGARDING FEDERALLY SPONSORED RESEARCH OR DEVELOPMENT

N.A.

FIELD OF THE INVENTION

The present invention relates to inflammation. More specifically, the present invention is concerned with the inhibition of the NRP1 pathway for the prevention or treatment of inflammation.

REFERENCE TO SEQUENCE LISTING

The electronic sequence listing, submitted herewith as an XML file named 7386-98565-04.xml (316,843 bytes), created on Mar. 23, 2023, is herein incorporated by reference in its entirety.

BACKGROUND OF THE INVENTION

Local acute inflammatory responses are predominantly beneficial and constitute the body's first line of defense against infection of the host. Conversely, acute systemic inflammation such as in septic shock is a leading cause of morbidity and mortality (58). When chronic, low-grade inflammation persists, it can be at the origin of a several systemic diseases ranging from type II Diabetes Mellitus, arthritis, cancer, a number of neuroinflammatory conditions and more.

Of all cytokines, receptors and other players thought to contribute to the inflammatory processes, one paradigm that has been largely overlooked is the influence of classical neuronal guidance cues and their receptors. These include semaphorin3A (SEMA3A, e.g., mRNA: NM_006080; and protein: NP_006071 and FIG. 21) and their receptor Neuropilin-1 (NRP1, e.g., mRNA: NM_001024628; and protein: NP_001019799, NM_003873 and FIG. 22 (isoform 2 or b, secreted) and 26 (isoform 1). NRP1 is expressed on both lymphoid and myeloid cells (59, 31). Yet its role in inflammation is largely unknown and especially in the context of cytokine production.

The Semaphorins were initially characterized as key players in axonal guidance during embryogenesis. It is now clear that the role of Semaphorins extends beyond axonal guidance and influence vascular systems, tumor growth and the immune response. The Semaphorin family counts at least 21 vertebrate genes and 8 additional genes in invertebrates. All Semaphorins contain a ~500 amino acid SEMA domain that is required for signaling. Class 3 Semaphorins (such as SEMA3A) are the only secreted members of the family. SEMA3A is synthesized as a disulphide-linked homodimer and dimerization is essential for signaling.

In neurons, binding of SEMA3A to its cognate receptor Neuropilin-1 (NRP1) provokes cytoskeletal collapse via plexins (60); the transduction mechanism in endothelial cells remains ill-defined. NRP1 has the particular ability to bind two structurally dissimilar ligands via distinct sites on its extracellular domain (27-29). It binds not only SEMA3A (46, 47) provoking cytoskeletal collapse but also $VEGF_{165}$ (28, 29, 47, 61) enhancing binding to VEGFR2 and thus increasing its angiogenic potential (62). Crystallographic evidence revealed that VEGF165 and SEMA3A do not directly compete for NRP1 but rather can simultaneously bind to NRP1 at distinct, non-overlapping sites (63). Moreover, genetic studies show that NRP1 distinctly regulates the effects of VEGF and SEMA3A on neuronal and vascular development (64). Finally, NRP1 has also been found to bind to TGF-β1 and to regulate its latent form.

NRP1 is a single-pass transmembrane receptor with a large 860 amino acid extracellular domain subdivided into 3 sub-domains (a1a2, b1b2 and c) and a short 40 amino acid intracellular domain (65). In neurons, binding of SEMA3A to NRP1 recruits Plexins, which transduce their intracellular signal (60) and provoke cytoskeletal collapse. The transduction mechanism in endothelial cells remains ill-defined. NRP1 binds SEMA3A (46, 47) primarily via its a1a2 (but possibly also b1-) domain (provoking cytoskeletal collapse) and VEGF165 (28, 29, 47, 61) via its b1b2 domain (enhancing binding to VEGFR2 and thus increasing its angiogenic potential (62). The elevated levels of SEMA3A in the ischemic retina may thus partake in forcing neovessels into the vitreous by collapsing and deviating the advancing tip cells away from the source of the repellent cue (21).

The CNS had long been considered an immune-privileged system, yet it is now clear that the brain, retina and spinal cord are subjected to complex immune-surveillance (1, 2). Immunological activity in the CNS is largely dependent on an innate immune response and is present in health and heightened in diseases such as diabetic retinopathy, multiple sclerosis, amyotrophic lateral sclerosis and Alzheimer's disease. This is apparent in the retina where an intensified, largely microglial/macrophage-based immune response is associated with the progression of several sight threatening diseases such as diabetic retinopathy (DR)(3-5), age related macular degeneration (AMD)(6-8) and retinopathy of prematurity (ROP)(9, 10). Together, these retinal diseases account for the principal causes of loss of sight in industrialized countries (6, 11, 12).

Many of the current line of treatments of inflammatory diseases and conditions suffer from important side-effects and deficient long-term safety profiles. Accordingly, there remains a need for novel pharmaceutical targets and methods of treatments.

The present description refers to a number of documents, the content of which is herein incorporated by reference in their entirety.

SUMMARY OF THE INVENTION

The present inventors have sought to determine the function of myeloid-resident NRP1 in the context of the innate immune response.

The present inventors have determined that SEMA3A, VEGF and TGF-β act as potent attractants for mononuclear phagocytes (MPs, e.g., microglia and macrophages) expressing the NRP1 receptor. Inhibition of NRP1 signaling in innate immune cells was shown to result in protection against MPs-dependent inflammation and tissue damage under a variety of conditions involving hyperactivation of the innate immune-response including proliferative retinopathies, septic shock and cerebral ischemia/stroke. Furthermore, the present inventors have designed various soluble NRP1-derived traps which inhibit SEMA3A signalling and shown that inhibition of SEMA3A significantly reduce the inflammatory response in various conditions.

Accordingly, the present invention relates to the inhibition of NRP1 cell signalling (e.g., NRP1 and its ligands) for the prevention or treatment of inflammatory diseases and conditions involving hyperactivation (i.e., pathological activation) of the innate immune response. Non-limiting examples of such disease and conditions include sepsis, stroke, cerebral ischemia, and various proliferative retinopathies.

More specifically, in an aspect, the present invention concerns a method of treating or preventing inflammation comprising inhibiting NRP1-dependent cell-signaling.

In another aspect, the present invention relates to a method of preventing or reducing hyperactivation of innate immune response comprising inhibiting NRP1-dependent cell-signaling. In an embodiment, the hyperactivation of innate immune response comprises i) secretion of IL-1β and TNFα and/or activation/recruitment of mononuclear phagocytes (MPs).

In an embodiment, inhibiting NRP1-dependent cell-signaling comprises: a) reducing NRP1 expression or activity; and/or b) reducing NRP1 ligand expression or activity. In an embodiment, the NRP1 ligand is SEMA3A, $VEGF_{165}$ or TGF-β. In a particular embodiment, the NRP1 ligand is SEMA3A.

In an embodiment, reducing NRP1 activity consists of inhibiting the binding of NRP1 to at least one NRP1 ligand. In an embodiment, inhibiting the binding of NRP1 to at least one NRP1 ligand comprises administering an NRP1 antibody (e.g., a SEMA3A antibody).

In another embodiment of the above methods, reducing NRP1 activity comprises administering an effective amount of an NRP1 trap which comprises soluble NRP1 polypeptide or a functional fragment thereof. In a particular embodiment, the NRP1 trap is as set forth in FIG. 19 or 20.

In a particular embodiment, the NRP1 trap of the present invention inhibits the binding of SEMA3A to NPR-1 but does not substantially inhibit the binding of VEGF to NRP1. In an embodiment, such NRP1 trap comprises the a1a2 domain of NRP1 but does not comprise the b1 and/or b2 subdomain(s) of NRP1. In another embodiment, such trap comprises a mutation in domain b1 at a position corresponding to tyrosine 297 of the NRP1 amino acid sequence as set forth in FIG. 22 which reduces or abrogates VEGF binding to the trap. In a specific embodiment, the mutation changes the tyrosine at position 297 to an alanine.

In specific embodiments, the NRP1 trap of the present invention: a) comprises domains a1, a2, b1, b2 and c and of NRP1; b) comprises domains a1, a2, b1 and b2 of NRP1; c) comprises domains a1, a2 and b1 of NRP1; d) comprises domains a1 and a2 of NRP1; e) comprises domain b1, wherein the b1 domain comprises a mutation in amino acid corresponding to tyrosine 297 of NRP1 which reduces or abrogates the binding to VEGF; f) comprises domain b1, wherein the b1 domain comprises a mutation in amino acid corresponding to tyrosine 297 of NRP1 which changes the tyrosine to an alanine; g) does not comprise domain c of NRP1; h) does not comprise domain b1 of NRP1; i) does not comprise domains b1 and b2 of NRP1; or j) does not comprise domains b1, b2 and c of NRP1.

In an embodiment of the above methods, inhibiting NRP1 ligand expression or activity comprises specifically inhibiting SEMA3A expression or SEMA3A binding to NRP1. In a particular embodiment, inhibiting SEMA3A binding to NRP1 comprises administering a SEMA3A antibody.

In a particular embodiment, the method of the present invention comprises reducing NRP1 expression by administering a NRP1 antisense, shRNA or siRNA.

In another embodiment, the method comprises reducing SEMA3A expression by administering a SEMA3A antisense, shRNA or siRNA.

In a further aspect, the present invention concerns a compound for the prevention or treatment of inflammation wherein the compound a) reduces NRP1 expression or activity; or b) reduces NRP1 ligand expression or activity.

In another aspect, the present invention relates to a compound for preventing or reducing hyperactivation of innate immune response, wherein the compound a) reduces NRP1 expression or activity; or b) reduces NRP1 ligand expression or activity.

In an embodiment, the compound is: i) A SEMA3A antibody; ii) A NRP1 antibody; iii) A NRP1 trap; iv) A SEMA3A antisense, shRNA or siRNA; or v) A NRP1 antisense, shRNA or siRNA. In another particular embodiment the compound is a NRP1 antibody or a NRP1 trap and said compound does not substantially reduce the binding of VEGF to NRP1.

In a particular embodiment, the compound is a NRP1 trap. In an embodiment, the NRP1 trap is as set forth in FIGS. 19, 20, 27 and Table 1.

In another embodiment, the NRP1 trap of the present invention inhibits the binding of SEMA3A to NPR-1 but does not substantially inhibit the binding of VEGF to NRP1. In an embodiment, such NRP1 trap comprises the a1a2 domain of NRP1 but does not comprise the b1 and/or b2 subdomain(s) of NRP1. In another embodiment, such trap comprises a mutation in domain b1 at a position corresponding to tyrosine 297 of the NRP1 amino acid sequence as set forth in FIG. 22 which reduces or abrogates VEGF binding to the trap. In a specific embodiment, the mutation changes the tyrosine at position 297 to an alanine.

In specific embodiments, the NRP1 trap of the present invention: a) comprises domains a1, a2, b1, b2 and c and of NRP1; b) comprises domains a1, a2, b1 and b2 of NRP1; c) comprises domains a1, a2 and b1 of NRP1; d) comprises domains a1 and a2 of NRP1; e) comprises domain b1, wherein the b1 domain comprises a mutation in amino acid corresponding to tyrosine 297 of NRP1 which reduces or abrogates the binding to VEGF; f) comprises domain b1, wherein the b1 domain comprises a mutation in amino acid corresponding to tyrosine 297 of NRP1 which changes the tyrosine to an alanine; g) does not comprise domain c of NRP1; h) does not comprise domain b1 of NRP1; i) does not comprise domains b1 and b2 of NRP1; or j) does not comprise domains b1, b2 and c of NRP1.

In an embodiment, the NRP1 trap of the present invention comprises: (i) amino acids 1-856 (preferably, 22 to 856) of the NRP1 polypeptide set forth in FIG. 26 (SEQ ID NO: 69); (ii) amino acids 1 to 583 (preferably 22 to 583) of the NRP1 polypeptide set forth in FIG. 26 (SEQ ID NO: 69); (iii) amino acids 1 to 424 (preferably 22-424) the NRP1 polypeptide set forth in FIG. 26 (SEQ ID NO: 69); (iv) amino acids 1 to 265 (preferably 22 to 265) the NRP1 polypeptide set forth in FIG. 26 (SEQ ID NO: 69); (v) 1 to 430 and 584 to 856 (preferably 22-430 and 584-856) the NRP1 polypeptide set forth in FIG. 26 (SEQ ID NO: 69); (vi) amino acids 1 to 274 and 584 to 856 (preferably 22-274 and 584 to 856) the NRP1 polypeptide set forth in FIG. 26 (SEQ ID NO: 69); (vii) amino acids 1 to 430 and 584 (preferably 22 to 430 and 584 to 856) of the NRP1 polypeptide set forth in FIG. 26 (SEQ ID NO: 69). In a particular embodiment, the above noted traps comprise one or more mutation to reduce VEGF or SEMA3A binding as described above.

In another aspect, the present invention provides compositions for i) treating and preventing inflammation or ii) for preventing or reducing the hyperactivation of the innate immune response, comprising one or more compounds of the present invention together with a pharmaceutical carrier.

The present invention also relates to the use of one or more compounds of the present invention in the manufacture of a medicament for i) treating and preventing inflammation or ii) for preventing or reducing the hyperactivation of the innate immune response.

In a related aspect, the present invention concerns the use of one or more compounds of the present invention for i) treating and preventing inflammation or ii) for preventing or reducing the hyperactivation of the innate immune response.

In a particular embodiment, the methods, compounds (e.g., NRP1 polypeptide traps, nucleic acids encoding same, vectors, cells comprising vectors, etc.), compositions and uses of the present invention are for treating or preventing inflammatory diseases and conditions selected from the group consisting of septic shock, arthritis, inflammatory bowel disease (IBD), cutaneous skin inflammation, diabetes, uveitis, diabetic retinopathy, age-related macular degeneration (AMD), retinopathy of prematurity, multiple sclerosis, amyotrophic lateral sclerosis (ALS), age-related cognitive decline/Alzheimer's disease or stroke.

In an embodiment, the methods, compounds, compositions and uses of the present invention are for treating or preventing septic shock, cerebral ischemia or stroke.

More specifically, in accordance with the present invention, there is provided the following items:

1. A method of treating or preventing inflammation comprising inhibiting NRP1-dependent cell-signaling in a subject.
2. A method of preventing or reducing hyperactivation of innate immune response comprising inhibiting NRP1-dependent cell-signaling in a subject.
3. The method of item 2, wherein said hyperactivation of innate immune response comprises i) secretion of IL-6, IL-1β and TNFα and/or recruitment of mononuclear phagocytes (MPs).
4. The method of any one of items 1-3, wherein inhibiting NRP1-dependent cell-signaling comprises: (a) reducing NRP1 expression or activity; and/or (b) reducing NRP1 ligand expression or activity; wherein said NRP1 ligand is SEMA3A, VEGF and/or TGF-β.
5. The method of item 4, wherein the method comprises (i) reducing NRP1 activity by inhibiting the binding of NRP1 to at least one NRP1 ligand.
6. The method of item 5, wherein the NRP1 ligand is SEMA3A, VEGF or TGF-β.
7. The method of item 5 or 6, wherein inhibiting the binding of NRP1 to at least one NRP1 ligand comprises administering an anti-NRP1 antibody or an NRP1 trap, wherein said trap comprises a NRP1 polypeptide or a functional fragment or variant thereof.
8. The method of item 7, wherein said NRP1 polypeptide corresponds to soluble NRP1 isoform 2.
9. The method of item 8, wherein said soluble NPR1 isoform 2 comprises or consists essentially of a polypeptide having an amino acid sequence as set forth in FIG. 22 without a signal peptide.
10. The method of item 7, wherein said NRP1 polypeptide corresponds to the extracellular domain of an NRP1 isoform 1 polypeptide.
11. The method of item 10, wherein said NRP1 isoform 1 polypeptide is as set forth in FIG. 26 and wherein said extracellular domain comprises amino acids 22 to 859 corresponding to the NRP1 polypeptide shown in FIG. 26 (SEQ ID NO:66).
12. The method of any one of items 7 to 11, wherein said NRP1 trap comprises an NRP1 polypeptide comprising (i) amino acids 22 to 609 of a NRP1 polypeptide as set forth in SEQ ID NO: 65; (ii) amino acids 22 to 859 of a NRP1 polypeptide as set forth in SEQ ID NO: 66; (iii) amino acids 22 to 859 of a NRP1 polypeptide as set forth in SEQ ID NO: 69 (iv) or a functional fragment or functional variant of (i), (ii) or (iii).
13. The method of any one of items 7 to 12, wherein said anti-NRP1 antibody inhibits the binding of SEMA3A to NPR-1 but does not substantially inhibit the binding of VEGF to NRP1 and wherein said NRP1 trap binds to SEMA3A but does not substantially bind to VEGF165 or has a reduced binding affinity for VEGF165 compared to SEMA3A binding affinity.
14. The method of item 13, wherein said NRP1 trap (i) lacks completely or partially domain b1 and/or b2 of NRP1; or (ii) comprises at least one amino acid point mutation which inhibits VEGF binding to NRP1.
15. The method of item 13, wherein said anti-NRP1 antibody does not bind to domain b1 and/or b2 of NRP1.
16. The method of item 14, wherein said point mutation comprises (a) an amino acid substitution or deletion in domain b1 at an amino acid residue corresponding to tyrosine 297 of an NRP1 amino acid sequence set forth in FIG. 22 or FIG. 26; (b) an amino acid substitution or deletion in domain b1 at an amino acid residue corresponding to aspartic acid 320 of an NRP1 amino acid sequence set forth in FIG. 22 or FIG. 26; and/or (c) an amino acid substitution or deletion in domain b1 at an amino acid residue corresponding to glutamic acid 319 of an NRP1 amino acid sequence set forth in FIG. 22 or FIG. 26.
17. The method of item 16, wherein said point mutation is a Y297A substitution; a D320K substitution and/or a E319K substitution.
18. The method of any one of item 7 to 12, wherein said NRP1 trap: (a) comprises domains a1, a2, b1, b2, and c and of said NRP1 polypeptide; (b) comprises domains a1, a2, b1 and b2 of said NRP1 polypeptide; (c) comprises domains a1, a2, and b1 of said NRP1 polypeptide; (d) comprises domains a1 and a2 said NRP1 polypeptide; (f) comprises domain b1 of said NRP1 polypeptide, wherein said domain b1 comprises at least one point mutation at an amino acid residue corresponding to (i) tyrosine 297; (ii) aspartic acid 320 and/or (iii) glutamic acid 319, of a NRP1 polypeptide comprising an amino acid sequence as set forth in FIG. 26, wherein said at least one mutation reduces or abrogates binding to $VEGF_{165}$; (g) lacks completely or partially domain c of said NRP1 polypeptide; (h) lacks completely or partially domain b1 of said NRP1 polypeptide; (i) lacks completely or partially domain b2 of said NRP1 polypeptide; (j) lacks domains b1 and b2 of said NRP1 polypeptide; or (k) lacks domains b1, b2 and c of said NRP1 polypeptide.

19. The method of item 18, wherein (i) said domain a1 comprises or consists essentially of an amino acids sequence corresponding to amino acids 27 to 141 of an NRP1 polypeptide as set forth in FIG. 26; (ii) said domain a2 comprises an amino acid sequence corresponding to amino acids 147 to 265 of an NRP1 polypeptide as set forth in FIG. 26; (iii) said domain b1 comprises an amino acids sequence corresponding to amino acids 275 to 424 of an NRP1 polypeptide as set forth in FIG. 26; (iv) said domain b2 comprises an amino acids sequence corresponding to amino acids 431 to 583 of an NRP1 polypeptide as set forth in FIG. 26; and/or (v) said domain c domain comprises an amino acids sequence corresponding to amino acids 645 to 811 of an NRP1 polypeptide as set forth in FIG. 26.

20. The method of item 18, wherein (i) said domain a1 comprises or consists essentially of an amino acids sequence corresponding to amino acids 22 to 148 of an NRP1 polypeptide as set forth in FIG. 26; (ii) said domain a2 comprises an amino acid sequence corresponding to amino acids 149 to 275 of an NRP1 polypeptide as set forth in FIG. 26; (iii) said domain b1 comprises an amino acids sequence corresponding to amino acids 276 to 428 of an NRP1 polypeptide as set forth in FIG. 26; (iv) said domain b2 comprises an amino acids sequence corresponding to amino acids 429 to 589 of an NRP1 polypeptide as set forth in FIG. 26; and/or (v) said domain c domain comprises an amino acids sequence corresponding to amino acids 590 to 859 of an NRP1 polypeptide as set forth in FIG. 26.

21. The method of item 7, wherein said method comprises inhibiting the binding of NRP1 to at least one NRP1 ligand by administering a NRP1 trap consisting essentially of a trap as set forth in Table 1 or a functional variant thereof.

22. The method of any one of items 7 to 20, wherein said NRP1 trap further comprises a protein purification domain.

23. The method of 22, wherein said purification domain is a polyhistidine tag.

24. The method of any one of items 7 to 20, wherein said NRP1 trap further comprises a FC domain.

25. The method of any one of items 22 to 24, wherein said NRP1 trap comprises a protease or peptidase cleavage site enabling said protein purification domain or FC domain to be removed from said NRP1 trap.

26. The method of item 25, wherein said protease or peptidase is a TEV protease cleavage site.

27. The method of item 26, wherein said TEV protease cleavage site comprises the amino acid sequence GSKENLYFQG.

28. The method of item 4, wherein the method comprises reducing NRP1 ligand expression or activity, and wherein the NRP1 ligand is SEMA3A.

29. The method of item 28, comprising reducing SEMA3A activity by inhibiting SEMA3A binding to NRP1 by administering an anti-SEMA3A antibody which binds to the SEMA domain of SEMA3A.

30. The method of 4, wherein said method comprises reducing NRP1 expression by administering a NRP1 antisense, shRNA or siRNA.

31. The method of 4, wherein said method comprises reducing SEMA3A expression by administering a SEMA3A antisense, shRNA or siRNA.

32. A NRP1 polypeptide trap comprising s a NRP1 polypeptide or a functional fragment or variant thereof which binds to SEMA3A, $VEGF_{165}$ and/or TGF-β.

33. The NRP1 polypeptide trap of item 32, wherein said NRP1 polypeptide corresponds to soluble NRP1 isoform 2.

34. The NRP1 polypeptide trap of item 33, wherein said soluble NPR1 isoform 2 comprises or consists essentially of a polypeptide having an amino acid sequence as set forth in FIG. 22 without a signal peptide.

35. The NRP1 polypeptide trap of item 34, wherein said NRP1 polypeptide corresponds to the extracellular domain of an NRP1 isoform 1 polypeptide.

36. The NRP1 polypeptide trap of item 35, wherein said NRP1 isoform 1 polypeptide is as set forth in FIG. 26 and wherein said extracellular domain corresponds to amino acids 22 to 859.

37. The NRP1 polypeptide trap of any one of items 32 to 36, wherein said NRP1 trap comprises an NRP1 polypeptide comprising (i) amino acids 22 to 609 of a NRP1 polypeptide as set forth in SEQ ID NO: 65; (ii) amino acids 22 to 859 of a NRP1 polypeptide as set forth in SEQ ID NO: 66; (iii) amino acids 22 to 859 of a NRP1 polypeptide as set forth in SEQ ID NO: 69 (iv) or a functional fragment or functional variant of (i), (ii) or (iii).

38. The NRP1 polypeptide trap of item any one of items 32 to 37, wherein NRP1 trap binds to SEMA3A but does not substantially bind to VEGF165 or has a reduced binding affinity for VEGF165 as compared to SEMA3A binding affinity.

39. The NRP1 polypeptide trap of item 38, wherein said NRP1 trap (i) lacks completely or partially domain b1 and/or b2 of NRP1; or (ii) comprises at least one amino acid point mutation which inhibits VEGF binding to NRP1.

40. The NRP1 polypeptide trap of item 39, wherein said point mutation comprises (a) an amino acid substitution or deletion in domain b1 at an amino acid residue corresponding to tyrosine 297 of an NRP1 amino acid sequence set forth in FIG. 22 or FIG. 26; (b) an amino acid substitution or deletion in domain b1 at an amino acid residue corresponding to aspartic acid 320 of an NRP1 amino acid sequence set forth in FIG. 22 or FIG. 26; and/or (c) an amino acid substitution or deletion in domain b1 at an amino acid residue corresponding to glutamic acid 319 of an NRP1 amino acid sequence set forth in FIG. 22 or FIG. 26.

41. The NRP1 polypeptide trap of item 40, wherein said mutation point is a Y297A substitution; a D320K substitution and/or a E319K substitution.

42. The NRP1 polypeptide trap of any one of items 32 to 38, wherein said trap: (a) comprises domains a1, a2, b1, b2, and c and of said NRP1 polypeptide; (b) comprises domains a1, a2, b1 and b2 of said NRP1 polypeptide; (c) comprises domains a1, a2, and b1 of said NRP1 polypeptide; (d) comprises domains a1 and a2 said NRP1 polypeptide; (e) comprises domain b1 of said NRP1 polypeptide, wherein said domain b1 comprises at least one point mutation at an amino acid residue corresponding to (i) tyrosine 297; (ii) aspartic acid 320 and/or (iii) glutamic acid 319, of a NRP1 polypeptide comprising an amino acid sequence as set forth in FIG. 26, wherein said at least one mutation reduces or abrogates binding to $VEGF_{165}$; (f) lacks completely or partially domain c of said NRP1 polypeptide; (g) lacks completely or partially domain b1 of said NRP1 polypeptide; (h) lacks completely or partially domain b2 of said NRP1 polypeptide; (i) lacks domains b1 and b2 of said NRP1 polypeptide; or (j) lacks domains b1, b2 and c of said NRP1 polypeptide.

43. The NRP1 polypeptide trap of item 42, wherein (i) said domain a1 comprises or consists essentially of an amino acids sequence corresponding to amino acids 27 to 141 of an NRP1 polypeptide as set forth in FIG. 26; (ii) said domain a2 comprises an amino acid sequence corresponding to amino acids 147 to 265 of an NRP1 polypeptide as set forth in FIG. 26; (iii) said domain b1 comprises an amino acids sequence corresponding to amino acids 275 to 424 of an NRP1 polypeptide as set forth in FIG. 26; (iv) said domain b2 comprises an amino acids sequence corresponding to amino acids 431 to 583 of an NRP1 polypeptide as set forth in FIG. 26; and/or (v) said domain c domain comprises an amino acids sequence corresponding to amino acids 645 to 811 of an NRP1 polypeptide as set forth in FIG. 26.

44. The NRP1 polypeptide trap of item 42, wherein (i) said domain a1 comprises or consists essentially of an amino acids sequence corresponding to amino acids 22 to 148 of an NRP1 polypeptide as set forth in FIG. 26; (ii) said domain a2 comprises an amino acid sequence corresponding to amino acids 149 to 275 of an NRP1 polypeptide as set forth in FIG. 26; (iii) said domain b1 comprises an amino acids sequence corresponding to amino acids 276 to 428 of an NRP1 polypeptide as set forth in FIG. 26; (iv) said domain b2 comprises an amino acids sequence corresponding to amino acids 429 to 589 of an NRP1 polypeptide as set forth in FIG. 26; and/or (v) said domain c domain comprises an amino acids sequence corresponding to amino acids 590 to 859 of an NRP1 polypeptide as set forth in FIG. 26.

45. The NRP1 polypeptide trap of item 32, wherein said trap consists essentially of a trap as set forth in Table 1 or a functional variant thereof.

46. The NRP1 polypeptide trap of any one of items 32 to 44, wherein said trap further comprises a protein purification domain.

47. The NRP1 polypeptide trap of item 46, wherein said purification domain is a polyhistidine tag.

48. The NRP1 polypeptide trap of any one of items 32 to 47, wherein said NRP1 trap further comprises a FC domain.

49. The NRP1 polypeptide trap of any one of items 46 to 48, wherein said NRP1 trap comprises a protease or peptidase cleavage site enabling said protein purification domain or FC domain to be removed from said NRP1 trap.

50. The NRP1 polypeptide trap of item 49, wherein said protease or peptidase cleavage site is a TEV protease cleavage site.

51. The NRP1 polypeptide trap of item 50, wherein said TEV protease cleavage site comprises the amino acid sequence GSKENLYFQG.

52. A nucleic acid encoding the NRP1 polypeptide trap of any one of items 32-51.

53. An expression vector comprising the nucleic acid of item 52.

54. A host cell comprising the vector of item 53.

55. A composition comprising the NRP1 polypeptide trap of any one of items 32 to 51, the nucleic acid of item 52, the vector of item 53 or the host cell of item 54 and a suitable carrier.

56. The composition of item 55 for (ii) for preventing or treating inflammation, or (ii) preventing or reducing hyperactivation of innate immune response.

57. A compound for preventing or treating inflammation, wherein said compound: (a) reduces NRP1 expression or activity; and/or (b) reduces NRP1 ligand expression or activity.

58. A compound for preventing or reducing hyperactivation of innate immune response, wherein said compound: (a) reduces NRP1 expression or activity; and/or (b) reduces NRP1 ligand expression or activity.

59. The compound of item 57 or 58, wherein said compound is: (i) A anti SEMA3A antibody; (ii) An anti VEGF165 antibody; (iii) A anti NRP1 antibody (iv) A NRP1 trap; (v) A SEMA3A antisense, shRNA or siRNA; (vi) A NRP1 antisense, shRNA or siRNA; or (vii) A VEGF antisense, shRNA or siRNA.

60. The compound item 59, wherein said compound is an NRP1 polypeptide trap.

61. A composition for treating or preventing inflammation comprising a compound as defined in any one of items 57-60 and a suitable carrier.

62. A composition for preventing or reducing hyperactivation of innate immune response comprising a compound as defined in of any one of items 57-60 and a suitable carrier.

63. Use of the NRP1 polypeptide trap of any one of items 32-51, the nucleic acid of item 52, the vector of item 53, the host cell of item 54 the compound of any one of items 57-60 or the composition of any one of items 55, 61 and 62 in the manufacture of a medicament for preventing or treating inflammation.

64. Use of the NRP1 polypeptide trap of any one of items 32-51, the nucleic acid of item 52, the vector of item 53, the host cell of item 54 the compound of any one of items 57-60 or the composition of any one of items 55, 61 and 62 in the manufacture of a medicament for preventing or treating inflammation.

65. Use of the NRP1 polypeptide trap of any one of items 32-51, the nucleic acid of item 52, the vector of item 53, the host cell of item 54 the compound as defined in any one of items 57-60 or the composition as defined in any one of items 55, 61 and 62 for preventing or treating hyperactivation of innate immune response.

66. Use of a the NRP1 polypeptide trap of any one of items 32-51, the nucleic acid of item 52, the vector of item 53, the host cell of item 54 the compound as defined in any one of items 57-60 or the composition as defined in any one of items 55, 61 and 62 for preventing or reducing hyperactivation of innate immune response.

67. The method of any one of items 1-31, wherein said subject suffers or is likely to suffer from septic shock, arthritis, inflammatory bowel disease (IBD), cutaneous skin inflammation, diabetes, uveitis, diabetic retinopathy, age-related macular degeneration (AMD), retinopathy of prematurity, multiple sclerosis, amyotrophic lateral sclerosis (ALS), age-related cognitive decline/Alzheimer's disease or stroke.

68. The method of any one of items 1-31, the NRP1 polypeptide trap of any one of items 32-51, the nucleic acid of item 52, the vector of item 53, the host cell of item 54, a compound as defined in any one of items 57-60 or a composition as defined in any one of items 55, 61 and 62 wherein said method, NRP1 polypeptide trap, nucleic acid, vector, host cell, compound, composition or use is for treating or preventing septic shock, arthritis, inflammatory bowel disease (IBD), cutaneous skin inflammation, diabetes, uveitis, diabetic retinopathy, age-related macular degeneration (AMD), retinopathy of prematurity, multiple sclerosis, amyotrophic lateral sclerosis (ALS), age-related cognitive decline/Alzheimer's disease or stroke.

69. The method of any one of items 1-31, the NRP1 polypeptide trap of any one of items 32-51, the nucleic acid of item 52, the vector of item 53, the host cell of item 54, a compound as defined in any one of items 57-60 or a composition as defined in any one of items 55, 61 and 62 wherein said method, NRP1 polypeptide trap, nucleic acid, vector, host cell, compound, composition or use is for treating or preventing septic shock or stroke.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the Appended Drawings:

FIGS. 1A-1T show that NRP1 identifies a population of microglia that is mobilized secondary to vascular injury. (FIG. 1A). Schematic depiction of the mouse model of oxygen-induced retinopathy (01R). The first phase (postnatal day 7-12 (P7-P12)), under 75% oxygen, induces vasoobliteration. The second phase (under room air) from postnatal day 12 to 17 (P7-P17) allows to attain maximal pre-retinal neovascularization. (FIG. 1R) Summary graph of MP accumulation in the retina over the course of OIR in WT and LysM-Cre/$Nrp1^{fl/fl}$ mice. (FIG. 1S, FIG. 1T) Representative FACS plots depicting that $Gr1^{-}/CD11b^{+}/F4/80^{+}$ cells express high levels of CX3CR1 and intermediate/low levels of CD45. CX3CR1high and CD45low cells express NRP1 in WT retinas (S) and do not express NRP1 in retinas from LysM-Cre/$Nrp1^{fl/fl}$ mice (FIG. 1T). Data is expressed as fold change relative to control ±SEM. *P<0.05, P<0.001, *P>0.0001;

FIGS. 2A-2L show that $NRP1^{+}$ myeloid cells localize to sites of pathological neovascularization in the retina. Confocal images of Isolectin B4 (vessel and microglia stain) and NRP1-stained retinal flatmounts at P14 with budding neovascular tufts in WT (FIG. 2A) and LysM-Cre/$Nrp1^{fl/fl}$ mice (FIG. 2G) and at P17 with mature tufts in WT (FIG. 2D) and LysM-Cre/$Nrp1^{fl/fl}$ mice (FIG. 2J). High magnification images reveal co-localization of NRP1-positive microglia (IBA1) with both nascent (FIG. 2B) and mature tufts (FIG. 2E) as confirmed by 3D reconstruction (FIG. 2C, FIG. 2D) in WT mice. (FIGS. 2C, 2F, 2I, 2L) show 3D reconstruction of tissue. White arrows in (FIG. 2A, right panel) point to sprouting tufts. White arrows in (FIG. 2B, FIG. 2E) point to $NRP1^{+}$ MPs associated with tufts. LysM-Cre/$Nrp1^{fl/fl}$ mice had less MPs and less tufting (FIGS. 2G-2K). For all IHCs, representative images of three independent experiments are shown. Scale bars (FIGS. 2A, 2D, 2G, 2J): 100 μm, (FIGS. 2B, 2E, 2H, 2K): 50 μm;

(FIG. 3H) PDR patients show some evidence of macular edema, including cystoid formation (white arrowhead) due to focal coalescence of extravasated fluid. (FIG. 3I) Vitreous humour analyzed by ELISA shows increased levels of SEMA3A protein by 5-fold in patients with PDR; n=17 for controls and 17 with PDR. (FIG. 3J) Western blot analysis of equal volumes of vitreous corroborates the increase in SEMA3A (~125 KDa and 95 KDa) in patients with PDR with respect to controls;

(FIG. 4A, FIG. 4B) Retinas from WT and myeloid deficient NRP1 k.o. mice (LysM-Cre/$Nrp1^{fl/fl}$ mice) under normoxic conditions or in OIR were collected between P10 and P17 and analyzed by RT-qPCR (oligonucleotide used were as disclosed in Example 11, Table 2). SEMA3A mRNA (FIG. 4A) expression was induced throughout OIR in both WT and LysM- Cre/Nrp1$^{fl/fl}$ retinas while VEGF (FIG. 4B) was significantly less induced in k.o. mice (LysM-Cre/Nrp1$^{fl/fl}$) compared to WT retinas (stars). Data are expressed as a fold change relative to respective normoxic controls for each time point ±SEM; n=4-7; *p<0.05, p<0.01, *p<0.001. (FIG. 4C) Laser capture micro-dissection (LCM) was performed on P14 mice with care being taken to select avascular retinal zones in OIR. (FIG. 4D, FIG. 4E) RT-qPCR on LCM of retinal layers in control and OIR avascular zones showed an induction in both SEMA3A (FIG. 4D) and VEGF (FIG. 4E) mRNA in the ganglion cell layer (GCL) during OIR retinas compared to normoxic retinas. VEGF was also induced in the inner nuclear layer of OIR retinas (FIG. 4E). Data are expressed as a fold change relative to normoxic GCL±SEM;

(FIG. 6A, FIG. 6B) Primary macrophages were isolated from WT or myeloid-deficient NRP1 k.o. mice (LysM-Cre/Nrp1$^{fl/fl}$ mice) and subjected to a transwell migration assay with vehicle, MCP-1 (100 ng/ml), SEMA3A (100 ng/ml) or VEGF (50 ng/ml) added to the lower chamber. Representative images of migrated cells stained with DAPI are shown (FIG. 6A). SEMA3A or VEGF promoted macrophage migration to similar extents as the positive control MCP-1 (FIG. 6B). To ascertain that SEMA3A and VEGF were stimulating macrophage chemotaxis, cells were pre-treated with the selective ROCK inhibitor Y-27632 (100 μg/ml) (FIG. 6B) which abolished chemotaxis. Macrophages from LysM-Cre/Nrp1$^{fl/fl}$ mice were unresponsive to SEMA3A or VEGF but responsive to MCP-1 (FIG. 6C). Data are expressed as a fold change relative to control (non-treated cells); n=6-22; p<0.01, *p<0.001. Scale bars: 100 μm (FIG. 6A);

(FIG. 7A) Quantification and representative images of choroid explants isolated from LysM-Cre/Nrp1$^{fl/fl}$ and LysM-Cre/Nrp1$^{fl/fl}$ mice (n=6; p=0.018). (FIG. 7B, FIG. 7C) Representative images of choroid explants from LysM-Cre/Nrp1$^{fl/fl}$ (FIG. 7B) and LysM-Cre/Nrp1$^{fl/fl}$ (FIG. 7C) mice following chlodronate liposome treatment (to deplete macrophages) and subsequent addition of exogenous macrophages (Ma). (FIG. 7D, FIG. 7E) Quantification of choroidal microvascular sprouting from LysM-Cre/Nrp1$^{fl/fl}$ (FIG. 7D) and LysM-Cre/Nrp1$^{fl/fl}$ (FIG. 7E) depicted in B and C (n=6, n.s.: not significant, * p<0.05, p<0.01, *p<0.001);

FIGS. 8A-8F show that deficiency in myeloid-resident NRP1 reduces vascular degeneration and pathological neovascularization in retinopathy. Wild-type, LysMCre/Nrp1$^{+/+}$ and LysM-Cre/Nrp1$^{fl/fl}$ mice were subjected to OIR and retinas collected at P12 and P17, flatmounted and stained with Isolectin B4. LysM-Cre/Nrp1$^{fl/fl}$ mice had less vasoobliteration at P12 (#3 in FIG. 8A, FIG. 8B) and reduced avascular areas (#3 in FIG. 8C, FIG. 8D) and preretinal neovascularization (#3 in FIG. 8E, FIG. 8F) at P17 compared to both control WT (#1) or control LysMCre/Nrp1$^{+/+}$ mice (#2). Results are expressed as percentage of avascular or neovascular area versus the whole retinal area; n=5−19. Scale bars: B&D: 1 mm and F:500 μm. p<0.01, *p<0.001;

FIG. 10 is a schematic depiction of the instant findings illustrating that during ischemic retinopathies such as that of diabetes, avascular zones of the retina, ischemic neurons and neural tissue produces ligands of NRP1 (SEMA3A and VEGF), which in turn act as potent chemo-attractive agents for pro-angiogenic microglia. The NRP1$^{+}$ microglia then partake in the pathogenesis of proliferative retinopathy;

FIG. 11A. Fold change in SEMA3A (left panel) and VEGF (right panel) in mice brain. FIG. 11B. Fold change in SEMA3A (left panel) and VEGF (right panel) in mice kidneys. FIG. 11C. Fold change in SEMA3A (left panel) and VEGF (right panel) in mice lungs. FIG. 11D. Fold change in SEMA3A (left panel) and VEGF (right panel) in mice liver;

FIG. 12A. Fold change in TNF-α (left panel) and IL-1β (right panel) in mice brain. FIG. 12B. Fold change in TNF-α (left panel) and IL-1β (right panel) in mice kidneys. FIG. 12C. Fold change in TNF-α (left panel) and IL-1β (right panel) in mice lungs. FIG. 12D. Fold change in TNF-α (left panel) and IL-1β (right panel) in mice liver;

FIGS. 13A-130 show that SEMA3A induces secretion of pro-inflammatory cytokines in myeloid cells via NRP1. Wild-type and NRP1 knock out (LyzM/NRP1$^{fl/fl}$) myeloid cells were treated with SEMA3A (100 ng/nml) or vehicle and IL-6 (FIG. 13A), TNF-α (FIG. 13B) and IL-1β (FIG. 13C) protein secretion was analyzed by Cytometric Bead Array (CBA);

Figure 14A:
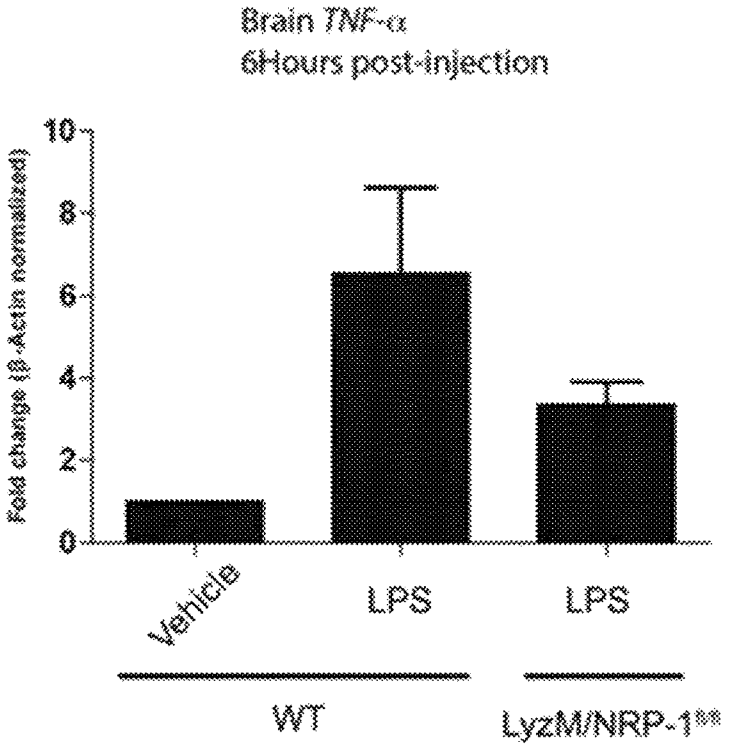
FIGS. 14A-14D show that myeloid deficiency in NRP1 reduces production of inflammatory cytokines during sepsis in vivo. NRP1 knock out mice (LyzM/NRP1$^{fl/fl}$) and control wild type mice were administered vehicle or LPS (15 mg/kg) to induce sepsis. Brains and livers were collected 6 hours post LPS injection and mRNA extracted. TNF-α (FIG.
Figure 14B:
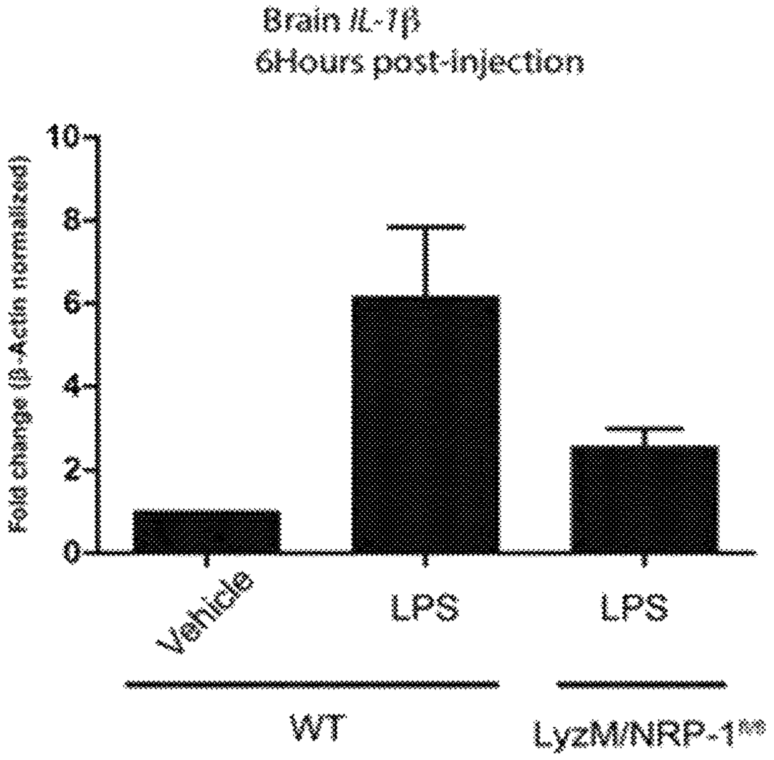
Figure 14D:
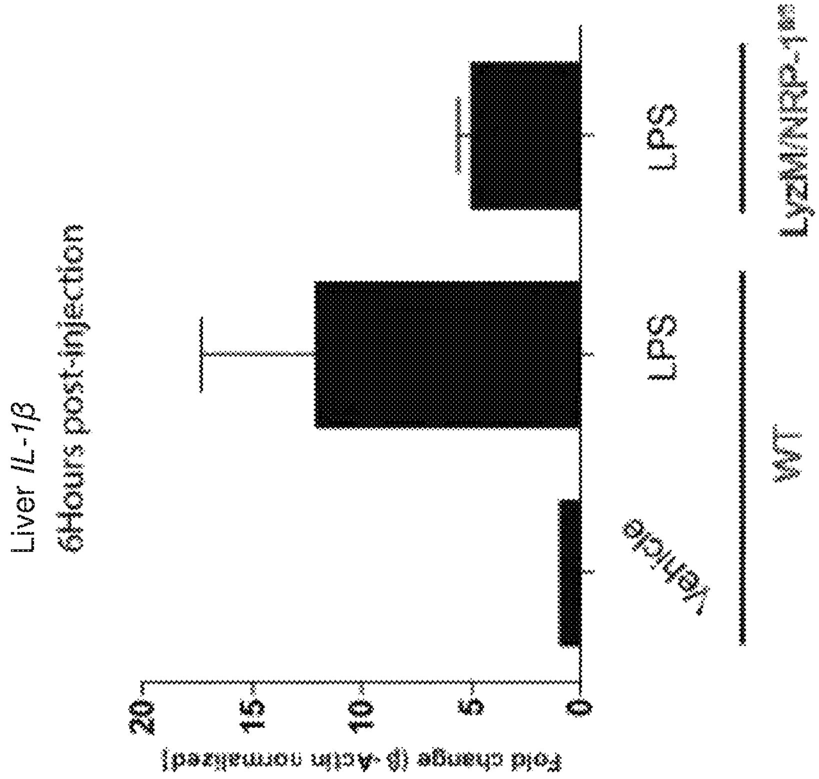
Figure 14C:
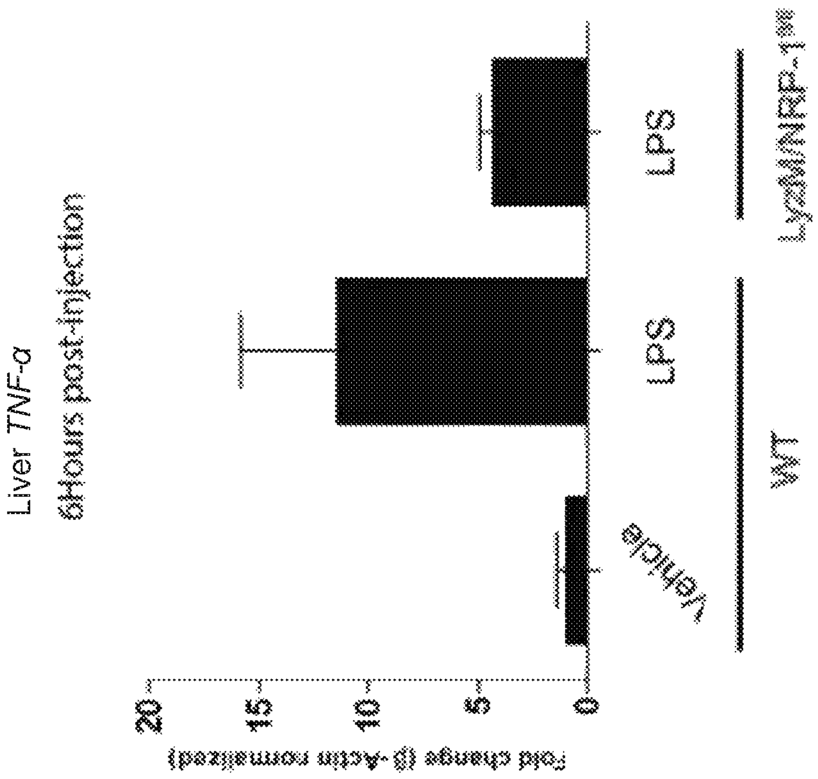
Figure 15A:
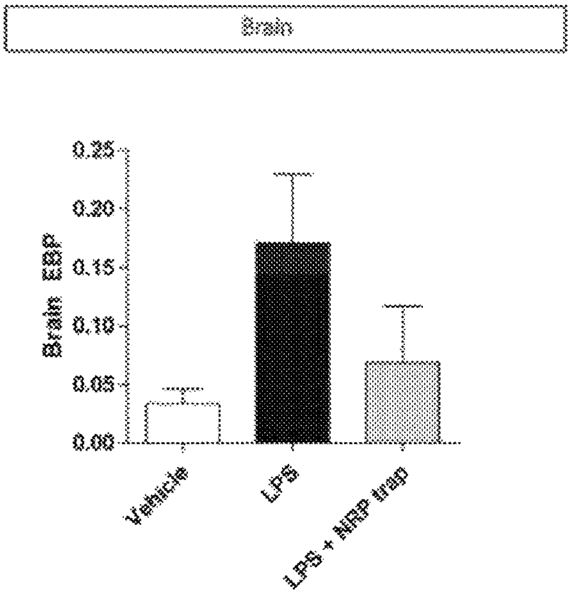
Figure 15B:
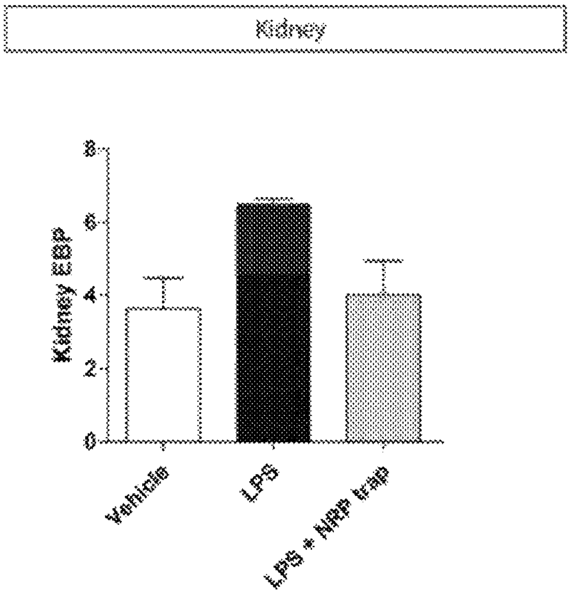
Figure 15C:
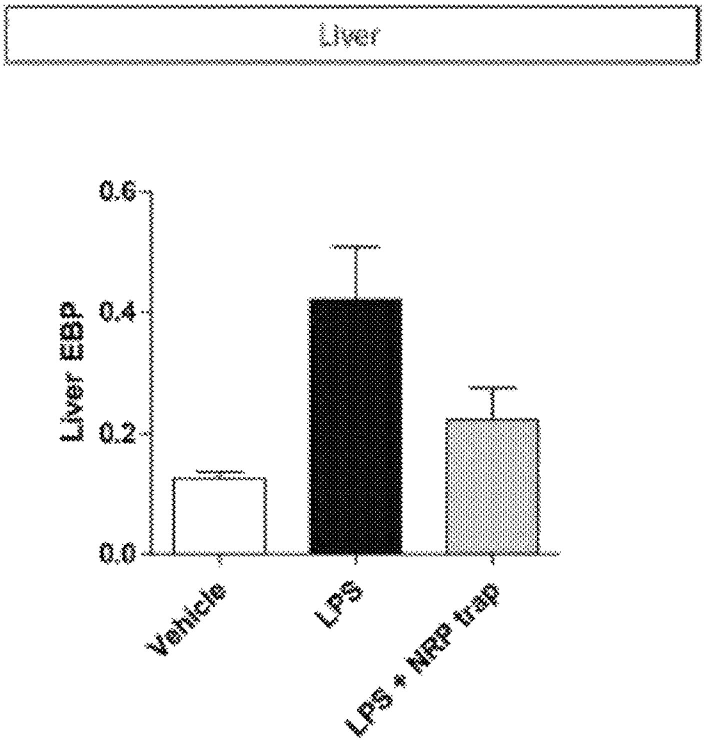
Figure 16A:
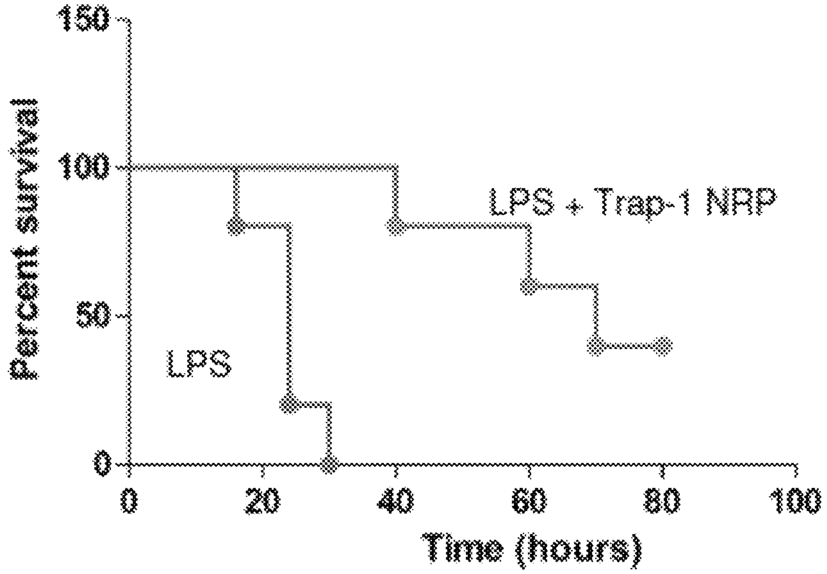
Figure 16B:
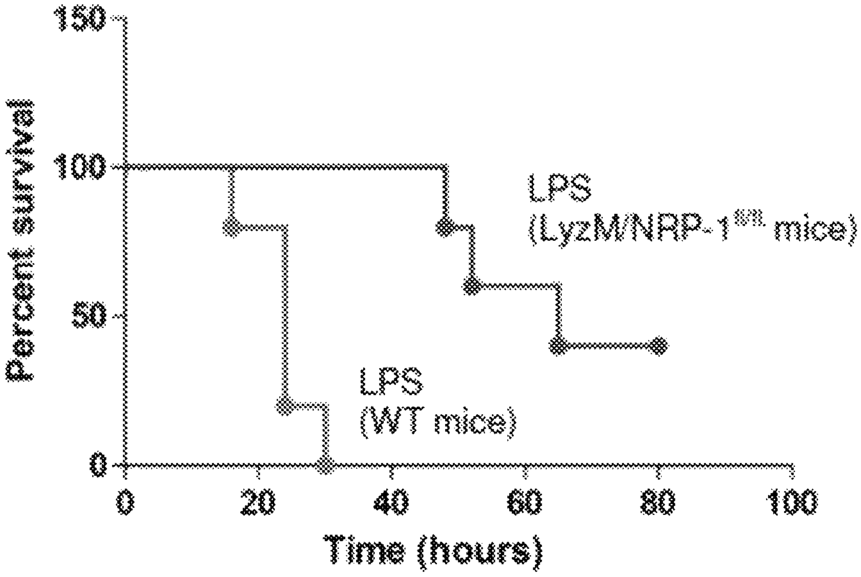
Figure 17A:
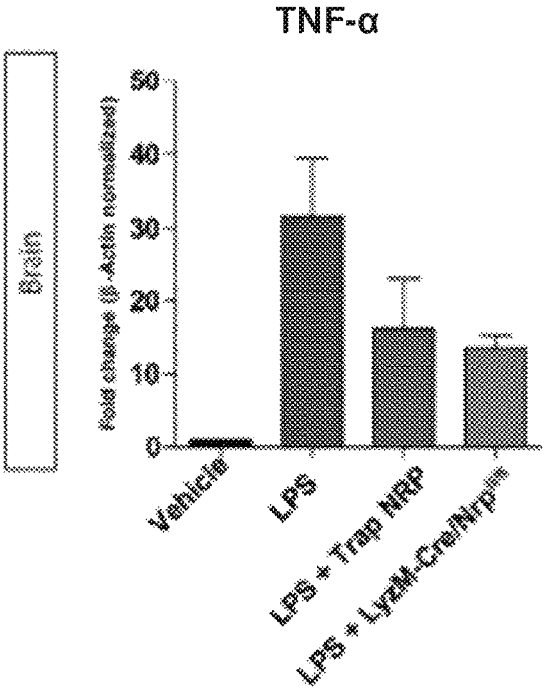
Figure 17B:
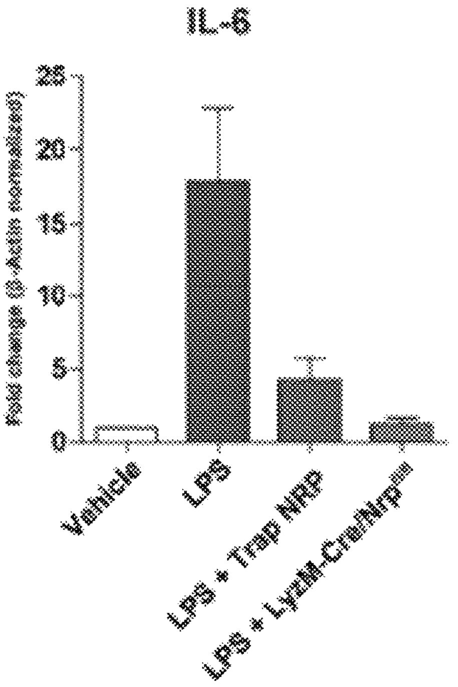
Figure 19A:
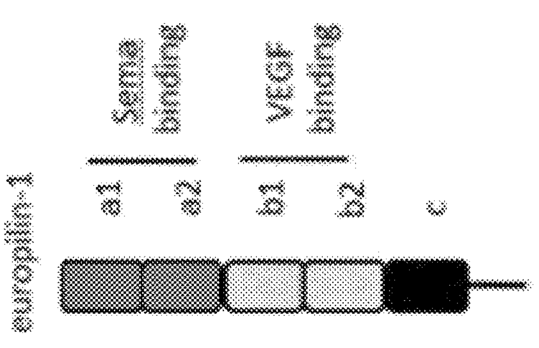
Figure 19B:
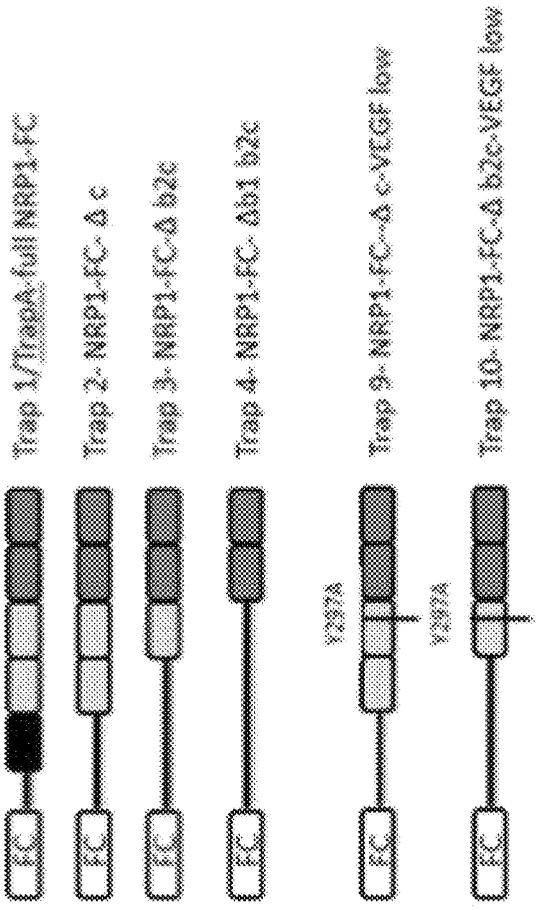
Figure 19C:
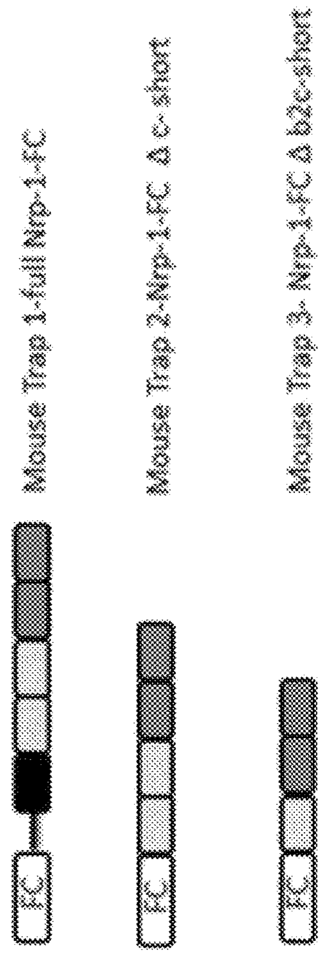
Figure 19D:
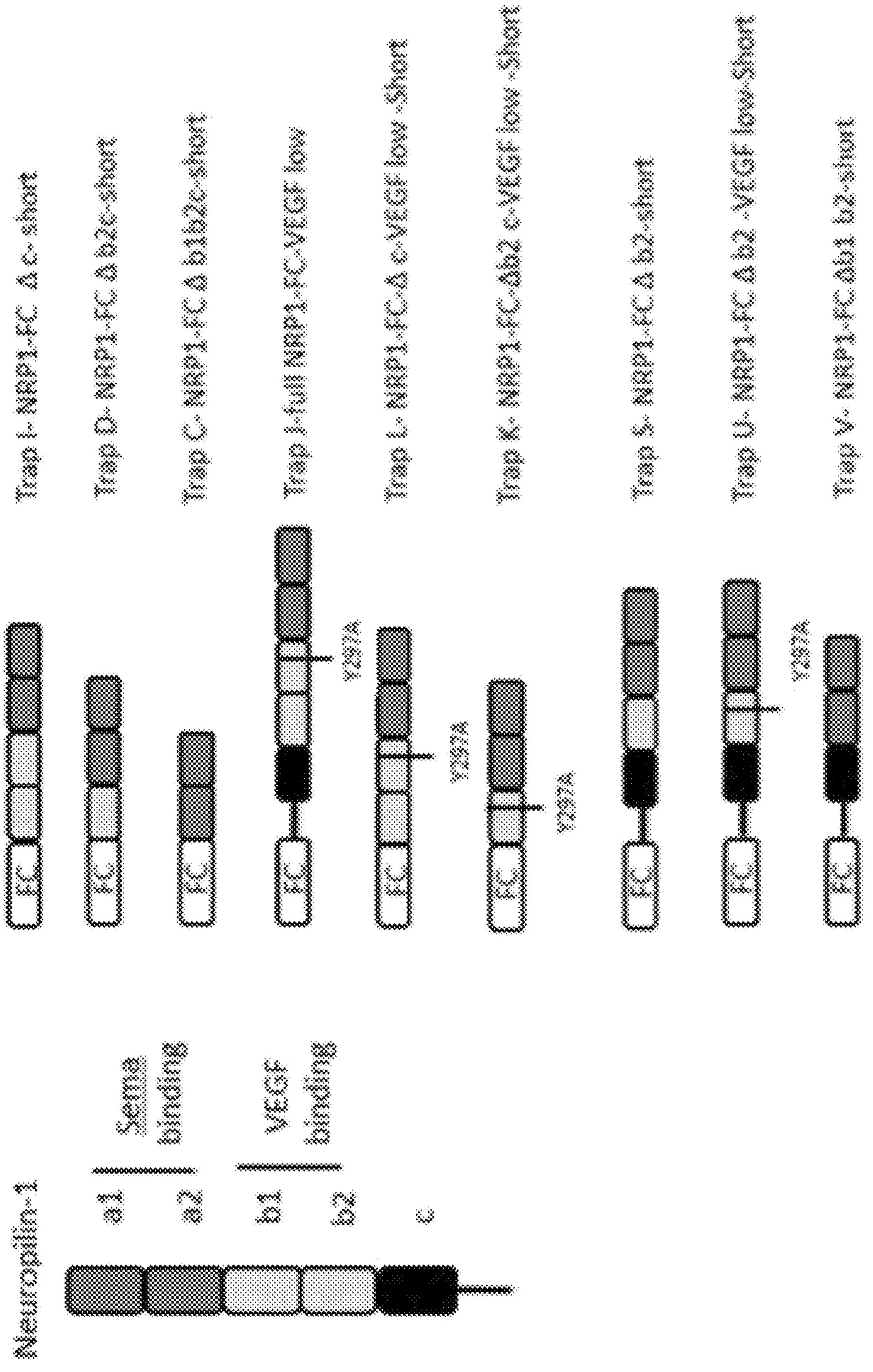
Figure 19E:
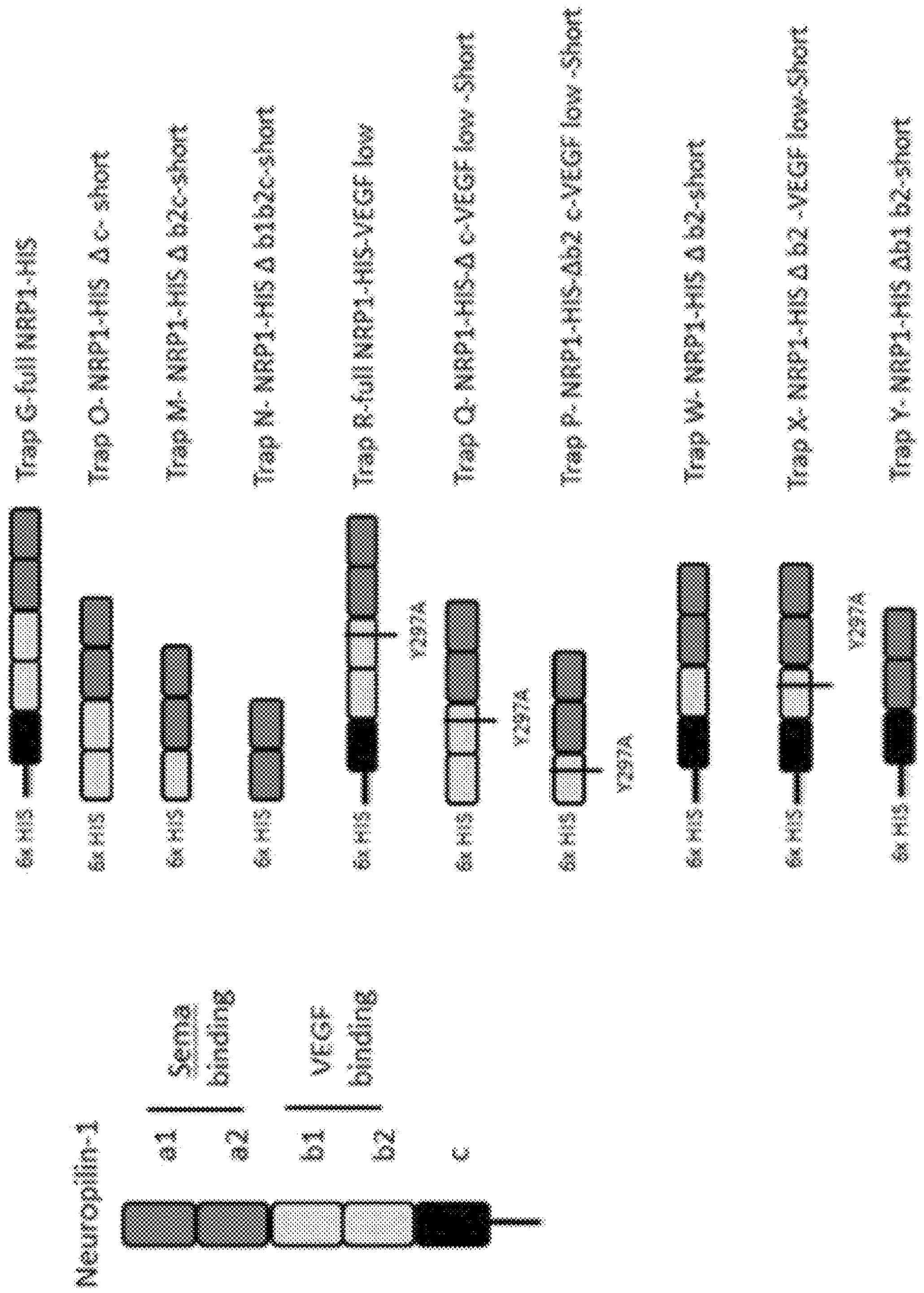
Figure 19F:
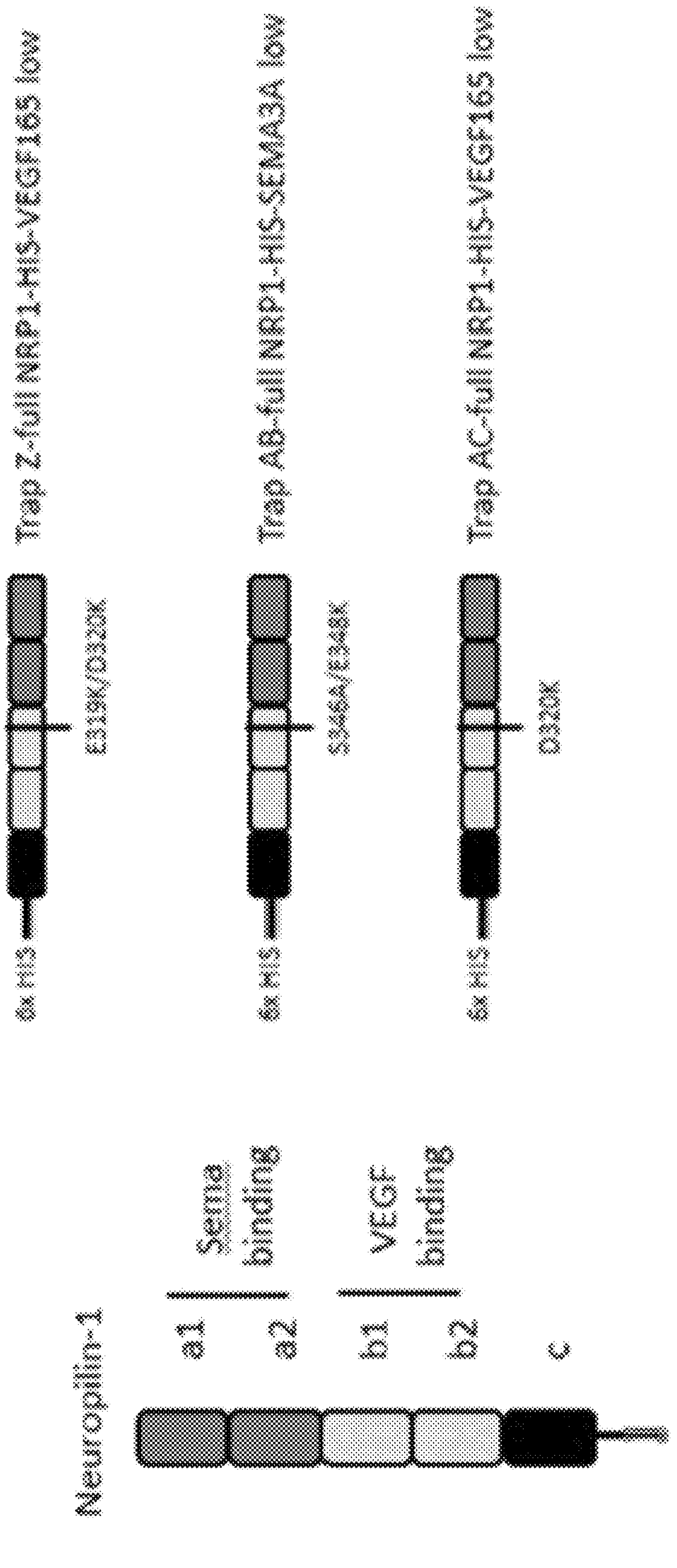
Figure 23A:
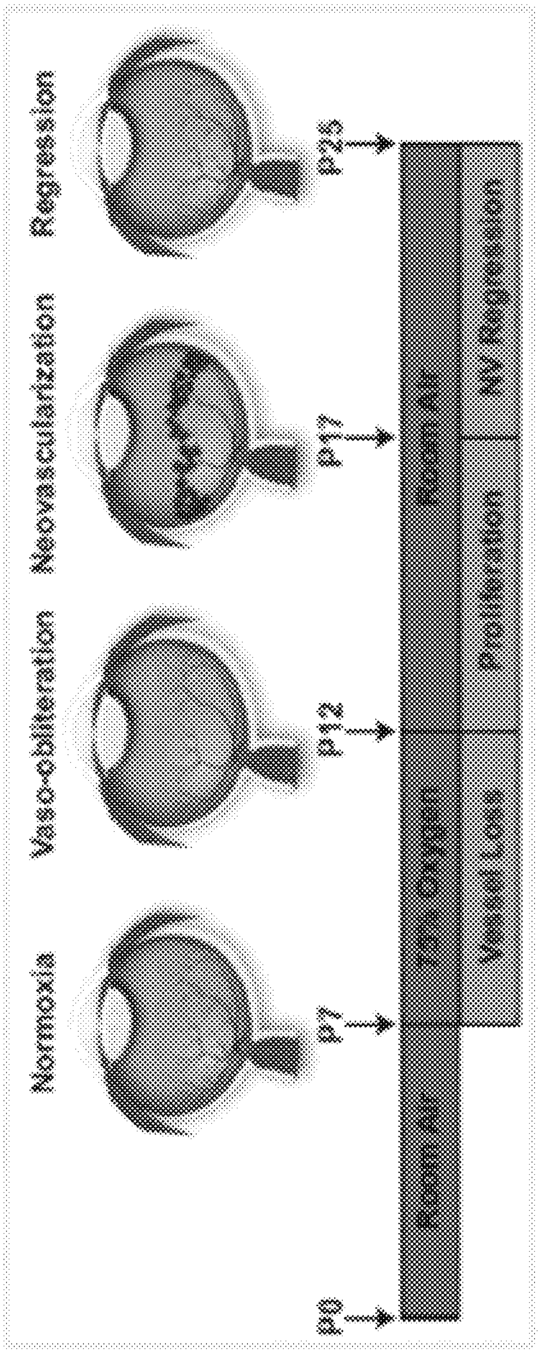
Figure 23B:
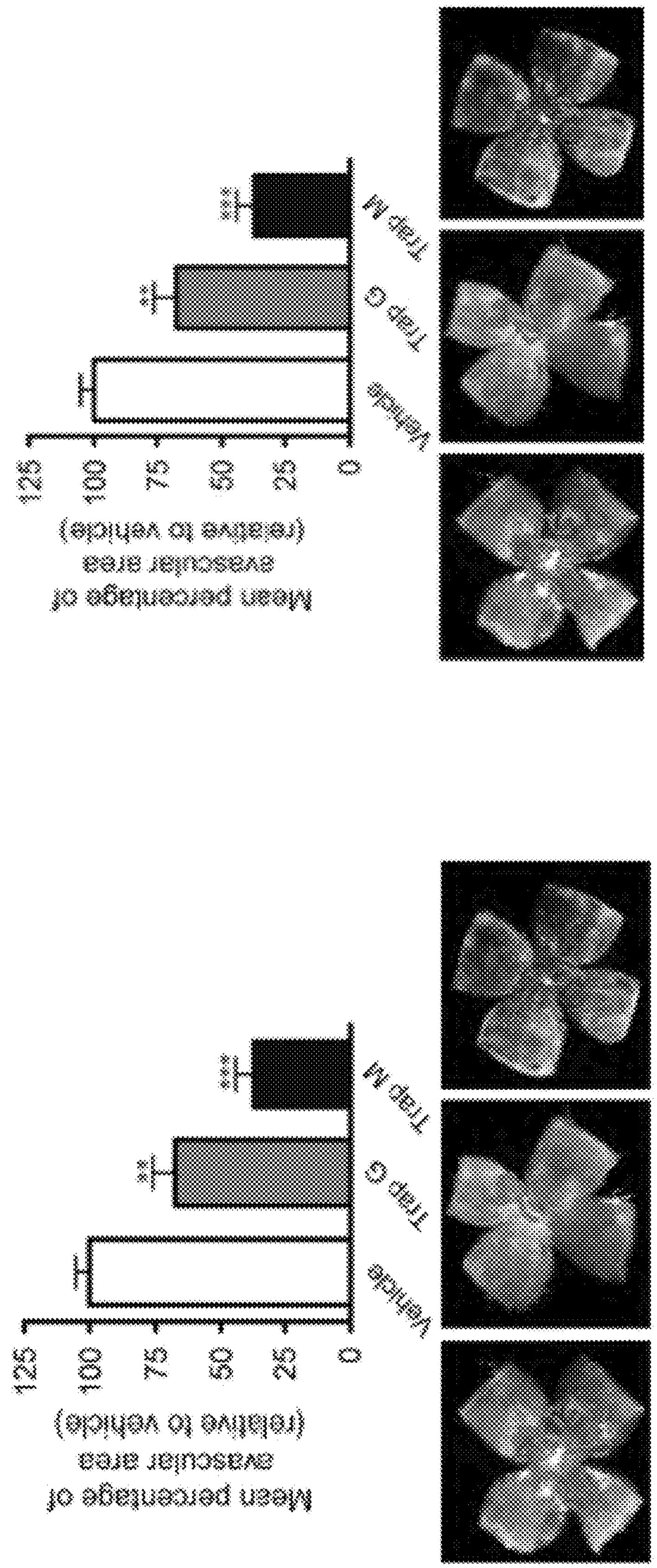
Figure 24A:
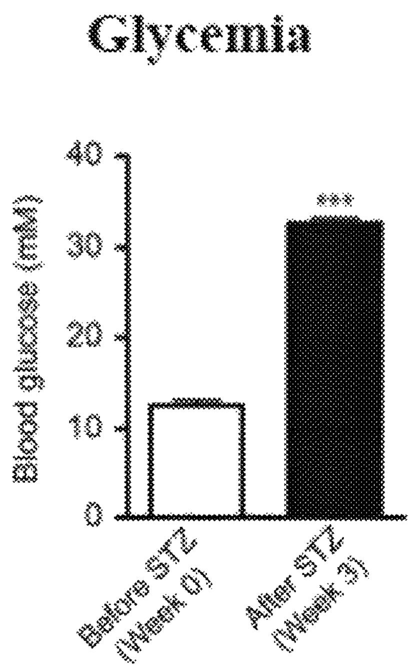
Figure 24B:
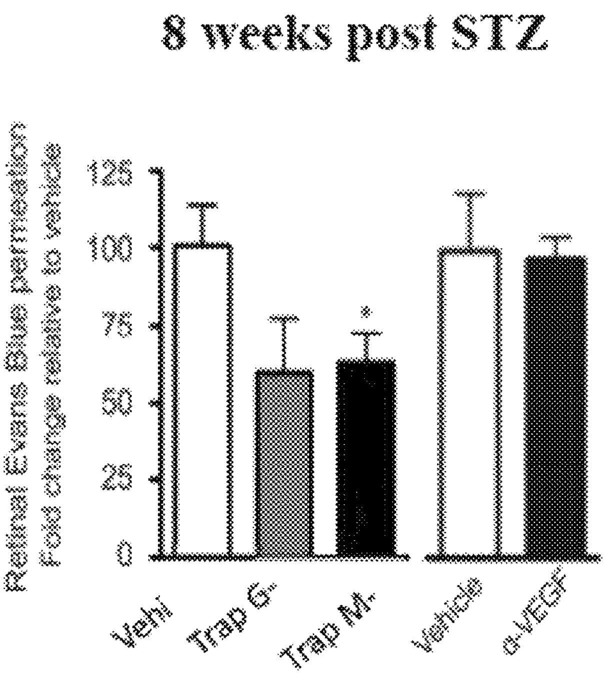
Figure 24C:
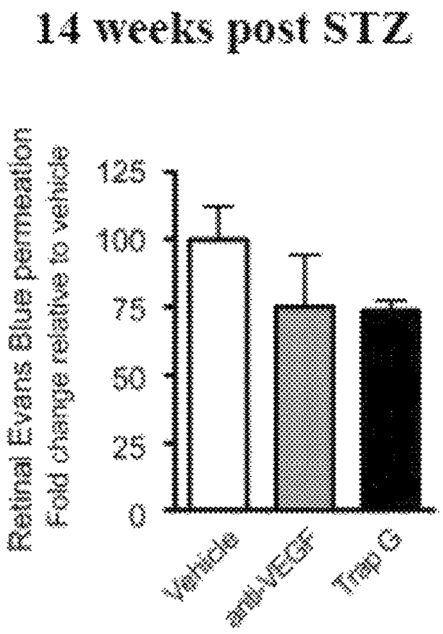
Figure 25A:
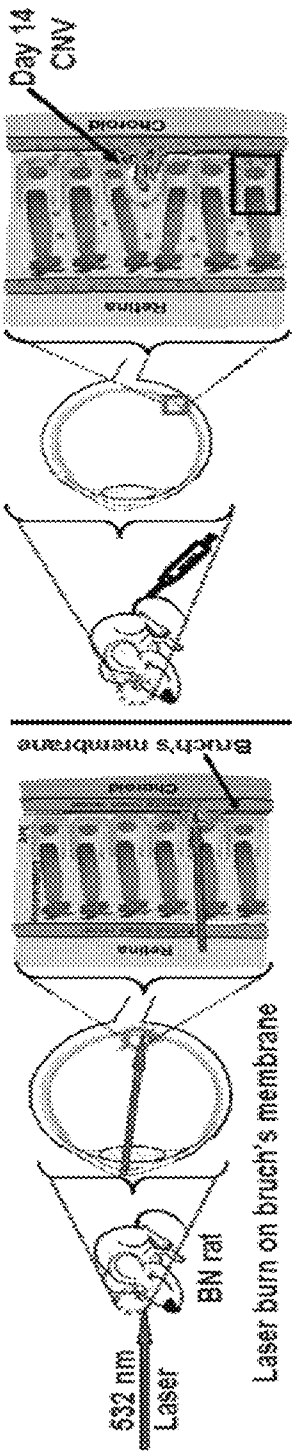
Figure 25B:
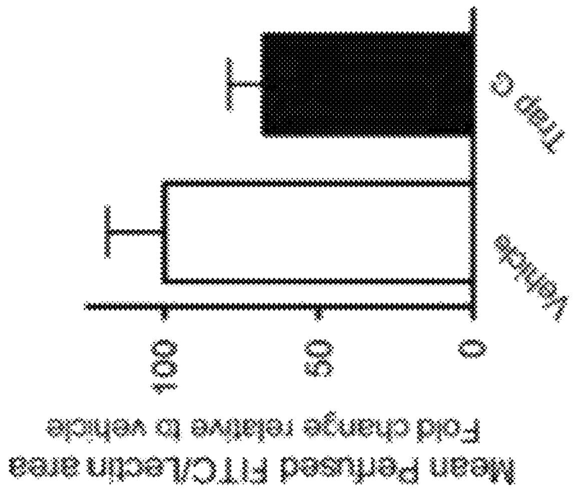
Figure 26B:
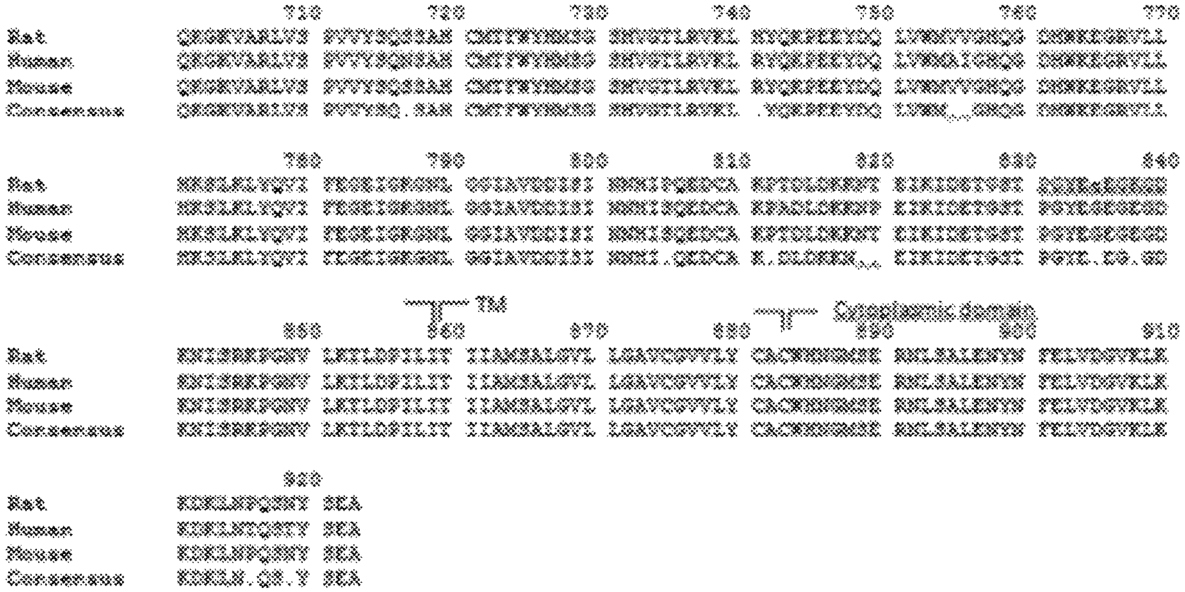
Figure 27B:
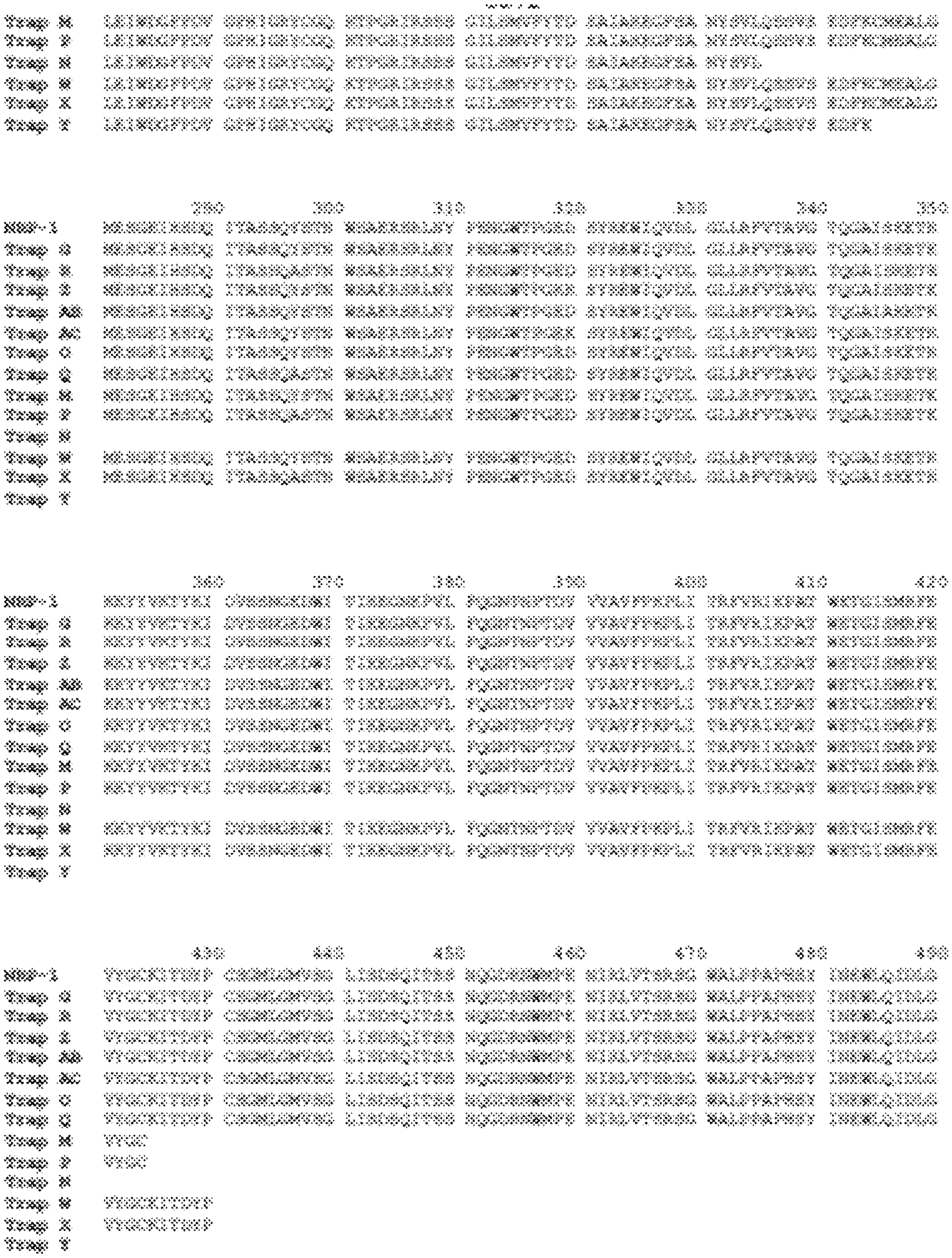

14A, FIG. 14C) and IL-1β (FIG. 14B, FIG. 14D) expression was analyzed by real-time RT-PCR and levels normalized with β-actin expression level;

FIGS. 15A-15C show that in vivo inhibition of NRP1 activity prevents sepsis-induced barrier function breakdown. Mice were administered with i) vehicle, ii) LPS (15 mg/kg); or iii) LPS (15 mg/kg) and an NRP1 trap (Trap-1, FIGS. 19C and 20X-20Y but without an FC domain, NP_032763, 4 ug/0.2 mg/kg, i.v.). Vascular permeability in brain (FIG. 15A), kidney (FIG. 15B) and liver (FIG. 15C) was then assessed using an Evan blue permeation assay (EBP);

FIGS. 16A-16B show that in vivo inhibition of NRP1 activity protects against sepsis. (FIG. 16A) Survival rate of control mice administered with i) a high dose of LPS (i.p., 25/mg/kg); or ii) an NRP1 trap (i.v., 0.2 mg/kg of Trap-1, FIGS. 19C and 20X-20Y but without an FC domain, NP_032763) followed by a high dose of LPS (i.p., 25/mg/kg). (FIG. 16B) Comparison of survival rate between myeloid-resident NRP1 knock out mice (LyzM/NRP1$^{fl/fl}$) and control mice administered with a high dose of LPS (i.p., 25/mg/kg);

FIGS. 17A-17B show that administration of NRP1 derived trap or myeloid deficiency in NRP1 lowers inflammatory cytokine production in septic shock. Wild-type mice were administered i) vehicle (n=3), ii) LPS (15 mg/kg, n=3) or iii) LPS and an NRP1 trap (Trap-1, FIGS. 19C and 20X-20Y but without an FC domain, NP_032763). Mice with NRP1 deficient myeloid cells (LyzM-Cre/Nrp$^{fl/fl}$) were administered LPS (15 mg/kg, n=3). Brains were collected 6 hours post LPS injection and production of TNF-α (FIG. 17A) and IL-6 (FIG. 17B) was measured;

FIGS. 18A-18E shows that administration of NRP1 derived trap protects against ischemic stroke. Mice were subjected to transient middle cerebral artery occlusion (MCAO) and administered vehicle or NRP1 trap and the size of the infarct (stroke) measured on coronal cerebral sections stained with cresyl violet. The unstained area corresponds to the damaged area. (FIG. 18A), Coronal cerebral sections of MCAO mice treated with vehicle. (FIG. 18B) Coronal cerebral sections of MCAO mice treated with NRP1 Trap-1 (see FIGS. 19C and 20X-20Y but without an FC domain, NP_032763). (FIG. 18C) Schematic representation of average infarct size in mice treated with vehicle or NRP1 trap following MCAO. (FIG. 18D) Neurological impairment (neuroscore) of mice treated with vehicle or NRP1 trap 1 h after MCAO. (FIG. 18E) Neurological impairment (neuroscore) of mice treated with vehicle or NRP1 trap 24 h after MCAO;

FIGS. 19A-19F show a schematic representation of the NRP1 protein and embodiments of NRP1-traps of the present invention. (FIG. 19A). WT NRP1 representation showing SEMA3A binding domain (mainly a1a2 with a small contribution of b1 and VEGF binding domain (b1b2). The c-domain is the MEM domain that is thought to contribute to NRP dimerization to other co-receptors. (FIGS. 19B, 19D-19F) Schematic representations of human-derived NRP1 (FIG. 19C) and mouse-derived NRP1 traps;

FIGS. 20A-20CC show the nucleic acid and protein sequences of the NRP1 traps depicted in FIGS. 19B and 19C. (FIGS. 20A-20B) Trap 1/TrappeA-full NRP1-FC amino acid (SEQ ID NO: 114) and nucleotide (SEQ ID NO: 2) sequences; (FIG. 20C) Trap 2-NRP1-FC-Δ c-amino acid sequence (SEQ ID NO: 115); (FIG. 20D) Trap 2-NRP1-FC-Δ c-nucleotide sequence (SEQ ID NO: 4); (FIG. 20E) Trap 3-NRP1-FC-A b2c-amino acid sequence (SEQ ID NO: 116); (FIG. 20F). Trap 3-NRP1-FC-A b2c-nucleotide sequence (SEQ ID NO: 6); (FIG. 20G) Trap 4-NRP1-FC-Δb1 b2c-amino acid sequence (SEQ ID NO: 117); (FIG. 20H) Trap 4-NRP1-FC-Δb1 b2c-nucleotide sequence (SEQ ID NO: 8); (FIGS. 201-20J) Trap 5/Trap I-NRP1-FC Δ c-short-amino acid (SEQ ID NO: 118) and nucleotide (SEQ ID NO: 10) sequences; (FIGS. 20K-20L) Trap 6/Trap D-NRP1-FC Δ b2c-short-amino acid (SEQ ID NO: 119) and nucleotide (SEQ ID NO: 12) sequences; (FIG. 20M) Trap 7/Trap C-NRP1-FC Δ b1 b2c-short-amino acid (SEQ ID NO: 120) and nucleotide (SEQ ID NO: 14) sequences; (FIGS. 20N-200) Trap 8/TrapJ-full NRP1-FC-VEGF low-amino acid (SEQ ID NO: 121) and nucleotide (SEQ ID NO: 16) sequences; (FIG. 20P) Trap 9-NRP1-FC-Δ c-VEGF low-amino acid sequence (SEQ ID NO: 122); (FIG. 20Q) Trap 9-NRP1-FC-Δ c-VEGF low-nucleotide sequence (SEQ ID NO: 18); (FIG. 20R) Trap 10-NRP1-FC-Δ b2c-VEGF low-amino acid sequence (SEQ ID NO:123); (FIG. 20S) Trap 10-NRP1-FC-Δ b2c-VEGF low-nucleotide sequence (SEQ ID NO: 20); (FIGS. 20T-20U) Trap 11/TrapL-NRP1-FC-Δ c-VEGF low—Short-amino acid (SEQ ID NO: 124) and nucleotide (SEQ ID NO:22) sequences; (FIGS. 20V-20W) Trap 12/TrapK-NRP1-FC-Δb2c-VEGF low—Short-amino acid (SEQ ID NO:125) and nucleotide (SEQ ID NO:24) sequences. (FIGS. 20X-20Y) Mouse Trap 1-full Nrp1-mFC amino acid (SEQ ID NO: 126) and nucleotide (SEQ ID NO: 26) sequences. (FIGS. 20Z-20AA) Mouse Trap 2-Nrp1-mFC Δ c-short amino acid (SEQ ID NO: 127) and nucleotide (SEQ ID NO: 28) sequences. (FIGS. 20BB-20CC) Mouse Trap 3-Nrp1-FC Δ b2c-short amino acid (SEQ ID NO: 128) and nucleotide (SEQ ID NO: 30) sequences;

FIG. 21 shows human SEMA3A precursor protein sequence (SEQ ID NO: 31). This sequence is further processed into mature form. Residues 1-20 correspond to the signal peptide;

FIG. 22 shows human soluble Neuropilin-1 (NRP1) receptor protein sequence (e.g., GenBank Acc. No. AAH07737.1-SEQ ID NO: 65). Domains a1, a2, b1, b2 and c are shown. Domain a1 consist of amino acids 23-148; domain a2 consist of amino acids 149-270; domain b1 consist of amino acids 271-428; domain b2 consists of amino acids 429-590 and domain c consists of amino acids 591-609;

FIGS. 23A-23B show that SEMA3A traps accelerate vascular regeneration and reduce pathological angiogenesis in ischemic mice retinas in an oxygen-induced retinopathy model. (FIG. 23A) Schematic depiction of the mouse model of oxygen-induced retinopathy (OIR) showing the four principal stages of retinopathy i.e., normoxia, vessel loss/vaso-obliteration, proliferation/neovascularization and neovascular (NV) regression. (FIG. 23B) Mean percentage (%) of avascular area (relative to vehicle) at P17 following intravitreal injection of histidine tagged Trap G or Trap M (Trap G-HIS (SEQ ID NO: 38) and TrapM-HIS (SEQ ID NO: 42)). Photographs of representative retinas showing avascular area are shown for each group. Mean percentage of neovascular area (relative to vehicle) at P17 following intravitreal injection of histidine tagged Trap G and Trap M. Photographs of representative retinas showing neovascular area are shown for each group. *p<0.05, p<0.01, *p<0.001. n=8-13 animals/group;

FIGS. 24A-24C show that SEMA3A trap prevents vascular leakage and edema in diabetic retinas. (FIG. 24A). Blood glucose levels of mice prior streptozotocin (STZ) treatment (week 0) and 3 weeks following STZ treatment (diabetic state). (FIG. 24B). Retinal Evans Blue permeation assay (measured at week 8) on mice retinas injected intravitreally with 0.5 ug/ml of Trap G, Trap M or 80 μg (1 ul)

of anti-$VEGF_{164}$ antibody (AF-493-NA, R&D) at 6 and 7 weeks following STZ administration. (FIG. 24C) Retinal Evans Blue permeation assay (measured at week 14) on mice retinas injected intravitreally with 0.5 ug/ml of Trap G or Trap M or anti-$VEGF_{164}$ antibody (AF-493-NA, Novus Biologicals) at 12 and 13 weeks post STZ treatment. *$p<0.05$, n=4, from 12 animals;

FIGS. 25A-25B show that NRP1 derived trap (anti SEMA3A and VEGF) reduces choroidal neovascularization in a model of age-related macular degeneration (AMD) (FIG. 25A). Schematic representation of the method used for inducing choroidal neovascularization in mice eyes. (FIG. 25B) Choroidal Neovascularization at day 14 post laser burn (mean perfused FITC/Lectin area). Mice eyes were injected intravitreally with Trap G right after laser burn:

FIGS. 26A-26B show an alignment between rat (Access. Nos. EDL96784, NP_659566, SEO ID NO: 68), human (SEQ ID NO: 66, Accession No. NM003873) and mouse (SEQ ID NO: 67, Accession No. NP_032763) together with an NRP1 consensus sequence (SEQ ID NO: 69). The NRP1 signal domain (amino acids 1-21), SEMA3a binding domains a1 (amino acids 22-148, SEQ ID NO:78), a2 (amino acids 149-175, SEQ ID NO:79), VEGF binding domains b1 (amino acids 276-428, SEQ ID NO:80) and b2 (amino acids 429-589, SEQ ID NO:81), domain c (amino acids 590-859, SEQ ID NO:82), transmembrane domain (amino acids 860-883, SEQ ID NO: 77) and cytoplasmic domain (amino acids 884-923) are identified; and FIGS. 27A-27H show protein sequence alignments between exemplary traps of the present invention shown in FIG. 19 but without any histidine or FC tags. (FIGS. 27A-27D). protein sequence alignment between exemplary traps but lacking the 6×His tag purification domains (G (SEQ ID NO:100), R (SEQ ID NO:101), Z (SEQ ID NO:102), AB (SEQ ID NO:103), AC (SEQ ID NO:104), 0 (SEQ ID NO:105), Q (SEQ ID NO:106), M (SEQ ID NO:107), P (SEQ ID NO:108), N (SEQ ID NO:109), W (SEQ ID NO: 110), X (SEQ ID NO: 111) and Y (SEQ ID NO: 112)) of the present invention comprising a 6×His tag purification domain. (FIGS. 27E-27H) protein sequence alignment between exemplary traps of the present invention but lacking the FC domain ((A (SEQ ID NO:100), I (SEQ ID NO:105), D (SEQ ID NO:107), C (SEQ ID NO:109), J (SEQ ID NO:101), L (SEQ ID NO:106), K (SEQ ID NO:108), S (SEQ ID NO:113), U (SEQ ID NO:111), V (SEQ ID NO:112)).

DESCRIPTION OF ILLUSTRATIVE EMBODIMENTS

The present inventors have identified a subset of mononuclear phagocytes (MPs) that responds to local chemotactic cues such as SEMA3A that are conserved between central neurons, vessels and immune cells. NRP1 expressing MP's were shown to enter the site of injury and to contribute to (i) tissue damage and/or (ii) pathological activation of the innate immune response in models of inflammatory conditions including various forms of inflammatory, proliferative retinopathies (e.g., proliferative diabetic retinopathy, retinopathy of prematurity and age-related macular degeneration), septic shock and cerebral ischemia/stroke.

The inventors demonstrated that stressed retinal neurons and neural tissue have the inherent ability to modulate the local innate immune response via unconventional chemotactic agents. NRP1 on microglia was found to be a potent chemoattractive receptor for SEMA3A, and VEGF and inhibition of NRP1 signaling in innate immune cells (e.g., using NRP1-derived traps or NRP1 or SEMA3A antibodies) resulted in protection against MP's induced inflammation and tissue damage.

Patients suffering from late-stage proliferative diabetic retinopathy (PDR) were shown to produce elevated levels of SEMA3A which counterintuitively acts as a potent attractant for Neuropilin-1 (NRP1)-positive MPs. These pro-angiogenic MPs are selectively recruited to sites of pathological neovascularization in response to locally produced SEMA3A as well as VEGF and TGF-β. Furthermore, SEMA3A was shown to be up-regulated in several organs during septic shock and to induce secretion of inflammatory cytokines by MP's. Inhibition of NRP1 also reduced the production of proinflammatory cytokines in sepsis.

Finally, NRP1-positive MPs were shown to play a critical role in inflammatory disease progression. Inhibition/abrogation of NRP1 myeloid-dependent activity was shown to protect against neovascular retinal disease (vascular degeneration and pathological neovascularization), septic shock and neural damages secondary to cerebral ischemia/stroke.

Together, these findings underscore the role of NRP1-positive MPs and their ligands in inflammation (and in particular in neuroinflammation) and demonstrate the therapeutic benefit of inhibiting NRP1 cell signaling to limit hyperactivation of innate immune response (e.g., tissue damage at the site of injury through recruitment of microglia/macrophages and/or induction of production and/or secretion of proinflammatory cytokines, and/or vascular leakage/edema). The present findings finds applications in the prevention and treatment of diseases and conditions characterized by sustained (e.g., chronic, persistent) or excessive/pathological inflammation involving MP recruitment and proinflammatory cytokines production and secretion such as septic shock, arthritis, inflammatory bowel disease (IBD), cutaneous skin inflammation, diabetes, uveitis and neuroinflammatory conditions such as diabetic retinopathy, age-related macular degeneration (AMD), retinopathy of prematurity, multiple sclerosis, amyotrophic lateral sclerosis (ALS), age-related cognitive decline/Alzheimer's disease and stroke.

Inhibition of NRP1-Mediated Cellular Activity

The present inventors have found that by inhibiting NRP1-dependent cell signaling (and in particular SEMA3A-mediated cell signaling), it is possible to protect against (prevent or treat) inflammatory diseases and conditions such as those involving hyperactivation of the innate immune response. In particular, inhibition of NRP1-mediated cell-signaling reduces the unwanted (pathological) recruitment of mononuclear phagocytes (MPs, e.g., microglia, macrophages) and the production/secretion of proinflammatory cytokines which contribute to tissue damage (e.g., increased vascular degeneration, pathologic neovascularization, cell death or cell damages), inflammation and edema.

Thus, in an aspect, the present invention relates to a method of treating or preventing inflammation comprising inhibiting NRP1-dependent cell-signaling. In a particular aspect, the inflammation is neuroinflammation.

As used herein, the term "inflammation" means a disease or condition which involves the activation of the innate immune response comprising i) the recruitment of mononuclear phagocytes (e.g., microglia or macrophages) expressing the NRP1 receptor at the site of inflammation or injury; and/or ii) the NRP1 dependent production/secretion of pro-inflammatory cytokines (e.g., IL-1β, TNF-α, IL-6). The classical signs of acute inflammation are pain, heat, redness, swelling, and loss of function. Inflammation can be classified as either acute or chronic. Acute inflammation is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. Prolonged (sustained) inflammation, known as chronic inflammation, leads to a progressive shift in the type of cells present at the site of inflammation and is characterized by simultaneous destruction and healing of the tissue from the inflammatory process. Non-limiting examples of inflammatory conditions which may be treated or prevented in accordance with methods of the present invention include septic shock, arthritis, inflammatory bowel disease (IBD), cutaneous skin inflammation, diabetes, uveitis and neuroinflammatory conditions such as diabetic retinopathy (including proliferative diabetic retinopathy (PDR)), age-related macular degeneration (AMD), retinopathy of prematurity, multiple sclerosis, amyotrophic lateral sclerosis (ALS), age-related cognitive decline/Alzheimer's disease and stroke.

In a particular embodiment the inflammatory disease or condition is not a retinopathy. In another embodiment, the inflammatory disease or condition is not diabetic retinopathy. In another embodiment, the inflammatory disease or condition is not macular edema. In another embodiment, the inflammatory disease or condition is not diabetic macular edema.

In a related aspect, the present invention concerns a method of inhibiting hyperactivation (or pathological activation) of the innate immune response comprising inhibiting NRP1-dependent cell-signaling. Such an hyperactivation of innate immune response, is typically associated with acute or chronic activation of any given cell population of the immune system (innate and adaptive, e.g., mononuclear cell recruitment in the organ/tissue) beyond levels required to maintain tissue homeostasis. This is often accompanied by heightened production of cytokines (e.g., TNF-alpha, IL-6), increased vascular permeability, and may result in compromised tissue function.

In another aspect, the present invention concerns a method of treating or preventing vascular degeneration comprising inhibiting NRP1-dependent cell-signaling.

In a further aspect, the present invention concerns a method of treating or preventing pathological neovascularization comprising inhibiting NRP1-dependent cell-signaling.

In another aspect, the present invention concerns a method of treating or preventing septic shock comprising inhibiting NRP1-dependent cell-signaling.

In a yet another aspect, the present invention concerns a method of treating or preventing neural damages secondary to cerebral ischemia/stroke comprising inhibiting NRP1-dependent cell-signaling.

Because NRP1-mediated cell signaling (e.g., MPs recruitment and production/secretion of pro-inflammatory cytokines) depends on the binding of NRP1 to its ligands (e.g., SEMA3A, VEGF and/or TGF-β), inhibition of NRP1-mediated cellular signaling can be achieved in at least two ways: i) by targeting the expression or activity of NRP1 directly (through the use of NRP1 antibodies, NRP1 derived traps or the like); or ii) by targeting the expression or activity of one or more of its ligands (e.g., SEMA3A, VEGF and/or TGF-β).

In embodiments, the above methods comprise preferentially or specifically inhibiting SEMA3A-mediated cell signalling. "Preferentially inhibiting" means that the level of inhibition of SEMA3A-mediated cell signalling is greater than that of other NRP1 ligands (e.g., VEGF165 and TGF-beta). In certain aspects, methods of the present invention substantially do not reduce or inhibit VEGF (e.g., VEGF165) and/or TGF-beta-mediated cell signalling that occur through the interaction with NRP1. In embodiments, compounds of the present invention (e.g., NRP1 traps) "preferentially bind" to one ligand over the others (e.g., preferentially bind SEMA3A over VEGF). Such preferential interaction may be determined by measuring the dissociation constant (Kd) for each ligand. In embodiments, interaction for one ligand (e.g., SEMA3A) over the others (e.g., VEGF) is at least 1.5, 2, 3, 4, 5, 6, 7, 8, 9, 10, 12, 15, 28, 20, 22, 25, 30, 35, 40, 45, 50, 60, 75, 80, 100, 200, 300, 400, 500, 1000 times greater or more. In embodiments the kD (e.g., in nM) for one ligand is at least 1.5, 2, 3, 4, 5, 6, 7, 8, 9, 10, 12, 15, 28, 20, 22, 25, 30, 35, 40, 45, 50, 60, 75, 80, 100, 200, 300, 400, 500, 1000 times smaller than the kD for one or more of the other ligands (e.g., VEGF).

In an embodiment, methods of the present invention comprise administration to a subject likely to suffer from inflammation (e.g., likely to suffer from an inflammatory disease or condition). In other embodiment, methods of the present invention comprise administration to a subject diagnosed from inflammation (e.g., likely to suffer from an inflammatory disease or condition). In an embodiment, the subject is a mammal, preferably a human.

NRP1 Traps

Inhibition of NRP1-mediated cellular signaling can be achieved using NRP1 traps of the present invention. As used herein, the terms, "NRP1 trap", or "NRP1 polypeptide trap" encompass naturally occurring soluble NRP1 polypeptide (e.g., such as NRP1 secreted isoform b FIG. 22, SEQ ID NO: 65)), and synthetic (e.g., recombinantly produced) NRP1 polypeptide traps including any functional soluble fragment of NRP1 (e.g., NRP1 isoform 1 or 2) or any functional variant of NRP1 which competes with endogenous NRP1 for ligand binding. In an embodiment, the NRP1 traps of the present invention do not exists in nature (i.e., are not naturally occurring) but are "derived" from naturally occurring NRP1 polypeptides (i.e., they are synthetic; e.g., NRP1 traps comprising the extracellular domain of NRP1 isoform 1 or a fragment or variant thereof). NRP1 traps the present invention initially comprise a signal peptide at their N-terminal end (e.g., amino acids 1-21 (SEQ ID NO: 70) of NRP1 shown in FIG. 26 (e.g., SEQ ID NO:69) which is cleaved upon secretion by the cells. Accordingly, NRP1 polypeptide traps of the present invention lack amino acids 1-21 when administered as purified polypeptides or when prepared as pharmaceutical compositions comprising a purified or substantially pure form. Nucleic acids encoding for NRP1 traps of the present invention (e.g., SEQ ID NOs: 2, 4, 6, 8, 10, 12, 14, 16, 18, 20, 22, 24, 26, 28, 34, 32, 34, 36, 39, 41, 43, 45, 47, etc. See also Table 1) comprise a polynucleotide sequence in 5' which encodes for a signal peptide (first 63 nucleotides encoding for the first 21 amino acids at the N-terminal end) which will allow the NRP1 trap to be synthesized and secreted by the cells. In a particular embodiment, the signal peptide corresponds to the first 20 amino acids of the NRP1 polypeptide set forth in SEQ ID NO: 65 (FIG. 22) or SEQ ID NO: 69 (FIG. 26). NRP1 traps of the present invention encompass functional variants of corresponding "wild-type" NRP1 polypeptides or fragment thereof (e.g., polymorphic variations naturally found in the population).

NRP1 traps of the present invention may or may not comprise further polypeptide domains (e.g., purification domains). Exemplary traps lacking purification domains and comprising only NRP1-derived sequences are shown in FIG. 27. Non-limiting examples of NRP1 traps that may be used in accordance with the present invention are given in FIGS. 19B-F, FIG. 20, FIG. 27 and are listed Table 1 below.

TABLE 1

Exemplary NRP1-derived traps which have been prepared in accordance with the present invention.

| Trap | Description | SEQ ID Nos. (aa and nts) |
|---|---|---|
| Trap 1/A | Human, "full" extracellular domain NRP1 (corresponding to amino acids 22 to 856 of NRP1 sequences shown on FIG. 26)-FC | SEQ ID NOS: 1, 2, 100 (aa without FC, includes SP) |
| Trap 2 | Human, NRP1-FC-Δc (275 aa linker) | SEQ ID NOs: 3, 4 |
| Trap 3 | Human, NRP1-FC-Δb2c (434 aa linker) | SEQ ID NOS: 5, 6 |
| Trap 4 | Human, NRP1-FC-Δb1b2c (593 aa linker) | SEQ ID NOs: 7, 8 |
| Trap 5/Trap I | Human, NRP1-FC-Δc-short | SEQ ID NOs: 9, 10, 105 (aa, without FC, includes SP) |
| Trap 6/TrapD | Human, NRP1-FC-Δb2c-short | SEQ ID NOs: 11, 12, 107, (aa, without FC, includes SP) |
| Trap 7/TrapC | Human, NRP1-FC-Δb1b2c-short | SEQ ID NOs: 13, 14 109, (aa, without FC, includes SP) |
| Trap 8/TrapJ | Human, "full" extracellular domain NRP1-FC-VEGF low (Y297A mutation) | SEQ ID NOS: 15, 16, 101 (aa, without FC, includes (SP) |
| Trap 9 | Human, NRP1-FC-Δc-VEGF low (Y297A mutation, 275 aa linker) | SEQ ID NOS: 17, 18 |
| Trap 10 | Human, NRP1-FC-Δb2c-VEGF low (Y297A mutation, 434 aa linker) | SEQ ID NOS: 19, 20 |
| Trap 11/Trap L | Human, NRP1-FC-Δc-VEGF low-short (Y297A mutation) | SEQ ID NOS: 21, 22, 106 (aa, without FC, includes SP) |
| Trap 12Trap K | Human, NRP1-FC-Δb2c-VEGF low-short (Y297A mutation) | SEQ ID NOs: 23, 24, 108 (aa, without FC, includes SP) |
| mTrap 1 | Mouse, "full" extracellular domain NRP1-FC Amino acids residues 22-856 | SEQ ID NOs: 25, 26 |
| mTrap 2 | Mouse, NRP1-FC-Δc-short | SEQ ID NOs: 27, 28 |
| mTrap 3 | Mouse, NRP1-FC-Δb2c-short | SEQ ID NOS: 29, 30 |
| Trap S | Human, NRP1-FC-Δb2-short | SEQ ID NOS: 31, 32, 113 (aa without FC, includes SP) |
| Trap U | Human, NRP1-FC-Δb2-VEGF low-short (Y297A mutation) | SEQ ID NOS: 33, 34, 111 (aa, without FC, includes SP) |
| Trap V | Human, NRP1-FC-Δb1b2-short | SEQ ID NOs: 35, 36, 112 (aa, without FC, includes SP) |
| Trap G | Human, "full" extracellular domain NRP1-His | SEQ ID NOS: 38, 39, 100 (aa without his tag, includes SP) |
| Trap O | Human, NRP1-His-Δc-short | SEQ ID NOs: 40, 41, 105 (aa without his tag, includes SP) |
| Trap M | Human, NRP1-His-Δb2c-short | SEQ ID NOs: 42, 43, 107 (aa without his tag, includes SP) |
| Trap N | Human, NRP1-His-Δb1b2c-short | SEQ ID NOs: 44, 45, 109 (aa without his tag, includes SP) |
| Trap R | Human, NRP1-His-Δc-VEGF low | SEQ ID NOs: 46, 47, 101 (aa without his tag) |
| Trap Q | Human, NRP1-His-Δc-VEGF low-short | SEQ ID NOS: 48, 49, 106 (aa without his tag, includes SP) |
| Trap P | Human, NRP1-His-Δb2c-VEGF low-short | SEQ ID NOs: 50, 51, 108 (aa without his tag, includes SP) |
| Trap W | Human, NRP1-His-Δb2-short | SEQ ID NOs: 52, 53, 110 (aa without his tag, includes SP |
| Trap X | Human, NRP1-His-Δb2-VEGF low-short | SEQ ID NOs: 54, 55, 111 (aa, without his tag, includes SP) |

TABLE 1-continued

Exemplary NRP1-derived traps which have been prepared in accordance with the present invention.

| Trap | Description | SEQ ID Nos. (aa and nts) |
|---|---|---|
| Trap Y | Human, NRP1-His-Δb1b2-short | SEQ ID NOS: 56, 57, 112 (aa, without his tag, includes SP) |
| Trap AB | Human, “full” extracellular domain NRP1-His-<br>SEMA3A low (S346A et E348K mutations) | SEQ ID NOs: 58, 59, 103<br>(aa, without his tag, includes SP) |
| Trap AC | Human, “full” extracellular domain NRP1-His-<br>VEGF-low<br>(D320K mutation) | SEQ ID NOs: 60, 61, 104<br>(aa without his tag, includes SP) |
| Trap Z | Human, “full” extracellular domain NRP1-His,<br>VEGF165-Low<br>(E319K/D320K mutations) | SEQ ID NOs: 62, 63, 102<br>(aa, without his tag, includes SP) |
| Trap 1bis | Human, Trap 1 without FC | SEQ ID NO: 83, 84 |

SP: Signal peptide

Given that NRP1 distinctly regulates the effects of its ligands on signal transduction and cellular responses, it may be advantageous to specifically inhibit the binding of one specific ligand to NRP1 but not that of the others. For example, as shown herein, at early time points of retinal disease, where SEMA3A levels are elevated, VEGF levels remain low and relatively unchanged compared to non-diabetic controls. Also, in septic shock, SEMA3A was the sole NRP1 ligand which had a long term effect and stayed up-regulated for more than 24 hours following induction of sepsis. Thus, given the differences in expression kinetics for each ligand and the fact that neutralization of one ligand (e.g., VEGF) may be ineffective in certain conditions (or be associated with undesired side effects), specific inhibition of one ligand (e.g., SEMA3A) binding to NRP1, (but not that of the other(s) (e.g., VEGF)) is advantageous. Thus, in certain aspects of the methods of the present invention, inhibition of SEMA3A-mediated cell signaling, is accomplished by providing NRP1 Traps having greater affinity for SEMA3 than VEGF or to which VEGF (e.g., VEGF165) does not bind or does not bind substantially.

Accordingly, in an embodiment, the soluble NRP1 polypeptide or functional fragment or variant thereof (NRP1 trap) of the present invention binds to all natural ligands of NRP1 (e.g., SEMA3A, VEGF and TGF-beta, e.g., a soluble NRP1 trap comprising the extracellular domain (e.g., amino acids 22-856 or 22-959 of SEQ ID NO: 66 or 69), Trap 1, (SEQ ID NO: 1) or Trap G (SEQ ID NO: 38)—See also, FIGS. 19 and 27 and Table 1). In an embodiment, the NRP1-derived trap of the present invention inhibits SEMA3 and VEGF signaling by binding to both SEMA3A and VEGF.

In another embodiment, the NRP1 trap of the present invention is a polypeptide which binds to SEMA3A but not to VEGF. For example the NRP1 trap may comprise the a1 (e.g., SEQ ID NO:71) and/or a2 subdomain(s) (e.g., SEQ ID NO:72) which bind(s) to SEMA3A but not the b1 (e.g., SEQ ID NO:73) and/or b2 (e.g., SEQ ID NO: 74) subdomain(s) required for VEGF binding (e.g., Trap M, (SEQ ID NO: 42), Trap N (SEQ ID NO: 44), Trap 12/Trap K(SEQ ID NO: 23), Trap 4 (SEQ ID NO:7), Trap 7/C (SEQ ID NO: 13), See also, FIGS. 19 and 27 and Table 1). In an embodiment, the NRP1-derived trap comprises domains a1 and a2 corresponding to amino acids 22 to 275 of the NRP1 amino acid sequence set forth in FIG. 26 (e.g., amino acids 22-275 of SEQ ID NO: 66 or SEQ ID NO: 22-275 of SEQ ID NO: 69). The NRP1 trap may also comprise a mutation (e.g., a deletion or substitution) which abrogates or reduces significantly the binding of VEGF to NRP1 but not that of SEMA3A to NRP1 (e.g., Trap 8/trap J (SEQ ID NO:15), Trap 9 (SEQ ID NO: 17), Trap 10 (SEQ ID NO: 19), TRAP 11/L (SEQ ID NO:21), Trap12/K (SEQ ID NO: 23), Trap U (SEQ ID NO: 34), Trap R (SEQ ID NO: 46), Trap Q (SEQ ID NO: 48), Trap P (SEQ ID NO: 50, Trap X (SEQ ID NO:54, Tarp AC (SEQ ID NO: 60), TRAP Z (SEQ ID NO: 62) See also, FIGS. 19 and 27 and Table 1). One non-limiting example of such mutation is a substitution at tyrosine 297 in the b1 domain of NRP1 (e.g., Y297A, FIGS. 19B-D, FIG. 27 and Table 1, e.g., Traps 8, 9, 10, 11, 12, V, R, Q, P and X). Other examples of such mutations comprise a substitution at the glutamic acid at position 319 and at aspartic acid at position 320 in NRP1 (e.g., E319K and D320K such as in Trap AC and Z (SEQ ID NOs: 60, 62)).

In another embodiment, the NRP1 trap is a soluble NRP1 polypeptide or functional fragment or variant thereof which binds to VEGF but not to SEMA3A. For example, the NRP1 trap may comprise the b1 (e.g., SEQ ID NO: 73) and/or b2 (e.g., SEQ ID NO: 74) domain(s) to bind to VEGF but not the a1 (e.g., SEQ ID NO: 71) and/or a2 (e.g., SEQ ID NO: 72) subdomain(s) which bind to SEMA3A. In an embodiment, the NRP1 trap comprises domains b1 b2 corresponding to amino acids 276 to 589 of the NRP1 amino acid sequence set forth in FIG. 26 (e.g., amino acids 276-589 of SEQ ID NO: 66 or 276-289 of SEQ ID NO: 69). In another embodiment, the NRP1 trap may comprise a mutation which reduces or abrogate SEMA3A binding but not that of VEGF. One non-limiting example of such mutation is a substitution at serine 346 and/or glutamic acid 348 of NRP1 (e.g., S346A and E348K mutations, such as in trap AB (SEQ ID NO: 58)—See also FIGS. 19 and 27).

In an embodiment, the soluble NRP1 polypeptide or functional fragment thereof comprises or consists of traps as set forth in FIGS. 19B-F, 20, 27 and Table 1.

In preferred embodiments, the NRP1 traps of the present invention lack the transmembrane domain (e.g., corresponding to amino acids residues 860 to 883 of the NRP1 polypeptide sequences shown in FIG. 26 (such as SEQ ID NO: 66 and 69)) and cytosolic domain (e.g., corresponding to amino acids residues 884-923 of the NRP1 polypeptide isoform 1 sequences shown in FIG. 26 (such as SEQ ID NO:

66 and 69)) found in for example NRP1 isoform 1. In embodiments, the NRP1 traps of the present invention lacks completely or partially domain c of NRP1. NRP1 isoform 1 comprises a larger c domain (see FIG. 26), while that of isoform 2 is shorter (e.g., amino acid sequence VLATEKPT-VIDSTIQSGIK (SEQ ID NO: 99) shown in FIG. 22). Particularly, domain c is not essential to SEMA3A and VEGF binding and thus may be excluded from the NRP1 traps used to inhibit NRP1-dependent cell signaling (or SEMA3A-mediated cell signaling). In an embodiment, the NRP1 trap lacks the c domain corresponding to amino acids 590 to 859 of the NRP1 amino acid sequence set forth in FIG. 26 (e.g., amino acids 590 to 859 of SEQ ID NO: 66 or SEQ ID NO: 69). In an embodiment the NRP1 traps of the present invention lack completely or partially the c domain of isoform 2 as set forth in FIG. 22 (e.g., SEQ ID NO: 99). In an embodiment, NRP1 traps of the present invention comprise domain c of NRP1 isoform 2. In another embodiment, the NRP1 derived trap lacks a portion of domain c corresponding to the amino acids set forth in SEQ ID NO: 75.

The soluble NRP1 polypeptide or functional fragment or variant thereof of the present invention may comprise one or more additional polypeptide domain(s) to increase in vivo stability and/or facilitate purification. For example, NRP1 traps of the present invention may include a FC domain (or part thereof such as the human FC domain set forth in SEQ ID NO: 37.) or a purification tag (e.g., a 6×-histidine tag). Such additional polypeptide domain(s) may be linked directly or indirectly (through a linker) to the soluble NRP1 polypeptide or functional fragment thereof.

The soluble NPR1 polypeptide or functional fragment thereof of the present invention may optionally include one or more polypeptide linkers. Such linkers may be used to link one or more additional polypeptide domain(s) to the soluble polypeptide of the present invention (e.g., a polypeptide domain which increases the stability of the polypeptide in vivo and/or a domain which facilitates purification of the polypeptide). Linker sequence may optionally include peptidase or protease cleavage sites which may be used to remove one or more polypeptide fragments or domains (e.g., removal of purification tag prior to in vivo administration of the soluble NRP1 polypeptides or functional fragment thereof). One non-limiting example of a linker or domain which enables cleavage of the polypeptide and removal of, for example, polypeptide domain(s) (e.g., 6×his tag purification domain) includes a polypeptide comprising a TEV protease cleavage site (e.g., GSKENLYFQ'G, SEQ ID NO:76). Many other TEV cleavage sites are known and many other protease/peptidase cleavage sites are known to the skilled person and may be introduced in the polypeptides of the present invention to optionally remove one or more polypeptide domains or fragments.

Polypeptide linkers may also be used to replace totally or partially domains which are normally found in the wild-type NRP1 polypeptide but which are absent in the soluble NRP1 polypeptide or functional fragment thereof of the present invention. For example, in the NRP1 traps of the present invention, synthetic linkers may replace totally or partially domains a1, a2, b1, b2 and c. The length of the linker may correspond to the entire length of the domain removed or to a portion of it. Such linkers may increase protein folding, stability or binding to NRP1 ligands. Non-limiting examples of NRP1 traps comprising linkers are shown in FIGS. 19 and 20 (e.g., Trap 2, Trap 3, Trap 4, Trap 9 and Trap 10 listed in Table 1). One non-limiting example of a useful polypeptide linker is a polyarginine polypeptide. Other linkers are known in the art and may be used in accordance with the present invention.

In an embodiment, the NRP1 trap of the present invention comprises: (i) amino acids 1-856 (preferably, 22 to 856) of the NRP1 polypeptide set forth in FIG. 26 (SEQ ID NO: 69); (ii) amino acids 1 to 583 (preferably 22 to 583) of the NRP1 polypeptide set forth in FIG. 26 (SEQ ID NO: 69); (iii) amino acids 1 to 424 (preferably 22-424) the NRP1 polypeptide set forth in FIG. 26 (SEQ ID NO: 69); (iv) amino acids 1 to 265 (preferably 22 to 265) the NRP1 polypeptide set forth in FIG. 26 (SEQ ID NO: 69); (v) 1 to 430 and 584 to 856 (preferably 22-430 and 584-856) the NRP1 polypeptide set forth in FIG. 26 (SEQ ID NO: 69); (vi) amino acids 1 to 274 and 584 to 856 (preferably 22-274 and 584 to 856) the NRP1 polypeptide set forth in FIG. 26 (SEQ ID NO: 69); (vii) amino acids 1 to 430 and 584 (preferably 22 to 430 and 584 to 856) of the NRP1 polypeptide set forth in FIG. 26 (SEQ ID NO: 69). In a particular embodiment, the above noted traps comprise one or more mutation to reduce VEGF or SEMA3A binding as described above.

In a related aspect, the present invention provides nucleic acids encoding the NRP1 traps (e.g., traps listed in Table 1 and shown on FIGS. 19, 20 and 27). Such nucleic acids may be included in an expression vector for expression in cells. Accordingly, the present invention further relates to vectors comprising nucleic acids encoding soluble NRP1 polypeptide or functional fragments thereof and cells comprising such expression vectors. Nucleic acids encoding a soluble NRP1 polypeptide or functional fragment thereof (i.e., NRP-derived trap) of the present invention may include a polynucleotide portion encoding a signal sequence (e.g., encoding amino acids 1-21 of SEQ ID NO: 65, 66 or 69, or SEQ ID NO: 70) for secretion by the cells. Furthermore, nucleic acids of the present invention include nucleic acids with and without a translation termination "stop" codon at their 3' end. The translation termination stop codon may be provided, for example, by an expression vector into which the nucleic acids of the present invention may be cloned.

As used herein, a "functional fragment" or "functional variant" of NRP1 (e.g., a functional fragment of soluble NRP1 polypeptide or polynucleotide of the present invention such as an NRP1) refers to a molecule which retains substantially the same desired activity as the original molecule but which differs by any modifications, and/or amino acid/nucleotide substitutions, deletions or additions (e.g., fusion with another polypeptide). Modifications can occur anywhere including the polypeptide/polynucleotide backbone (e.g., the amino acid sequence, the amino acid side chains and the amino or carboxy termini). Such substitutions, deletions or additions may involve one or more amino acids or in the case of polynucleotide, one or more nucleotide. The substitutions are preferably conservative, i.e., an amino acid is replaced by another amino acid having similar physico-chemical properties (size, hydrophobicity, charge/polarity, etc.) as well known by those of ordinary skill in the art. Functional fragments of the soluble NRP1 include a fragment or a portion of a soluble NRP1 polypeptide (e.g., the a1 and/or a2 domain(s)) or a fragment or a portion of a homologue or allelic variant of NRP1 which retains inhibiting activity, i.e., binds to SEMA3A, VEGF and/or TGF-β and inhibits the transduction of NRP1-mediated cellular activity. Non-limiting examples of NRP1-mediated cellular activity include i) vascular hyperpermeability; ii) MPs activation and recruitment; iii) inducement of apoptosis; iv) induction of pro-inflammatory cytokines (e.g., TNF-α, IL-1β) production and/or secretion. In an embodiment, the NRP1 polypeptide is at least 80, 85, 88, 90, 95, 98 or 99% identical to the polypeptide sequence of FIG. 22 (NRP1 isoform 2, SEQ ID NO: 65) or amino acids 1-859 or 22-859 of the NRP1 isoform 1 set forth in FIG. 26 (SEQ ID Nos: 66 and 69). In an embodiment, the NRP1 functional fragment comprises subdomains a1, a2, b1, b2 and/c which are/is at least 80, 85, 88, 90, 95, 98 or 99% identical to subdomain(s) a1 (e.g., SEQ ID NO: 71 or amino acids 22-148 of SEQ ID NO: 66), a2 (e.g., SEQ ID NO: 72, or amino acids 149-275 of SEQ ID NO: 66), b1 (e.g., SEQ ID NO:73 or amino acids), b2 (e.g., SEQ ID NO: 74 or amino acids 429-589 of SEQ ID NO:66) and/or c (e.g., SEQ ID NO: 75 or amino acids 590-859 of SEQ ID NO: 66) of NRP1 as depicted in FIG. 22 or 26 (SEQ ID NOs:65 and 66 respectively). In an embodiment, the NRP1 is a functional variant which includes variations (conservative or non-conservative substitution(s) and/or deletion(s)) in amino acids which are not conserved between rat, mouse and human NRP1 (see FIG. 26 and consensus sequence set forth in SEQ ID NO: 69). Preferably, the NRP1 polypeptide/polynucleotide or fragment thereof is human.

TABLE 2

Non-limiting examples of substitutions in the soluble NRP1 polypeptide/NRP1 traps of the present invention.

| WT Amino acid (with ref. to FIG. 26, SEQ ID NO: 66) | Domain | Exemplary substitution(s) |
|---|---|---|
| N24 | a1 | Serine |
| E26 | a1 | Lysine |
| D29 | a1 | Glycine |
| S35 | a1 | Asparagine |
| D62 | a1 | Glutamic acid |
| M68 | a1 | Isoleucine |
| F90 | a1 | Isoleucine |
| N96 | a1 | Glycine |
| H98 | a1 | Arginine |
| F99 | a1 | Leucine |
| R100 | a1 | Tryptophan |
| P110 | a1 | Serine |
| T153 | a2 | Alanine |
| S155 | a2 | Threonine |
| S170 | a2 | Cysteine |
| V177 | a2 | Isoleucine |
| P196 | a2 | Glutamine |
| D219 | a2 | Glutamic acid |
| I242 | a2 | Valine |
| 269 | a2 | Isoleucine |
| 298 | b1 | Glycine |
| A303 | b1 | valine |
| N323 | b1 | Lysine |
| K359 | b1 | Arginine |
| I360 | b1 | Valine |
| V362 | b1 | Isoleucine |
| T371 | b1 | Serine |
| I372 | b1 | Leucine |
| P378 | b1 | Alanine |
| V379 | b1 | Isoleucine |
| L380 | b1 | Isoleucine |
| V392 | b1 | Phenylalanine, leucine |
| A393 | b1 | Glycine |
| P396 | b1 | Proline, serine |
| A409 | b1 | Valine |
| T410 | b1 | Serine |
| T410 | b1 | Serine |
| S449 | b2 | Alanine |
| G453 | b2 | Alanine |
| S469 | b2 | Threonine |
| A476 | b2 | Serine |
| S479 | b2 | Proline |
| I481 | b2 | Threonine |
| I487 | b2 | Valine |
| E491 | b2 | Aspartic acid |

TABLE 2-continued

Non-limiting examples of substitutions in the soluble NRP1 polypeptide/NRP1 traps of the present invention.

| WT Amino acid (with ref. to FIG. 26, SEQ ID NO: 66) | Domain | Exemplary substitution(s) |
|---|---|---|
| 498 | b2 | Valine |
| G518 | b2 | Alanine |
| M528 | b2 | Threonine |
| A553 | b2 | Alanine |
| P555 | b2 | Serine, threonine |
| A556 | b2 | Proline |
| G572 | b2 | Serine |
| A587 | c | Valine |
| L599 | c | Proline |
| D601 | c | Histidine |
| V634 | c | Isoleucine |
| N667 | c | Serine |
| 669 | c | Alanine |
| K672 | c | Arginine |
| S674 | c | Arginine |
| N717 | c | Serine |
| R741 | c | Histidine |
| A755 | c | Valine |
| I756 | c | Valine |
| S805 | c | Proline |
| A813 | c | Threonine |
| P820 | c | Threonine |
| G835 | c | deletion |
| E838 | c | Lysine |
| E854 | c | Aspartic acid |
| T410 | b1 | Serine |
| S449 | b2 | Alanine |

Antibodies

NRP1 cellular activity can be inhibited by using an agent which blocks NRP1 binding to one or more of its ligands (e.g., SEMA3A, VEGF and/or TGF-β). One example of such agent is an antibody which binds to NRP1 and blocks the binding of NRP1 to SEMA3A, VEGF and/or TGF-β.

Alternatively, inhibition of NRP1-mediated cellular signaling can be achieved by using an agent which blocks the binding of an NRP1 ligand to the NRP1 polypeptide. Non-limiting examples of such agent includes an antibody which binds to SEMA3A, VEGF or TGF-β and blocks their respective binding to NRP1.

In a particular aspect of the present invention, antibodies targeting NRP1 block SEMA3A binding to the receptor but do not substantially interfere with VEGF and/or TGF-β binding to NRP1. In an embodiment, the anti NRP1 antibody binds to the a1a2 domains of the NRP1 polypeptide. In another embodiment, the anti NRP1 antibody binds to subdomains a1 or a2 of the NRP1 polypeptide.

As noted above, anti SEMA3A antibodies may be used to inhibit (i.e., reduce completely or partially) NRP1-mediated cellular signaling by blocking SEMA3A binding to NRP1. Useful anti SEMA3A antibodies bind to the SEMA domain of SEMA3A and block the interaction with NRP1. In embodiments the anti-SEMA3A antibodies used in accordance with the present invention include antibodies binding to SEMA3A polypeptide domains comprising amino acid residues 252-260, 359-366 or 363-380 of SEMA3A. SEMA3A antibodies which inhibit the binding of SEMA3A to NRP1 are known in art and may be used in accordance with the present invention.

As used herein, the expression "anti NRP1 antibody" refers to an antibody that specifically binds to (interacts with) a NRP1 protein and displays no substantial binding to other naturally occurring proteins other than the ones sharing the same antigenic determinants as the NRP1 protein.

Similarly, the expression "anti SEMA3A antibody", "anti VEGF antibody" or "anti TGF-β antibody" refers to an antibody that specifically binds to (interacts with) a SEMA3A, VEGF or TGF-β protein respectively and displays no substantial binding to other naturally occurring proteins other than the ones sharing the same antigenic determinants as the targeted SEMA3A/VEGF/TGF-β protein.

Antibodies that can be used in accordance with the present invention include polyclonal, monoclonal, humanized as well as chimeric antibodies. The term antibody or immunoglobulin is used in the broadest sense, and covers monoclonal antibodies (including full length monoclonal antibodies), polyclonal antibodies, multispecific antibodies and antibody fragments so long as they exhibit the desired biological activity. Antibody fragments comprise a portion of a full length antibody, generally an antigen binding or variable region thereof. Examples of antibody fragments include Fab, Fab', F(ab')2, and Fv fragments, diabodies, linear antibodies, single-chain antibody molecules, single domain antibodies (e.g., from camelids), nanobodies, shark NAR single domain antibodies, and multispecific antibodies formed from antibody fragments. Antibody fragments can also refer to binding moieties comprising CDRs or antigen binding domains including, but not limited to, VH regions (VH, VH-VH), anticalins, PepBodies™, antibody-T-cell epitope fusions (Troybodies) or Peptibodies.

Anti-human NRP1/sem3A/VEGF/TGF-β antibodies have been previously prepared and are also commercially available from various sources including Santa Cruz, AbCam, and Cell Signaling.

In general, techniques for preparing antibodies (including monoclonal antibodies, hybridomas and humanized antibodies when their sequences are known) and for detecting antigens using antibodies are well known in the art and various protocols are well known and available.

Inhibition of the Expression of NRP1 or NRP1 Ligands

Various approaches are available for decreasing the expression (at the mRNA or protein level) of NRP1 or its ligands (e.g., SEMA3A, VEGF or TGF-β) to inhibit NRP1 mediated cell signaling and thus reduce inflammation and hyperactivation of innate immune response (i.e., i) production and/or secretion of pro-inflammatory cytokines; ii) recruitment of mononuclear phagocytes (MPs); iii) vascular hyperpermeabilization; and/or iv) edema, v) neuronal damage, choroidal neovascularization etc.). Non-limiting example includes the use of small hairpin shRNA (RNAi), antisense, ribozymes, TAL effectors targeting the NRP1, SEMA3A, VEGF or Tgf-β promoter or the like.

Expression in cells of shRNAs, siRNAs, antisense oligonucleotides or the like can be obtained by delivery of plasmids or through viral (e.g., lentiviral vector) or bacterial vectors.

Therefore, in alternative embodiments, the present invention provides antisense, shRNA molecules and ribozymes for exogenous administration to effect the degradation and/or inhibition of the translation of mRNA of interest. Preferably, the antisense, shRNA molecules and ribozymes target human NRP1, SEMA3A, VEGF and/or Tgf-β expression. Examples of therapeutic antisense oligonucleotide applications include: U.S. Pat. No. 5,135,917, issued Aug. 4, 1992; U.S. Pat. No. 5,098,890, issued Mar. 24, 1992; U.S. Pat. No. 5,087,617, issued Feb. 11, 1992; U.S. Pat. No. 5,166,195 issued Nov. 24, 1992; U.S. Pat. No. 5,004,810, issued Apr. 2, 1991; U.S. Pat. No. 5,194,428, issued Mar. 16, 1993; U.S. Pat. No. 4,806,463, issued Feb. 21, 1989; U.S. Pat. No. 5,286,717 issued Feb. 15, 1994; U.S. Pat. Nos. 5,276,019 and 5,264,423; BioWorld Today, Apr. 29, 1994, p. 3.

Preferably, in antisense molecules, there is a sufficient degree of complementarity to the mRNA of interest to avoid non-specific binding of the antisense molecule to non-target sequences under conditions in which specific binding is desired, such as under physiological conditions in the case of in vivo assays or therapeutic treatment or, in the case of in vitro assays, under conditions in which the assays are conducted. The target mRNA for antisense binding may include not only the information to encode a protein, but also associated ribonucleotides, which for example form the 5'-untranslated region, the 3'-untranslated region, the 5' cap region and intron/exon junction ribonucleotides. A method of screening for antisense and ribozyme nucleic acids that may be used to provide such molecules as Shc inhibitors of the invention is disclosed in U.S. Pat. No. 5,932,435.

Antisense molecules (oligonucleotides) of the invention may include those which contain intersugar backbone linkages such as phosphotriesters, methyl phosphonates, short chain alkyl or cycloalkyl intersugar linkages or short chain heteroatomic or heterocyclic intersugar linkages, phosphorothioates and those with $CH_2$—NH—O—$CH_2$, $CH_2$—N($CH_3$)—O—$CH_2$ (known as methylene(methylimino) or MMI backbone), $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$). Oligonucleotides having morpholino backbone structures may also be used (U.S. Pat. No. 5,034,506). In alternative embodiments, antisense oligonucleotides may have a peptide nucleic acid (PNA, sometimes referred to as "protein nucleic acid") backbone, in which the phosphodiester backbone of the oligonucleotide may be replaced with a polyamide backbone wherein nucleosidic bases are bound directly or indirectly to aza nitrogen atoms or methylene groups in the polyamide backbone (Nielsen et al., 1991, Science 254:1497 and U.S. Pat. No. 5,539,082). The phosphodiester bonds may be substituted with structures which are chiral and enantiomerically specific. Persons of ordinary skill in the art will be able to select other linkages for use in practice of the invention.

Oligonucleotides may also include species which include at least one modified nucleotide base. Thus, purines and pyrimidines other than those normally found in nature may be used. Similarly, modifications on the pentofuranosyl portion of the nucleotide subunits may also be effected. Examples of such modifications are 2'-O-alkyl- and 2'-halogen-substituted nucleotides. Some specific examples of modifications at the 2' position of sugar moieties which are useful in the present invention are OH, SH, $SCH_3$, F, OCN, $O(CH_2)_n NH_2$ or $O(CH_2)_n CH_3$ where n is from 1 to about 10; $C_1$ to $C_{10}$ lower alkyl, substituted lower alkyl, alkaryl or aralkyl; Cl; Br; CN; $CF_3$; $OCF_3$; O—, S—, or N-alkyl; O-, S-, or N-alkenyl; $SOCH_3$; $SO_2 CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. One or more pentofuranosyl groups may be replaced by another sugar, by a sugar mimic such as cyclobutyl or by another moiety which takes the place of the sugar.

In some embodiments, the antisense oligonucleotides in accordance with this invention may comprise from about 5 to about 100 nucleotide units. As will be appreciated, a nucleotide unit is a base-sugar combination (or a combination of analogous structures) suitably bound to an adjacent nucleotide unit through phosphodiester or other bonds forming a backbone structure.

In a further embodiment, expression of a nucleic acid encoding a polypeptide of interest (e.g., SEMA3A or NRP1), or a fragment thereof, may be inhibited or prevented using RNA interference (RNAi) technology, a type of post-transcriptional gene silencing. RNAi may be used to create a pseudo "knockout", i.e. a system in which the expression of the product encoded by a gene or coding region of interest is reduced, resulting in an overall reduction of the activity of the encoded product in a system. As such, RNAi may be performed to target a nucleic acid of interest or fragment or variant thereof, to in turn reduce its expression and the level of activity of the product which it encodes. Such a system may be used for functional studies of the product, as well as to treat disorders related to the activity of such a product. RNAi is described in for example published US patent applications 20020173478 (Gewirtz; published Nov. 21, 2002) and 20020132788 (Lewis et a1.; published Nov. 7, 2002). Reagents and kits for performing RNAi are available commercially from for example Ambion Inc. (Austin, TX, USA) and New England Biolabs Inc. (Beverly, MA, USA).

The initial agent for RNAi in some systems is a dsRNA molecule corresponding to a target nucleic acid. The dsRNA (e.g., shRNA) is then thought to be cleaved into short interfering RNAs (siRNAs) which are 21-23 nucleotides in length (19-21 bp duplexes, each with 2 nucleotide 3' overhangs). The enzyme thought to effect this first cleavage step has been referred to as "Dicer" and is categorized as a member of the RNase III family of dsRNA-specific ribonucleases. Alternatively, RNAi may be effected via directly introducing into the cell, or generating within the cell by introducing into the cell a suitable precursor (e.g. vector encoding precursor(s), etc.) of such an siRNA or siRNA-like molecule. An siRNA may then associate with other intracellular components to form an RNA-induced silencing complex (RISC). The RISC thus formed may subsequently target a transcript of interest via base-pairing interactions between its siRNA component and the target transcript by virtue of homology, resulting in the cleavage of the target transcript approximately 12 nucleotides from the 3' end of the siRNA. Thus the target mRNA is cleaved and the level of protein product it encodes is reduced.

RNAi may be effected by the introduction of suitable in vitro synthesized siRNA (shRNAs) or siRNA-like molecules into cells. RNAi may for example be performed using chemically-synthesized RNA. Alternatively, suitable expression vectors may be used to transcribe such RNA either in vitro or in vivo. In vitro transcription of sense and antisense strands (encoded by sequences present on the same vector or on separate vectors) may be effected using for example T7 RNA polymerase, in which case the vector may comprise a suitable coding sequence operably-linked to a T7 promoter. The in vitro-transcribed RNA may in embodiments be processed (e.g. using *E. coli* RNase III) in vitro to a size conducive to RNAi. The sense and antisense transcripts are combined to form an RNA duplex which is introduced into a target cell of interest. Other vectors may be used, which express small hairpin RNAs (shRNAs) which can be processed into siRNA-like molecules. Various vector-based methods and various methods for introducing such vectors into cells, either in vitro or in vivo (e.g., gene therapy) are known in the art.

Accordingly, in an embodiment expression of a nucleic acid encoding a polypeptide of interest (or a fragment thereof e.g., soluble NRP1, NRP1 derived traps, may be inhibited by introducing into or generating within a cell an siRNA or siRNA-like molecule corresponding to a nucleic acid encoding a polypeptide of interest (e.g., SEMA3A or NRP1), or a fragment thereof, or to an nucleic acid homologous thereto. "siRNA-like molecule" refers to a nucleic acid molecule similar to an siRNA (e.g., in size and structure) and capable of eliciting siRNA activity, i.e., to effect the RNAi-mediated inhibition of expression. In various embodiments such a method may entail the direct administration of the siRNA or siRNA-like molecule into a cell, or use of the vector-based methods described above. In an embodiment, the siRNA or siRNA-like molecule is less than about 30 nucleotides in length. In a further embodiment, the siRNA or siRNA-like molecule is about 21-23 nucleotides in length. In an embodiment, siRNA or siRNA-like molecule comprises a 19-21 bp duplex portion, each strand having a 2 nucleotide 3' overhang. In embodiments, the siRNA or siRNA-like molecule is substantially identical to a nucleic acid encoding a polypeptide of interest, or a fragment or variant (or a fragment of a variant) thereof. Such a variant is capable of encoding a protein having activity similar to the polypeptide of interest.

A variety of viral vectors can be used to obtain shRNA/RNAi expression in cells including adeno-associated viruses (AAVs), adenoviruses, and lentiviruses. With adeno-associated viruses and adenoviruses, the genomes remain episomal. This is advantageous as insertional mutagenesis is avoided. It is disadvantageous in that the progeny of the cell will lose the virus quickly through cell division unless the cell divides very slowly. AAVs differ from adenoviruses in that the viral genes have been removed and they have diminished packing capacity. Lentiviruses integrate into sections of transcriptionally active chromatin and are thus passed on to progeny cells. With this approach there is increased risk of insertional mutagenesis; however, the risk can be reduced by using an integrase-deficient lentivirus.

Pharmaceutical Compositions and Kits

Agents which inhibit NRP1-dependent cell signaling (i.e., NRP1 inhibitors) of the present invention can be administered to a human subject by themselves or in pharmaceutical compositions where they are mixed with suitable carriers or excipient(s) at doses to treat or prevent the targeted disease or condition or to raise the desired cellular response.

Mixtures of these compounds (e.g., NRP1 trap, antibodies, dominant negative, small inhibitory peptides or the like) can also be administered to the subject as a simple mixture or in suitable formulated pharmaceutical compositions. A therapeutically effective dose further refers to that amount of the compound or compounds sufficient to result in the prevention or treatment of the targeted inflammatory disease or condition (e.g., such as septic shock, arthritis, inflammatory bowel disease (IBD), cutaneous skin inflammation, diabetes, uveitis and neuroinflammatory conditions such as diabetic retinopathy, age-related macular degeneration (AMD), retinopathy of prematurity, multiple sclerosis, amyotrophic lateral sclerosis (ALS), age-related cognitive decline/Alzheimer's disease) or to provide the desired cellular or physiological response (e.g., amount sufficient to i) reduce edema, ii) reduce activation/recruitment of mononuclear phagocytes (e.g., microglia or macrophages), iii) reduce production or secretion of inflammatory cytokines (e.g., IL-1β, TNF-α, IL-6, etc.); iv) reduce pathological neovascularization; v) reduce vascular degeneration, etc.,).

As used herein "pharmaceutically acceptable carrier" or "excipient" includes any and all solvents, dispersion media, coatings, antibacterial and antifungal agents, physiological media, and the like that are physiologically compatible. In embodiments the carrier is suitable for ocular administration. In other embodiments the carrier is suitable for systemic administration. In other embodiments the carrier is suitable for oral administration.

Pharmaceutically acceptable carriers include sterile aqueous solutions or dispersions and sterile powders for the extemporaneous preparation of sterile injectable solutions or dispersion. The use of such media and agents, such as for ocular, systemic or oral application, is well known in the art. Except insofar as any conventional media or agent is incompatible with the compounds of the invention, use thereof in the compositions of the invention is contemplated. Supplementary active compounds can also be incorporated into the compositions.

Techniques for formulation and administration of the compounds of the instant application may be found in "Remington's Pharmaceutical Sciences," Mack Publishing Co., Easton, PA, latest edition.

The present invention also concerns kits or commercial packages for use in the methods of the present invention. Such kits may comprise compounds of the present invention (e.g., compounds which inhibit NRP1 cell signaling, including SEMA3A-mediated cell signaling such as traps, antibodies, shRNA, cells, vectors, nucleic acids) optionally with instructions to use the kit.

Routes of Administration/Formulations

Suitable routes of administration may, for example, include systemic, oral and ocular (eye drops or intraocular injections). Preferred routes of administration comprise eye drops and intraocular injections for eye conditions, oral for chronic inflammatory conditions and systemic for sepsis and certain neuronal conditions such as stroke. The formulations may also be in the form of sustained release formulations.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen. For injection, the agents of the invention may be formulated in aqueous solutions, preferably in physiologically compatible buffers such as Hanks's solution, Ringer's solution, or physiological saline buffer.

The compounds may be formulated for ocular administration e.g., eye drops or ocular injections. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Furthermore, one may administer the drug in a targeted drug delivery system, for example, in a liposome coated with a cell-specific antibody or other delivery system (e.g., to target for example a specific tissue (e.g., brain) or cell type (e.g., microglia or macrophages)). Nanosystems and emulsions are additional well-known examples of delivery vehicles or carriers for drugs. Another example is the Encapsulated Cell Therapy (ECT) delivery system from Neurotech's, for eye diseases. ECT is a genetically engineered ocular implant that enables continuous production of therapeutic proteins to the eye for over 2 years. Additionally, the therapy is reversible by simply removing the implant. The ECT implant is inserted into the vitreous through a single incision and sutured in place in a 20-minute outpatient surgical procedure.

Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated, Determination of the effective amounts is well within the capability of those skilled in the art.

The effective dose of the compound inhibits the cellular signaling function of NRP1 sufficiently to reduce or prevent one or more physiological or cellular responses (e.g., vascular hyperpermeability, blood retinal barrier leakage, edema, MPs activation and/or recruitment, proinflammatory cytokines production and/or secretion, neovascularization, neuronal damage, etc.) or to prevent or treat a given inflammatory disease or condition, without causing significant adverse effects. Certain compounds which have such activity can be identified by in vitro assays that determine the dose-dependent inhibition of NRP1-mediated cell signaling inhibitors (e.g., agents which directly target the expression or activity of NRP1 or agents which targets the expression or activity (e.g., binding) of ligands of NRP1.

For any compound used in the method of the invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of the cellular signaling function of NRP1, usually in response to inflammatory mediators such as Il-1β or other activating stimulus such as hypoxia, ischemia, cellular stress, ER stress, etc.

A therapeutically effective amount refers to that amount of the compound that results in amelioration of symptoms in a subject. Similarly, a prophylactically effective amount refers to the amount necessary to prevent or delay symptoms in a patient (e.g., NRP1-mediated vascular hyperpermeability, spotted and/or blurry vision, pericytes loss, macular edema, retinal swelling, blood retinal barrier leakage, mononuclear phagocytes recruitment, production and secretion of pro-inflammatory cytokines, vascular degeneration, pathological neovascularization, neuronal damage, etc.). Toxicity and therapeutic efficacy of such compounds can be determined by standard pharmaceutical procedures in cell cultures or experimental animals, e.g., determining the maximum tolerated dose (MTD) and the ED (effective dose for 50% maximal response). The dose ratio between toxic and therapeutic effects is the therapeutic index and it can be expressed as the ratio between MID and ED50, Compounds which exhibit high therapeutic indices are preferred. The exact formulation, route of administration and dosage can be chosen by the individual physician in view of the patient's condition.

Dosage amount and interval may be adjusted individually to provide levels of the active compound which are sufficient to maintain the NRP1 modulating effects, or minimal effective concentration (MEG). The MEG will vary for each compound but can be estimated from in vitro data; e. g, the concentration necessary to achieve substantial inhibition of SEMA3A expression or activity (e.g., binding to NRP1 receptor) Dosages necessary to achieve the MEG will depend on individual characteristics and route of administration.

The amount of composition administered will, of course, be dependent on the subject being treated, on the subject's weight, the severity of the affliction, the manner of administration and the judgment of the prescribing physician.

Definitions

For clarity, definitions of the following terms in the context of the present invention are provided.

As used herein, the term "Neuropilin-1 receptor" or "NRP1" receptor refers to neuropilin-1 and its isoforms, and allelic/polymorphic forms (e.g., HGNC: 8004; Entrez Gene: 8829; Ensembl: ENSG00000099250; OMIM: 602069; and UniProtKB: 014786; GenBank Acc. No. AAH07737.1, FIG. 22, SEQ ID NO: 65). NRP1 is a non-tyrosine kinase multifunctional receptor having the particular ability to bind three structurally dissimilar ligands via distinct sites on its extracellular domain. It binds SEMA3A[18,19] (for example provoking cytoskeletal collapse) and $VEGF_{165}$, enhancing binding to VEGFR2 (for example increasing its angiogenic potential). It also binds to TGF-β. Moreover, genetic studies show that NRP1 distinctly regulates the effects of VEGF and SEMA3A on neuronal and vascular development. Hence, depending on the ligand, NRP1-mediated cellular response varies.

The basic structure of neuropilin-1 comprises 5 domains: Three extracellular domains (a1a2 (CUB), b1b2 (FV/FVIII) and c (MAM)), a transmembrane domain and a cytoplasmic domain (See FIGS. 19A and 22 and SEQ ID NO: 65 and 66 and 68). The a1a2 domain is homologous to complement components C1r and C1s (CUB) which generally contain 4 cysteine residues forming disulfide bridges. This domain binds SEMA3A. Domains b1b2 (FV/FVIII) binds to VEGF. Amino acid Y297 in subdomain b1 is important for binding to VEGF as substitution of Y297 to an alanine significantly reduces VEGF binding to NRP1. There exists several splice variants isoforms and soluble forms of NRP1 which are all encompassed by the present invention.

"Homology" and "homologous" refers to sequence similarity between two peptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a nucleic acid/polynucleotide sequence is "homologous" to another sequence if the two sequences are substantially identical and the functional activity of the sequences is conserved (as used herein, the term 'homologous' does not infer evolutionary relatedness). Two nucleic acid sequences are considered substantially identical if, when optimally aligned (with gaps permitted), they share at least about 50% sequence similarity or identity, or if the sequences share defined functional motifs. In alternative embodiments, sequence similarity in optimally aligned substantially identical sequences may be at least 60%, 70%, 75%, 80%, 85%, 90%, 95%, 98% or 99% identical. As used herein, a given percentage of homology between sequences denotes the degree of sequence identity in optimally aligned sequences. An "unrelated" or "non-homologous" sequence shares less than 40% identity, though preferably less than about 25% identity, with any of the nucleic acids and polypeptides disclosed herein.

Substantially complementary nucleic acids are nucleic acids in which the complement of one molecule is substantially identical to the other molecule. Two nucleic acid or protein sequences are considered substantially identical if, when optimally aligned, they share at least about 70% sequence identity. In alternative embodiments, sequence identity may for example be at least 75%, at least 80%, at least 85%, at least 90%, at least 95%, at least 98%, or at least 99%. Optimal alignment of sequences for comparisons of identity may be conducted using a variety of algorithms, such as the local homology algorithm of Smith and Waterman, 1981, Adv. Appl. Math 2: 482, the homology alignment algorithm of Needleman and Wunsch, 1970, J. Mol. Biol. 48:443, the search for similarity method of Pearson and Lipman, 1988, Proc. Natl. Acad. Sci. USA 85: 2444, and the computerised implementations of these algorithms (such as GAP, BESTFIT, FASTA and TFASTA in the Wisconsin Genetics Software Package, Genetics Computer Group, Madison, WI, U.S.A.). Sequence identity may also be determined using the BLAST algorithm, described in Altschul et al., 1990, J. Mol. Biol. 215:403-10 (using the published default settings). Software for performing BLAST analysis may be available through the National Center for Biotechnology Information. The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, Proc. Natl. Acad. Sci. USA 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridisation to filter-bound sequences under moderately stringent conditions may, for example, be performed in 0.5 M NaHPO4, 7% sodium dodecyl sulfate (SDS), 1 mM EDTA at 65° C., and washing in 0.2×SSC/0.1% SDS at 42° C. (see Ausubel, et a1. (eds), 1989, Current Protocols in Molecular Biology, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO4, 7% SDS, 1 mM EDTA at 65° C., and washing in 0.1×SSC/0.1% SDS at 68° C. (see Ausubel, et a1. (eds), 1989, supra). Hybridization conditions may be modified in accordance with known methods depending on the sequence of interest (see Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York). Generally, stringent conditions are selected to be about 5° C. lower than the thermal melting point for the specific sequence at a defined ionic strength and pH. For example, in an embodiment, the compound of the present invention is an antisense/RNAi or shRNA that hybridizes to an NRP1 or SEMA3A nucleic acid sequence (preferably a human sequence).

As used herein the term "treating" or "treatment" in reference to inflammatory diseases or conditions (e.g., retinopathies, cerebral ischemia, stroke, sepsis, ect.) is meant to refer to a reduction/improvement in one or more symptoms or pathological physiological responses associated with said disease or condition. Non-limiting examples include edema, swelling, itching, pain, vascular hyperpermeability; blood retinal barrier integrity, increase in SEMA3A, VEGF and/or TGF-beta expression, mononuclear phagocyte recruitment/chemotaxis, production and/or secretion of proinflammatory cytokines, vascular or neuronal degeneration, etc.

As used herein the term "preventing" or "prevention" in reference to inflammatory diseases or conditions is meant to refer to a reduction in the progression or a delayed onset of at least one symptom associated with the disease or condition.

The articles "a," "an" and "the" are used herein to refer to one or to more than one (i.e., to at least one) of the grammatical object of the article.

The term "including" and "comprising" are used herein to mean, and re used interchangeably with, the phrases "including but not limited to" and "comprising but not limited to".

The terms "such as" are used herein to mean, and is used interchangeably with, the phrase "such as but not limited to".

The present invention is illustrated in further details by the following non-limiting examples.

Example 1

Materials and Methods (Examples 2-9 and 12)

Generation of LyzM-cre/Nrpfl/fl mice. C57Bl/6 wild-type (WT) were purchased from The Jackson Laboratory. LyzM-Cre (Lyz2tm1(cre)Ifo/J; no. 004781) and NRP1 floxed mice (Nrp1tm2Ddg/J; no. 005247) were purchased from The Jackson Laboratory and bread to obtain LyzM-cre/Nrpfl/fl with NRP1-deficient myeloid cells.

$O_2$-induced retinopathy. Mouse pups (WT or LyzM-Cre (Jackson Laboratory) or LysM-Cre/Nrp1$^{fl/fl}$) and their fostering mothers (CD1, Charles River) were exposed to 75% $O_2$ from postnatal day 7 (P7) to day 12 and returned to room air (52). This model serves as a proxy to human ocular neovascular diseases such as diabetic retinopathy characterized by a late phase of destructive pathological angiogenesis (53, 54). Upon return to room air, hypoxia-driven neovascularization (NV) develops from P14 onwards (26). Eyes were enucleated at different time points and the retinas dissected for FACS analysis or mRNA analysis as described. In other experiments, dissected retinas were flatmounted and incubated overnight with fluoresceinated isolectin B4 (1:100) in 1 mM $CaCl_2$) to determine extent of avascular area or neovascularization area at P17 using ImageJ and the SWIFT-NV method (55).

FACS of digested retinas and spleen. Retinas from WT or LysM-Cre/Nrp1$^{fl/fl}$ mice were homogenized and incubated in a solution of 750 U/mL DNaseI (Sigma) and 0.5 mg/mL of collagenase D (Roche) for 15 min at 37° C. with gentle shaking. Homogenates were then filtered with a 70 μm cell strainer and washed in PBS+3% fetal bovine serum. Spleen samples were homogenized and incubated with 1 mg/mL of collagenase D for 10 min at 37° C. Homogenates were washed in PBS+3% fetal bovine serum and the pellets were resuspended and incubated in lysis buffer (10 mM $KCHO_3$; 150 mM $NH_4Cl$; 0.1 mM EDTA) for 5 min at room temperature. Cell suspensions (retina or spleen) were incubated with LEAF™ purified anti-mouse CD16/32 (Biolegend) for 15 min at room temperature to block Fc receptors. Cells were then incubated for 30 min at room temperature with the following antibodies: FITC anti-mouse/human CD11b (Biolegend), PE/CY7 anti-mouse Ly-6G/Ly-6C (Gr-1; Biolegend), Pacific Blue™ anti-mouse F4/80 (Biolegend), 7AAD (BD Biosciences) and anti-mNeuropilin-1 Allophycocyanin conjugated Rat IgG2A (R&D Systems) or Rat IgG2A Isotype Control Allophycocyanin conjugated (R&D Systems).

For analysis of CX3CR1 and CD45 expression, additional extracellular staining was performed using the above mentioned antibodies supplemented with Alexa Fluor 700 anti-mouse CD45.2 (Biolegend) and anti-mouse CX3CR1 Phycoerythrin conjugated Goat IgG (R&D Systems) or Goat IgG Isotype. Control Phycoerythrin conjugated FACS was performed on a LSRII (BD Biosciences) device and data were analysed using FlowJo™ software (version 7.6.5).

BrdU injections. Wild-type mice subjected to OIR or kept in normoxic conditions were injected intraperitoneally with 5-bromo-2-deoxyuridine (BrdU; Sigma) at the dose of 1 mg/mouse dissolved in PBS at P13.

Analysis of BrdU incorporation. The staining was performed on the retinal cells from P14 WT mice. Samples were obtained as described above. Extracellular staining was performed as described above (CD45.2 (intermediate/low); Gr−1−; CD11b+,F4/80+; 7AAD). Cells were then fixed with Cytofix/Cytoperm™ Buffer (BD Biosciences) for 30 min and permeabilised with Perm/Wash™ Buffer (BD Biosciences) for 10 min. Next, cells were treated with 300 ug/mL of DNAse for 1 h at 37° C. and washed with Perm/Wash™. Intracellular staining of BrdU was performed using anti-BrdU-PE antibodies (Ebioscience) or mouse IgG1$_K$ Isotype Control PE conjugated (Ebioscience) for 25 min at 4° C. Cells were then washed in Perm/Wash™ and resuspended in PBS+3% fetal bovine serum before FACS analysis on a LSRII (BD Biosciences).

Vitrectomy. All patients previously diagnosed with PDR were followed and operated by a single vitreoretinal surgeon (FAR). Control patients were undergoing surgical treatment for non-vascular pathology (ERM (epiretinal membrane) or MH (macular hole)) by the same surgeon. In an operating room setting, patients underwent surgery under local retro/peribulbar anesthesia. A 5% povidone-iodine solution was used to clean the periocular skin and topical instillation into the eye and within the cul-de-sac was left in place for 5 minutes. Three-port 25-gauge transconjunctival pars plana vitrectomy was performed through 25-gauge valved cannulas (Alcon). Under microscope visualization using a wide-angle viewing system (Resight™, Zeiss), undiluted vitreous was collected with a 25-gauge vitrector. After vitreous biopsy, the infusion line was opened and vitrectomy and membrane peeling was performed in the usual fashion to treat diabetic vitreous hemorrhage and tractional retinal detachment. This was followed by panretinal endolaser photocoagulation, fluid-air exchange, and intravitreal anti-VEGF injection.

Quantification of SEMA3A protein by ELISA. Vitreous samples were frozen on dry ice and immediately after biopsy and stored at −80°. Samples were centrifuged at 15000×g for 5 minutes at 4° C. prior to analysis. SEMA3A levels were quantified in supernatants using enzyme-linked immunosorbent assays (ELISAs) following manufacturer's instructions (USCN Life Science Inc.).

Assessment of SEMA3A protein levels by Western-blot. Equal volumes of vitreous fluid (20 uL) from PDR and control patients were assessed by standard SDS-PAGE technique for the presence of SEMA3A (Abcam).

Real-time PCR analysis. RNA was isolated using the GenElute™ Mammalian Total RNA Miniprep Kit (Sigma) and digested with DNase I to prevent amplification of genomic DNA. Reversed transcription was performed using M-MLV reverse transcriptase (Life Technologies) and gene expression analyzed using Sybr™ Green (BioRad) in an ABI Biosystems Real-Time PCR machine. β-actin was used as a reference gene (see Table 2 in Example 10 for details on the sequence of the oligonucleotides used.

Immunohistochemistry. For visualization of pan-retinal vasculature, flatmount retinas were stained with stained with Rhodamine labeled Griffonia (Bandeiraea) *Simplicifolia* Lectin I (Vector Laboratories, Inc.) in 1 mM $CaCl_2$ in PBS for retinal vasculature and anti-rat Neuropilin-1 antibody, (goat IgG; R&D Systems) and IBA1 (rabbit polyclonal; Wako).

Primary peritoneal macrophages culture. Adult WT or LyzMcre/NRP1fl/fl mice were anesthetized with 2% isoflurane in oxygen 2 L/min and then euthanized by cervical dislocation. Then, a small incision in abdominal skin of mouse was performed. Skin was pulled to each size of the mouse and peritoneal cavity was washed with 5 ml of PBS plus 3% FBS for 2 min. Then, the harvested cells were centrifuged for 5 min at 1000 rpm, resuspended in medium (DMEM F12 plus 10% FBS and 1% Streptomycin/Penicillin) and plated. After 1 h of culture at 37° C. under a 5% $CO_2$ atmosphere the medium was changed and cells were cultured for the next 24 h in the same conditions before use in cytokine or transwell migration assay.

Transwell migration assay. Migration assays were performed in 24-well plates with 8 μm pore inserts. Primary peritoneal macrophages (5×105 cells) resuspended in 200 μl of medium (DMEM F12 plus 10% FBS and 1% Streptomycin/Penicillin) were added to the upper chamber. 800 μl of medium with or without migratory factors: MCP-1 (100 ng/ml), SEMA3A (100 ng/ml), and $VEGF_{165}$ (50 ng/ml) was added to the lower chamber. Cells were allowed to migrate through the insert membrane overnight at 37° C. under a 5% $CO_2$ atmosphere. In some experiments, cells were first pretreated with Y-27632 (Sigma), selective ROCK (Rho-associated coiled coil forming protein serine/threonine kinase) inhibitor (100 μg/ml) for 1 h at 37° C. The inserts were then washed with PBS, and nonmigrating cells were swabbed from the upper surface of the insert membrane with cotton buds. Then the membranes with migrated cells were fixed with 4% paraformaldehyde (PFA) for 20 minutes, washed twice with PBS and mounted on the slide. The cells were stained using mounting medium with DAPI (Vector Laboratories, Inc.). Then, 9 random fields per each membrane were photographed using an inverted fluorescence microscope at 20× magnification and the cells were counted using ImageJ software.

Choroidal explants and microvascular sprouting assay. The ex vivo choroid explants and quantification of microvascular sprouting as described previously (56). Briefly, choroids from LysM-Cre/$Nrp1^{+/+}$ and LysM-Cre/$Nrp1^{fl/fl}$ mice (n=6 for each condition) were dissected shortly after enucleating eyes. After plating segmented choroids into 24 well tissue culture plates and covering with Matrigel™ (BD Biosciences), samples were treated with either EGM™-2 medium, EGM-2 medium with PBS filled liposome (liposome-PBS), or EGM™-2 medium with Dichloromethylene-diphosphonic acid disodium salt filled liposome (liposome-Clodronate) (Sigma). The packaging of liposomes was performed according to (57). Twelve hours later, liposomes containing passenger compounds were removed from the wells followed by washing with PBS. Macrophages from primary peritoneal macrophage cultures (from either LysM-Cre/$Nrp1^{+/+}$ or LysM-Cre/$Nrp1^{fl/fl}$ mice) were added to choroidal explant cultures to investigate the impact of macrophages on microvascular sprouting.

Soluble recombinant NRP1. Wild-type mice subjected to OIR were intravitreally injected with rmNRP1 trap-1 (FIGS. 19C and 20X-20Y, SEQ ID NO: 25) from plasmid (29) or R&D Systems at P12.

Recombinant proteins used. Recombinant mouse CCL2/JE/MCP-1 (from *E. coli*) (R&D Systems) concentration used in vitro 100 ng/ml. Recombinant human SEMA3A Fc chimera (from murine myeloma cell line, NS0) (R&D Systems) concentration used in vitro 100 ng/ml. -Recombinant human $VEGF_{165}$ (PeproTech) concentration used in vitro 50 ng/ml.

Statistical analyses. Data are presented as mean±s.e.m. Student's T-test and ANOVA were used, where appropriate, to compare the different groups; a $P<0.05$ was considered statistically different. For ELISA, statistical analysis was performed using nonparametric Mann-Whitney test (GraphPad Prism).

Study approval: Human samples. We obtained approval of human clinical protocol and informed consent form by Maisonneuve-Rosemont Hospital (HMR) ethics committee (Ref. CER: 10059) and recruitment of patients for local core vitreal biopsy sampling from patients afflicted with T1DM or T2DM. The entire procedure was performed as an outpatient procedure in the minor procedure room within the ambulatory clinic from the Department of Ophthalmology at Maisonneuve-Rosemont Hospital. All instruments were opened and handled in a sterile manner. The study conforms to the tenets of the declaration Helsinki.

Study approval: Animals. All studies were performed according to the Association for Research in Vision and Ophthalmology (ARVO) Statement for the Use of Animals in Ophthalmic and Vision Research and were approved by the Animal Care Committee of the University of Montreal in agreement with the guidelines established by the Canadian Council on Animal Care. C57Bl/6 wild-type (WT) were purchased from The Jackson Laboratory. LyzM-Cre (Lyz2tm1(cre)Ifo/J; no. 004781) and Neuropilin 1 floxed mice (Nrp1tm2Ddg/J; no. 005247) were purchased from The Jackson Laboratory.

TABLE 3

| Characteristics of Vitrectomy Patients | | | | | |
|---|---|---|---|---|---|
| Sample | Age | Db type | Duration (years) | Retinopathy | Analysis |
| C1 | 74 | na | na | MH | WB/ELISA |
| C2 | 54 | na | na | MMD | WB/ELISA |
| C3 | 72 | na | na | ERM | WB/ELISA |
| C4 | 77 | na | na | ERM | WB/ELISA |
| C5 | 82 | na | na | MH | WB/ELISA |
| C6 | 62 | na | na | ERM | ELISA |
| C7 | 65 | na | na | MH | ELISA |
| C8 | 69 | na | na | ERM | ELISA |
| C9 | 75 | na | na | MH/Cataract | ELISA |
| C10 | 77 | na | na | Ret. Det. | ELISA |
| C11 | 69 | na | na | ERM | ELISA |
| C12 | 68 | na | na | ERM | ELISA |
| C13 | 81 | na | na | ERM | ELISA |
| C14 | 70 | na | na | ERM | ELISA |
| C15 | 65 | na | na | MH | ELISA |
| C16 | 74 | na | na | MH | ELISA |
| C17 | 75 | na | na | MH | ELISA |
| PDR1 | 62 | 2 | 13 | PDR | WB/ELISA |
| PDR2 | 79 | 2 | 33 | PDR | WB/ELISA |
| PDR3 | 73 | 2 | 15 | PDR | WB/ELISA |
| PDR4 | 74 | 2 | 10 | PDR | WB/ELISA |
| PDR5 | 54 | 1 | 20 | PDR | WB/ELISA |
| PDR6 | 60 | 2 | 34 | PDR | WB/ELISA |
| PDR7 | 77 | 2 | 34 | PDR | WB/ELISA |
| PDR8 | 71 | 2 | 10 | PDR | ELISA |
| PDR9 | 35 | — | — | PDR | ELISA |
| PDR10 | 69 | 2 | 40 | PDR | ELISA |
| PDR11 | 78 | — | 5 | PDR | ELISA |
| PDR12 | 36 | 2 | — | PDR | ELISA |
| PDR13 | 81 | 1 | 30 | PDR | ELISA |
| PDR14 | 70 | 2 | 30 | PDR | ELISA |
| PDR15 | 74 | — | 35 | PDR | ELISA |
| PDR16 | 67 | 2 | 30 | PDR | ELISA |
| PDR17 | 69 | 2 | 2 | PDR | ELISA |

MH: Macular hole
MMD: Myopic Macular Degeneration
ERM: Epiretinal Membrane
PDR: Proliferative Diabetic Retinopathy
Ret. Det.: Retinal Detachement

Example 2

Figure 1A:
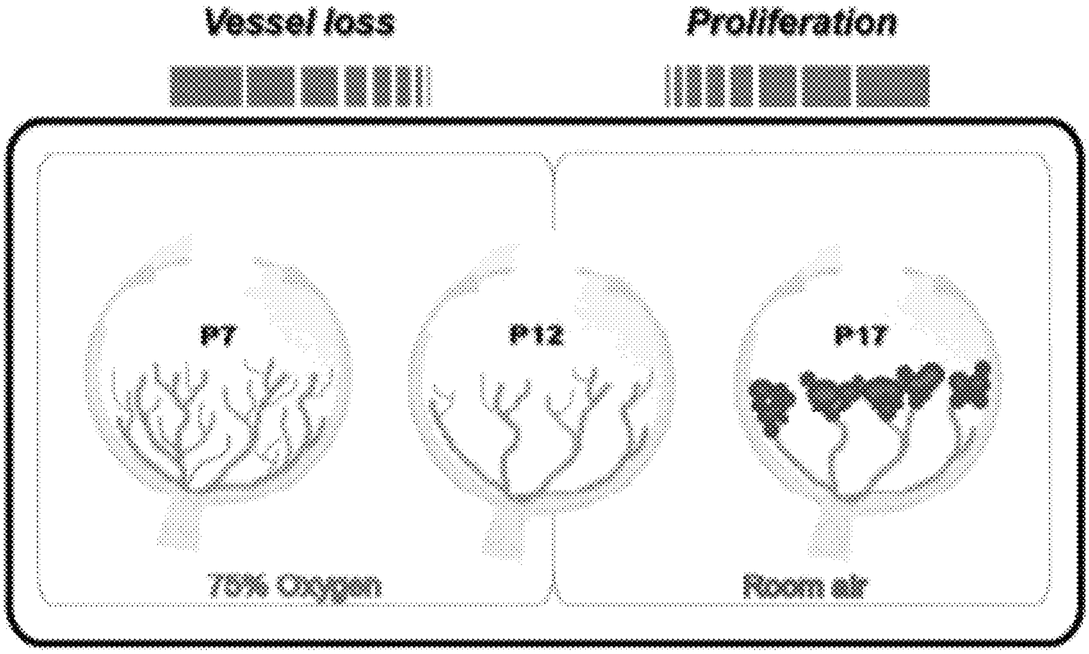
Figures 1B, 1C, 1D:
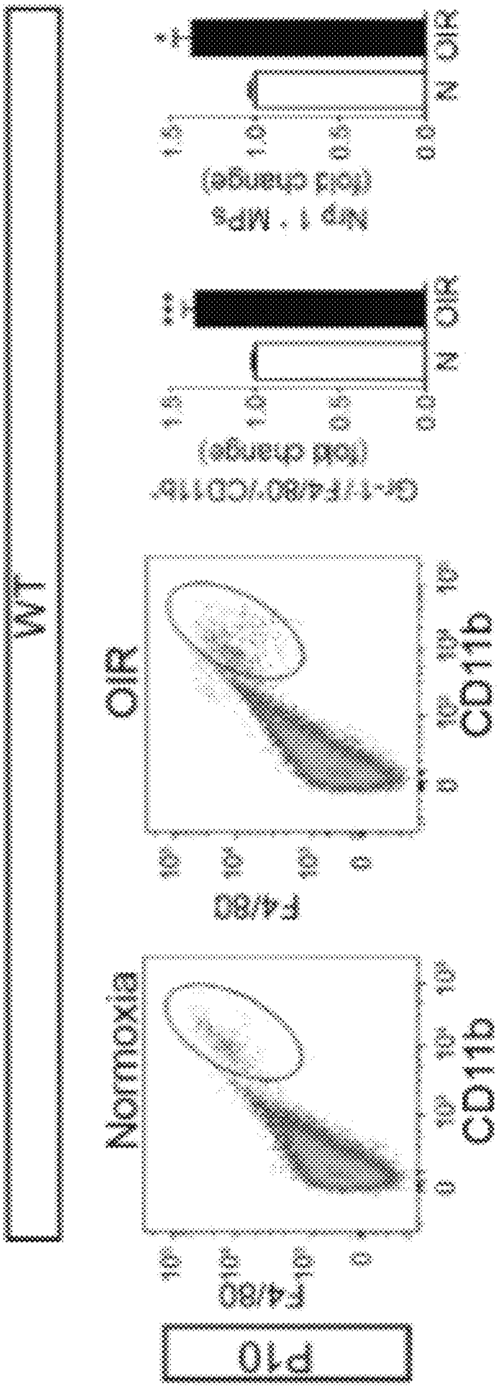
(FIGS. 1B, 1E and 1H) show representative FACS plots of CD11b+/F4−80+/Gr−$1^{-}$ cells (microglia) in retinas collected at P10 (FIG. 1B), P14 (FIG. 1E) and P17 (FIG. 1H) from WT OIR and Normoxic control mice.
(FIGS. 1C, 1F and 1I) show the fold change in the number of retinal microglia in Normoxia (N) and OIR at P10 (FIG. 1C), P14 (FIG. 1F) and P17 (FIG. 1I). The number of retinal microglia was significantly increased in OIR at all points analyzed (FIGS. 1C, 1F and 1I); n=7-8 (Normoxia, (N)), n=7-8 (OIR) (total of 28-32 retinas per condition; each "n" comprises 4 retinas).
(FIGS. 1D, 1G and 1J) show the fold change in the number of NRP1 positive MPs at P10 (FIG. 1D), P14 (FIG. 1G) and P17 (FIG. 1J). A proportional increase in the number of NRP1-positive microglia was observed in OIR retinas (FIGS. 1D, 1G and 1J); n=3-5 (Normoxia, (N)), n=3-5 (01R) (total of 12-20 retinas per condition; each "n" is comprised of 4 retinas).
Figures 1E, 1F, 1G:
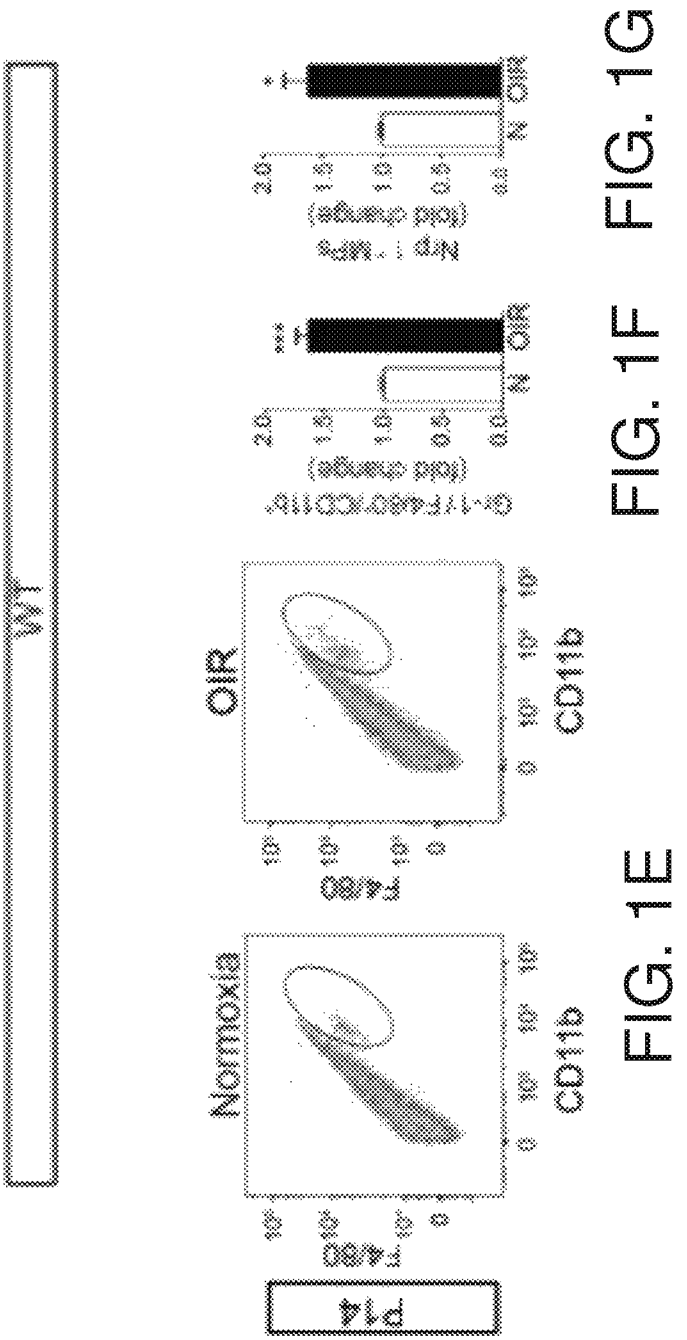
Figures 1H, 1I, 1J:
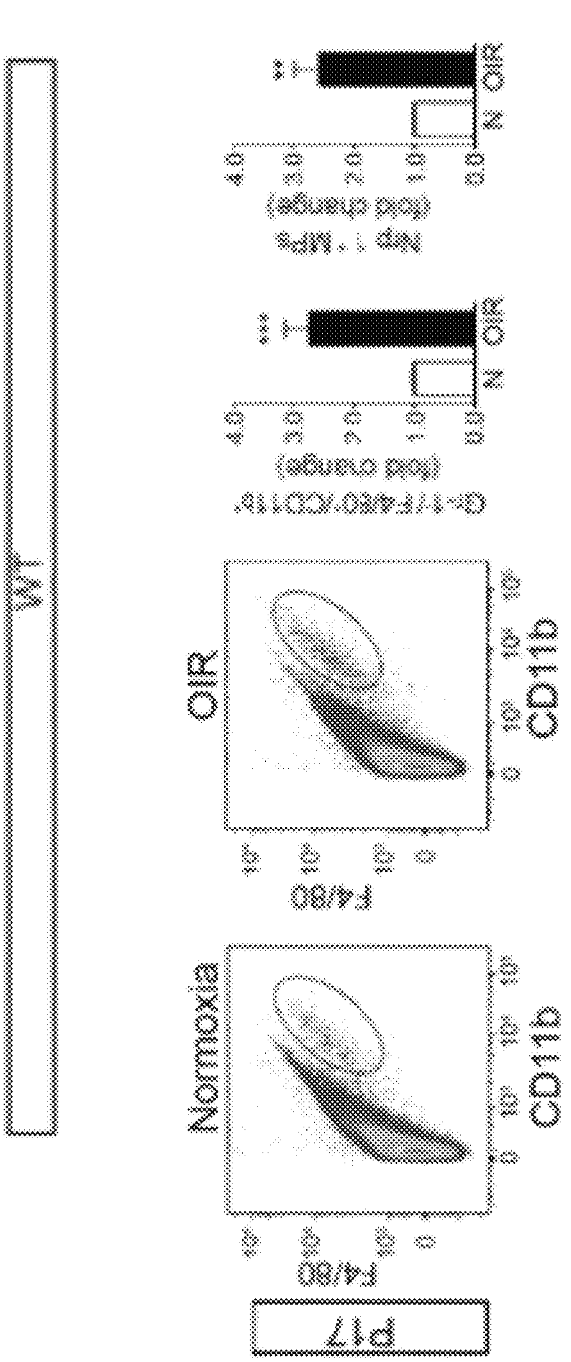

Nrp1 Identifies a Population of Mononuclear Phagocytes (MPs) that are Mobilized Secondary to Vascular Injury To determine whether MPs (mononuclear phagocytes) such as microglia or macrophages partake in the vascular pathogenesis associated with proliferative retinopathies, FACS analysis was first carried-out on whole mouse retinas to elucidate the kinetics of macrophage/microglial accumulation throughout the evolution of oxygen-induced retinopathy (OIR, FIG. 1A, 75% oxygen from P7-P12 (postnatal day 7-12) to induce vasoobliteration and room air until P17 to attain maximal pre-retinal neovascularization (26,33)) (FIG. 1B,E,H). Results revealed significantly higher numbers of retinal macrophage/microglial cells (Gr−1−, F4/80+, CD11b+, cells, data not shown) in OIR at all time points analysed including a 36% increase during the vaso-obliterative phase at P10 (P=0.0004) (FIG. 1C), a 63% rise during the neovascular phase at P14 (P<0.0001) (FIG. 1F) and a 172% surge during maximal neovascularization at P17 (P=0.0006) (FIG. 1I).

Importantly, at each time point investigated, we observed a proportional increase in NRP1-positive MPs in OIR with a rise of 37% at P10 (P=0.0240) (FIG. 1D), 61% at P14 (P=0.0196) (FIG. 1G) and 155% at P17 (P=0.0058) (FIG. 1J) suggesting that this subpopulation of NRP1-positive MPs was being recruited to the neuroretina during the progression of the disease. For all OIR experiments, weights of mouse pups were recorded (data not shown) to ascertain adequate metabolic health (35).

Figure 1K:
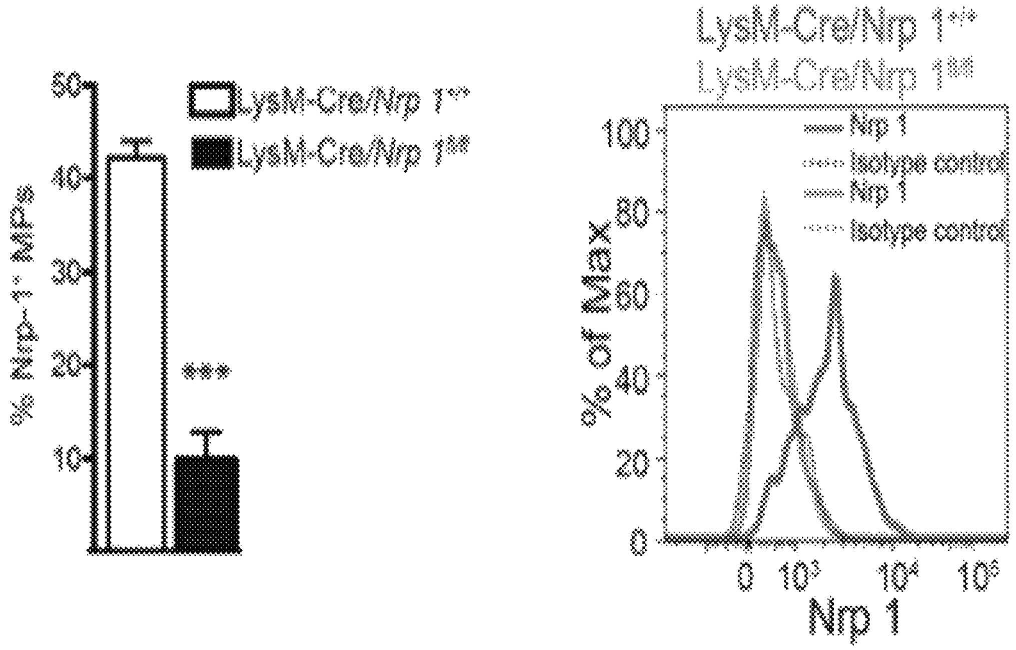
(FIG. 1K). To investigate the role of MP-resident NRP1, LysM-Cre/$Nrp1^{fl/fl}$ mice which have significantly compromised NRP1 expression in retinal microglia were generated (n=3 (WT), n=4 (LysM-Cre/$Nrp1^{fl/fl}$, total of 12-16 retinas per condition). Left panel shows the % of NPR-1 positive MPs in WT (LysM-Cre/$NRP1^{+/+}$) and mice deficient in NRP1 in their myeloid cells (LysM-Cre/$Nrp1^{fl/fl}$) as determined by FACS (right panel).
Figures 1L, 1M:
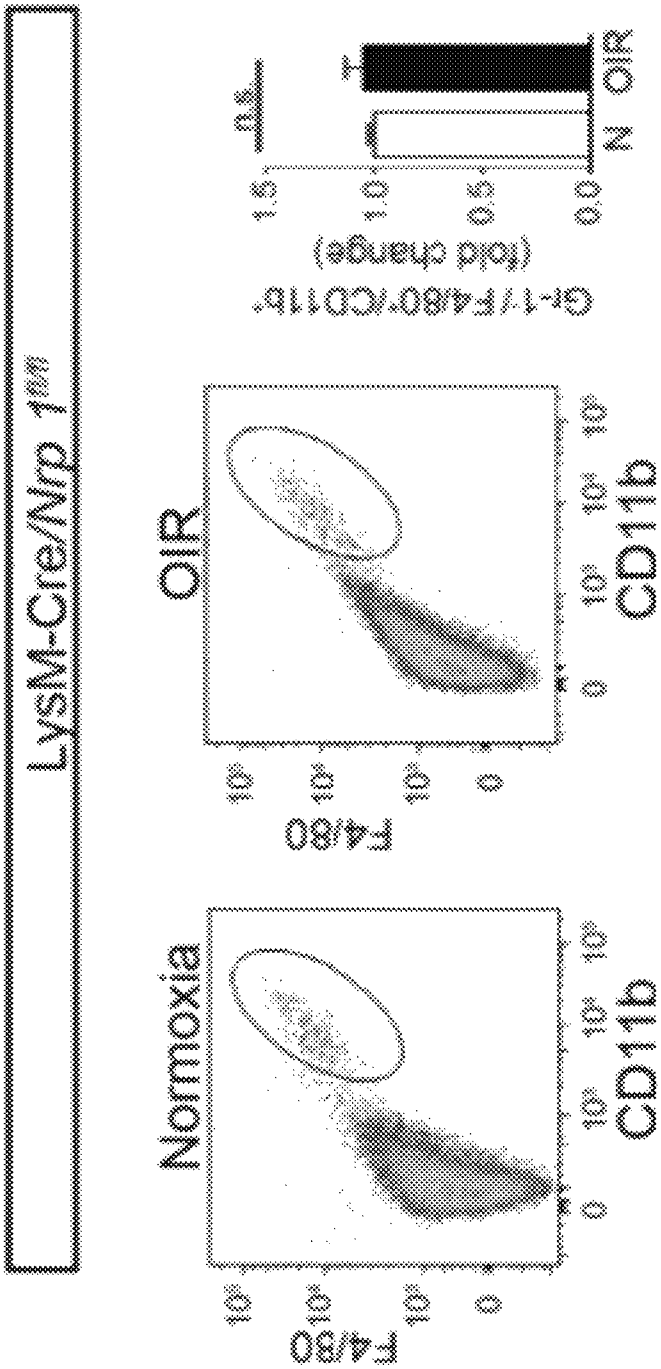
(FIGS. 1L, 1N and 1P), FACS analysis at P10 (FIG. 1L), P14 (FIG. 1N) and P17 (FIG. 1P) to quantify the number of MPs in LysM-Cre/$Nrp1^{fl/fl}$ mice retinas in Normoxia and OIR.
(FIGS. 1M, 10 and 1Q) show the fold change in the number of MPs in LysM-Cre/$Nrp1^{fl/fl}$ mice retinas in normoxia and OIR. FACS analysis at P10 and P14 during the proliferative phase of OIR (FIG. 1L, FIG. 1N) reveals that MP-resident NRP1 is essential for MP infiltration into the ischemic retina as LysM-Cre/$Nrp1^{fl/fl}$ mice did not show an increase in numbers of CD11b+/F4−80+/Gr−$1^{-}$ cells in OIR at these time points (FIG. 1M, FIG. 1O). At P17, MPs infiltrate independent of NRP1 (P, Q). n=7-8 (N), n=7-9 (OIR) (total of 28-36 retinas per condition; each "n" comprises 4 retinas).
Figure 1O:
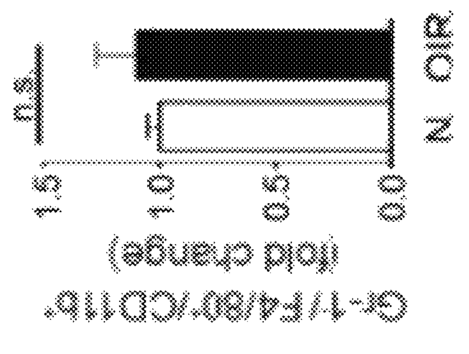
Figure 1N:
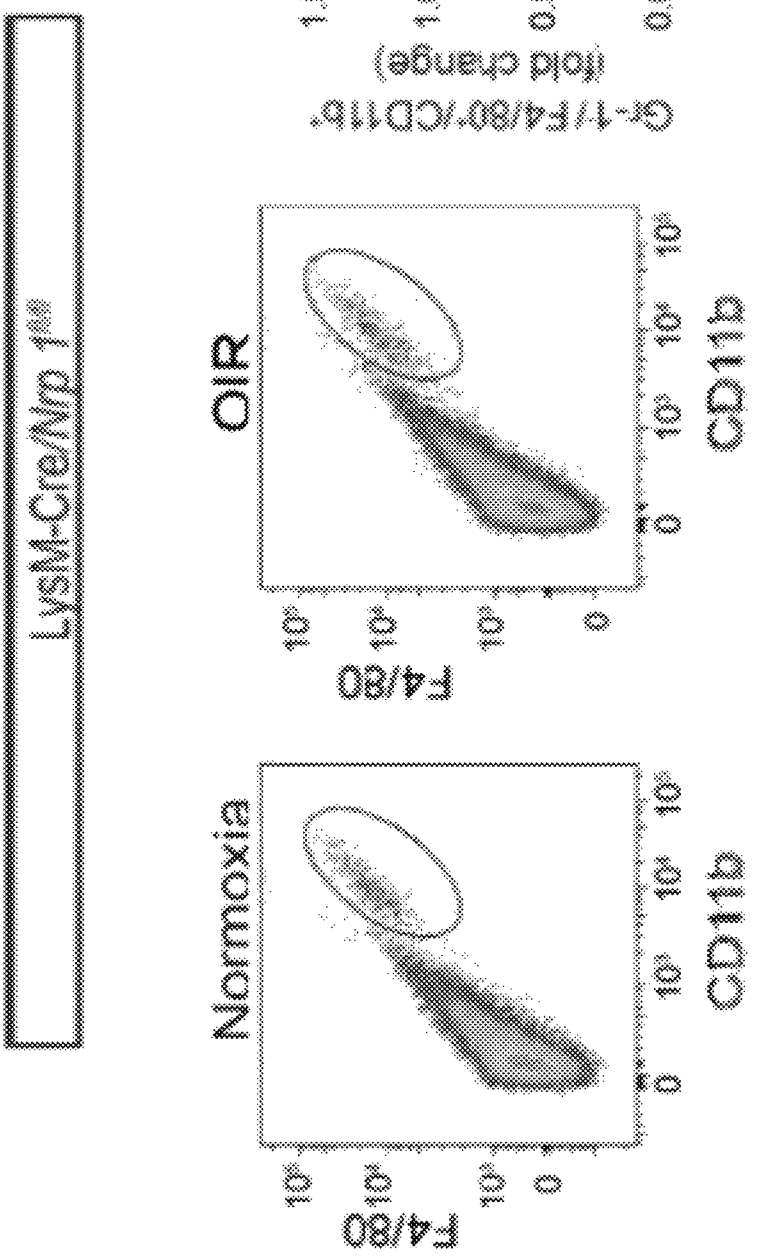
Figure 1P:
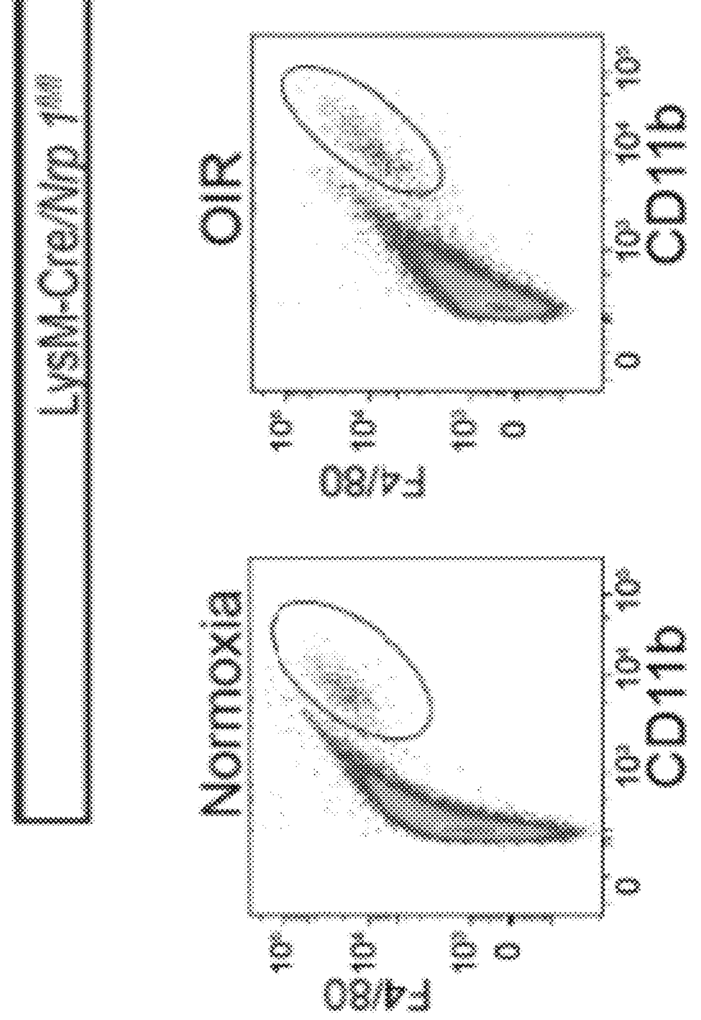
Figure 1Q:
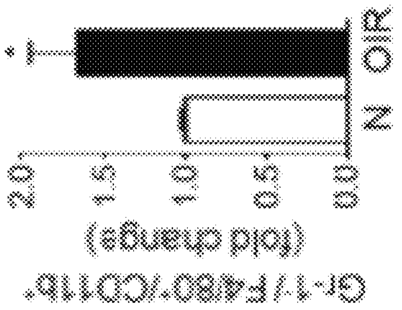

In order to establish the role of MP-resident NRP1 in retinopathy, a myeloid specific knockout of NRP1 was generated by intercrossing Nrp1 floxed mice with LysM-Cre mice(36) yielding LysM-Cre/Nrp1$^{fl/fl}$ progeny. The resulting mice showed an ~80% decrease in NRP1 expression in retinal MPs when compared to LysM-Cre/Nrp1$^{+/+}$ littermate controls (P=0.0004) (FIG. 1K). Of note, mice tested negative for the rd8 mutation of the Crb1 gene (37). LysM-Cre/Nrp1$^{fl/fl}$ mice did not show any difference in body weight, size, or open-field activity when compared with littermates throughout the period of experimentation (from P1-P17) (data not shown) and had similar numbers of resident retinal microglia (data not shown). Remarkably, deletion of NRP1 on myeloid cells fully abrogated the entry of macrophages/microglia at P10 and P14 OIR (FIG. 1L-O) revealing the critical role for this receptor in MP chemotaxis during the early stages of ischemic retinal injury. At P17, following maximal pathological neovascularization, MP infiltration occurs largely independent of NRP1 (FIG. 1P, Q and R). Consistent with a potential microglial identity, the NRP1-expressing Gr1−/CD11b+/F4/80+ cells identified above express high levels of CX3CR1 and intermediate/low levels of CD45 (FIG. 1S and data not shown). As expected, in LysM-Cre/Nrp1$^{fl/fl}$ retinas, CD45low/CX3CR1 high MPs are devoid of NRP1 (FIG. 1T).

Example 3

Figures 2A, 2B, 2C, 2D, 2E, 2F:
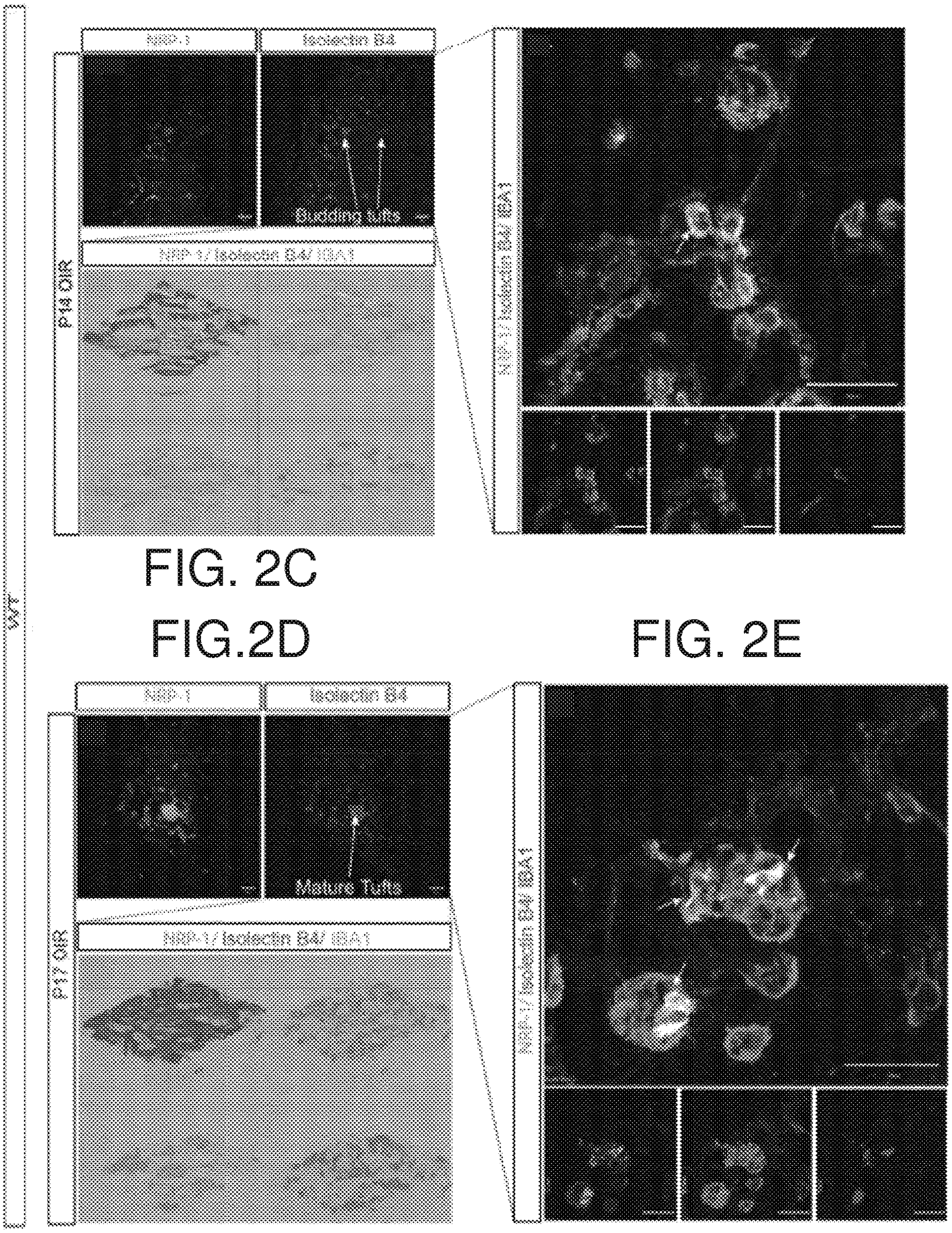

Nrp1$^{+}$ Myeloid Cells Localize to Sites of Pathological Neovascularization in the Retina Given the pronounced influx of NRP1$^{+}$ macrophage/microglia during OIR, the localization of these cells during the progression of disease was next determined. Immunofluorescence on retinal flatmounts revealed that NRP1-positive macrophage/microglia (co-labelled with IBA1 and NRP1) were intimately associated with nascent pathological tufts at P14 of OIR (FIG. 2A-C) as well as mature tufts at P17 of OIR (FIG. 2D-F). White arrows in FIGS. 2B and 2E point to NRP1-positive MPs associated with pre-retinal tufts. NRP1 was also expressed by endothelial cell on the endothelium of neovascular tufts as previously reported (21). Consistent with data presented in FIG. 1, LysM-Cre/Nrp1fl/fl mice had lower numbers of macrophage/microglia and less pronounced neovascularization (see below for full quantification) (FIG. 2 G-K).

Example 4

Figure 3A:
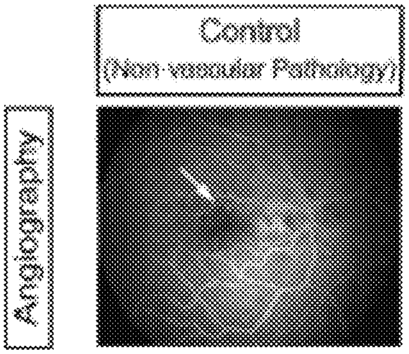
FIGS. 3A-3J show that the NRP1 ligand, SEMA3A, is induced in patients suffering from proliferative diabetic retinopathy. Angiographies, funduscopies, spectral-domain optical coherence tomography (SD-OCT) and three-dimensional (3D) retinal maps obtained from patients selected for the study. Control patients had non-vascular pathologies and were compared to patients with proliferative diabetic retinopathy (PDR). Control ERM patients shows signs of non-diabetes-related retinal damage such as (FIG. 3A, FIG. 3B) tractional tension on vasculature (arrow) secondary to (FIG. 3C) fibrotic tissue (white arrow), posterior vitreous detachment (arrowhead) and macular bulging (angiography and 3D map). Retinas from PDR patients have (FIG. 3E) neovascularization (inset) with (FIG. 3D) highly permeable microvessels as evidenced by leakage of fluorescent dye (inset), (FIG. 3F) microaneurysms (inset arrows) and (FIG. 3G) fibrous scar tissue (arrow), indicative of advanced retinopathy.
Figure 3B:
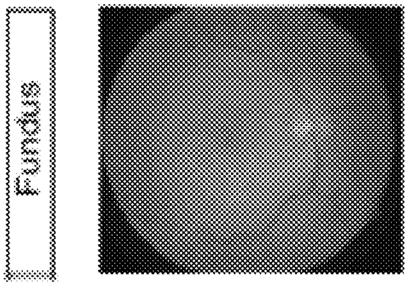
Figure 3C:
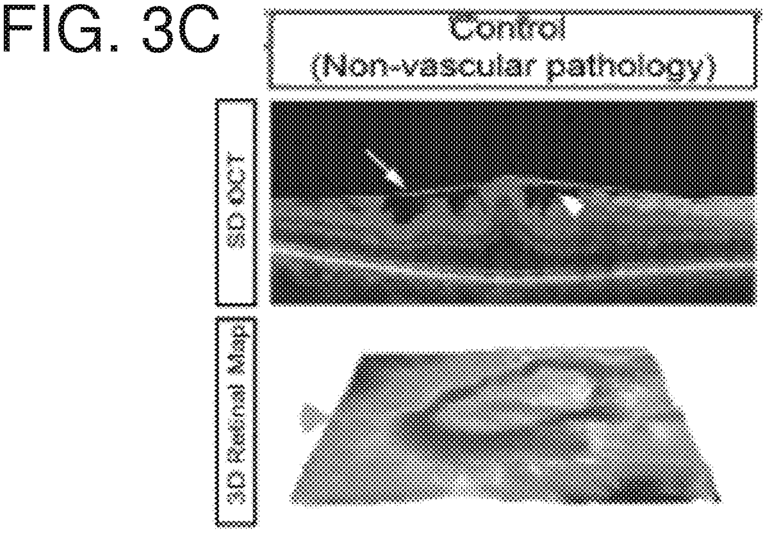
Figures 3D, 3E, 3F, 3G:
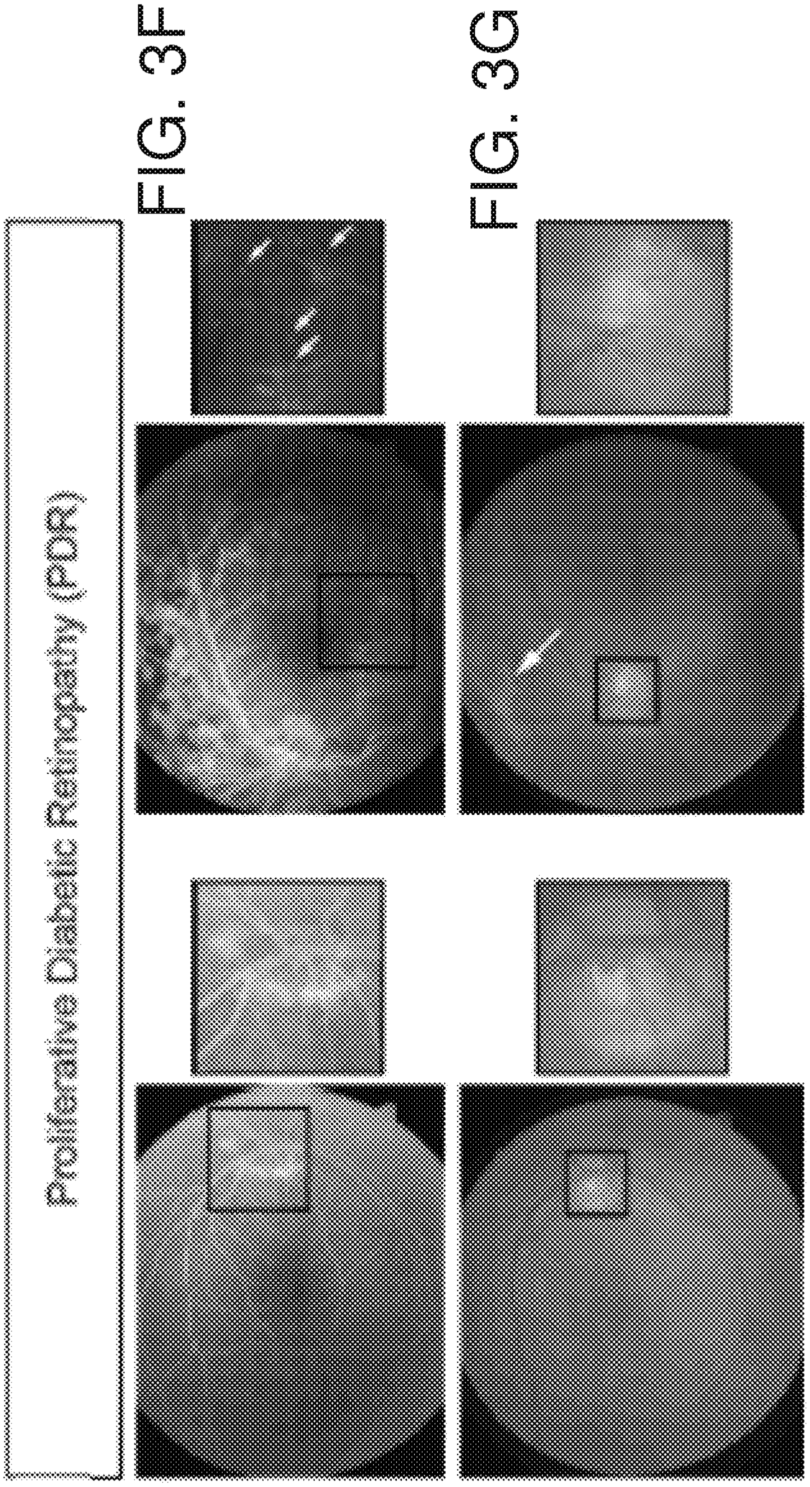
Figure 3H:
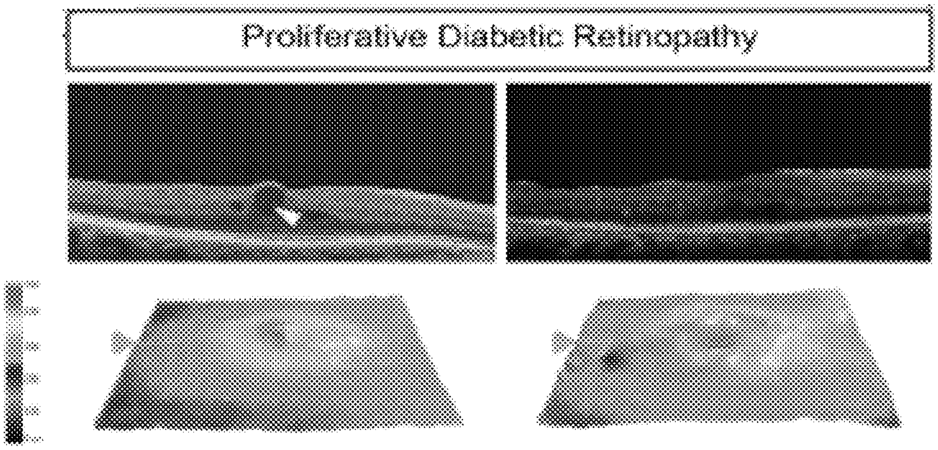

SEMA3A is Elevated in the Vitreous of Patients Suffering from Active Proliferative Diabetic Retinopathy To establish the clinical relevance of our findings on the obligate role of NRP1 in MP chemotaxis in retinopathy, the concentrations of SEMA3A directly in the vitreous of patients suffering from active PDR was determined. Seventeen samples of undiluted vitreous were obtained from patients suffering from PDR and 17 from control patients with nonvascular pathology. Detailed characteristics of patients are included in Table 1 (Example 1). Control patients (20) presented with non-vascular pathology and showed signs of non-diabetes-related retinal damage such as tractional tension on vasculature (FIG. 3A,B (white arrow)) secondary to fibrotic tissue and macular bulging (FIG. 3C). In contrast, all retinas from PDR patients showed signs of disc (FIG. 3D) or pre-retinal neovascularization (FIG. 3F), with highly permeable microvessels (leakage of fluorescent dye) (FIG. 3D,G insets), microaneurisms (FIG. 3D-G) and fibrous scar tissue, indicative of advanced retinopathy (FIG. 3G). In addition, patients showed some evidence of macular edema due to compromised vascular barrier function, including cystoid formation (white arrowhead) due to focal coalescence of extravasated fluid (FIG. 3H).

Figure 3I:
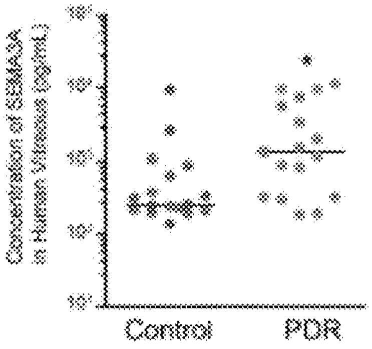
Figure 3J:
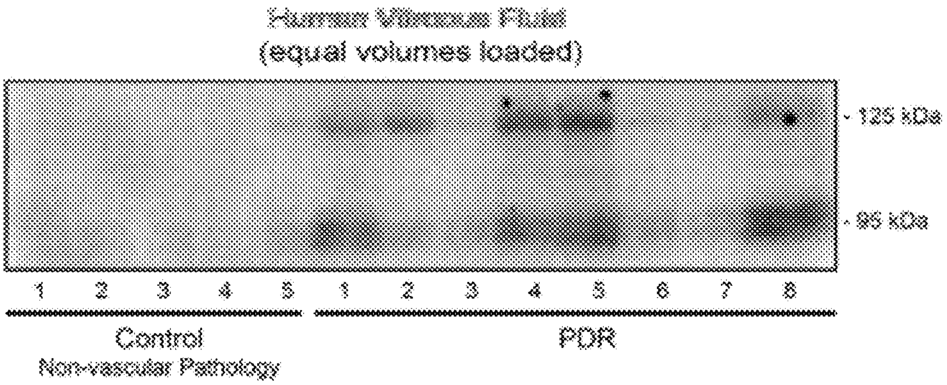

Consistent with a role in PDR, ELISA-based detection of SEMA3A revealed a 5-fold higher concentrations of the protein in the vitreous humor of patients with PDR when compared to vitreous from control patients (P=0.0132) (FIG. 3I). Results were confirmed by Western blot analysis on equal volumes of vitreous where SEMA3A (125 and 95 kDa isoforms)(38, 39) were elevated in patients with PDR (FIG. 3J). Thus, upregulation of SEMA3A in the vitreous is induced in diabetic ocular pathology.

Example 5

NRP1 Ligands are Induced in the Retinal Ganglion Cell Layer During OIR

Figure 4A:
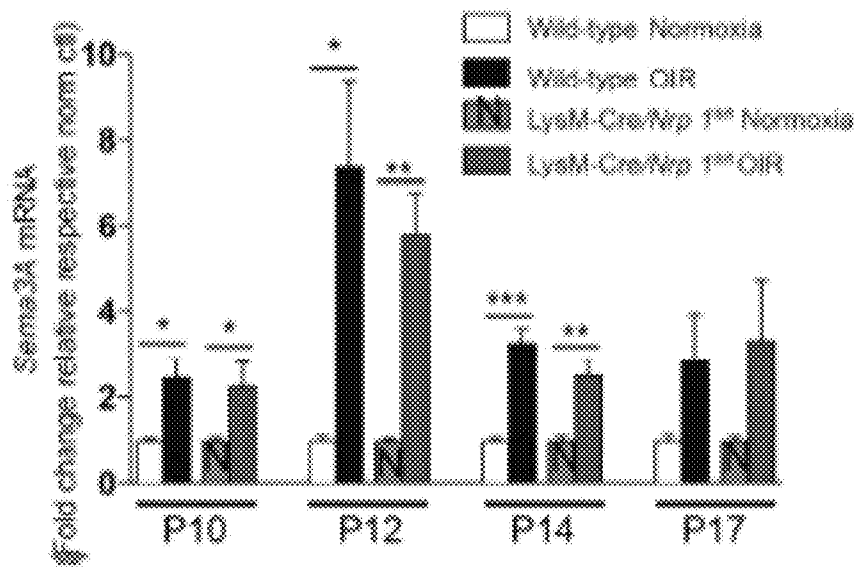
FIGS. 4A-4E show that ligands of NRP1 are induced in the retinal ganglion cell layer during OIR.
Figure 4B:
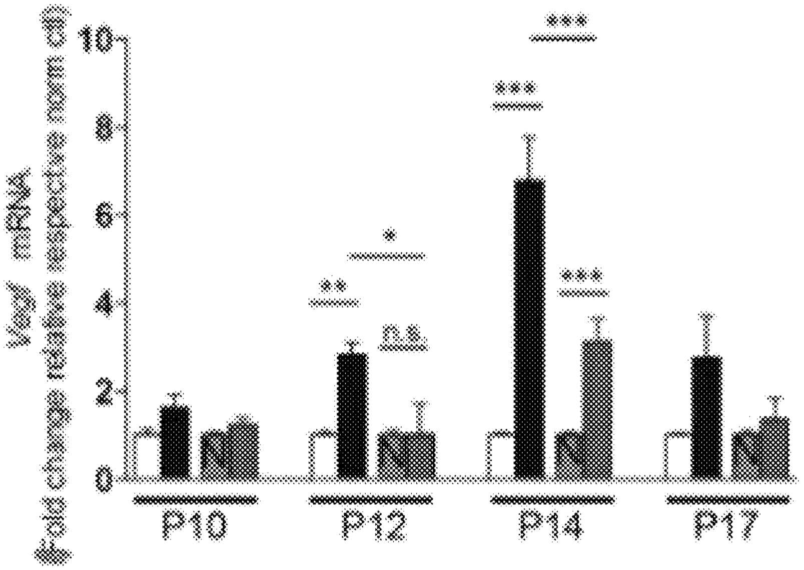

To obtain an accurate kinetic profile of expression of the two prominent ligands of NRP1 in proliferative retinopathy, levels of SEMA3A and VEGF messages in the mouse model of OIR were determined. Real-time quantitative PCR (RT-qPCR) on whole retinas revealed that SEMA3A was robustly induced in OIR both during the hyperoxic (vaso-degenerative) phase at P10 and the ischemic/neovascular stage from P12 to P17 (FIG. 4A). The observed induction occurred in both wild-type and LysM-Cre/Nrp1fl/fl retinas. Conversely, as expected, VEGF transcripts rose exclusively in the ischemic phase of OIR from P12 to P17 (FIG. 4B). Importantly, VEGF was significantly less induced in LysM-Cre/Nrp1fl/fl when compared to wild-type retinas (minimally increased at P12 (P=0.0451) and ~55% lower at P14 when compared wild-type OIR (P=0.0003)) (FIG. 4B) indicative of a healthier retina.

Figure 4C:
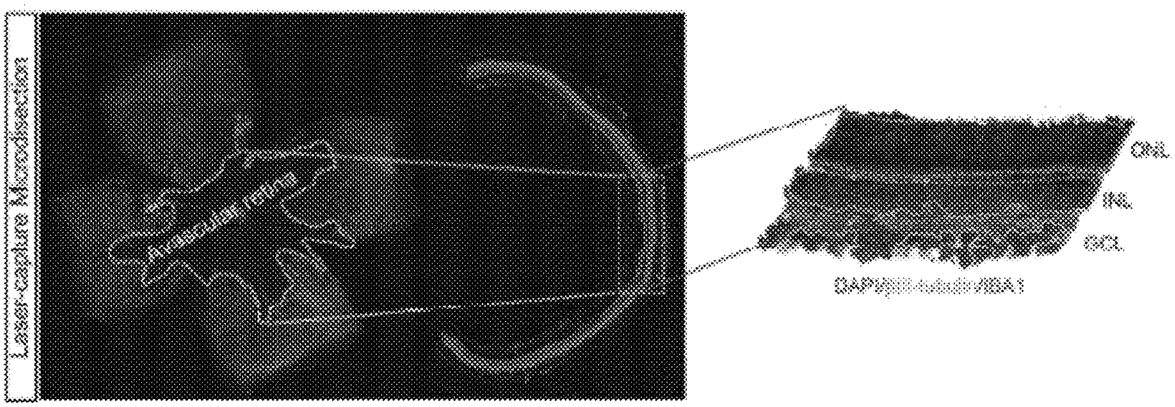
Figure 4D:
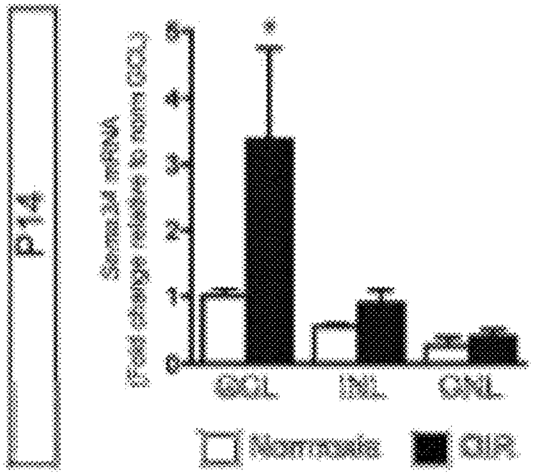
Figure 4E:
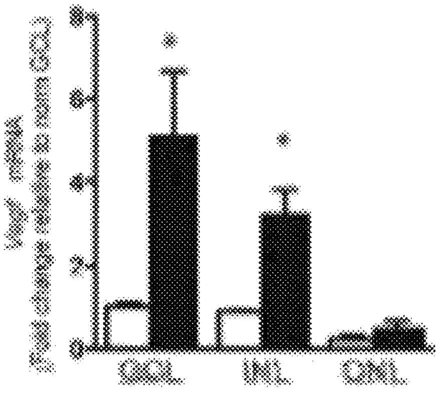

Next, laser capture micro-dissection (LCM) followed by RT-qPCR was performed on retinal layers in avascular zones to pinpoint the source of SEMA3A and VEGF messages in OIR (FIG. 4C). Both SEMA3A and VEGF where robustly induced in the ganglion cell layer with VEGF also increasing in the inner nuclear layer (FIG. 4D, E). Thus, the source of both ligands is geographically consistent with the localization of retinal MPs (FIG. 2).

Example 6

Figure 5A:
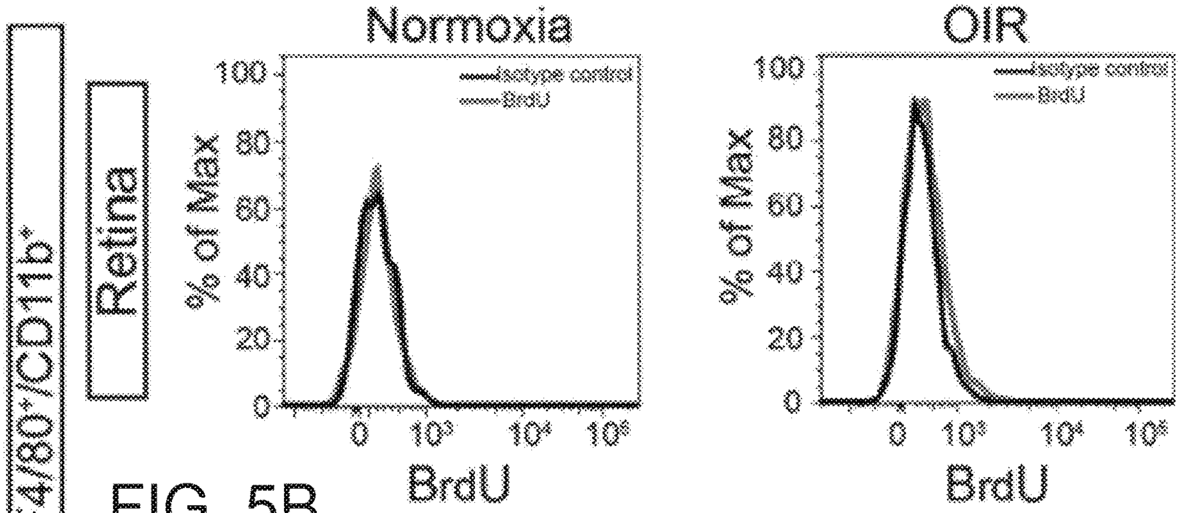
FIGS. 5A-5C show that NRP1$^{+}$ MPs do not proliferate in the retina after vascular injury. Representative FACS histograms of CD11b+/F4−80+/Gr−1$^{-}$ cells obtained from retinas (FIG. 5A) and spleens (FIG. 5B) collected at P14 from WT OIR (right panel) and Normoxic (left panel) control mice injected with BrdU at P13. The number of BrdU$^{+}$ cells was considerably higher in spleens but did not change significantly between OIR and Normoxic mice (FIG. 5C). n=4 (Normoxic, N), n=4 (01R) (total of 16 retinas per condition; each "n" is comprised of 4 retinas). Data are expressed as a percentage of BrdU+Gr−1$^{-}$/CD11b+/F4−80+ cells ±SEM.
Figure 5B:
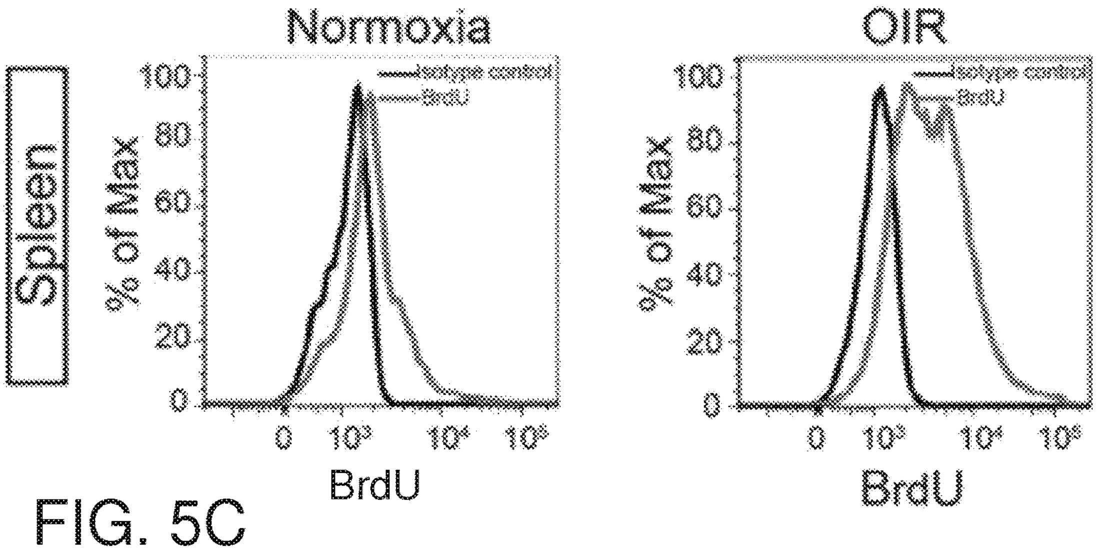
Figure 5C:
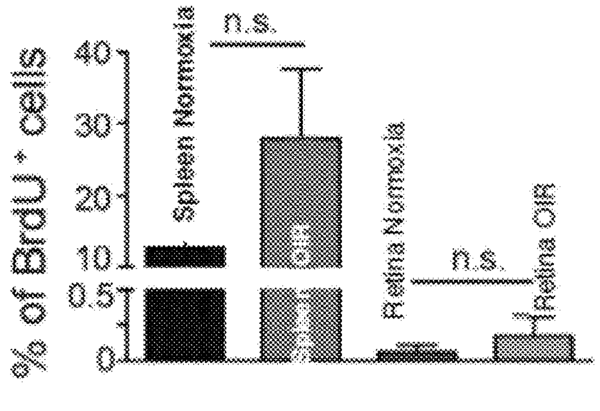

Mononuclear Phagocytes (MPS) do not Proliferate in the Retina after Vascular Injury In order to determine if the noted rise in NRP1+ MPs was due to an influx from systemic circulation or an increase in MP proliferation within the retina, the local retinal proliferation of these cells was investigated. Mice were systemically injected with BrdU at P13 (24 hours prior to sacrifice) and FACS analysis was carried out on retinas (FIG. 5A) and spleens (FIG. 5B). Within the retina, Gr1−/CD11b+/F4/80+ MPs did not show significant proliferation (P=0.4708). Considerably more proliferation was observed in spleens. No significant difference was observed between Normoxia and OIR (FIG. 5C). The lack of proliferation of MPs in the retina suggest that noted accretion NRP1+ MPs during retinopathy has a systemic origin.

Example 7

SEMA3A and $VEGF_{165}$ Mobilize MPs Via NRP1

Figure 6A:
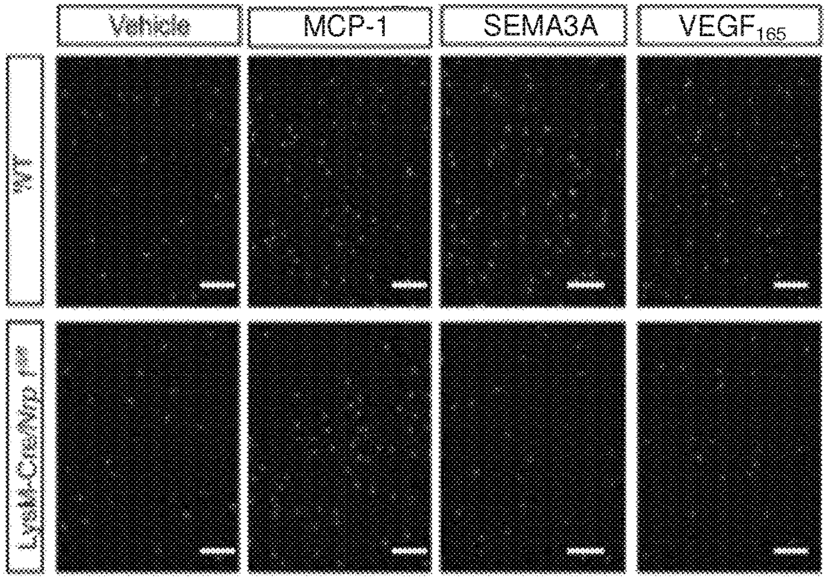
FIGS. 6A-6C show that SEMA3A and VEGF are chemo-attractive towards macrophages via NRP1.
Figure 6B:
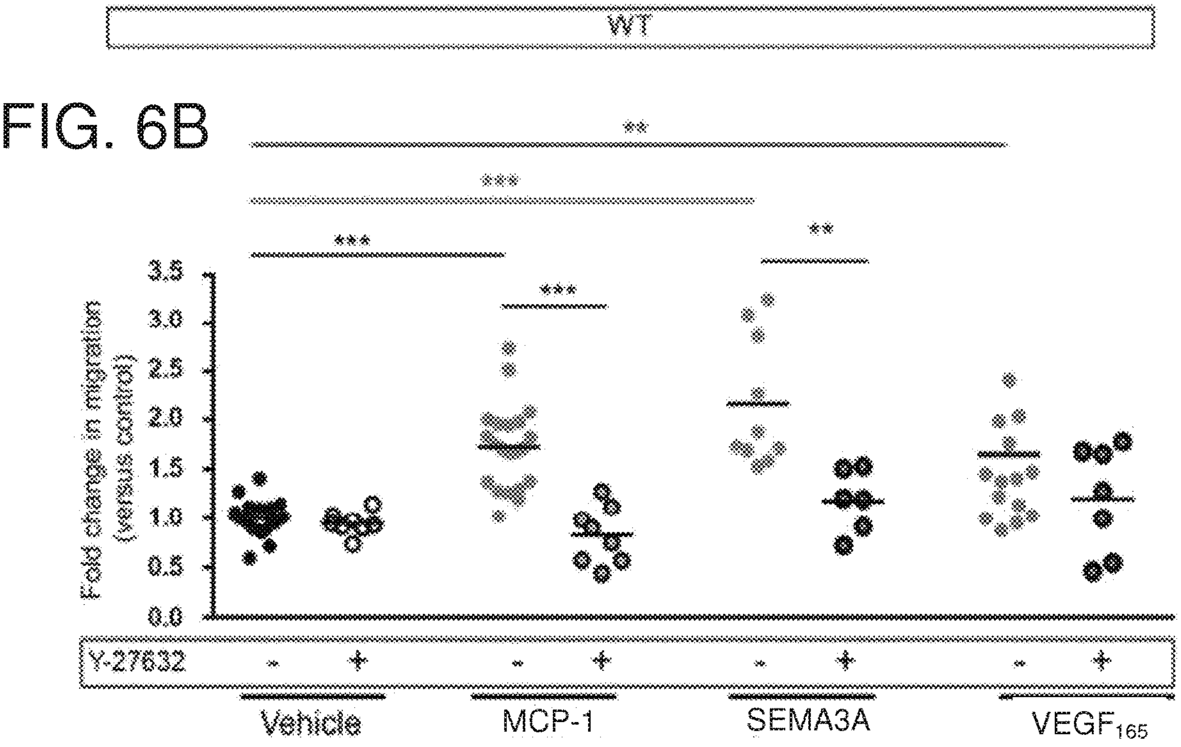
Figure 6C:
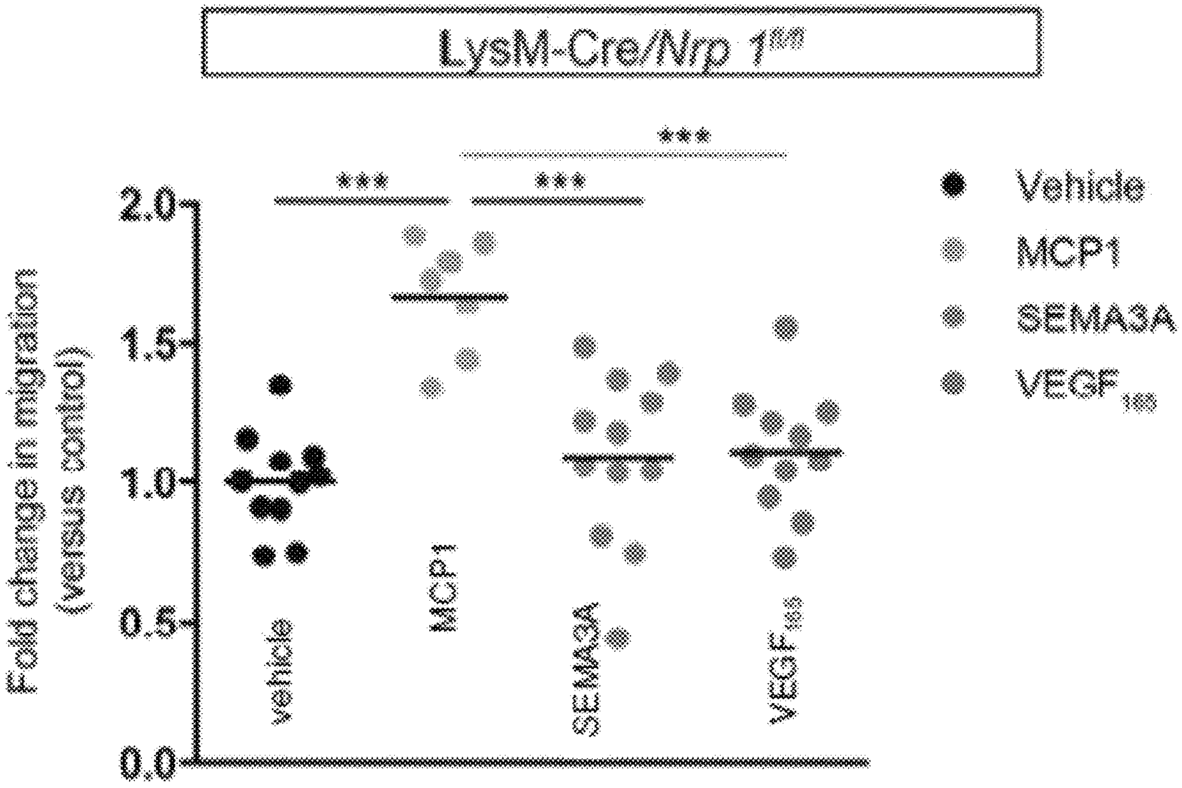

In light of the requirement of NRP1 for myeloid cell mobilization to sites of vascular lesion (FIG. 1) as well as the induction of the principal ligands of NRP1 in retinopathy (FIG. 3-4) and the likely systemic origin of these cells (FIG. 5), the propensity of these cues to provoke chemotaxis of MPs was determined. Primary macrophage cultures were isolated from wild-type mice and subjected to a Transwell Boyden chamber migration assay. Both SEMA3A (100 ng/ml) (P<0.0001) and $VEGF_{165}$ (50 ng/ml) (P=0.0027) provoked macrophage chemotaxis to similar magnitudes as positive control MCP-1 (100 ng/ml) (P<0.0001) (FIGS. 6A, B). These data were validated by demonstrating that Y-27632, a selective inhibitor ROCK (Rho-associated coiled coil forming protein serine/threonine kinase) abolished their chemotactic properties. ROCK is downstream of NRP1 signaling (40) and is known to mediate monocyte migration (41). VEGF migration was partially yet not significantly diminished suggesting a contribution from alternate receptors such as VEGFR1 as recently reported (33). Consistent with a role for NRP1 in SEMA3A and VEGF-mediated chemotaxis, macrophages from LysM-Cre/$Nrp1^{fl/fl}$ mice were uniquely responsive to MCP-1 and not mobilized by SEMA3A or VEGF (FIG. 6C).

Example 8

NRP1+ Macrophages Potentiate Microvascular Sprouting Ex Vivo

Figure 7A:
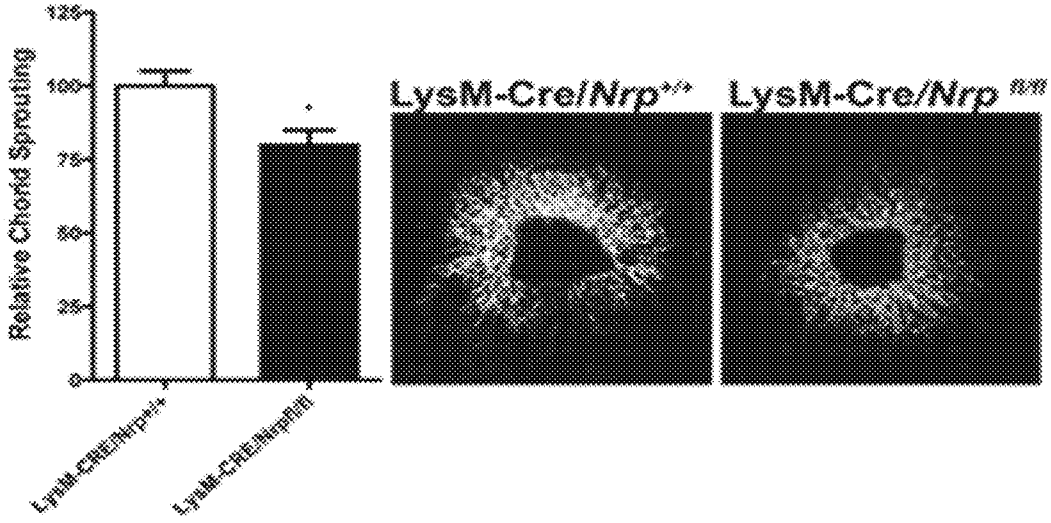
FIGS. 7A-7E show that Nrp1$^{+}$ macrophages promote microvascular growth in ex vivo choroid explants.
Figure 7B:
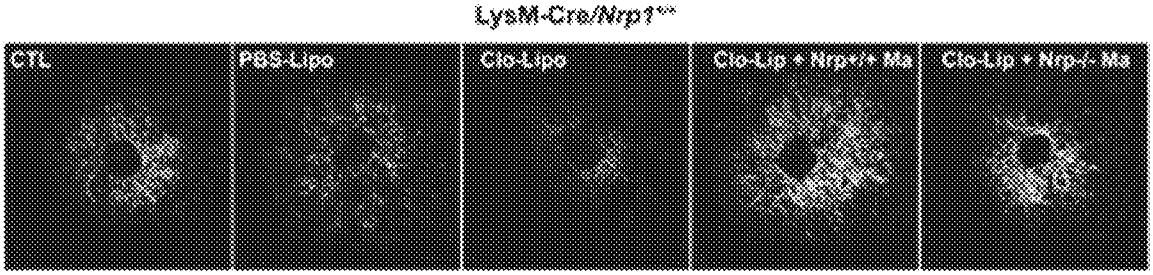
Figure 7C:
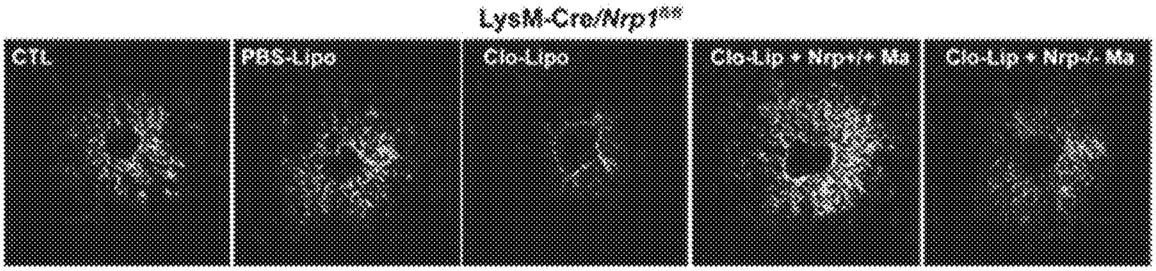
Figure 7D:
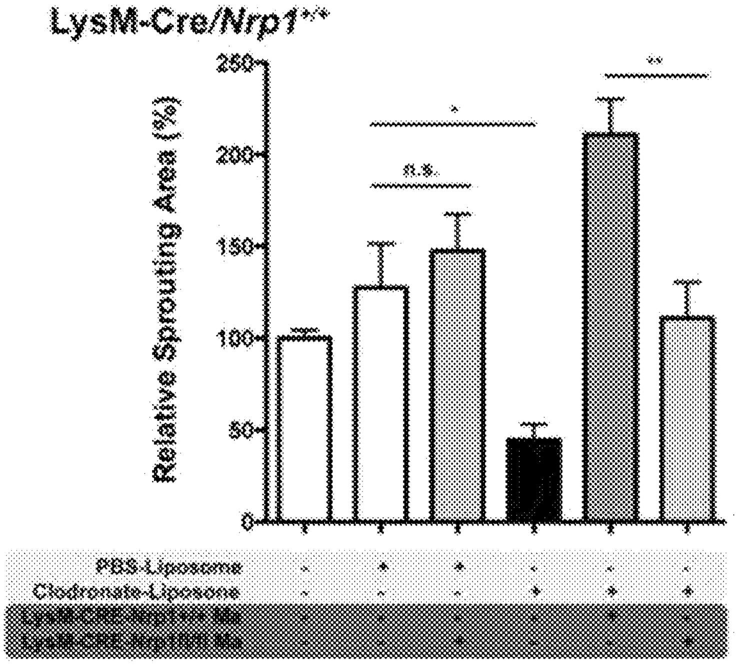
Figure 7E:
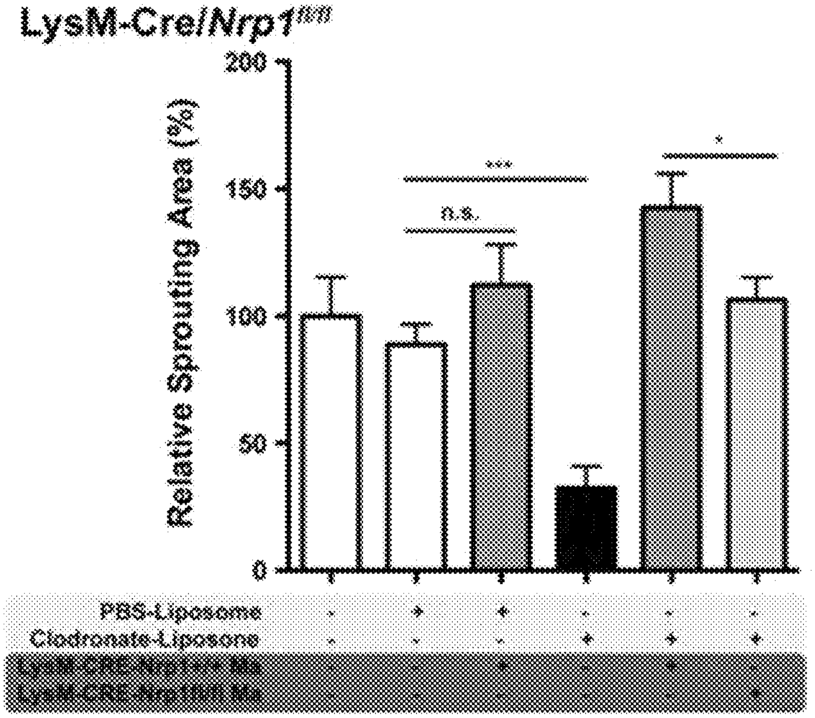

To investigate the impact of NRP1 expressing macrophages on microvascular angiogenesis, choroid tissue from either LysM-Cre/$Nrp1^{+/+}$ mice or LysM-Cre/$Nrp1^{fl/fl}$ mice was isolated and grew in Matrigel™ to assess microvascular sprouting. Choroids from LysM-Cre/$Nrp1^{fl/fl}$ mice sprout ~20% less microvessels when compared to ones from LysM-Cre/$Nrp1^{+/+}$ mice (P=0.018) (FIG. 7A). To investigate the role of $NRP1^{+}$ macrophages in promoting microvascular sprouting, clodronate-liposomes were used to eliminate endogenous macrophages from the isolated choroid tissues. In explants from both LysM-Cre/$Nrp1^{fl/fl}$ and LysM-Cre/$Nrp1^{+/+}$ mice, PBS containing liposomes (i.e. vehicle control) had no impact on vascular sprouting, but clodronate-liposomes reduced microvascular sprouting by ~60% (P=0.0114 for LysM-Cre/$Nrp1^{+/+}$ choroid and P=0.0007 for LysM-Cre/$Nrp1^{fl/fl}$ choroid) (FIGS. 7B-E). To verify whether $NRP1^{+}$ macrophages have a propensity to promote angiogenesis, peritoneal macrophages were extracted from LysM-Cre/$Nrp1^{+/+}$ or LysM-Cre/$Nrp1^{fl/fl}$ mice and introduced into choroid explant cultures that had previously been treated with clodronate liposomes and washed. LysM-Cre/$Nrp1^{+/+}$ macrophages robustly potentiated microvascular sprouting by 50-100% when compared to macrophages from LysM-Cre/$Nrp1^{fl/fl}$ mice (P=0.0068 for LysM-Cre/$Nrp1^{+/+}$ choroid and P=0.0491 for LysM-Cre/$Nrp1^{fl/fl}$ choroid) (FIGS. 7D and E) and independent of the genotype of the choroidal explant.

Example 9

Figure 8A:
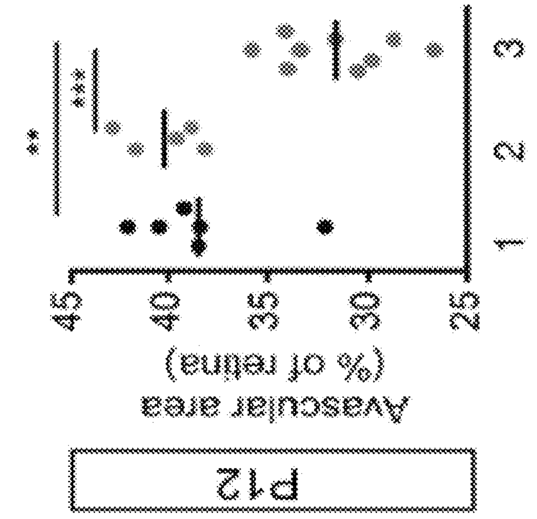
Figure 8B:
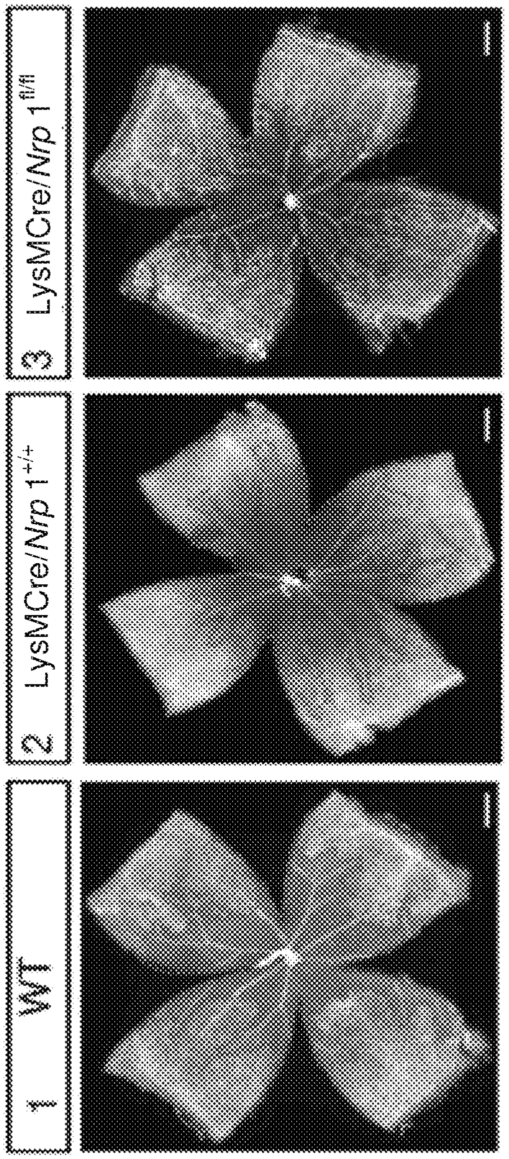

Deficiency in Myeloid-Resident NRP1 Reduces Vascular Degeneration and Pathological Neovascularization in Retinopathy Given the obligate role of NRP1 cell signaling in MP infiltration during the early stages of OIR (FIG. 1), the impact of myeloid cell-specific ablation of NRP1 on the progression of disease was next determined. Upon exit from 75% $O_2$ at P12, LysM-Cre/Nrp1fl/fl mice showed significantly lower levels of retinal vasoobliteration when compared to wild-type (p=0.0011) and LysM-Cre/Nrp1+|+ (P<0.0001) controls (FIGS. 8A, B). This may be attributed to lower levels of IL-1β present in the retinas of LysM-Cre/Nrp1fl/fl mice (Data not shown). Importantly, at P17 when pathological neovascularization peaks (26), deletion of myeloid-resident NRP1 profoundly reduced avascular areas (~35% when compared to wild-type (P<0.0001) and ~30% compared to LysM-Cre/$Nrp1^{+|+}$ mice (P=0.0008)) (FIGS. 8C, D). In turn, significant reductions in destructive preretinal neovascularization associated with ischemic retinopathy were observed (~36% when compared to wild-type (P=0.0008) and ~34% compared to LysM-Cre/Nrp1+|+ mice (P=0.0013)) (FIGS. 8E, F).

Example 10

Preparation of Soluble SEMA3A Neutralizing Traps

High affinity traps to inhibit/neutralize SEMA3A were generated. These traps were derived from Neuropilin 1 (NRP1) and were optionally coupled to 6×-His tag or FC proteins (see FIGS. 19, 20 and 27, and Table 1). Various variants comprising either the entire NRP1 extracellular domain or functional variants capable of maintaining SEMA3A binding were generated. Traps containing a b1 domain (which binds to VEGF) and including a neutralizing VEGF165 mutation were generated. The traps were shown to be highly expressed and secreted in transformed human cells. Simple purification and formulation protocols were developed to produce trap samples for SAR and in vivo efficacies studies to follow.

Methods

Cell culture and material. The human Neuropilin 1 (GenBank™ accession NM_003873, SEQ ID NO: 66) was acquired from Origene Inc. The Origen clone comprises a conservative mutation at amino acid 140 which changes the leucine for an isoleucine. The 293T (ATCC) cells were grown in Dulbecco's modified Eagle's medium supplemented with 10% fetal calf serum. The pFUSE-hIgG1-Fc1 vector was purchased from InvivoGen Inc.

Cloning. The extracellular domain of Neuropilin-1 (residues 1-856), or portions of it, were PCR amplified from Origene clone RC217035 using the Phusion™ high fidelity polymerase (New England Biolabs) and cloned in the EcoR1-BglII of pFUSE-hIgG1-Fc1 in frame with the human FC-1 coding sequence. Constructs coding for the soluble versions of the traps were generated by inserting a sequence coding for a TEV protease cleavage site followed by 6×His residues and a stop codon upstream of the FC coding portion of the corresponding FC constructs. Additional deletions (b1, b1b2) or VEGF165 binding mutations (e.g., Y297A) were introduced using the Q5 site directed mutagenesis kit (NEB). All construct sequences were verified by Sanger sequencing (Genome Quebec). The nucleotides and amino acid sequences of the assembled traps are depicted in FIGS. 20 and 27.

Evaluation of traps' expression in human cells. Constructs coding for the mouse and human traps were transfected in 293T cells. Cells were grown for 48 hrs post transfection in FreeStyle™ 293 medium (Invitrogen). Cell lysates were prepared from 293T cells 48 hours post-transfections. Cells were extensively washed with PBS and lysed in ice cold lysis buffer (50 mM HEPES pH7.5, 150 mM NaCL, 1.5 mM MgCl2, 1% Triton X-100 and 10% glycerol) supplemented with standard amounts of protease inhibitors (AEBSF, TPCK,TLCK, aprotinin, leupeptin, pepstatin and E64, Sigma). Cell lysates were cleared by micro centrifugation (12000 g, 20 minutes). Lysates concentrations were determined by standard micro BCA (Sigma). Equal amounts of protein were loaded on 5-20% PAGE-SDS gradient gels and transfered to PVDF (Amersham). Cleared conditioned media from transfected cells were incubated with either Protein A sepharose (Pharmacia) or Talon resin (Clontech) for FC or 6×His tag. Resins were washed with PBS and diluted in 2×PAGE-SDS sample buffer prior to gel separation and transfer. The antibody used in immunoblottings were the anti-human Neuropilin-1 (Cell signaling), the mouse monoclonal anti-6×-HIS (In Vitrogen) and the reporter HRP linked anti-human, mouse and rabbit IgG (BioRAD). All antibodies were used at a 1/2000 dilution. Chemiluminescent signal was captured using a Fuji imaging system after incubation of membranes with ECL (Amersham).

Traps expression and purification. 293-T cells were transfected with plasmids encoding the various traps by either the Polyethylamine (PEI) or the calcium phosphate precipitation standard transfections methods. The next day cells were washed twice with serum free media and fed with serum free complete media (Free style 293 media, InVitrogen). Conditioned medium was collected after 60-72 hrs of growth in serum free media and cleared from cellular debris by swing bucket centrifugation (2000 RPM, 20 minutes). FC traps were purified from conditioned media of transfected 293T cells by passage on Protein A or G sepharose (Pharmacia) followed by extensive washes with PBS and elutions with 0.1 M glycine pH 3.0. Elution fractions were neutralised immediately by the addition of 1/10 volume 1 M Tris pH 8 and 1/10 volume of 10×PBS pH 7.4. Soluble 6×HIS tagged traps were purified from conditioned media of transfected 293T cell by passage on Talon agarose (Clontech) followed by extensive washes with PBS and stepwise imidazole elutions (Range 10-150 uM typically). Samples of purification fractions of traps were analysed on 5-15% or 5-20% gradient PAGE-SDS gels. Gels were stained using the Safely Blue staining kit (InVitrogen).

Sterile formulation of purified traps for in vivo injections. Purifications elution fractions from 40 ml of conditioned media were pooled and diluted to a total volume of 10 ml in PBS. Diluted trap proteins were sterilized by filtration through a 0.2 uM low protein binding filter (Progene). Protein solutions were concentrated and buffer exchanged with PBS on sterile PES concentration devices (Pierce, nominal MWCO 30 KD). Sterile concentrated Traps samples (~30-50 ul) were analysed and stained on PAGE-SDS as described above.

Example 11

Affinity of Traps for SEMA3A and VEGF

Production of AP-$VEGF_{165}$. the coding sequence of the human VEGF165 variant 1 (NM_001025366) was subcloned in the pAPtag5 vector (GenHunter), in-frame with an Alkaline Phosphatase domain (AP-VEGF$_{165}$). HEK293T cells were transfected with the AP-VEGF165 construct using a polyethylenimine (PEI) transfection method. Following the overnight transfection step, cells were cultured for an additional 60 hr in serum free media (Invitrogen). The cell media were collected and concentrated on a PES device (Pierce). The concentrated AP-VEGF165 ligand was analysed on PAGE-SDS and quantified using SimplyBlue safe stain (Life technologies).

Sema 3A and AP-VEGF$_{165}$ binding assays. Saturation curves for the determinations of KD of binding to SEMA 3A or VEGF165 were obtained as follow. Wells of high protein binding 96 well plates (Maxisorp, Nunc) were coated with purified traps diluted in PBS and blocked afterward with binding buffer (PBS containing 2% casein and 0.05% Tween 20). The SEMA3A-FC (R&D systems) or AP-VEGF165 ligands were diluted in binding buffer over an extensive range of concentrations and added to wells. Following an overnight incubation, wells were washed with PBS containing 0.05% tween. Bound SEMA3a-FC was detected using an HRP-linked anti-Human IgG (Biorad) and ECL substrate (Pierce). Alternatively, bound AP-VEGF165 was detected using CPD star substrate (Roche). The Chemiluminescent signal was acquired on a TECAN reader. Dissociation constant (KD) were determined by non-linear curve fitting using the Graph Pad prism software.

The relative affinity of traps of the present invention to SEMA3A and VEGF has been assessed. Traps were prepared as described in Example 10. Schematic representation of traps tested is also provided in FIG. 19.

TABLE 4

Dissociation constant of SEMA3A and VEGF for various Traps

| Trap | SEMA 3A-FC binding (nM) | VEGF165 binding (nM) | SEQ ID NOS: (aa and nts) |
|---|---|---|---|
| G | 0.8 | 6.75 | SEQ ID NOs: 38, 39 |
| O | 1.05 | N.D. | SEQ ID NOs: 40, 41 |
| M | 0.95 | 20.13 | SEQ ID NOs: 42, 43 |
| N | >1000 | >250 | SEQ ID Nos: 44, 45 |
| R | 6.15 | N.D. | SEQ ID NOs: 46, 47 |
| W | 1.14 | 20.73 | SEQ ID NOs: 52, 53 |
| Y | >750 | N.D. | SEQ ID NOs: 56, 57 |
| Z | 4.44 | 66.96 | SEQ ID NOs: 62, 63 |
| AB | N.D. | 29.51 | SEQ ID NOs: 58, 59 |
| AC | 4 | No binding | SEQ ID NOs: 60, 61 |

Soluble NRP1 traps of the present invention bind more efficiently to SEMA3A than VEGF. Such preference for SEMA3A was found surprising since SEMA3A and VEGF are considered to normally have the same general affinity for NRP1. Increased affinity for SEMA3A may be advantageous in conditions where SEMA3A inhibition is preferred over inhibition of VEGF and may reduce side effects associated with VEGF inhibition.

Example 12

Figure 9A:
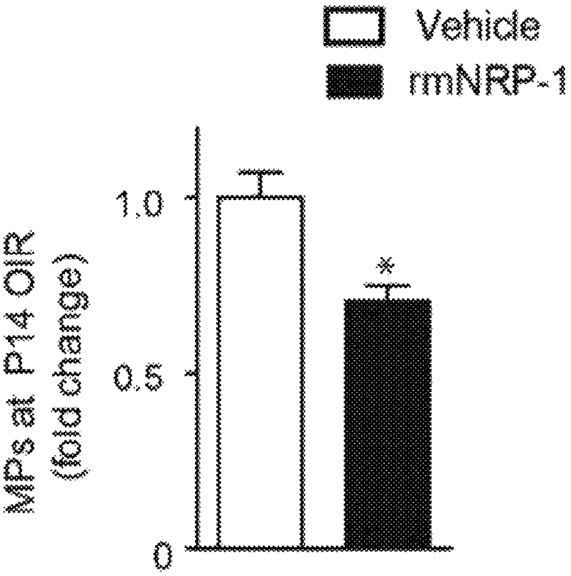
FIGS. 9A-9C show that therapeutic intravitreal administration of soluble NRP1 reduces MP infiltration and pathological neovascularization in retinopathy. WT mice were subjected to OIR and injected intravitreally at P12 with soluble recombinant mouse NRP1 (rmNRP1 comprising domains a1, a2, b1, b2 and c, see also FIGS. 19C and 20X-20Y) as a trap to sequester OIR-induced ligands of NRP1. At P14, FACS analysis revealed a decrease of over 30% in the number of retinal MPs in rmNRP1 injected retinas (FIG. 9A). Data are expressed as a fold change relative to control (vehicle-injected retinas) ±SEM; n=3-4 (total of 12-16 retinas per condition; each "n" comprises 4 retinas). Treatment with rmNRP1 efficiently decreased pathological neovascularization at P17 when compared to vehicle-injected eyes (FIG. 9B, FIG. 9C). Results are expressed as percentage of neovascular area versus the whole retinal area; n=11. Scale bars: 500 μm. *p<0.05, **p<0.01.
Figure 9B:
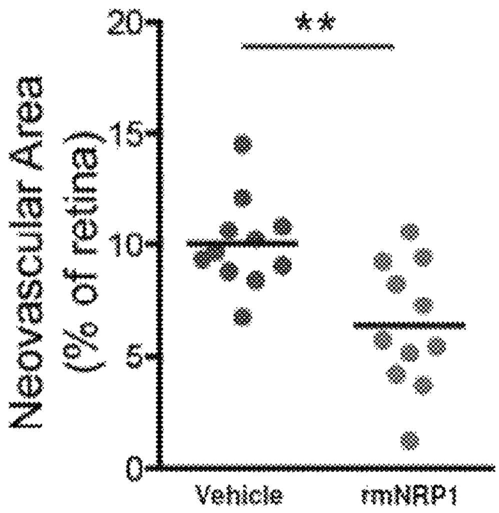
Figure 9C:
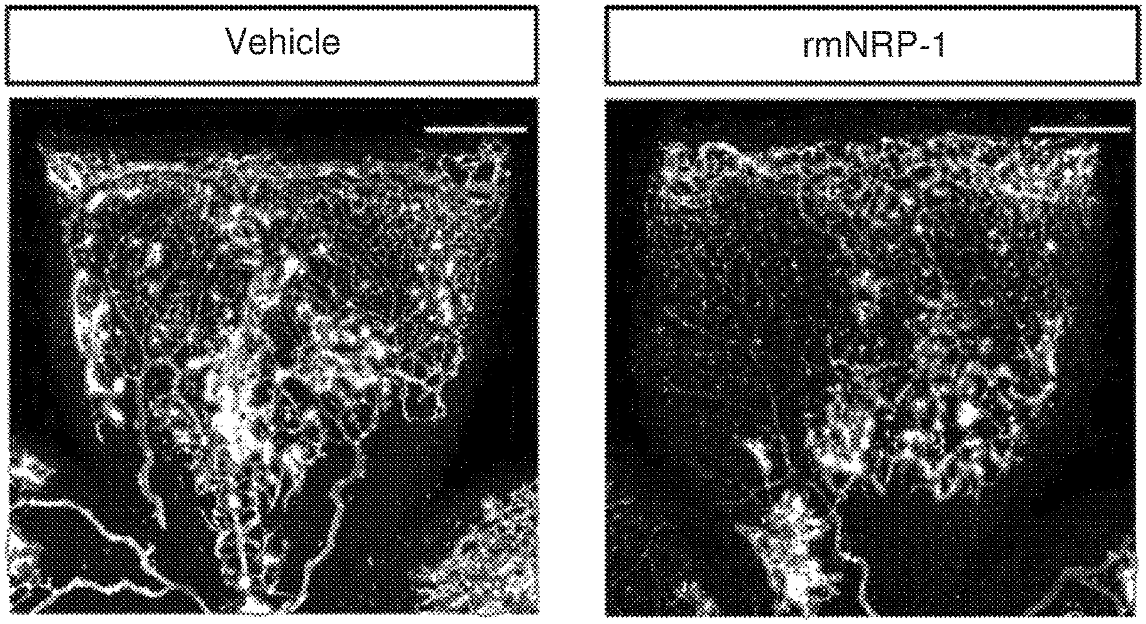
Figure 10:
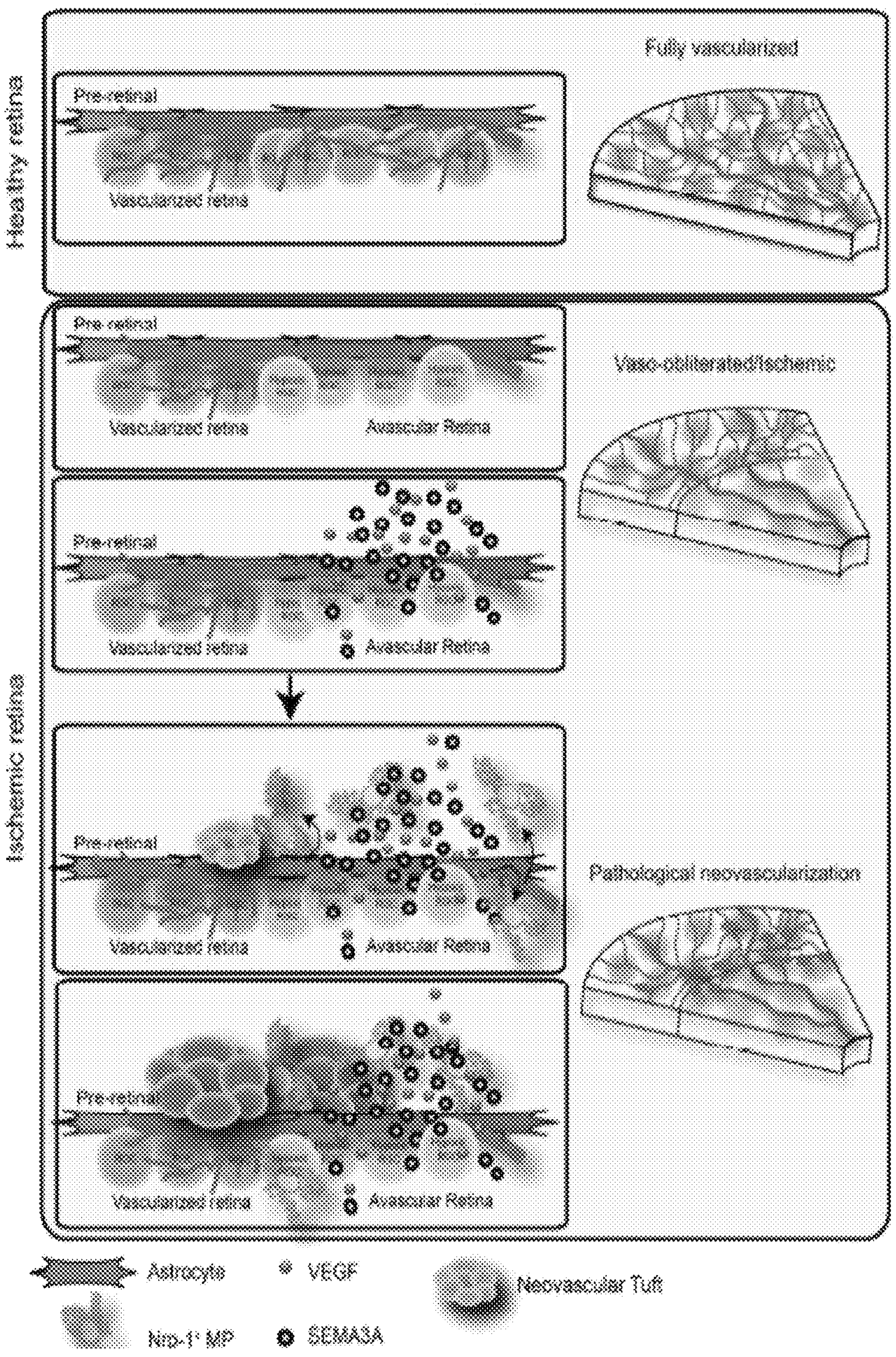
Figure 11A:
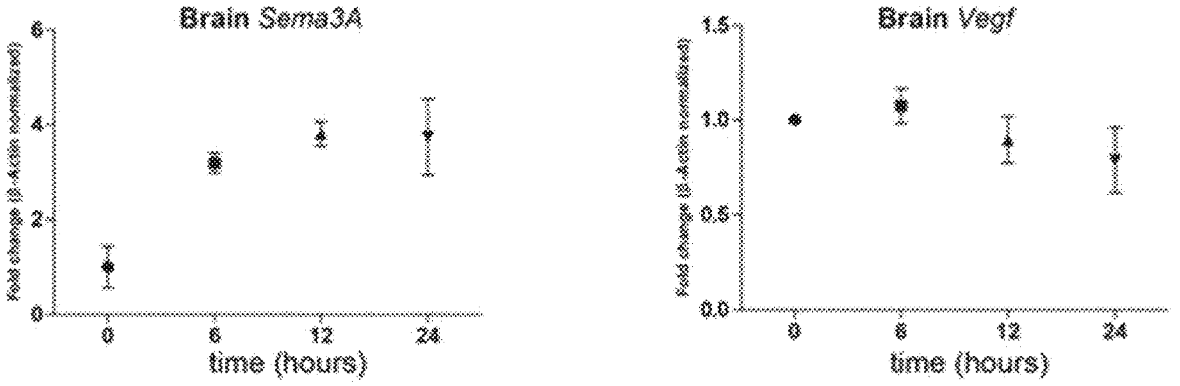
FIGS. 11A-11D show that SEMA3A is upregulated in several organs during septic shock. mRNA levels of SEMA3A (left panels) and VEGF (right panels) were assessed by qRT-PCR following LPS-induced (15 mg/kg) sepsis in mice. SEMA3A and VEGF mRNA levels were normalized with β-actin expression and fold changes in mRNA levels were determined at 0, 6, 12 and 24 hours following LPS administration.
Figure 11B:
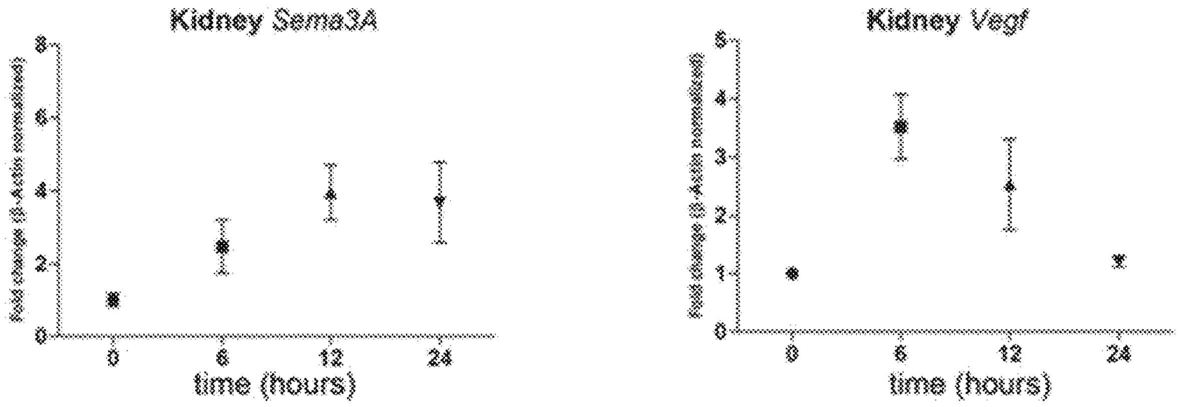
Figure 11C:
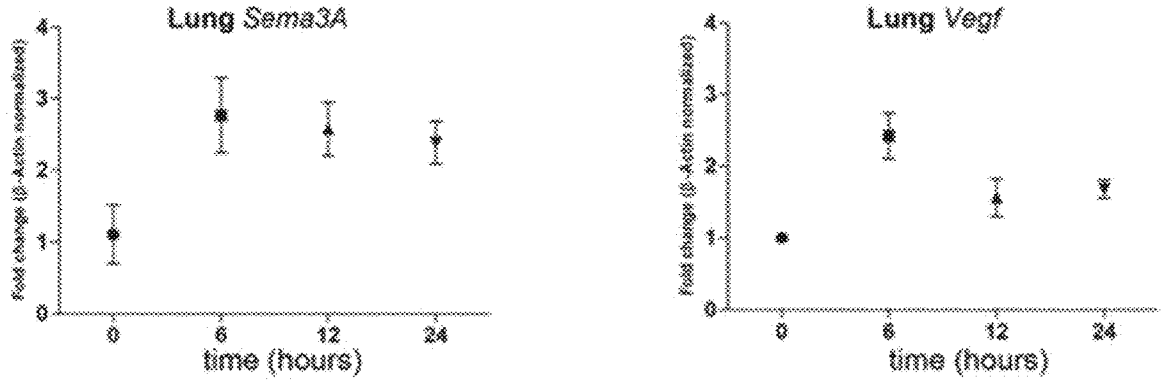
Figure 11D:
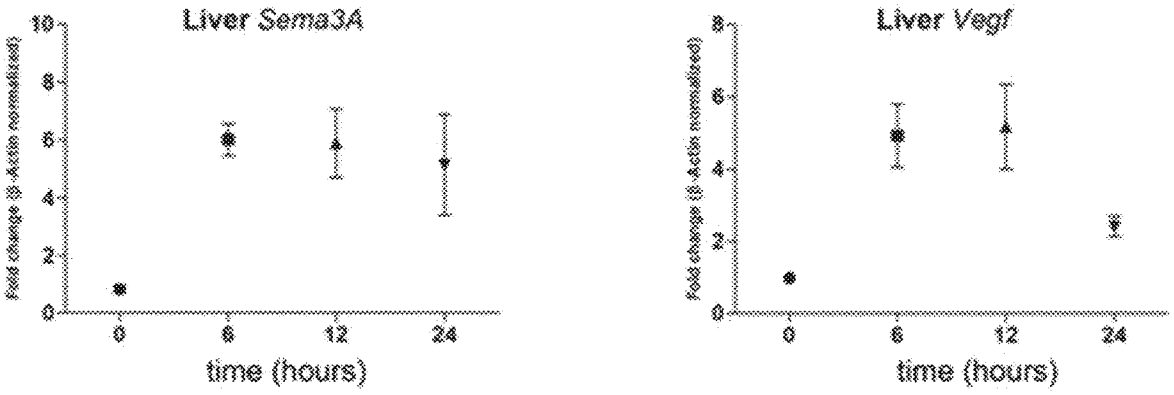
Figure 12A:
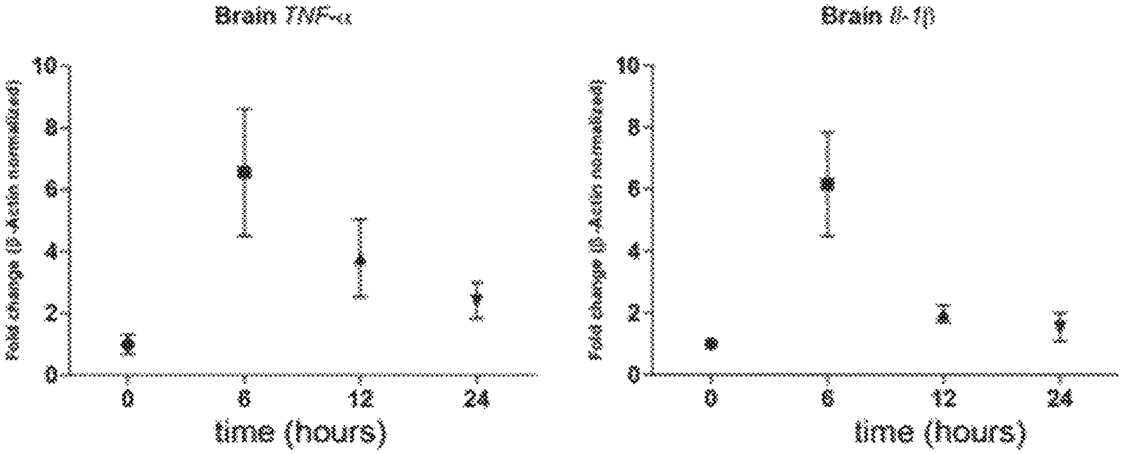
FIGS. 12A-12D show cytokines expression following LPS-induced sepsis. mRNA levels of TNF-α and IL-1β were assessed by qRT-PCR following LPS-induced sepsis (15 mg/kg) in mice. mRNA levels were normalized with β-actin expression an fold changes in mRNA levels were determined at 0, 6, 12 and 24 hours following LPS administration.
Figure 12B:
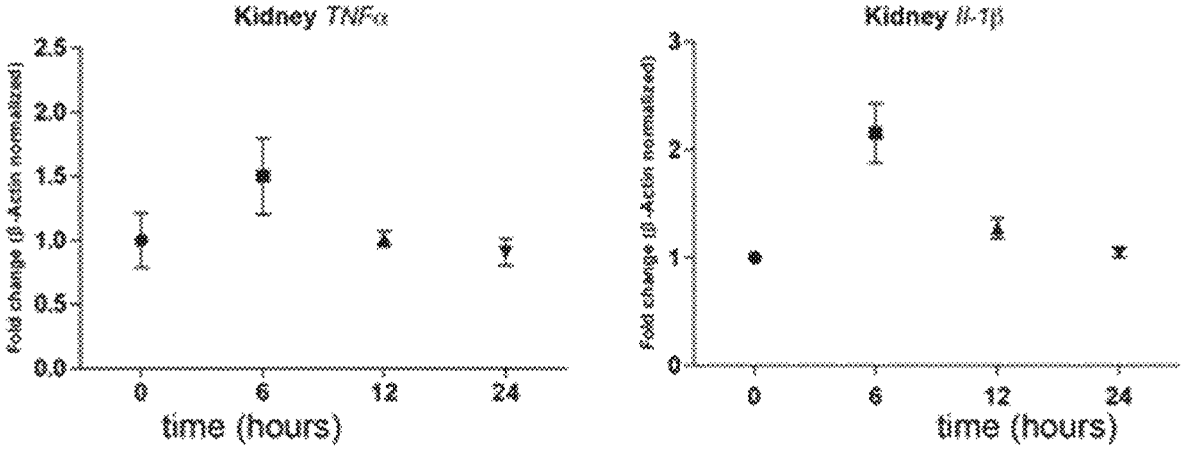
Figure 12C:
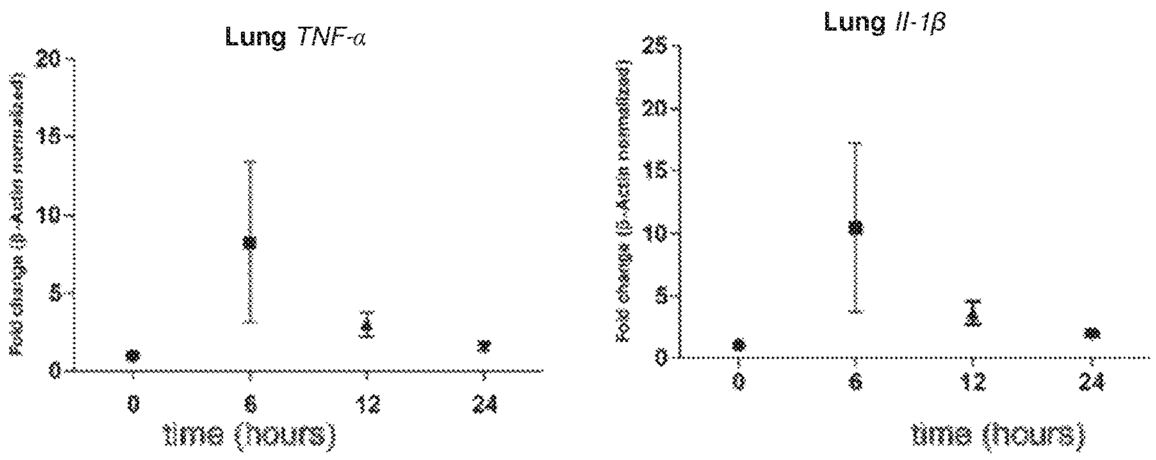
Figure 12D:
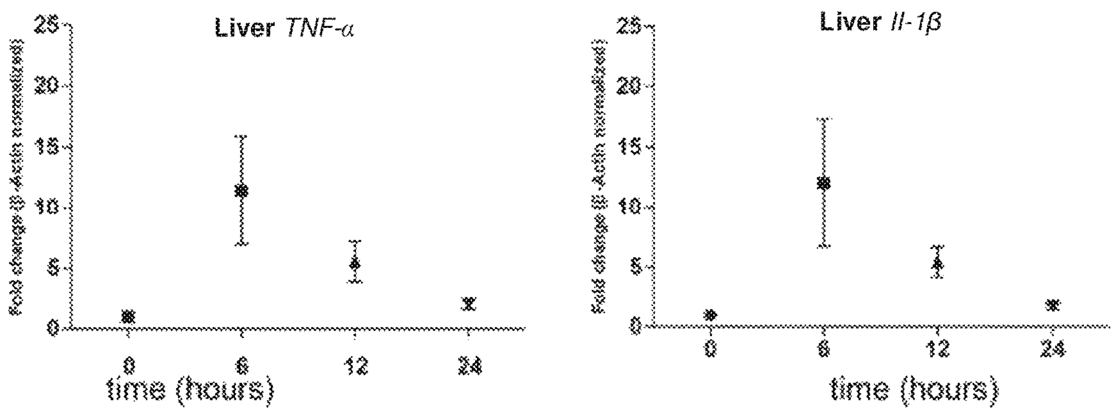

Therapeutic Intravitreal Administration of Soluble NRP1 Reduces MP Infiltration and Pathological Neovascularization in Retinopathy To determine the translational potential of the above findings, a soluble recombinant mouse (rm)NRP1 mTrap 1 polypeptide (FIGS. 19C and 20X-20Y comprising domains a1, a2, b1, b2 and c of SEQ ID NO. 25) was next employed as a trap to sequester OIR-induced ligands of NRP1. A single intravitreal injection of rmNRP1 at P12 lead to a 30% reduction at P14 (P=0.0282) in the number of microglia present in retinas subjected to OIR (FIG. 9A). This finding attests to the potency of soluble NRP1 (1 μl of 50 μg/ml) to compromise microglial mobilization. Intravitreal administration of soluble NRP1 provoked a significant ~40% decrease in pathological pre-retinal angiogenesis when compared to vehicle injected controls (P=0.0025) (FIGS. 9B,C). Together, these data suggest that neutralization of ligands of NRP1 is an effective strategy to reduce destructive neovascularization in retinopathy.

Example 13

Materials and Methods for Sepsis Model—Examples 14 to 19

Mouse model of sepsis. Studies were performed according to the regulations from the Canadian Guidelines for the Use of Animals in Research by the Canadian Council on Animal Care. LPS injections were delivered intraperitoneally (i.p) in 6-8 weeks old C57BL/6 mice.

Survival assay. For generation of survival data, mice were challenged with a single intraperitoneal injection of LPS at 25 mg/kg, in a volume of nearly 100 ul adjusted to mouse weight. Mice were then monitored until reaching critical limit points defined by the Canadian Council of Animal Care.

Measurement of pro-inflammatory cytokines. For assessment of pro-inflammatory cytokines, mice were challenged i.p. with a single intraperitoneal injection of LPS at 15 mg/kg and sacrificed at various time points up to 24 hours. Tissues (Brain, Liver, Kidney) were removed and mRNA was isolated using the GenElute™ Mammalian Total RNA Miniprep Kit (Sigma) and digested with DNase I to prevent amplification of genomic DNA. Reversed transcription was performed using M-MLV reverse transcriptase and gene expression analyzed using SybrGreen in an ABI Biosystems Real-Time PCR machine, β-actin was used as a reference gene.

Primary peritoneal macrophages culture. Adult WT or LyzMcre/NRP1fl/fl mice were anesthetized with 2% isoflurane in oxygen 2 L/min and then euthanized by cervical dislocation. Then, a small incision in abdominal skin of mouse was performed. Skin was pulled to each size of the mouse and peritoneal cavity was washed with 5 ml of PBS plus 3% FBS for 2 min. Then, the harvested cells were centrifuged for 5 min at 1000 rpm, resuspended in medium (DMEM F12 plus 10% FBS and 1% Streptomycin/Penicillin) and plated. After 1 h of culture at 37° C. under a 5% $CO_2$ atmosphere the medium was changed.

Cytometric Bead Array (CBA). CBA was performed according to manufacturer's guidelines (BD Bioscience). Macrophages were isolated from wild type or LyzMcre/NRP1fl/fl mice and subjected to SEMA3A (100 ng/ml) or vehicle for 12 hours and processed by CBA.

Trap and anti-VEGF antibody administration. Mice experimental model of sepsis were treated with human or mice NRP1 trap-1 (FIGS. 19B, C and 20A-20B, 20X-20Y, SEQ ID NO: 25 or SEQ ID NO: 83) or VEGF neutralizing antibody (R&D Systems, AF-493-NA).

Experimental design: 3 mice per group. Groups: 1—Vehicle, 2—LPS, and 3—LPS+NRP1 Trap 1—Vehicle: NaCl, 2—LPS: 15 mg/kg; and 3-LPS+NRP1-trap: Mice received i.v. a single injection of 4 ug (in a volume of 100 uL) of recombinant mouse NRP1-trap corresponding to 0.2 mg/kg, few minutes after LPS injection.

Permeability tests. For permeability assays, mice were challenged i.p. with a single intraperitoneal injection of LPS at 15 mg/kg, and sacrificed 24 hrs later for tissue sampling. Changes in liver, kidney, and brain vascular permeability were assessed by quantifying Evans Blue (EB) extravasation in tissue. After 24 hrs, a solution of 10 mg/ml of EB was injected intravenously (55 mg/kg). Two hours later, mice were sacrificed and perfused through the heart with PBS. Tissues were then removed, allowed to dry at room temperature 24 hrs, and dry weights were determined. EB was extracted in formamide overnight at 65° C. EB was then measured at 620 and 740 nm in spectrophotometer.

Real-time PCR analysis. RNA was isolated using the GenElute™ Mammalian Total RNA Miniprep Kit (Sigma) and digested with DNase I to prevent amplification of genomic DNA. Reversed transcription was performed using M-MLV reverse transcriptase (Life Technologies) and gene expression analyzed using SybrGreen (BioRad) in an ABI Biosystems Real-Time PCR machine. β-actin was used as a reference gene. See Table 3 below for details on the sequence of the oligonucleotides used.

TABLE 3

Primer sequences used for RT-PCR analysis

| Target | Primer sequence | SEQ ID NO: |
|---|---|---|
| β-actin (fwd) | GAC GGC CAG GTC ATC ACT ATT G | SEQ ID NO: 85 |
| β-actin (rev) | CCA CAG GAT TCC ATA CCC AAG A | SEQ ID NO: 86 |
| SEMA3A (fwd) | GCT CCT GCT CCG TAG CCT GC | SEQ ID NO: 87 |
| SEMA3A (rev) | TCG GCG TTG CTT TCG GTC CC | SEQ ID NO: 88 |
| VEGF (fwd) | GCC CTG AGT CAA GAG GAC AG | SEQ ID NO: 89 |
| VEGF (rev) | CTC CTA GGC CCC TCA GAA GT | SEQ ID NO: 90 |
| Tnf-α (fwd) | CCC TCA CAC TCA GAT CAT CTT CT | SEQ ID NO: 91 |
| Tnf-α (rev) | GCT ACG TGG GCT ACA G | SEQ ID NO: 92 |
| IL-1β (fwd) | CTG GTA CAT CAG GAC CTC ACA | SEQ ID NO: 93 |
| IL-1β (rev) | GAG CTC CTT AAC ATG CCC TG | SEQ ID NO: 94 |
| IL-6 (fwd) | AGA CAA AGC CAG AGT CCT TCA GAG A | SEQ ID NO: 95 |
| IL-6 (Rev) | GCC ACT CCT TCT GTG ACT CGA GC | SEQ ID NO: 96 |

Example 14

Semaphorin 3A is Upregulated in Several Organs During Septic Shock

Given the link between SEMA3A, NRP1 and the innate immune response in OIR (as demonstrated in Examples 2-9 above), the implication of the NRP1-dependent cellular response in general systemic inflammation was next assessed. This was first explored by determining the kinetics of SEMA3A expression during septic shock.

LPS was administrated (15 mg/kg) to 6-8 weeks old C57BL/6 mice (n=5) and mice were sacrificed at 0, 4, 8, 12 and 24 hours following LPS administration. Key organs such as brain, kidney, lung and liver were collected and mRNA isolated. Levels of SEMA3A mRNA were robustly induced in all organs analyzed as soon as 6 hours after LPS injection and persisted for 24 hours (FIG. 11A-D). Similarly, expression levels of another NRP1 ligand, VEGF, were also profoundly increased in kidney (FIG. 11B), lung (FIG. 11C) and liver (FIG. 11D) within the first 6 hours of septic shock. Increases in classical pro-inflammatory cytokines TNF-α and IL1-β rose at 6 hours post LPS administration and diminished similarly to VEGF mRNA (FIG. 12). Hence, of all investigated mediators of inflammation, SEMA3A had a long-term kinetic profile and stayed elevated for at least 24 hours following induction of sepsis. This particular expression profile for SEMA3A suggests that its contribution to septic shock may be long lasting when compared to other cytokines.

Example 15

SEMA3A Induces Secretion of Pro-Inflammatory Cytokines in Myeloid Cells Via NRP1

Given the contribution of monocytes and myeloid cells to the acute inflammatory response and the presence of NRP1 on myeloid cells, the contribution of SEMA3A and myeloid-resident NRP1 in the production of inflammatory cytokines was determined.

Figure 13A:
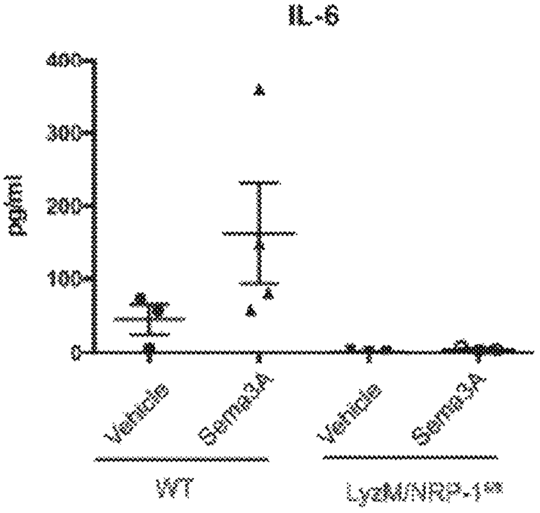
Figure 13B:
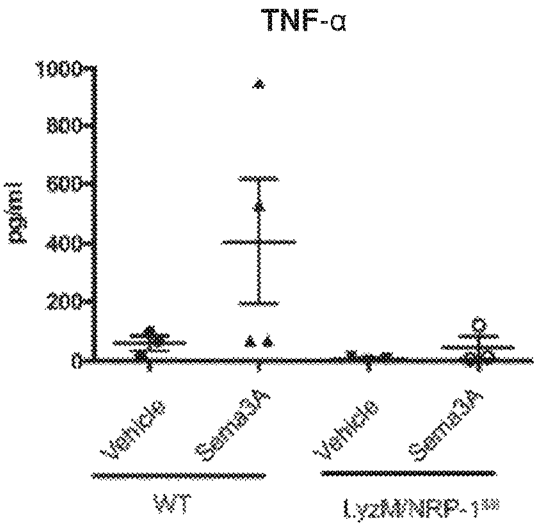
Figure 13C:
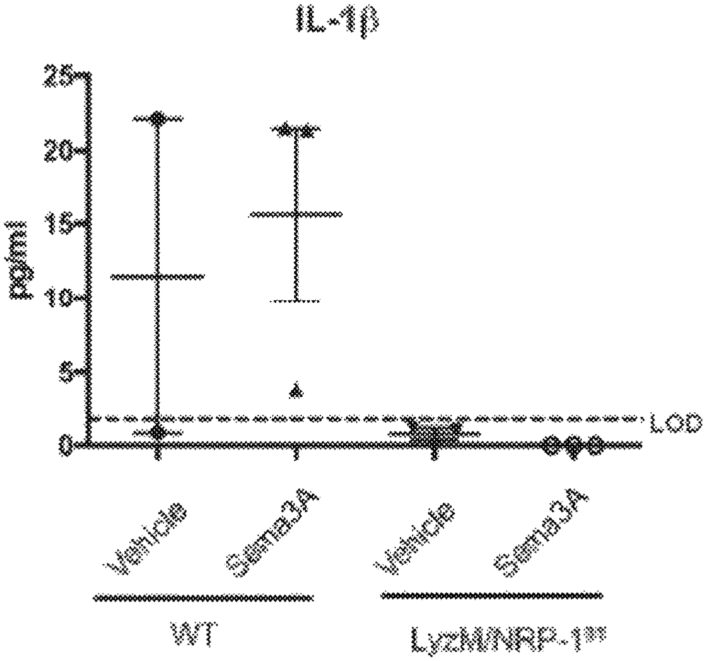

Isolated macrophages were exposed to SEMA3A (100 ng/ml) or vehicle and the production of cytokines was analyzed by Cytometric Bead Array (CBA). Results presented in FIG. 13 indicate that SEMA3A can induce the production/secretion of pro-inflammatory cytokines, known to contribute to septic shock such as IL-6 (FIG. 13A) and TNF-α (FIG. 13B). Of particular importance, a specific knockout of NRP1 (LyzM/NRP1$^{fl/fl}$) in myeloid cells abrogated SEMA3A-induced production of IL-6 and TNF-α. Notably, vehicle-treated control LyzM/NRP1$^{fl/fl}$ macrophages showed lesser production of IL-6, TNF-α and IL-1β then wild-type controls, highlighting the role of myeloid-resident NRP1 in sepsis-induced inflammation.

Example 16

Deficiency in Myeloid-Resident NRP1 Reduces Production of Pro-Inflammatory Cytokines In Vivo in Sepsis Because myeloid-resident NRP1 was important for the release of pro-inflammatory cytokines such as IL-6 and TNF-α in vitro, its contribution was next explored in vivo. LyzM/NRP1$^{fl/fl}$ and control wild-type mice were administered vehicle or LPS (15 mg/kg) and brains and livers were collected 6 hours post LPS injection. Real-time PCR analysis of TNF-α (FIGS. 14A,C) and IL-1b (FIG. 14B,D) levels revealed a robust drop in these cytokines in LyzM/NRP1$^{fl/fl}$. These results underscore the profound contribution of NRP1 and its ligands to the development of sepsis in vivo.

Example 17

Inhibition of NRP1 Signalling Prevents Sepsis-Induced Barrier Function Breakdown One of the pathological features of severe septic shock though to contribute to organ failure is the compromise of blood barriers (blood and air in lung, blood and urine in the kidney, blood and bile in liver, and humoral molecules in the brain). Given a role for SEMA3A in the breakdown of the blood retinal barrier (46) and the present novel data on the expression of SEMA3A during sepsis, the effect of neutralizing SEMA3A with a trap derived from the extracellular domain of human NRP1 was assessed (Trap-1, without FC, FIGS. 19B, SEQ ID NO:83). Using an Evans Blue Permeation (EBP) assay, we found that in all organs studied namely brain (FIG. 15A), kidney (FIG. 15B) and liver (FIG. 15C), a pronounced reduction in LPS-induced barrier function breakdown was observed when mice were treated with 4 ug of NRP1 derived trap (0.2 mg/kg, i.v.). These results strongly suggest that traps of soluble NRP1 and their derivatives are compelling therapeutic agents to counter sepsis.

Example 18

NRP1-Derived Trap Protects Against Sepsis

To determine the therapeutic benefits of neutralization of NRP1 ligands or NRP1 inhibition during sepsis, survival studies were performed. A high dose of LPS (25 mg/kg) was administered to mice. Mice were then monitored, and ethically sacrificed, when appropriate endpoints were achieved. In the second group, mice were injected i.v. with 4 ug of recombinant Trap-1 without FC (0.2 mg/kg, FIGS. 19B and 20A-20B, SEQ ID NO: 83) followed by LPS intraperitoneal injection. In the control group, 5/5 mice (100%) died within first 30 hrs (FIG. 16A) following LPS injection. Conversely, all mice treated with the trap were still alive after 30 hours and showed significant improved survival rate after 60 hours (3/5). Mortality was thus reduced from 100% (in the control group) after 30 hours to 40% (FIG. 16A) after 60 hours. Furthermore, 40% of Trap treated-mice remained alive 80 hours following LPS injection. Thus, survival time was at least doubled in 60% of the case and almost tripled in 40% of the case when cell signaling through NRP1 was inhibited.

Similar results were obtained with mice harboring a specific knock out of NPR1 in myeloid cells (FIG. 16B). Absence of NRP1 in myeloid cells increased survival time and reduced sepsis-induced mortality (3/5) from 100% to 40% (FIG. 16B) after 30 hours and from 100% to 40% after 60 hours. Also, 40% of NRP1 K.O. mice remained alive 80 hours following LPS injection.

Taken together, these results highlight the therapeutic value of inhibiting NRP1-dependent cell signaling in sepsis treatment.

Example 19

NRP1-Derived Trap Lowers Production of Inflammatory Cytokines in Septic Shock Given the therapeutic benefit of NRP1-trap on survival rates in septic shock, the impact of neutralization of NRP1 ligands on production of inflammatory cytokines during septic shock was next determined. Wild-type mice were administered i) vehicle (n=3); ii) LPS (15 mg/kg) (n=3) or iii) LPS and NRP1 mouse Trap 1 (without FC, FIG. 19C SEQ ID NO: 25, but without FC region) and brains were collected 6 hours post LPS injection. Injection of NRP1 trap-1 profoundly reduced production of TNF-α (FIG. 17A) and IL-6 (FIG. 17B). Similarly, mice with NRP1 deficient myeloid cells (LyzM-Cre/Nrp$^{fl/fl}$) (n=3) produced considerably less TNF-α and IL-6, underscoring the contribution of this cellular pathway to the progression of septic shock.

Example 20

Materials and Method for the Cerebral Ischemia/stroke Model Described in Example 21

The mice used in this study were 2- to 3-month-old male C57Bl/6 mice (22-28 g).

MCAO model. MCAO mouse model was performed using the intraluminal suture technique described by Rousselet et a1. (66). Briefly, mice were anesthetized in a chamber with 3% isoflurane in oxygen (1 L/min) and analgesized with buprenorphine (0.1 mg/kg body weight subcutaneously). Anesthesia was maintained during the operation using 1.5% isoflurane in oxygen provided via a face mask. The rectal temperature was recorded and kept stable at 37±0.5° C. with a heating pad. After a midline incision at the neck, the right carotid bifurcation was exposed and the common carotid artery (CCA) was temporarily occluded using 5-0 silk suture. The bifurcation of the right internal common carotid artery (ICA) and external common carotid artery (ECA) was separated. A permanent suture was placed around the ECA, as distally as possible, and another temporary suture slightly tight was placed on the ECA distal to the bifurcation. The right ICA was temporarily occluded with 5-0 silk suture to avoid bleeding. Then, a small hole in the ECA was cut between permanent and temporary sutures through which a 12 mm-long 6-0 silicon-coated (about 9-10 mm was coated with silicon) monofilament suture was introduced. The filament was advanced from the ECA into the lumen of the ICA until it blocked the origin of the middle cerebral artery (MCA) in the circle of Willis. Sham animals were obtained by inserting the monofilament into the CCA, but without advancing it to the MCA. The suture on the ECA was tightly tied to fix the monofilament in position. Thirty minutes after MCAO, the monofilament was completely removed to allow reperfusion. The temporary suture on the CCA was also removed to allow blood recirculation. After the wound was closed, 1 ml of saline solution was injected subcutaneously to avoid postsurgical dehydration. The mouse was placed in a cage and kept on the heating pad for 1 h. Meantime, when the mouse was fully awake from anesthesia, it was checked for some basic motor deficits (circling while walking and bending while hold by tail; indicators of the success of the operation) and NRP1-Trap-1 without FC (FIG. 19B SEQ ID NO:83) at the dose of 0.4 ug in 125 ul of PBS was administered to the tail vein (about 15 min after reperfusion had been started). Control animals operated in the same way as NRP1-treated animals received, after MCAO, a vehicle (PBS). Because post-surgical weight loss is generally observed, mashed food was placed in a Petri dish to encourage eating.

Determination of infarct volume. Following neurological evaluation (see section below) performed 24 h after MCAO the animals were deeply anesthetized with 3% isoflurane in oxygen (1 L/min) and decapitated. The brains were immediately isolated and transferred into isopentane cooled on dry ice and then stored at −80° C. Then, the frozen brains were coronally cut into 20-μm sections in a cryostat at −22° C. and every $15^{th}$ slice was mounted on positively charged glass slides. Cerebral sections were stained with cresyl violet for 15 min. Each section was photographed. The areas of infarction were delineated on the basis of the relative lack of staining in the ischemic region and measured by using NIH ImageJ software. Infarct area in each section was determined as the total area of the contralateral hemisphere minus the non-affected area of the ipsilateral hemisphere.

Neurological evaluation. One hour after operation, as well as 24 h after MCAO, animals were subjected to a series of motor tests performed. The examinations and scoring were as follows: 0, Normal; 1, Contralateral front or rear limb flexion upon lifting of the whole animal by the tail; 2, Circling to the contralateral side while walking and C-shaped lateral bending while hold by tail; 4 Circling to the contralateral side while walking and C-shaped lateral bending while hold by tail with limb flexion; 5, Comatose or moribund. The magnitude of the obtained neuroscore is directly proportional to the severity of impairment.

Example 21

NRP1-Trap Protects Against Cerebral Ischemia and Stroke

Figure 18A:
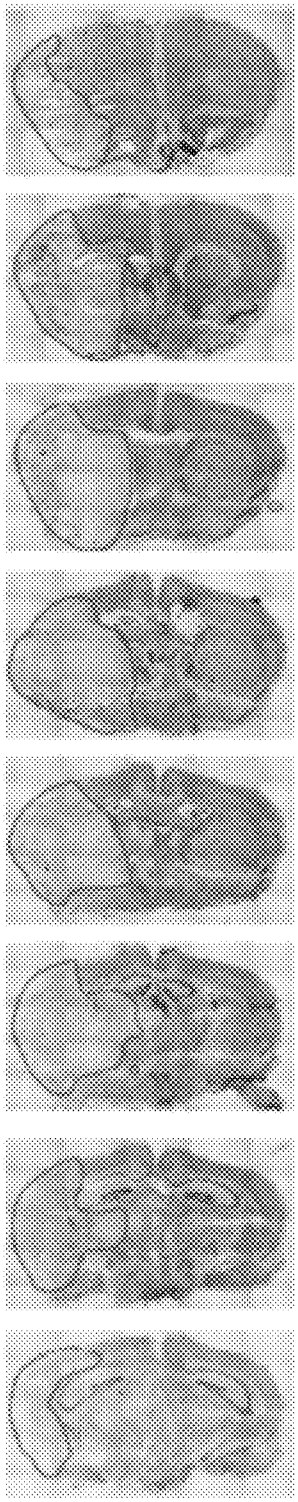
Figure 18B:
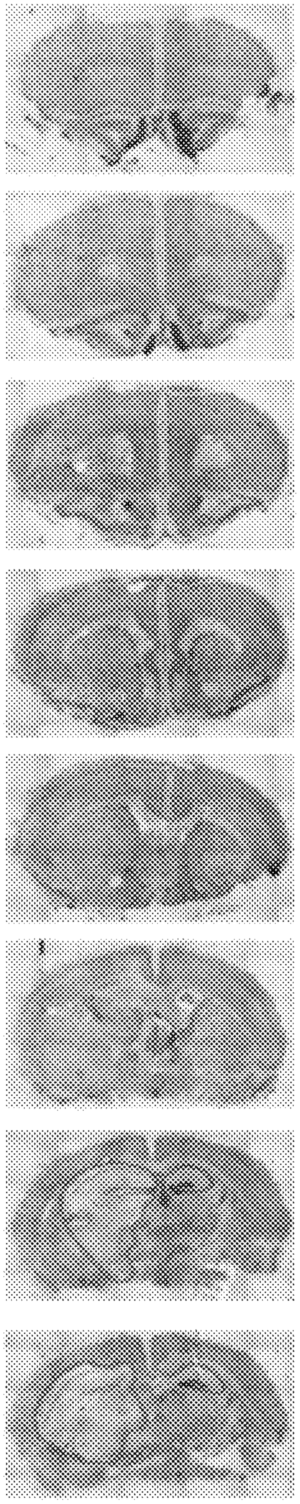
Figure 18C:
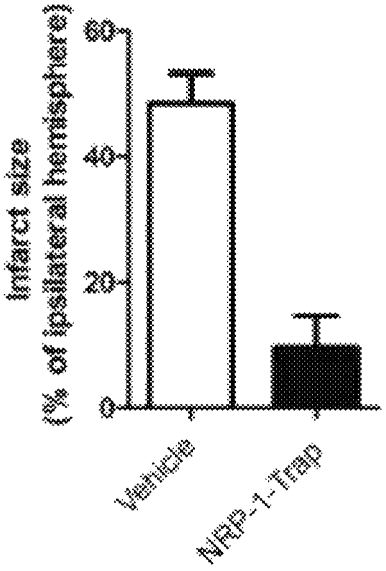

In order to assess the outcome of SEMA3A neutralization on cerebral ischemia or stroke, adult (8-12-week-old) mice were subjected to the transient middle cerebral artery occlusion (MCAO) model. Experimental details are provided in Example 20. Briefly, following termination of MCAO, mouse NRP1-trap (Trap-1, without FC,), 0.4 ug in 125 ul of PBS, (FIG. 19C, FIG. 20X-20Y; SEQ ID NO: 25) was administered to the tail vein (about 15 min after reperfusion had been started). In order to visualize brain damage induced by MCAO, coronal cerebral sections were stained with cresyl violet. On each section, the unstained area corresponded to the ischemic region of the brain (FIG. 18A). Measurement of these areas on serial coronal sections revealed that 24 h after MCAO, the infarcted zone constituted 48% of the ipsilateral hemisphere in occluded mice compared to sham operated animals whose brains were not injured. NRP1 treatment reduced brain damage; the infarct volume of the ipsilateral hemisphere was decreased by 80% (FIG. 18B,C).

Figure 18D:
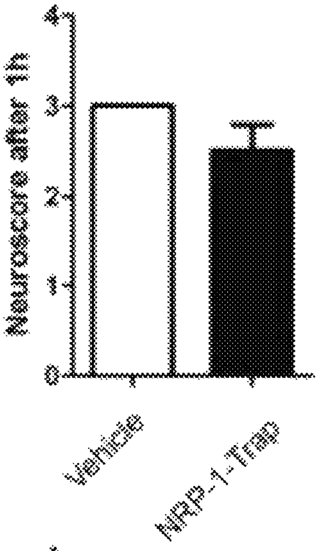
Figure 18E:
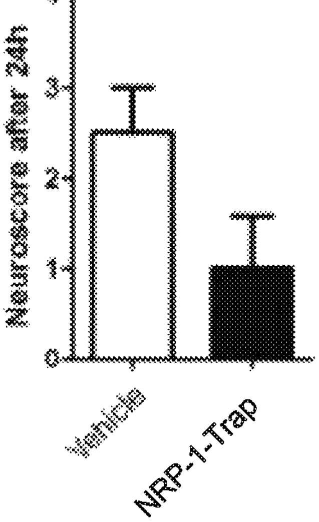

Neurological impairment was assessed by neurological scoring of the presence of limb flexion, C-shaped lateral bending of the body and circling movements. MCAO mice that were not showing circling and bending behaviour 1 hour after operation were excluded from the further study (FIG. 18D). Forelimb or hindlimb flexion, C-shaped lateral bending of the body, circling movements were observed in mice subjected to MCAO compared to sham operated animals. NRP1 treatment dramatically improved neurological scores of ischemic mice by 60% compared to non-treated MCAO mice when evaluated 24 hours after surgery (FIG. 18E).

Taken together, these results show that inhibition of the NRP1 pathway protects against cerebral ischemia and stroke and reduce the neurological impairment associated with cerebral ischemia and stroke.

Example 22

Neuropilin-Derived Traps Enhance Vascular Regeneration and Prevent Pathological Neovascularization in Ischemic Retinas in Mouse Model of Diabetic Retinopathy and Retinopathy of Prematurity Pathological vascular degeneration as well as pre-retinal vascular proliferation were studied using the well-established mouse model of oxygen-induced proliferative retinopathy (OIR)(Smith et al., 1994). This model is based on retinopathy of prematurity (ROP) and is regularly used as a proxy for the proliferative (angiogenic phase) of diabetic retinopathy and ROP.

Nursing mothers and their pups were exposed to 75% oxygen from P7-P12. Both vasodegenerative (assessed at P12) and vaso-proliferative (assessed at P17) phases are present and are highly reproducible making evaluation of interventions on disease progression accurate and swift. Trap G (SEQ ID NO: 38), or Trap M (lacking the b2 and c domains, SEQ ID NO: 42), was injected into the vitreous at P12 (1 ul at 0.5 ug/ul). Dissected retinas were flatmounted and incubated overnight with fluoresceinated isolectin B4 (1:100) in 1 mM $CaCl_2$ to determine extent of avascular area or neovascularization area at P17. Avascular areas were determined in lectin stained retinas as zones devoid of staining. Neovascularization was determined as areas of saturated lectin staining which demarcates pre-retinal tufts (54, 55).

Trap G, was shown to effectively enhance vascular regeneration by over 40% when compared to vehicle control (FIG. 23B). Similarly, Trap G was shown to inhibit pathological neovascularization by ~45% (FIG. 23C). Trap-M enhanced vascular regeneration by ~60% (FIG. 23B) and inhibited pathological neovascularization by ~60% when compared to vehicle controls (FIG. 23C). Hence, Trap M, with compromised VEGF binding, more effectively prevents pathological angiogenesis and more readily leads to enhanced vascular regeneration in the ischemic retina.

Example 23

Neuropilin-Derived Traps Decrease Vascular Leakage in Diabetic Retinas

The influence of Traps on vascular leakage/permeability in diabetic retinopathy was also studied in the streptozotocin (STZ) model of Type 1 diabetes. STZ (55 mg/kg) was administered over 5 consecutive days to ~6 week-old C57BL/6J mice and glycemia was monitored. Mice were considered diabetic if their non-fasted glycemia was higher than 17 mM (300 mg/dL). Mice were administered intravitreally with 0.5 ug (0.5 ug/ul) of Trap G (SEQ ID NO: 38) or M (SEQ ID NO: 42) or with mouse anti-VEGF antibody (AF-493-NA, from R&D) at 6 and 7 weeks after STZ administration. Alternatively, mice were injected intravitreally at 12 and 13 weeks post STZ and vascular permeability assessed at 14 weeks. Mice were hyperglycemic/diabetic at least 3 weeks prior to intravitreal injections with SEMA traps (see FIG. 24A) or anti VEGF antibody. Retinal vascular leakage was determined by Evans Blue assay at 8 weeks post STZ injections as follows. Retinal Evans Blue (EB) permeation was performed using 3 retinas per reading. Evan Blue was injected at 45 mg/kg intravenously and allowed to circulate for 2 hours prior to retinal extraction. Evans Blue Permeation was quantified in retinas by fluorimetry (620 nm max absorbance-740 nm min absorbance (background) with a TECAN Infinite® M1000 PRO. Evan Blue Permeation (EBP) [measured in uL/(grams*hour)] was calculated as follows: [EB (ug)/Wet retinal weight (g)]/[plasma EB (ug/uL)*Circulation time (hours)]. Evans Blue permeation was expressed relative to controls.

Both Trap-G (SEQ ID NO: 38) and Trap-M (SEQ ID NO: 42) significantly reduced vascular permeability by over 40% (FIG. 24B). The mouse anti-VEGF antibody (AF-493-NA) did not prevent vascular permeability at this early stage. Trap G was effective at reducing vascular leakage as was the anti-VEGF neutralizing Ab at P17 (FIG. 24C), *p<0.05, n=4, from 12 animals.

Example 24

Neuropilin-Derived Traps Decrease Choroidal Neovascularization in Model of Age-Related Macular Degeneration The effect of NRP1 trap G (SEQ ID NO: 38) on choroidal neovascularization (CNV) was determined in a mouse model of age-related macular degeneration (AMD). To induce CNV and thus mimic wet AMD in mice, laser coagulations on 6-8-week-old mice (1-2 disc diameters) were performed from the papillae using an Argon laser (532 nm) mounted on a Coherent slit lamp (400 mW, 50 ms and 50 μm) (Combadiere et al., 2007). Following laser burn, treated mice were injected intravitreally with 0.5 ug of Trap G. Fourteen days (P14) later, choroids were radially incised, flat-mounted and stained with the endothelial cell marker fluoresceinated Isolectin B4 (animals were also optionally perfused with fluorescein dextran to visualize luminal vessels) and volumes of CNV were measured by scanning laser confocal microscopy (Takeda et al., 2009).

Trap G was shown to significantly reduce choroidal neovascularization at day 14 post laser-burn (FIG. 25 B).

The scope of the claims should not be limited by the preferred embodiments set forth in the examples, but should be given the broadest interpretation consistent with the description as a whole.

REFERENCES

1. Lampron, A., Elali, A., and Rivest, S. 2013. Innate immunity in the CNS: redefining the relationship between the CNS and Its environment. *Neuron* 78:214-232.
2. Ousman, S. S., and Kubes, P. 2012. Immune surveillance in the central nervous system. *Nat Neurosci* 15:1096-1101.
3. Adamis, A. P., and Berman, A. J. 2008. Immunological mechanisms in the pathogenesis of diabetic retinopathy. *Semin Immunopathol* 30:65-84.
4. Antonetti, D. A., Klein, R., and Gardner, T. W. 2012. *Diabetic retinopathy. N Engl J Med* 366:1227-1239.
5. Joussen, A. M., Poulaki, V., Le, M. L., Koizumi, K., Esser, C., Janicki, H., Schraermeyer, U., Kociok, N., Fauser, S., Kirchhof, B., et al. 2004. A central role for inflammation in the pathogenesis of diabetic retinopathy. *FASEB J* 18:1450-1452.
6. Ambati, J., and Fowler, B. J. 2012. Mechanisms of age-related macular degeneration. *Neuron* 75:26-39.
7. Sennlaub, F., Auvynet, C., Calippe, B., Lavalette, S., Poupel, L., Hu, S. J., Dominguez, E., Camelo, S., Levy, O., Guyon, E., et al. 2013. CCR2(+) monocytes infiltrate atrophic lesions in age-related macular disease and mediate photoreceptor degeneration in experimental subretinal inflammation in Cx3cr1 deficient mice. *EMBO Mol Med* 5:1775-1793.
8. Combadiere, C., Feumi, C., Raoul, W., Keller, N., Rodero, M., Pezard, A., Lavalette, S., Houssier, M., Jonet, L., Picard, E., et al. 2007. CX3CR1-dependent subretinal microglia cell accumulation is associated with cardinal features of age-related macular degeneration. *J Clin Invest* 117:2920-2928.
9. Dammann, O. 2010. Inflammation and retinopathy of prematurity. *Acta Paediatr* 99:975-977.
10. Tremblay, S., Miloudi, K., Chaychi, S., Favret, S., Binet, F., Polosa, A., Lachapelle, P., Chemtob, S., and Sapieha, P. 2013. Systemic inflammation perturbs developmental retinal angiogenesis and neuroretinal function. *Invest Ophthalmol Vis Sci* 54:8125-8139.
11. Hartnett, M. E., and Penn, J. S. 2012. Mechanisms and management of retinopathy of prematurity. *N Engl J Med* 367:2515-2526.
12. Kempen, J. H., O'Colmain, B. J., Leske, M. C., Haffner, S. M., Klein, R., Moss, S. E., Taylor, H. R., and Hamman, R. F. 2004. The prevalence of diabetic retinopathy among adults in the United States. *Arch Ophthalmol* 122:552-563.
13. Sapieha, P., Hamel, D., Shao, Z., Rivera, J. C., Zaniolo, K., Joyal, J. S., and Chemtob, S. 2010. Proliferative retinopathies: angiogenesis that blinds. *Int J Biochem Cell Biol* 42:5-12.
14. Robinson, G. S., Ju, M., Shih, S. C., Xu, X., McMahon, G., Caldwell, R. B., and Smith, L. E. 2001. Nonvascular role for VEGF: VEGFR-1, 2 activity is critical for neural retinal development. *FASEB J* 15:1215-1217.
15. Saint-Geniez, M., Maharaj, A. S., Walshe, T. E., Tucker, B. A., Sekiyama, E., Kurihara, T., Darland, D. C., Young, M. J., and D'Amore, P. A. 2008. Endogenous VEGF is required for visual function: evidence for a survival role on muller cells and photoreceptors. *PLoS One* 3:e3554.
16. Hellstrom, A., Smith, L. E., and Dammann, O. 2013. Retinopathy of prematurity. *Lancet.*
17. Sapieha, P. 2012. Eyeing central neurons in vascular growth and reparative angiogenesis. *Blood* 120:2182-2194.
18. Kern, T. S., and Barber, A. J. 2008. Retinal ganglion cells in diabetes. *J Physiol* 586:4401-4408.
19. Binet, F., Mawambo, G., Sitaras, N., Tetreault, N., Lapalme, E., Favret, S., Cerani, A., Leboeuf, D., Tremblay, S., Rezende, F., et al. 2013. Neuronal ER Stress Impedes Myeloid-Cell-Induced Vascular Regeneration through IRE1alpha Degradation of Netrin-1. *Cell Metab* 17:353-371.
20. Cerani A, T. N., Menard C, Lapalme E, Patel C, Sitaras N, Beaudoin F, Leboeuf D, De Guire V, Binet F, Dejda A, Rezende F, Miloudi K, Sapieha P. 2013. Neuron-Derived Semaphorin 3A is an Early Inducer of Vascular Permeability in Diabetic Retinopathy via Neuropilin-1. *Cell Metabolism.,* 18(4): 505-518.
21. Joyal, J.-S., Sitaras, N., Binet, F., Rivera, J. C., Stahl, A., Zaniolo, K., Shao, Z., Polosa, A., Zhu, T., Hamel, D., et al. 2011. Ischemic neurons prevent vascular regeneration of neural tissue by secreting semaphorin 3A. *Blood* 117:6024-6035.
22. Checchin, D., Sennlaub, F., Levavasseur, E., Leduc, M., and Chemtob, S. 2006. Potential role of microglia in retinal blood vessel formation. *Invest Ophthalmol Vis Sci* 47:3595-3602.

23. Connor, K. M., SanGiovanni, J. P., Lofqvist, C., Aderman, C. M., Chen, J., Higuchi, A., Hong, S., Pravda, E. A., Majchrzak, S., Carper, D., et al. 2007. Increased dietary intake of omega-3-polyunsaturated fatty acids reduces pathological retinal angiogenesis. *Nat Med* 13:868-873.
24. Sapieha, P., Stahl, A., Chen, J., Seaward, M. R., Willett, K. L., Krah, N. M., Dennison, R. J., Connor, K. M., Aderman, C. M., Liclican, E., et al. 2011. 5-Lipoxygenase Metabolite 4-HDHA Is a Mediator of the Antiangiogenic Effect of {omega}-3 Polyunsaturated Fatty Acids. *Sci Transl Med* 3:69ra12.
25. Stahl, A., Sapieha, P., Connor, K. M., Sangiovanni, J. P., Chen, J., Aderman, C. M., Willett, K. L., Krah, N. M., Dennison, R. J., Seaward, M. R., et al. 2010. Short communication: PPAR gamma mediates a direct antiangiogenic effect of omega 3-PUFAs in proliferative retinopathy. *Circ Res* 107(4):495-500.
26. Smith, L. E., Wesolowski, E., McLellan, A., Kostyk, S. K., D'Amato, R., Sullivan, R., and D'Amore, P. A. 1994. Oxygen-induced retinopathy in the mouse. *Invest Ophthalmol Vis Sci* 35:101-111.
27. Lee, P., Goishi, K., Davidson, A. J., Mannix, R., Zon, L., and Klagsbrun, M. 2002. Neuropilin-1 is required for vascular development and is a mediator of VEGF-dependent angiogenesis in zebrafish. *Proc Natl Acad Sci USA* 99:10470-10475.
28. Gluzman-Poltorak, Z., Cohen, T., Shibuya, M., and Neufeld, G. 2001. Vascular endothelial growth factor receptor-1 and neuropilin-2 form complexes. *J Biol Chem* 276:18688-18694.
29. Mamluk, R., Gechtman, Z., Kutcher, M. E., Gasiunas, N., Gallagher, J., and Klagsbrun, M. 2002. Neuropilin-1 binds vascular endothelial growth factor 165, placenta growth factor-2, and heparin via its b1b2 domain. *J Biol Chem* 277:24818-24825.
30. Soker, S., Takashima, S., Miao, H. Q., Neufeld, G., and Klagsbrun, M. 1998. Neuropilin-1 is expressed by endothelial and tumor cells as an isoform-specific receptor for vascular endothelial growth factor. *Cell* 92:735-745.
31. Fantin, A., Vieira, J. M., Gestri, G., Denti, L., Schwarz, Q., Prykhozhij, S., Peri, F., Wilson, S. W., and Ruhrberg, C. 2010. Tissue macrophages act as cellular chaperones for vascular anastomosis downstream of VEGF-mediated endothelial tip cell induction. *Blood* 116:829-840.
32. Carrer, A., Moimas, S., Zacchigna, S., Pattarini, L., Zentilin, L., Ruozi, G., Mano, M., Sinigaglia, M., Maione, F., Serini, G., et al. 2012. Neuropilin-1 identifies a subset of bone marrow Gr1-monocytes that can induce tumor vessel normalization and inhibit tumor growth. *Cancer Res* 72:6371-6381.
33. Casazza, A., Laoui, D., Wenes, M., Rizzolio, S., Bassani, N., Mambretti, M., Deschoemaeker, S., Van Ginderachter, J. A., Tamagnone, L., and Mazzone, M. 2013. Impeding Macrophage Entry into Hypoxic Tumor Areas by SEMA3A/Nrp1 Signaling Blockade Inhibits Angiogenesis and Restores Antitumor Immunity. *Cancer Cell* 24:695-709.
34. Ritter, M. R., Banin, E., Moreno, S. K., Aguilar, E., Dorrell, M. I., and Friedlander, M. 2006. Myeloid progenitors differentiate into microglia and promote vascular repair in a model of ischemic retinopathy. *J Clin Invest* 116:3266-3276.
35. Stahl, A., Chen, J., Sapieha, P., Seaward, M. R., Krah, N. M., Dennison, R. J., Favazza, T., Bucher, F., Lofqvist, C., Ong, H., et al. 2010. Postnatal Weight Gain Modifies Severity and Functional Outcome of Oxygen-Induced Proliferative Retinopathy. *Am J Pathol.* 177(6): 2715-2733.
36. Clausen, B. E., Burkhardt, C., Reith, W., Renkawitz, R., and Forster, I. 1999. Conditional gene targeting in macrophages and granulocytes using LysMcre mice. *Transgenic Res* 8:265-277.
37. Mattapallil, M. J., Wawrousek, E. F., Chan, C. C., Zhao, H., Roychoudhury, J., Ferguson, T. A., and Caspi, R. R. 2012. The Rd8 mutation of the Crb1 gene is present in vendor lines of C57BL/6N mice and embryonic stem cells, and confounds ocular induced mutant phenotypes. *Invest Ophthalmol Vis Sci* 53:2921-2927.
38. Klebanov, O., Nitzan, A., Raz, D., Barzilai, A., and Solomon, A. S. 2009. Upregulation of Semaphorin 3A and the associated biochemical and cellular events in a rat model of retinal detachment. *Graefes Arch Clin Exp Ophthalmol* 247:73-86.
39. Koppel, A. M., and Raper, J. A. 1998. Collapsin-1 covalently dimerizes, and dimerization is necessary for collapsing activity. *J Biol Chem* 273:15708-15713.
40. Neufeld, G., and Kessler, O. 2008. The semaphorins: versatile regulators of tumour progression and tumour angiogenesis. *Nat Rev Cancer* 8:632-645.
41. Worthylake, R. A., and Burridge, K. 2003. RhoA and ROCK promote migration by limiting membrane protrusions. *J Biol Chem* 278:13578-13584.
42. Dammann, O., Brinkhaus, M. J., Bartels, D. B., Dordelmann, M., Dressler, F., Kerk, J., Dork, T., and Dammann, C. E. 2009. Immaturity, perinatal inflammation, and retinopathy of prematurity: a multi-hit hypothesis. *Early Hum Dev* 85:325-329.
43. Kastelan, S., Tomic, M., Gverovic Antunica, A., Salopek Rabatic, J., and Ljubic, S. 2013. Inflammation and pharmacological treatment in diabetic retinopathy. *Mediators Inflamm* 2013:213130.
44. Silva, P. S., Cavallerano, J. D., Sun, J. K., Aiello, L. M., and Aiello, L. P. 2010. Effect of systemic medications on onset and progression of diabetic retinopathy. *Nat Rev Endocrinol* 6:494-508.
45. Cerani, A., Tetreault, N., Menard, C., Lapalme, E., Patel, C., Sitaras, N., Beaudoin, F., Leboeuf, D., De Guire, V., Binet, F., et al. 2013. Neuron-derived semaphorin 3A is an early inducer of vascular permeability in diabetic retinopathy via neuropilin-1. *Cell Metab* 18:505-518.
46. Miao, H. Q., Soker, S., Feiner, L., Alonso, J. L., Raper, J. A., and Klagsbrun, M. 1999. Neuropilin-1 mediates collapsin-1/semaphorin III inhibition of endothelial cell motility: functional competition of collapsin-1 and vascular endothelial growth factor-165. *J Cell Biol* 146: 233-242.
47. Klagsbrun, M., and Eichmann, A. 2005. A role for axon guidance receptors and ligands in blood vessel development and tumor angiogenesis. *Cytokine Growth Factor Rev* 16:535-548.
48. Guttmann-Raviv, N., Shraga-Heled, N., Varshaysky, A., Guimaraes-Sternberg, C., Kessler, O., and Neufeld, G. 2007. Semaphorin-3A and semaphorin-3F work together to repel endothelial cells and to inhibit their survival by induction of apoptosis. *J Biol Chem* 282: 26294-26305.

49. Neufeld, G., Sabag, A. D., Rabinovicz, N., and Kessler, O. 2012. Semaphorins in angiogenesis and tumor progression. *Cold Spring Harb Perspect Med* 2:a006718.

50. Bussolino, F., Valdembri, D., Caccavari, F., and Serini, G. 2006. Semaphoring vascular morphogenesis. *Endothelium* 13:81-91.

51. Yancopoulos, G. D. 2010. Clinical application of therapies targeting VEGF. *Cell* 143:13-16.

52. Miloudi, K., Dejda, A., Binet, F., Lapalme, E., Cerani, A., and Sapieha, P. 2014. Assessment of vascular regeneration in the CNS using the mouse retina. *J Vis Exp.* 88: e51351.

53. Sapieha, P., Joyal, J. S., Rivera, J. C., Kermorvant-Duchemin, E., Sennlaub, F., Hardy, P., Lachapelle, P., and Chemtob, S. 2010. Retinopathy of prematurity: understanding ischemic retinal vasculopathies at an extreme of life. *J Clin Invest* 120:3022-3032.

54. Stahl, A., Connor, K. M., Sapieha, P., Chen, J., Dennison, R. J., Krah, N. M., Seaward, M. R., Willett, K. L., Aderman, C. M., Guerin, K. I., et al. 2010. The mouse retina as an angiogenesis model. *Invest Ophthalmol Vis Sci* 51:2813-2826.

55. Stahl, A., Connor, K. M., Sapieha, P., Willett, K. L., Krah, N. M., Dennison, R. J., Chen, J., Guerin, K. I., and Smith, L. E. 2009. Computer-aided quantification of retinal neovascularization. *Angiogenesis* 12:297-301.

56. Shao, Z., Friedlander, M., Hurst, C. G., Cui, Z., Pei, D. T., Evans, L. P., Juan, A. M., Tahir, H., Duhamel, F., Chen, J., et al. 2013. Choroid sprouting assay: an ex vivo model of microvascular angiogenesis. *PLoS One* 8:e69552.

57. Van Rooijen, N., and van Kesteren-Hendrikx, E. 2003. "In vivo" depletion of macrophages by liposome-mediated "suicide". *Methods Enzymol* 373:3-16.

58. Deutschman, C. S., and Tracey, K. J. 2014. Sepsis: current dogma and new perspectives. Immunity 40:463-475.

59. Bruder, D., Probst-Kepper, M., Westendorf, A. M., Geffers, R., Beissert, S., Loser, K., von Boehmer, H., Buer, J., and Hansen, W. 2004. Neuropilin-1: a surface marker of regulatory T cells. Eur J Immunol 34:623-630.

60. Takahashi, T., Fournier, A., Nakamura, F., Wang, L. H., Murakami, Y., Kalb, R. G., Fujisawa, H., and Strittmatter, S. M. 1999. Plexin-neuropilin-1 complexes form functional semaphorin-3A receptors. Cell 99:59-69.

61. Klagsbrun, M., Takashima, S., and Mamluk, R. 2002. The role of neuropilin in vascular and tumor biology. Adv Exp Med Biol 515:33-48.

62. Soker, S., Miao, H. Q., Nomi, M., Takashima, S., and Klagsbrun, M. 2002. VEGF165 mediates formation of complexes containing VEGFR-2 and neuropilin-1 that enhance VEGF165-receptor binding. J Cell Biochem 85:357-368.

63. Appleton, B. A., Wu, P., Maloney, J., Yin, J., Liang, W. C., Stawicki, S., Mortara, K., Bowman, K. K., Elliott, J. M., Desmarais, W., et al. 2007. Structural studies of neuropilin/antibody complexes provide insights into semaphorin and VEGF binding. EMBO J 26:4902-4912.

64. Vieira, J. M., Schwarz, Q., and Ruhrberg, C. 2007. Role of the neuropilin ligands $VEGF_{164}$ and SEMA3A in neuronal and vascular patterning in the mouse. Novartis Found Symp 283:230-235; discussion 235-241.

65. Geretti, E., Shimizu, A., and Klagsbrun, M. 2008. Neuropilin structure governs VEGF and semaphorin binding and regulates angiogenesis. Angiogenesis 11:31-39.

66. Rousselet, E., Kriz, J., Seidah, N. G. Mouse model of intraluminal MCAO: cerebral infarct evaluation by cresyl violet staining. J Vis Exp. 2012 Nov. 6; (69). pii: 4038. doi: 10.3791/4038.

67. Combadiere, C., C. Feumi, W. Raoul, N. Keller, M. Rodero, A. Pezard, S. Lavalette, M. Houssier, L. Jonet, E. Picard, P. Debre, M. Sirinyan, P. Deterre, T. Ferroukhi, S. Y. Cohen, D. Chauvaud, J. C. Jeanny, S. Chemtob, F. Behar-Cohen, and F. Sennlaub. 2007. CX3CR1-dependent subretinal microglia cell accumulation is associated with cardinal features of age-related macular degeneration. J Clin Invest 117:2920-2928.

68. Takeda, A., J. Z. Baffi, M. E. Kleinman, W. G. Cho, M. Nozaki, K. Yamada, H. Kaneko, R. J. Albuquerque, S. Dridi, K. Saito, B. J. Raisler, S. J. Budd, P. Geisen, A. Munitz, B. K. Ambati, M. G. Green, T. Ishibashi, J. D. Wright, A. A. Humbles, C. J. Gerard, Y. Ogura, Y. Pan, J. R. Smith, S. Grisanti, M. E. Hartnett, M. E. Rothenberg, and J. Ambati. 2009. CCR3 is a target for age-related macular degeneration diagnosis and therapy. Nature 460:225-230.

The invention claimed is:

1. A fusion polypeptide comprising (i) a neuropilin-1 (NRP1) polypeptide consisting of an amino acid sequence having at least 98% identity with residues 22-430 of SEQ ID NO: 66, and (ii) a fragment crystallizable (Fc) domain fused to the amino-terminal end of the NRP1 polypeptide, wherein said fusion polypeptide does not comprise the b2 and c domains of native human NRP1.

2. The fusion polypeptide of claim 1, wherein said NRP1 polypeptide consists of an amino acid sequence having at least 99% identity with residues 22-430 of SEQ ID NO: 66.

3. The fusion polypeptide of claim 1, wherein said NRP1 polypeptide consists of residues 22-430 of SEQ ID NO: 66.

4. The fusion polypeptide of claim 1, wherein said Fc domain is a human Fc domain.

5. The fusion polypeptide of claim 1, wherein said Fc domain is fused directly to the amino-terminal end of the NRP1 polypeptide.

6. A pharmaceutical composition comprising the fusion polypeptide of claim 1 and a pharmaceutically acceptable carrier.

7. The pharmaceutical composition of claim 6, which is an ophthalmic pharmaceutical composition.

8. The pharmaceutical composition of claim 7, wherein the pharmaceutically acceptable carrier is an aqueous or oily carrier.

9. The pharmaceutical composition of claim 7, wherein the pharmaceutically acceptable carrier is a physiological saline buffer.

10. The pharmaceutical composition of claim 7, wherein the composition is a suspension, solution or emulsion.

11. The pharmaceutical composition of claim 7, wherein said composition is an injectable formulation.

12. A method for reducing ocular inflammation in a subject, comprising administering in the eye of the subject an effective amount of the pharmaceutical composition of claim 7.

13. The method of claim 12, wherein the subject suffers from diabetic retinopathy or age-related macular degeneration.

14. The method of claim 13, wherein the subject suffers from diabetic retinopathy.

15. The method of claim 13, wherein the subject suffers from age-related macular degeneration.

* * * * *